United States Patent
Boulet et al.

(10) Patent No.: US 11,731,984 B2
(45) Date of Patent: Aug. 22, 2023

(54) KRAS G12C INHIBITORS

(71) Applicant: Eli Lilly and Company, Indianapolis, IN (US)

(72) Inventors: Serge Louis Boulet, Fishers, IN (US); Kevin Charles Fortner, Indianapolis, IN (US); Deqi Guo, Carmel, IN (US); David Michael Hyman, Westport, CT (US); Sheng-Bin Peng, Carmel, IN (US); Chong Si, Zionsville, IN (US)

(73) Assignee: Eli LIlly and Company, Indianapolis, IN (US)

( * ) Notice: Subject to any disclaimer, the term of this patent is extended or adjusted under 35 U.S.C. 154(b) by 245 days.

(21) Appl. No.: 17/111,676

(22) Filed: Dec. 4, 2020

(65) Prior Publication Data

US 2021/0179633 A1  Jun. 17, 2021

Related U.S. Application Data

(60) Provisional application No. 62/946,586, filed on Dec. 11, 2019.

(51) Int. Cl.
| | |
|---|---|
| *A61K 39/00* | (2006.01) |
| *C07D 498/04* | (2006.01) |
| *A61P 35/00* | (2006.01) |
| *A61K 33/243* | (2019.01) |
| *A61K 31/4985* | (2006.01) |
| *A61K 31/506* | (2006.01) |
| *A61K 31/517* | (2006.01) |
| *A61K 31/519* | (2006.01) |
| *A61K 31/5377* | (2006.01) |
| *A61K 31/553* | (2006.01) |
| *A61K 31/555* | (2006.01) |
| *A61K 39/395* | (2006.01) |
| *C07D 487/04* | (2006.01) |

(52) U.S. Cl.
CPC ........ *C07D 498/04* (2013.01); *A61K 31/4985* (2013.01); *A61K 31/506* (2013.01); *A61K 31/517* (2013.01); *A61K 31/519* (2013.01); *A61K 31/5377* (2013.01); *A61K 31/553* (2013.01); *A61K 31/555* (2013.01); *A61K 33/243* (2019.01); *A61K 39/3955* (2013.01); *A61P 35/00* (2018.01); *C07D 487/04* (2013.01)

(58) Field of Classification Search
CPC ............... C07D 498/04; C07D 487/04; A61K 31/4985; A61K 31/506; A61K 31/517; A61K 31/519; A61K 31/553
See application file for complete search history.

(56) References Cited

U.S. PATENT DOCUMENTS

2009/0318412 A1   12/2009   Matsumoto

FOREIGN PATENT DOCUMENTS

| CN | 112390818 A | 2/2021 |
|---|---|---|
| TW | 201906848 A | 2/2016 |
| TW | I659021 B | 5/2019 |
| TW | 201922739 A1 | 6/2019 |
| TW | 201938555 A1 | 10/2019 |
| WO | 2018/206539 | 11/2018 |
| WO | 2019/051084 | 3/2019 |
| WO | 2019/215203 A1 | 11/2019 |
| WO | 2020/081282 | 4/2020 |
| WO | 2020/178282 | 9/2020 |

OTHER PUBLICATIONS

Johnson et al Cancer Treatment Reviews vol. 2 p. 1 (1975). (Year: 1975).*
Patent Cooperation Treaty International Search Report pertaining to International Application No. PCT/US2020/063272; dated Mar. 4, 2021, 5 pages.
Patent Cooperation Treaty Written Opinion of the International Searching Authority pertaining to International Application No. PCT/US2020/063272; dated Mar. 4, 2021, 8 pages.
Taiwan Search Report in Taiwan Application No. 109142894, dated Aug. 4, 2021, 1 page (English translation only).

* cited by examiner

*Primary Examiner* — Sheela J. Huff
(74) *Attorney, Agent, or Firm* — Cedric A. D'Hue

(57) ABSTRACT

The present invention provides compounds of the formula:

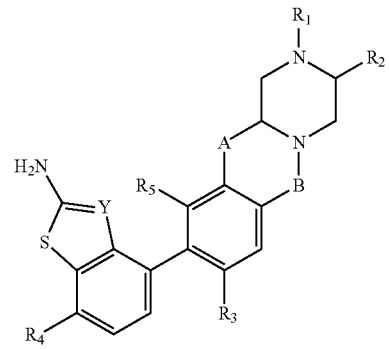

where $R_1$, $R_2$, $R_3$, $R_4$, $R_5$, A, B, and Y are as described herein, pharmaceutically acceptable salts thereof, and methods of using these compounds and salts for treating patients for cancer.

23 Claims, No Drawings

KRAS G12C INHIBITORS

The present invention relates to novel tricyclic heterocyclic compounds and pharmaceutically acceptable salts thereof, pharmaceutical compositions including the tricyclic heterocyclic compounds and salts, and methods of using the compounds and salts to treat cancers such as lung cancer, colorectal cancer, pancreatic cancer, bladder cancer, cervical cancer, endometrial cancer, ovarian cancer, cholangiocarcinoma or esophageal cancer.

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division. KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers and have been demonstrated to activate multiple downstream signaling pathways. Despite the prevalence of KRas mutations, it has been a difficult therapeutic target. (Cox, A. D. *Drugging the Undruggable RAS: Mission Possible? Nat. Rev. Drug Disc.* 2014, 13, 828-851; Pylayeva-Gupta, y et al. *RAS Oncogenes: Weaving a Tumorigenic Web.* Nat. Rev. Cancer 2011, 11, 761-774).

WO2015/054572 and WO2016/164675 disclose certain quinazoline derivatives capable of binding to KRas G12C. WO2016/044772 also discloses methods of using such quinazoline derivatives. WO2020/0081282 discloses KRas G12C inhibitors. WO2018/206539 and WO2020/178282 disclose certain heteroaryl compounds capable of binding to KRas G12C RAS proteins.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. There is also a need to provide small molecule KRas inhibitors that exhibit greater efficacy at the same or reduced KRas inhibitory activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward or undesired effects. The present invention addresses one or more of these needs by providing novel KRas inhibitors.

The present invention provides a compound of Formula I:

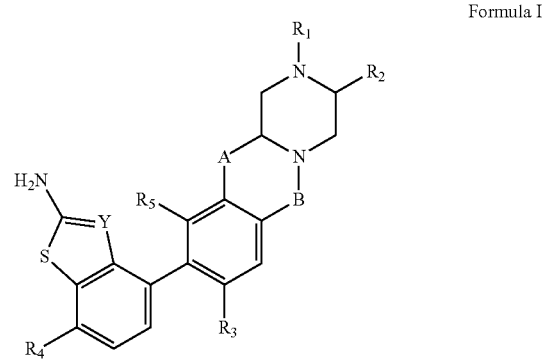

Formula I or a pharmaceutically acceptable salt thereof, wherein:
A is —OCH$_2$—, —N(R$_6$)CH$_2$—, —OCH$_2$CH$_2$—, —N(R$_6$)CH$_2$CH$_2$—, —CH$_2$OCH$_2$—, or —CH$_2$N(R$_6$)CH$_2$—;
B is —CH$_2$— or —C(O)—;
Y is —C(CN)— or —N—;
R$_1$ is —CN, —C(O)C≡CR$_8$, or a group of the formula

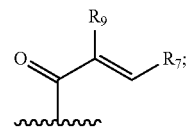

R$_2$ is H, methyl, or —CH$_2$CN;
R$_3$ and R$_5$ are each independently H, halogen, —C$_{0-3}$ alkyl-cyclopropyl, —C$_{1-6}$ alkyl optionally substituted 1-3 times with R$_{10}$, or —O—C$_{1-6}$ alkyl optionally substituted 1-3 times with R$_{10}$;
R$_4$ is H, halogen, or —C$_{1-6}$ alkyl optionally substituted 1-3 times with R$_{10}$;
R$_6$ is H or —C$_{1-6}$ alkyl optionally substituted 1-3 times with R$_{10}$;
R$_7$ is H, halogen, —NR$_{11}$R$_{12}$, —CH$_2$NR$_{11}$R$_{12}$, —C$_{1-6}$ alkyl optionally substituted 1-3 times with R$_{10}$ or R$_{13}$, —C$_{0-3}$ alkyl cyclopropyl, or —O—C$_{1-6}$ alkyl optionally substituted 1-3 times with R$_{10}$ or R$_{13}$;
R$_8$ is H, —C$_{1-4}$ alkyl optionally substituted 1-3 times with R$_{10}$, or —C$_{3-6}$ cycloalkyl optionally substituted 1-3 times with R$_{10}$;
R$_9$ is H, halogen, —CN, —C$_{0-3}$ alkyl-C$_{3-6}$ cycloalkyl, or —C$_{1-6}$ alkyl optionally substituted 1-3 times with R$_{10}$;
R$_{10}$ is independently at each occurrence halogen, oxygen, hydroxy, —C$_{1-4}$ alkyl, or —O—C$_{1-4}$ alkyl;
R$_{11}$ and R$_{12}$ are each independently H, —C$_{1-4}$ alkyl, or —C$_{1-4}$ heteroalkyl, wherein R$_{11}$ and R$_{12}$ may combine to form a heterocycloalkyl; and
R$_{13}$ is independently at each occurrence —N—C$_{1-4}$ alkyl.

As used herein, the term halogen means fluoro (F), chloro (Cl), bromo (Br), or iodo (I). As used herein, the term alkyl means saturated linear or branched-chain monovalent hydrocarbon radicals of one to six carbon atoms, e.g., "—C$_{1-6}$ alkyl." Examples of alkyls include, but are not limited to, methyl, ethyl, propyl, 1-propyl, isopropyl, butyl, pentyl, and hexyl. As used herein, the term heteroalkyl means saturated linear or branched-chain monovalent hydrocarbon radicals containing two to five carbon atoms and at least one heteroatom, e.g., "—C$_{1-4}$ heteroalkyl." As used herein, the term cycloalkyl means saturated monovalent cyclic molecules with three to six carbon atoms, e.g., "—$C_{3-6}$ cycloalkyl." Examples of cycloalkyl groups include, but are not limited to, cyclopropyl, cyclobutyl, cyclopentyl, and cyclohexyl. As used herein, the term cycloheteroalkyl means saturated monovalent cyclic molecules with two to five carbon atoms and at least one heteroatom, e.g., "—$C_{3-6}$ cycloheteroalkyl." Examples of cycloheteroalkyl groups include, but are not limited to, pyrrolidine, piperidine, imidazolidine, pyrazolidine, and piperazine.

In cases where a zero is indicated, e.g., —$C_{0-3}$ alkyl-$C_{3-6}$ cycloalkyl, the alkyl component of the substituent group can be absent, thus, if $R_9$ of Formula I is a cyclopropyl group with no lead alkyl, the substituent would be described by the —$C_{0-3}$ alkyl-cyclopropyl substituent as described for $R_9$ (i.e., the substituent group would be —$C_0$-cyclopropyl).

Regarding $R_{11}$ and $R_{12}$, the two groups may combine with the nitrogen they are attached to when chemistry allows to form a heterocycloalkyl. Examples of said heterocycloalkyl groups include, but are not limited to, piperidine, piperazine, and morpholine.

In an embodiment the present invention provides a compound of Formula Ia

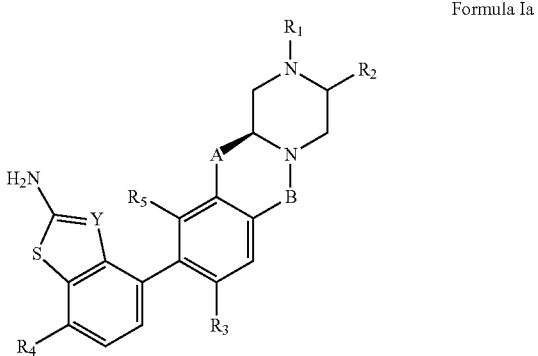

Formula Ia where $R_1$, $R_2$, $R_3$, $R_4$, $R_5$, A, B, and Y are as defined above, or a pharmaceutically acceptable salt thereof.

In an embodiment the present invention provides a compound of Formula I or Ia wherein A is —$OCH_2$—, —$N(R_6)CH_2$—, —$OCH_2CH_2$—, —$N(R_6)CH_2CH_2$—, or a pharmaceutically acceptable salt thereof. In a further embodiment the present invention provides a compound of formula I or Ia wherein A is —$OCH_2$— or —$OCH_2CH_2$—, or a pharmaceutically acceptable salt thereof. In yet a further embodiment the present invention provides a compound of formula I or Ia wherein A is —$OCH_2CH_2$—, or a pharmaceutically acceptable salt thereof.

In a further embodiment the present invention provides a compound of Formula I or Ia wherein B is —C(O)—, or a pharmaceutically acceptable salt thereof.

In a further embodiment the present invention provides a compound of Formula I or Ia wherein Y is —C(CN)— or a pharmaceutically acceptable salt thereof.

In a further embodiment the present invention provides a compound of Formula I or Ia wherein Y is —N—, or a pharmaceutically acceptable salt thereof.

In a further embodiment the present invention provides a compound of Formula I or Ia wherein $R_1$ is —CN, —C(O)C≡$CR_8$, or a pharmaceutically acceptable salt thereof. In yet a further embodiment the present invention provides a compound of Formula I or Ia wherein $R_1$ is a group of the formula

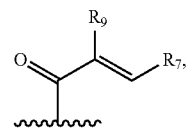

or a pharmaceutically acceptable salt thereof.

In a further embodiment the present invention provides a compound of Formula I or Ia wherein $R_2$ is H or methyl, or a pharmaceutically acceptable salt thereof. In yet a further embodiment the present invention provides a compound of Formula I or Ia wherein $R_2$ is H, or a pharmaceutically acceptable salt thereof.

In a further embodiment the present invention provides a compound of Formula I or Ia wherein $R_3$ is H, halogen, methyl, methoxy, ethyl, isopropyl, or cyclopropyl, or a pharmaceutically acceptable salt thereof. In yet a further embodiment the present invention provides a compound of Formula I or Ia wherein $R_3$ is halogen, (preferably F or Cl), or a pharmaceutically acceptable salt thereof.

In a further embodiment the present invention provides a compound of Formula I or Ia wherein $R_4$ is H or halogen, or a pharmaceutically acceptable salt thereof. In yet a further embodiment the present invention provides a compound of Formula I or Ia wherein $R_4$ is H or F, or a pharmaceutically acceptable salt thereof.

In a further embodiment the present invention provides a compound of Formula I or Ia wherein $R_5$ is halogen (preferably Cl) or a pharmaceutically acceptable salt thereof.

In a further embodiment the present invention provides a compound of formula I or Ia wherein $R_6$ is H or $CH_3$, or a pharmaceutically acceptable salt thereof.

In a further embodiment the present invention provides a compound of Formula I or Ia wherein $R_9$ is H, F, Cl, —$CH_2F$, —$CF_3$, or —$CH_2OH$, or a pharmaceutically acceptable salt thereof. In yet a further embodiment the present invention provides a compound of Formula I or Ia wherein $R_9$ is H, or a pharmaceutically acceptable salt thereof.

In a further embodiment the present invention provides a compound of Formula I or Ia wherein $R_7$ is H, —$CHF_2$, —$CH_2F$, —$CH_2OH$, —$CH_2OCH_3$, —$CH_2N(CH_3)_2$, or —$CH_2$-morpholine, or a pharmaceutically acceptable salt thereof. In yet a further embodiment the present invention provides a compound of Formula I or Ia wherein $R_7$ is H, or a pharmaceutically acceptable salt thereof.

In yet a further embodiment the present invention provides a compound of Formula I or Ia wherein $R_9$ is H and $R_7$ is H, —$CHF_2$, —$CH_2F$, —$CH_2OH$, —$CH_2OCH_3$, —$CH_2N(CH_3)_2$, or —$CH_2$-morpholine, or a pharmaceutically acceptable salt thereof.

In yet a further embodiment the present invention provides a compound of Formula I or Ia wherein $R_9$ is H, F, Cl, —$CH_2F$, —$CF_3$, or —$CH_2OH$ and $R_7$ is H, or a pharmaceutically acceptable salt thereof.

In yet a further embodiment the present invention provides a compound of Formula I or Ia wherein $R_7$ and $R_9$ are both H, or a pharmaceutically acceptable salt thereof.

In yet a further embodiment the present invention provides a compound of Formula I or Ia wherein $R_1$ is —CN, —C(O)C≡$CR_8$ and $R_8$ is H, methyl, —$CH_2F$, or —$CH_2OH$ or a pharmaceutically acceptable salt thereof.

In yet a further embodiment the present invention provides a compound of Formula I or Ia wherein $R_1$ is a group of the formula

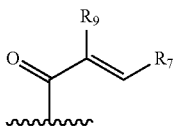

and R₇ and R₉ are both H, or a pharmaceutically acceptable salt thereof.

In yet a further embodiment the present invention provides a compound of Formula I or Ia wherein R₁ is a group of the formula

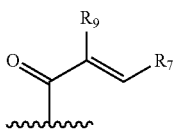

and R₇ is tert-butyl and R₉ is —CN, or a pharmaceutically acceptable salt thereof.

In yet a further embodiment the present invention provides a compound of Formula I or Ia wherein A is —OCH₂—, —N(R₆)CH₂—, —OCH₂CH₂—, —N(R₆)CH₂CH₂—, and B is —C(O)—, or a pharmaceutically acceptable salt thereof.

In yet a further embodiment the present invention provides a compound of Formula I or Ia wherein A is —OCH₂— or —OCH₂CH₂— and B is —C(O)—, or a pharmaceutically acceptable salt thereof.

In yet a further embodiment the present invention provides a compound of Formula I or Ia wherein A is —OCH₂CH₂— and B is —C(O)—, or a pharmaceutically acceptable salt thereof.

In yet a further embodiment the present invention provides a compound of Formula I or Ia wherein A is —OCH₂—, —N(R₆)CH₂—, —OCH₂CH₂—, —N(R₆)CH₂CH₂—, B is C(O) and R₂ is H or —CH₃, or a pharmaceutically acceptable salt thereof.

In yet a further embodiment the present invention provides a compound of Formula I or Ia wherein A is —OCH₂— or —OCH₂CH₂—, B is —C(O)— and R₂ is H or methyl, or a pharmaceutically acceptable salt thereof.

In yet a further embodiment the present invention provides a compound of Formula I or Ia wherein A is —OCH₂CH₂—, B is —C(O)— and R₂ is H or methyl, or a pharmaceutically acceptable salt thereof.

In yet a further embodiment the present invention provides a compound of Formula I or Ia wherein A is —OCH₂—, —N(R₆)CH₂—, —OCH₂CH₂—, —N(R₆)CH₂CH₂—, B is —C(O)— and R₂ is H, or a pharmaceutically acceptable salt thereof.

In yet a further embodiment the present invention provides a compound of Formula I or Ia wherein A is —OCH₂— or —OCH₂CH₂—, B is —C(O)— and R₂ is H, or a pharmaceutically acceptable salt thereof.

In yet a further embodiment the present invention provides a compound of Formula I or Ia wherein A is —OCH₂CH₂—, B is —C(O)— and R₂ is H, or a pharmaceutically acceptable salt thereof.

In yet a further embodiment the present invention provides a compound of Formula I or Ia wherein A is —OCH₂CH₂— and R₂ is H or methyl, or a pharmaceutically acceptable salt thereof.

In yet a further embodiment the present invention provides a compound of Formula I or Ia wherein A is —OCH₂CH₂— and R₂ is H, or a pharmaceutically acceptable salt thereof.

In yet a further embodiment the present invention provides a compound of Formula I or Ia wherein B is —C(O)— and R₂ is H or methyl, or a pharmaceutically acceptable salt thereof.

In yet a further embodiment the present invention provides a compound of Formula I or Ia wherein B is —C(O)— and R₂ is H, or a pharmaceutically acceptable salt thereof.

In yet a further embodiment the present invention provides a compound of Formula I or Ia wherein R₃ and R₅ are each independently selected from H, halogen or methyl, or a pharmaceutically acceptable salt thereof.

In yet a further embodiment the present invention provides a compound of Formula I or Ia wherein R₃ or R₅ are halogen, or a pharmaceutically acceptable salt thereof.

In yet a further embodiment the present invention provides a compound of Formula I or Ia wherein R₃ and R₅ are halogen, or a pharmaceutically acceptable salt thereof.

In yet a further embodiment the present invention provides a compound of Formula I or Ia wherein R₃ and R₅ are each independently selected from F or Cl, or a pharmaceutically acceptable salt thereof.

In yet a further embodiment the present invention provides a compound of Formula I or Ia wherein Y is —C(CN)— and R₄ is H or halogen (preferably F or Cl), or a pharmaceutically acceptable salt thereof.

In yet a further embodiment the present invention provides a compound of Formula I or Ia wherein Y is —N— and R₄ is H or halogen (preferably F or Cl), or a pharmaceutically acceptable salt thereof.

In yet a further embodiment the present invention provides a compound of Formula I or Ia wherein Y is —C(CN)—, and R₃ and R₅ are each independently selected from methyl or halogen, or a pharmaceutically acceptable salt thereof.

In yet a further embodiment the present invention provides a compound of Formula I or Ia wherein Y is —C(CN)—, and R₃ and R₅ are each halogen (preferably F or Cl), or a pharmaceutically acceptable salt thereof.

In yet a further embodiment the present invention provides a compound of Formula I or Ia wherein Y is —N—, R₃ and R₅ are each independently selected from methyl or halogen, or a pharmaceutically acceptable salt thereof.

In yet a further embodiment the present invention provides a compound of Formula I or Ia wherein Y is —N—, R₃ and R₅ are each halogen (preferably F or Cl), or a pharmaceutically acceptable salt thereof.

In yet a further embodiment the present invention provides a compound of Formula I or Ia wherein A is —OCH₂—, —OCH₂CH₂—, —N(R₆)CH₂CH₂—, —CH₂OCH₂—, or —CH₂N(R₆)CH₂, B is —CH₂— or —C(O)—; Y is —C(CN)— or —N—; R₁ is —CN, —C(O)C≡CR₈, or a group of the formula

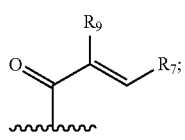

R₂ is H or methyl; R₃ and R₅ are each H, F, Cl or methyl; R₄ is H or F; R₆ is H or methyl; R₇ is H, —CHF₂, —CH₂F, —CH₂OH, —CH₂OCH₃, —CH₂N(CH₃)₂, —CH₂-morpholine or tert-butyl; $R_8$ is methyl, —$CH_2F$ or —$CH_2OH$; and $R_9$ is H, F, Cl, —$CH_2F$, —$CF_3$, —$CH_2OH$ or CN; or a pharmaceutically acceptable salt thereof.

In yet a further embodiment the present invention provides a compound of Formula I or Ia wherein A is —$OCH_2$— or —$OCH_2CH_2$—; B is —$CH_2$— or —C(O)—; Y is —C(CN)— or —N—; $R_2$, $R_7$, and $R_5$ are each H; $R_4$ is H or halogen; $R_3$ and $R_5$ are each halogen; or a pharmaceutically acceptable salt thereof.

The present invention further provides a compound of the Formula II:

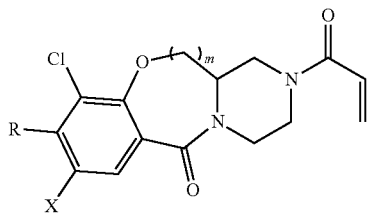

Formula II

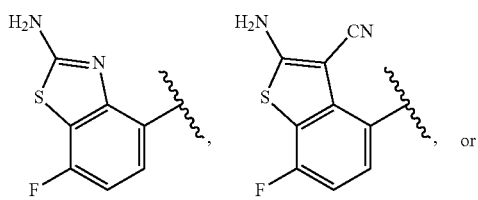

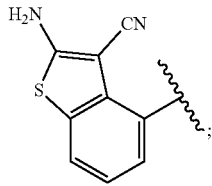

wherein R is
X is Cl or F;
and m is 1 or 2.
or a pharmaceutically acceptable salt thereof.

The present invention also provides a compound of the Formula IIa:

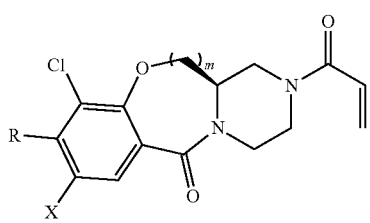

Formula IIa

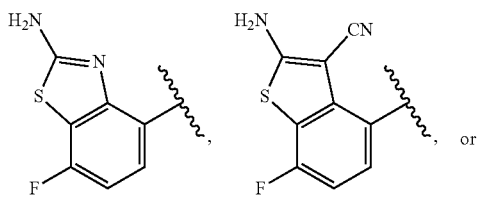

wherein R is
X is Cl or F;
and m is 1 or 2.
or a pharmaceutically acceptable salt thereof.

Another way to describe the compound of Formula II is with Formula Ib:

Formula Ib (structure shown)

or a pharmaceutically acceptable salt thereof, wherein:
A is —$OCH_2$— or —$OCH_2CH_2$—;
Y is —C(CN)— or —N—;
$R_3$ is Cl or F;
$R_4$ is H or F when Y is C(CN); and
$R_4$ is F when Y is N.

Another way to describe the compound of Formula IIa is with Formula Ib, wherein A is

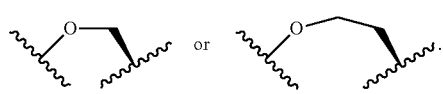

The present invention also provides a compound selected from any one of Formulae III-VI below:

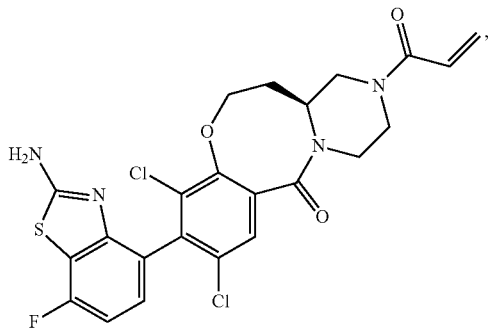

Formula III

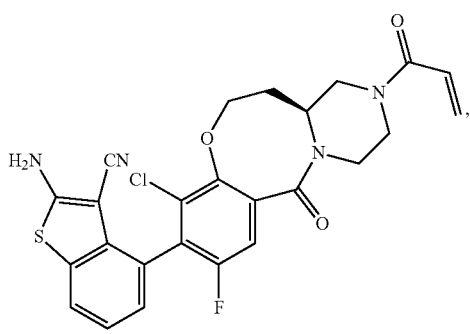

Formula IV

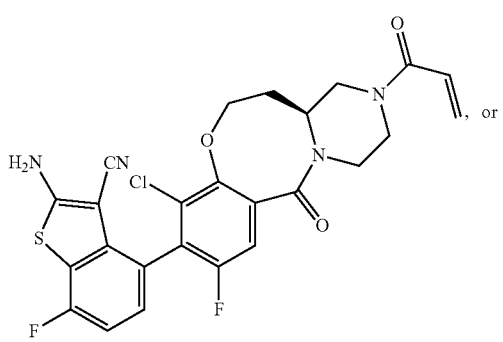

Formula V, or

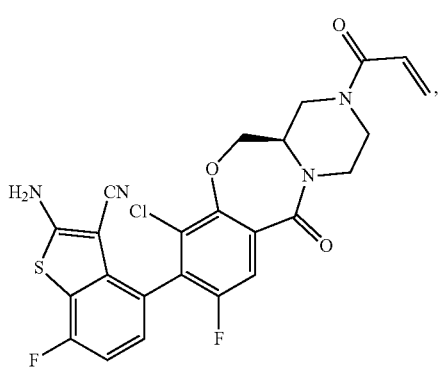

Formula VI or a pharmaceutically acceptable salt thereof.

In another form, the present invention provides a compound of Formula III which is:

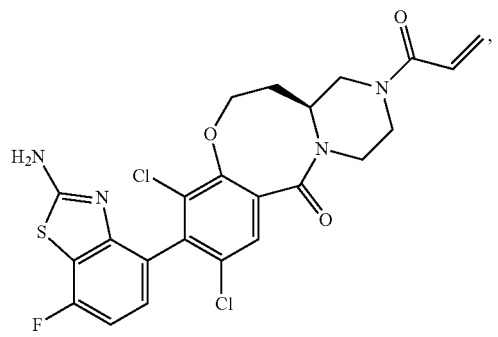

Formula III or a pharmaceutically acceptable salt thereof.

In another form, the present invention provides a compound of Formula IV which is:

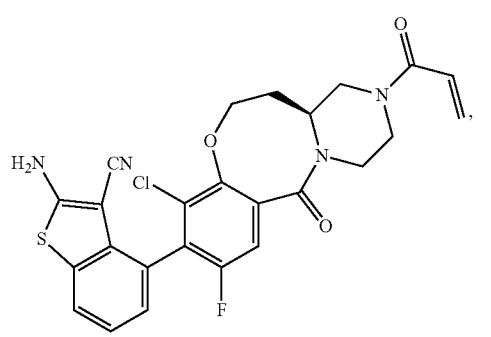

Formula IV or a pharmaceutically acceptable salt thereof.

In another form, the present invention provides a compound of Formula V which is:

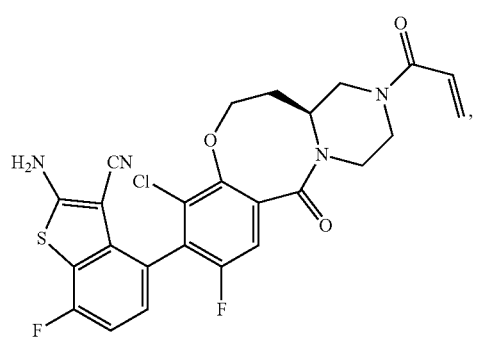

Formula V or a pharmaceutically acceptable salt thereof.

In another form, the present invention provides a compound of Formula VI which is:

Formula VI

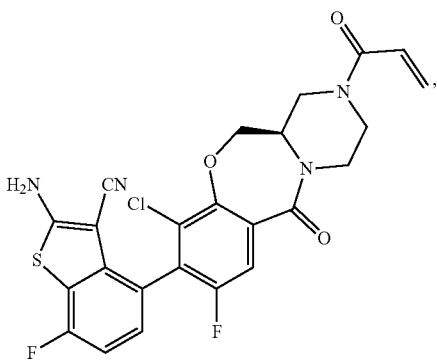

or a pharmaceutically acceptable salt thereof.

The present invention also provides a pharmaceutical composition comprising a compound according to any one of Formulae I-VI, or a pharmaceutically acceptable salt thereof, and a pharmaceutically acceptable carrier, diluent, or excipient.

The present invention also provides a method of treating cancer, comprising administering to a patient in need thereof, an effective amount of a compound according to any one of Formulae I-VI, or a pharmaceutically acceptable salt thereof. In various embodiments, the cancer is lung cancer, colorectal cancer, pancreatic cancer, bladder cancer, cervical cancer, endometrial cancer, ovarian cancer, cholangiocarcinoma, or esophageal cancer. In preferred embodiments, the cancer is non-small cell lung cancer, pancreatic cancer, or colorectal cancer. In still more preferred embodiments, the cancer is non-small cell lung cancer.

In still yet another form, the present invention comprises a method of treating cancer, comprising administering to a patient in need thereof, an effective amount of a compound according to any one of Formulae I-VI, or a pharmaceutically acceptable salt thereof, in which the cancer has one or more cells that express a mutant KRas G12C protein. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In yet another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating a patient with a cancer that has a KRAS G12C mutation comprising administering to a patient in need thereof an effective amount of a compound according to any one of Formulae I-VI or a pharmaceutically acceptable salt thereof.

The present invention also provides a method of modulating a mutant KRas G12C enzyme in a patient in need thereof, by administering a compound according to any one of Formulae I-VI, or a pharmaceutically acceptable salt thereof. Preferably the method comprises inhibiting a human mutant KRas G12C enzyme.

The present invention also provides a method of treating cancer in a patient in need thereof, wherein the patient has a cancer that was determined to express the KRas G12C mutant protein. The method comprises administering to a patient an effective amount of a compound according to any one of Formulae I-VI, or a pharmaceutically acceptable salt thereof. The G12C mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g. G12C mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

The present invention also provides a compound or a pharmaceutically acceptable salt thereof, according to any one of Formulae I-VI for use in therapy. The compound or a pharmaceutically acceptable salt thereof, can be for use in treating cancer. Preferably, the cancer is lung cancer, colorectal cancer, pancreatic cancer, bladder cancer, cervical cancer, endometrial cancer, ovarian cancer, cholangiocarcinoma, or esophageal cancer. In preferred embodiments the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from: KRas G12C mutant non-small cell lung cancer, KRas G12C mutant colorectal cancer, and KRas G12C mutant pancreatic cancer. In another embodiment, the cancer is non-small cell lung cancer, and one or more cells express KRas G12C mutant protein. In another embodiment, the cancer is colorectal cancer, and one or more cells express KRas G12C mutant protein. In another embodiment, the cancer is pancreatic cancer, and one or more cells express KRas G12C mutant protein. In another embodiment, the patient has a cancer that was determined to have one or more cells expressing the KRas G12C mutant protein prior to administration of the compound or a pharmaceutically acceptable salt thereof.

The present invention also provides for the use of a compound according to any one of Formulae I-VI, or a pharmaceutically acceptable salt thereof, in the manufacture of a medicament for treating cancer. Preferably, the cancer is lung cancer, colorectal cancer, pancreatic cancer, bladder cancer, cervical cancer, endometrial cancer, ovarian cancer, cholangiocarcinoma, or esophageal cancer. In preferred embodiments, the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer.

The present invention also provides a method of treating cancer, comprising administering to a patient in need thereof, an effective amount of a compound according to any one of Formulae I-VI, or a pharmaceutically acceptable salt thereof, and one or more of a PD-1 inhibitor, a PD-L1 inhibitor, a CD4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof, a platinum agent, and pemetrexed, or a pharmaceutically acceptable salt thereof, in which the cancer has one or more cells that express a mutant KRas G12C protein. The present invention also provides a compound according to any one of Formulae I-VI, or a pharmaceutically acceptable salt thereof, for use in simultaneous, separate or sequential combination with one or more of a PD-1 or PD-L1 inhibitor, a CD4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof, a platinum agent, and pemetrexed, or a pharmaceutically acceptable salt thereof, in the treatment of cancer. The present invention also provides a combination comprising a compound according to any one of Formulae I-VI, or a pharmaceutically acceptable salt thereof, and one or more of a PD-1 or PD-L1 inhibitor, a CD4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof, a platinum agent, and pemetrexed, or a pharmaceutically acceptable salt thereof, for simultaneous, separate, or sequential use in the treatment of cancer.

The present invention also provides a method of treating cancer, comprising administering to a patient in need thereof, an effective amount of a compound according to any one of Formulae I-VI, or a pharmaceutically acceptable salt thereof, and a PD-1 or PD-L1 inhibitor, in which the cancer has one or more cells that express a mutant KRas G12C protein. The present invention also provides a compound according to any one of Formulae I-VI, or a pharmaceutically acceptable salt thereof, for use in simultaneous, separate or sequential combination with a PD-1 or PD-L1 inhibitor, for use in the treatment of cancer. The present invention also provides a combination comprising a compound according to any one of Formulae I-VI, or a pharmaceutically acceptable salt thereof, and a PD-1 or PD-L1 inhibitor, for simultaneous, separate, or sequential use in the treatment of cancer. In one embodiment, the compound is a compound of Formula I-VI or a pharmaceutically acceptable salt thereof. In another embodiment, the PD-1 or PD-L1 inhibitor is pembrolizumab. In another embodiment, the PD-1 or PD-L1 inhibitor is nivolumab. In another embodiment, the PD-1 or PD-L1 inhibitor is cimiplimab. In another embodiment, the PD-1 or PD-L1 inhibitor is sintilimab. In another embodiment, the PD-1 or PD-L1 inhibitor is atezolizumab. In another embodiment, the PD-1 or PD-L1 inhibitor is avelumab. In another embodiment, the PD-1 or PD-L1 inhibitor is durvatumab. In another embodiment, the PD-1 or PD-L1 inhibitor is lodapilimab. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating cancer, comprising administering to a patient in need thereof, an effective amount of a compound according to any one of Formulae I-VI, or a pharmaceutically acceptable salt thereof, and a CDK4/CDK6 inhibitor, or a pharmaceutically acceptable salt thereof, in which the cancer has one or more cells that express a mutant KRas G12C protein. The present invention also provides a compound according to any one of Formulae I-VI, or a pharmaceutically acceptable salt thereof, for use in simultaneous, separate or sequential combination with a CDK4/CDK6 inhibitor, or a pharmaceutically acceptable salt thereof, for use in the treatment of cancer, in which the cancer has one or more cells that express a mutant KRas G12C protein. The present invention also provides a combination comprising a compound according to any one of Formulae I-VI, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12C protein. In another embodiment, the CDK4/CDK6 inhibitor is abemaciclib. In another embodiment, the CDK4/CDK6 inhibitor is palbociclib. In another embodiment, the CDK4/CDK6 inhibitor is ribociclib. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating cancer, comprising administering to a patient in need thereof, an effective amount of a compound according to any one of Formulae I-VI, or a pharmaceutically acceptable salt thereof, and an EGFR inhibitor, or a pharmaceutically acceptable salt thereof, in which the cancer has one or more cells that express a mutant KRas G12C protein. The present invention also provides a compound according to any one of Formulae I-VI, or a pharmaceutically acceptable salt thereof, for use in simultaneous, separate or sequential combination with an EGFR inhibitor, or a pharmaceutically acceptable salt thereof, for the treatment of cancer. The present invention also provides a combination comprising a compound according to any one of Formulae I-VI, or a pharmaceutically acceptable salt thereof, and an EGFR inhibitor, or a pharmaceutically acceptable salt thereof, for simultaneous, separate, or sequential use in the treatment of cancer. In one embodiment, the compound is a compound of Formulae I-VI or a pharmaceutically acceptable salt thereof. In another embodiment, the EGFR inhibitor is erlotinib. In another embodiment, the EGFR inhibitor is afatinib. In another embodiment, the EGFR inhibitor is gefitinib. In another embodiment, the EGFR inhibitor is cetuximab. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating cancer, comprising administering to a patient in need thereof, an effective amount of a compound according to any one of Formulae I-VI, or a pharmaceutically acceptable salt thereof, and an ERK inhibitor, or a pharmaceutically acceptable salt thereof, in which the cancer has one or more cells that express a mutant KRas G12C protein. The present invention also provides a compound according to any one of Formulae I-VI, or a pharmaceutically acceptable salt thereof, for use in simultaneous, separate or sequential combination with an ERK inhibitor, or a pharmaceutically acceptable salt thereof, for the treatment of cancer, in which the cancer has one or more cells that express a mutant KRas G12C protein. The present invention also provides a combination comprising a compound according to any one of Formulae I-VI, or a pharmaceutically acceptable salt thereof, and an ERK inhibitor, or a pharmaceutically acceptable salt thereof, for simultaneous, separate, or sequential use in the treatment of cancer. In one embodiment, the compound is a compound of Formulae I-VI or a pharmaceutically acceptable salt thereof. In another embodiment, the ERK inhibitor is LY3214996 In another embodiment, the ERK inhibitor is LTT462. In another embodiment, the ERK inhibitor is KO-947. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating cancer, comprising administering to a patient in need thereof, an effective amount of a compound according to any one of Formulae I-VI, or a pharmaceutically acceptable salt thereof, and a platinum agent, in which the cancer has one or more cells that express a mutant KRas G12C protein. The present invention also provides a compound according to any one of Formulae I-VI, or a pharmaceutically acceptable salt thereof, for use in simultaneous, separate or sequential combination with a platinum agent, or a pharmaceutically acceptable salt thereof, for the treatment of cancer, in which the cancer has one or more cells that express a mutant KRas G12C protein. The present invention also provides a combination comprising a compound according to any one of Formulae I-VI, or a pharmaceutically acceptable salt thereof, and a platinum agent, for simultaneous, separate, or sequential use in the treatment of cancer. In one embodiment, the compound is a compound of Formulae I-VI or a pharmaceutically acceptable salt thereof. In another embodiment, the platinum agent is cisplatin. In another embodiment, the platinum agent is carboplatin. In another embodiment, the platinum agent is oxaliplatin. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The present invention also provides a method of treating cancer, comprising administering to a patient in need thereof, an effective amount of a compound according to any one of Formulae I-VI, or a pharmaceutically acceptable salt thereof, and pemetrexed, in which the cancer has one or more cells that express a mutant KRas G12C protein. The present invention also provides a compound according to any one of Formulae I-VI, or a pharmaceutically acceptable salt thereof, for use in simultaneous, separate or sequential combination with pemetrexed, for the treatment of cancer, in which the cancer has one or more cells that express a mutant KRas G12C protein. The present invention also provides a combination comprising a compound according to any one of Formulae I-VI, or a pharmaceutically acceptable salt thereof, and pemetrexed, for simultaneous, separate, or sequential use in the treatment of cancer, in which the cancer has one or more cells that express a mutant KRas G12C protein. In one embodiment, the compound is a compound of Formulae I-VI, or a pharmaceutically acceptable salt thereof. In another embodiment, the cancer is non-small cell lung carcinoma, in which the cancer has one or more cells that express a KRas G12C mutant protein. In another embodiment, a platinum agent is also administered to the patient. In another embodiment, the platinum agent is cisplatin. In another embodiment, the platinum agent is carboplatin. In another embodiment, the platinum agent is oxaliplatin. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. In another embodiment, the present invention comprising a method of treating KRas G12C mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

The pharmaceutical compositions for the present invention may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in treating a disorder or disease, such as a cancerous lesion or progression of abnormal cell growth and/or cell division. The attending physician, as one skilled in the art, can readily determine an effective amount by the use of conventional techniques and by observing results obtained under analogous circumstances. Dosages per day of treatment normally fall within a range of between about 1 mg per day or twice daily and 1000 mg per day or twice daily, more preferably 100 mg per day or twice daily and 900 mg per day or twice daily. Factors considered in the determination of an effective amount or dose of a compound include: whether the compound or its salt will be administered; the co-administration of other agents, if used; the species of patient to be treated; the patient's size, age, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Preferred pharmaceutical compositions can be formulated as a tablet or capsule for oral administration, a solution for oral administration, or an injectable solution. The tablet, capsule, or solution can include a compound of the present invention in an amount effective for treating a patient in need of treatment for cancer.

As used herein, the terms "treating", "to treat", or "treatment", includes slowing, reducing, or reversing the progression or severity of an existing symptom, disorder, condition, which can include specifically slowing the growth of a cancerous lesion or progression of abnormal cell growth and/or cell division.

As used herein, the term "patient" refers to a mammal in need of treatment. Preferably, the patient is a human that is in need of treatment for cancer, for example, KRas G12C mutant bearing cancers.

Certain abbreviations are defined as follows: "ACN" refers to acetonitrile; AIBN" refers to azobisisobutyronitrile; "Boc-Gly-OH" refers to N-(tert-butoxycarbonyl)glycine; "DCM" refers to dichloromethane; "DIEA" refers to N,N-diisopropyl ethylamine; "DMAP" refers to 4-dimethylaminopyridine; "DMEM" refers to Dulbecco's modified Eagle's medium; "DMF" refers to N,N-dimethylformamide; "DMSO" refers to dimethylsulfoxide; "DNA" refers to deoxyribonucleic acid; "DPEPhosPdCl$_2$" refers to dichloro-bis(diphenylphophinophenyl)ether palladium (II); "DTT" refers to dithiothreitol; "EDTA" refers to ethylenediaminetetraacetic acid; "EGTA" refers to ethylene glycol-bis(β-aminoethyl ether)-N,N,N',N'-tetraacetic acid; "ELISA" refers to enzyme-linked immunosorbent assay; "ERK" refers to extracellular signal-regulated kinases; "EtOAc" refers to ethyl acetate; "EtOH" refers to ethanol; "FBS" refers to fetal bovine serum; "GDP" refers to guanosine diphosphate; "GTP" refers to guanosine triphosphate; "HPLC" refers to high-performance liquid chromatography; "HRP" refers to horseradish peroxidase; "IPA" refers to isopropyl alcohol; "IPAm" refers to isopropyl amine; "LC-ES/MS" refers to liquid chromatograph-electrospray mass spectrometry; "LC-MS" refers to liquid chromatography mass spectrometry; "MAPK" refers to mitogen-activated protein kinases; "MeOH" refers to methanol; "NaOMe" refers to sodium methoxide; "NB S" refers to N-bromosuccinimide; "NCS" refers to N-chlorosuccinimide; "NMP" refers to 1-methylpyrrolidin-2-one; "PCR" refers to polymerase chain reaction; "RPMI" refers to Roswell Park Memorial Institute; "SCX" refers to strong cation exchange; "TEA" refers to triethylamine; "TFA" refers to trifluoracetic acid; and "THF" refers to tetrahydrofuran.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "*Stereochemistry of Organic Compounds*", Wiley-Interscience, 1994). The present invention includes certain compounds, which are atropisomers and which can exist in different conformations or as different rotomers. Atropisomers are compounds, which exist in different conformations arising from restricted rotation about a single bond. Atropisomers can be isolated as separate chemical species if the energy barrier to rotation about the single bond is sufficiently high enough and the rate of interconversion is slow enough to allow the individual rotomers to be separated from each other. The present inventions contemplates all of the isomers, enantiomers, diastereomers, and atropisomers disclosed herein or that could be made using the compounds disclosed herein.

A compound of any one of Formulae I-VI is readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures, some of which are illustrated in the Preparations and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

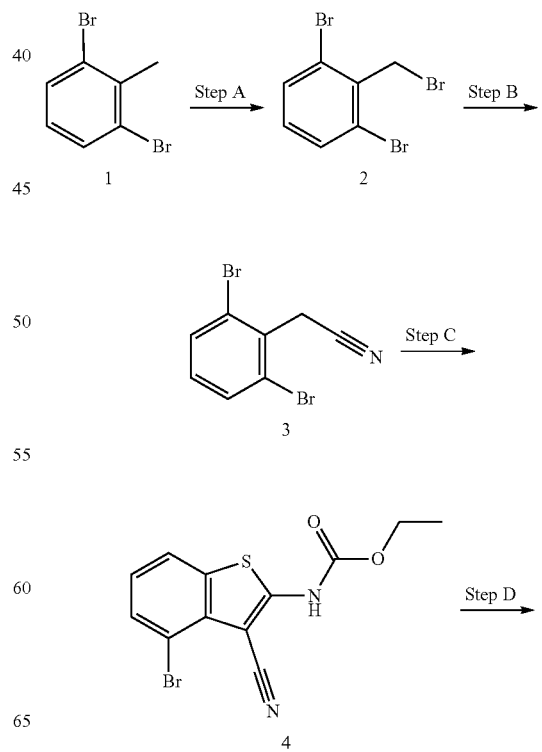

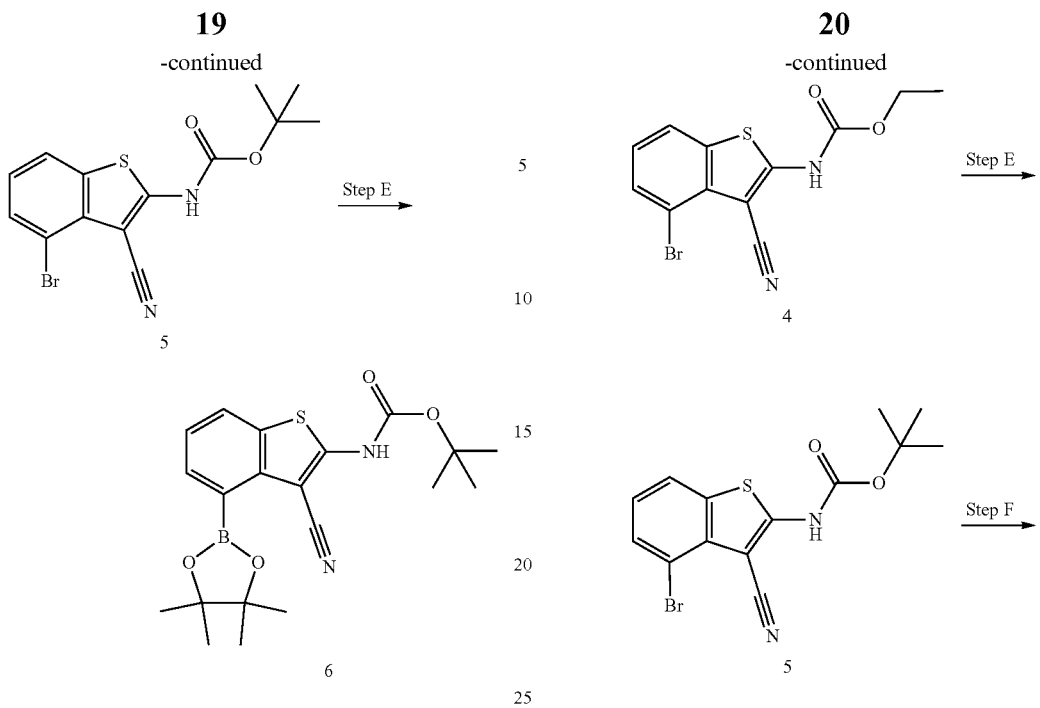

Scheme 1, step A depicts the bromination of compound (1) using NBS and AIBN in a suitable solvent such as CCl₄ to give compound (2). Step B shows the nucleophilic substitution on compound (2) using potassium cyanide refluxing in a suitable solvent system such as EtOH and water to give compound (3). The addition of ethoxycarbonyl isothiocyanate to compound (3) using sodium hydride in a suitable solvent such as DMF and subsequent cyclization to compound (4) is shown in step C. The basic deprotection of compound (4) with aqueous NaOH in refluxing DMSO and subsequent reprotection using di-tert-butyl dicarbonate with a suitable base such as DIEA and catalytic DMAP in a solvent system such as THF and DMF to give compound (5) is depicted in step D. Step E shows the reaction of the bromine of compound (5) with bis(pinacolato)diboron using a suitable base such as potassium acetate and a catalyst-ligand system such as palladium acetate and 1,1'-bis(diisopropylphosphino)ferrocene in a suitable solvent such as 1,4-dioxane to give compound (6). One skilled in the art will recognize that a variety of catalyst-ligand combinations could be used to afford this reaction.

Scheme 2

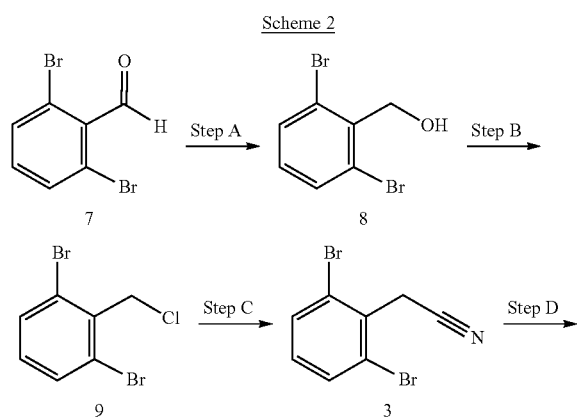

Scheme 2 depicts an alternate route for the synthesis of compound (6). Step A depicts the reduction of the benzaldehyde (7) using an appropriate reducing agent such as sodium borohydride in an appropriate solvent such as EtOH to give compound (8). Step B shows the chlorination of compound (8) using thionyl chloride in an appropriate solvent such as DCM to give compound (9). Step C depicts the nucleophilic substitution on compound (9) using potassium cyanide in an appropriate solvent such as DMSO to give compound (3). The addition of ethoxycarbonyl isothiocyanate to compound (3) using sodium hydride in a suitable solvent such as DMF and subsequent cyclization utilizing L-proline and CuI to give compound (4) is shown in step D. The basic deprotection of compound (4) with aqueous NaOH in refluxing DMSO and subsequent reprotection using di-tert-butyl dicarbonate with a suitable base such as DIEA and catalytic DMAP in a solvent such as THF to give compound (5) is depicted in step E. Step F shows the reaction of the bromine of compound (5) with bis(pinacolato)diboron using a suitable base such as potassium acetate and a catalyst-ligand system such as palladium acetate and bis(2-diphenylphosphinophenyl)ether in a suitable solvent such as 1,4-dioxane to give compound (6). One skilled in the art will recognize that a variety of catalyst-ligand combinations could be used to afford this reaction.

Scheme 3

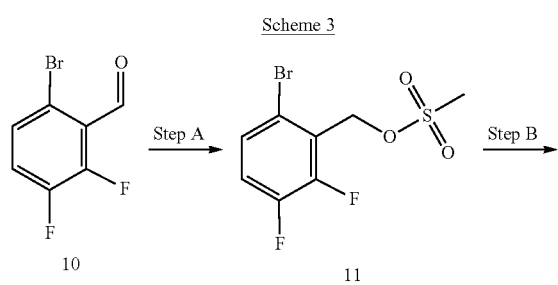

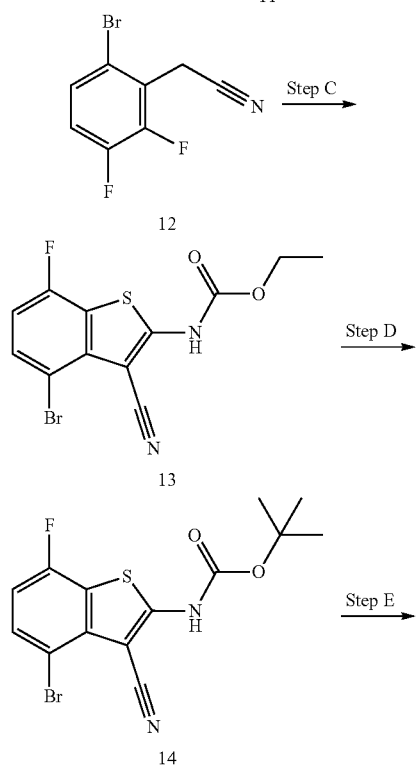

to those found in scheme 1, step D. Step E shows the reaction of the bromine of compound (14) with bis(neopentylglycolato)diboron using a suitable base such as potassium acetate and a catalyst-ligand system such as DPEPhosPdCl$_2$ in a suitable solvent such as 1,4-dioxane to give compound (15). One skilled in the art will recognize that a variety of catalyst-ligand combinations could be used to afford this reaction.

Scheme 4

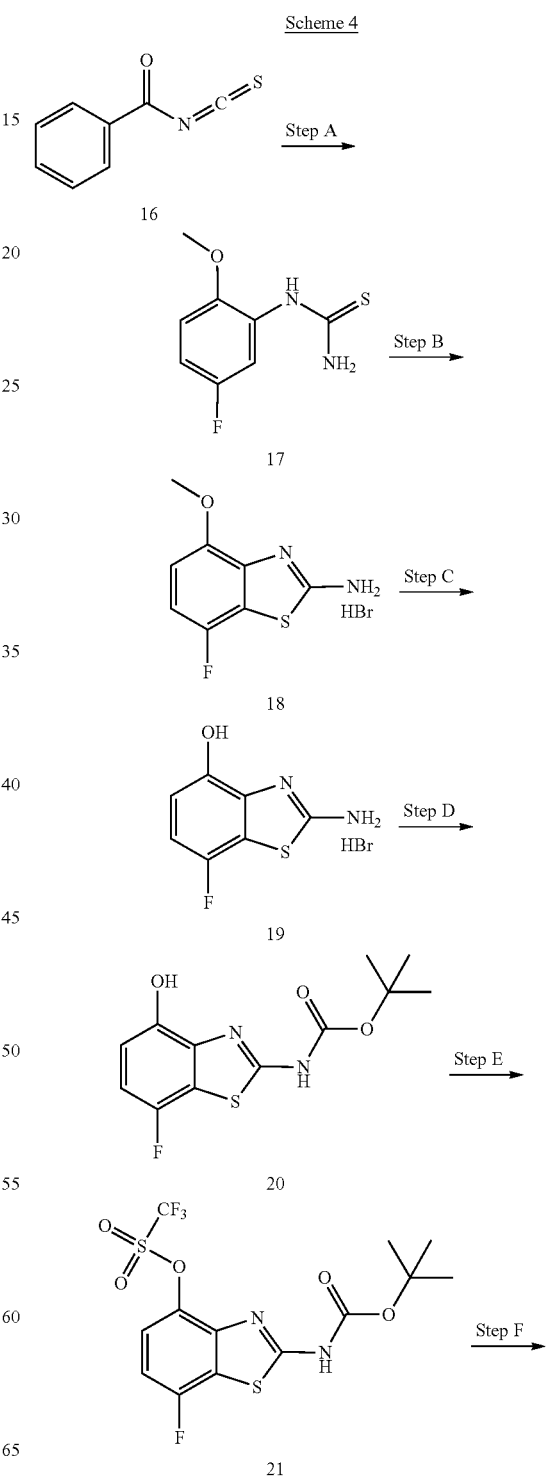

Scheme 3, step A depicts the reduction of the compound (10) aldehyde with sodium borohydride in MeOH and subsequent mesylation using methane sulfonic anhydride with a suitable base such as DIEA in a solvent such as THF to give compound (11). The conditions used for the transformation of compound (11) to compound (12) are essentially analogous to those found in scheme 1, step B. The addition of ethoxycarbonyl isothiocyanate to compound (12) using potassium tert-butoxide in a suitable solvent such as DMF and subsequent cyclization to compound (13) is shown in step C. The conditions used for the transformation of compound (13) to compound (14) are essentially analogous

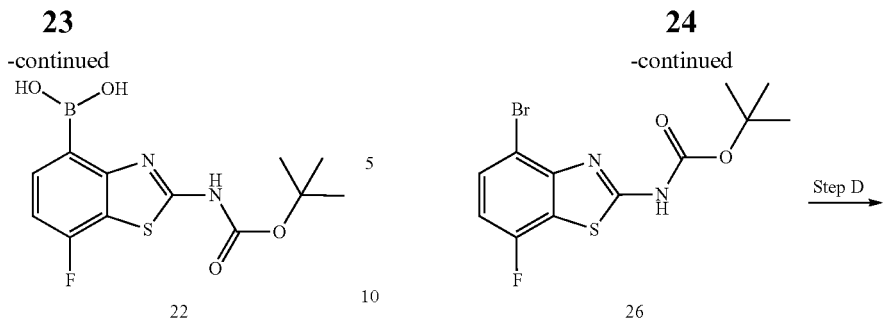

Scheme 4, step A depicts the formation of a thiourea from the reaction of compound (16) and 5-fluoro-2-methoxyaniline, while maintaining a cool reaction temperature, followed by a basic deprotection to afford compound (17). Step B shows the cyclization of compound (17) in chloroform after the addition of bromine to provide compound (18). Step C depicts the demethylation of compound (18) which may be achieved by addition of $BBr_3$ while maintaining a cold reaction mixture under an inert atmosphere to give compound (19). Step D shows the protection of compound (19) with di-tert-butyl dicarbonate using a suitable base such as TEA and catalytic DMAP in a solvent system such as 1,4-dioxane to give compound (20). Compound (20) is treated with a base such as pyridine followed by trifluoromethansulfonic anhydride in a solvent such as DCM to give compound (21) as shown is step E. Step F depicts the reaction of the triflate of compound (21) with bis(pinacolato) diboron using a suitable base such as potassium acetate and a catalyst such as tetrakis(triphenylphosphine)palladium(0) in a suitable solvent such as 1,4-dioxane to give compound (22). One skilled in the art will recognize that a variety of catalyst-ligand combinations could be used to afford this reaction.

Scheme 5 depicts an alternate route for the synthesis of compound (22). Step A depicts the thiourea formation from the reaction of compound (23) and 2-bromo-5-fluoroaniline in a solvent such as THF followed by a basic deprotection to afford compound (24). Step B shows the bromination and cyclization of compound (24) using an appropriate brominating agent such as pyridinium tribromide in a solvent such as sulfuric acid to give compound (25). Step C shows the protection of compound (25) with di-tert-butyl dicarbonate using a suitable base such as DMAP in a solvent system such as DCM to give compound (26). Step D depicts the transformation of compound (26) to compound (22) through treatment with sodium hydride in a solvent such as THF at low temperatures followed by the addition of n-butyllithium and triisopropyl borate.

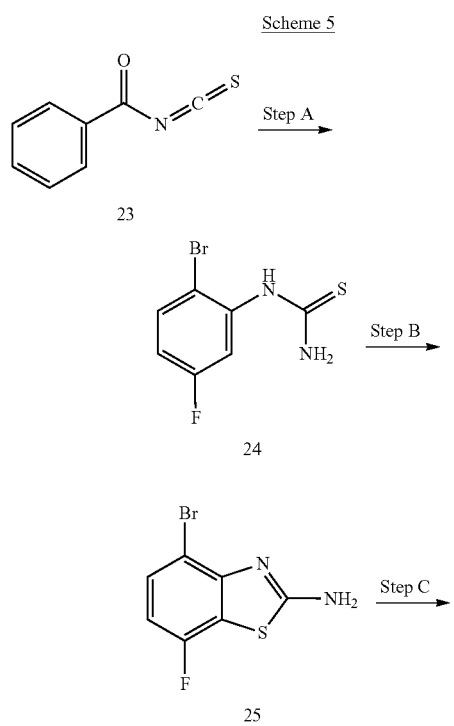

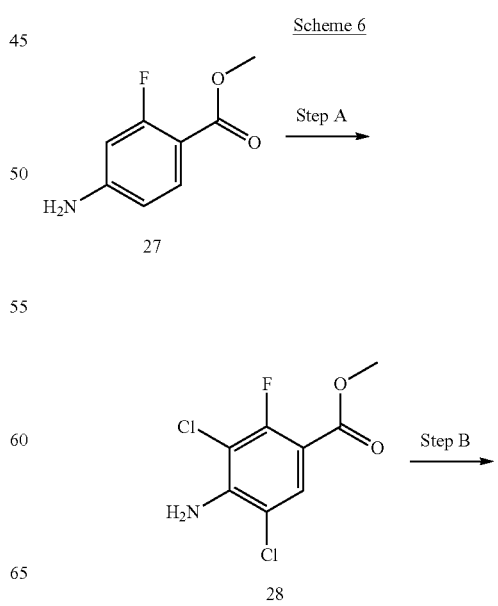

Scheme 8

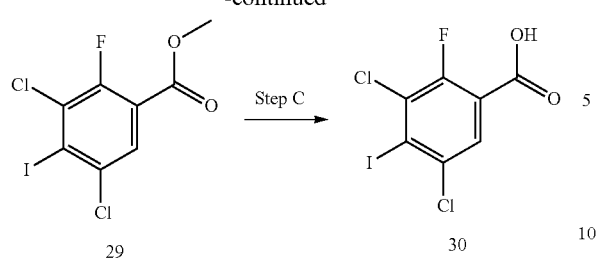
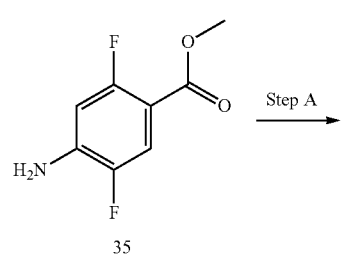

Scheme 6, step A depicts the chlorination of compound (27) with NCS in an appropriate solvent such as DMF to give compound (28). Step B shows a Sandmeyer reaction to convert the aniline nitrogen of compound (28) to an iodine, the conditions of which will be known by one skilled in the art, to give compound (29). Step C shows the basic hydrolysis of the ester of compound (29) to the acid of compound (30).

Scheme 7

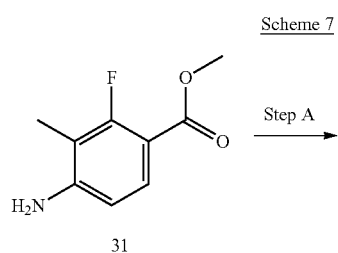

Scheme 8, step A is performed in a manner essentially analogous to the method in step A of Scheme 6 to give compound (36). Step B shows a Sandmeyer reaction to convert the aniline nitrogen of compound (36) to a bromine, the conditions of which will be known by one skilled in the art, to give compound (37). Step C is performed in a manner essentially analogous to the method in step C of Scheme 6 to give compound (38).

Scheme 9

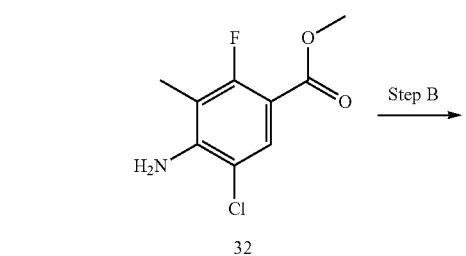

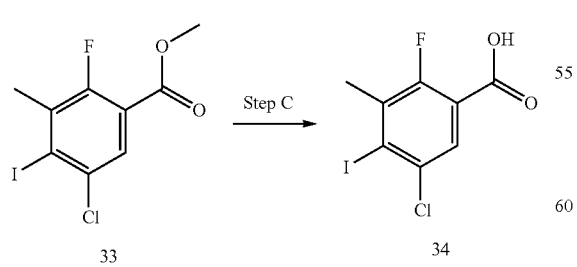

Scheme 7, steps A-C are performed in a manner essentially analogous to the methods found in steps A-C of Scheme 6 to give compounds (32-34).

Scheme 9, step A is performed in a manner essentially analogous to the method in step A of Scheme 6 to give compound (40). Step B is performed in a manner essentially analogous to the method in step B of Scheme 8 to give compound (41).

Scheme 10

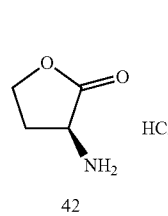
42

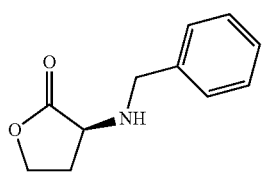
43

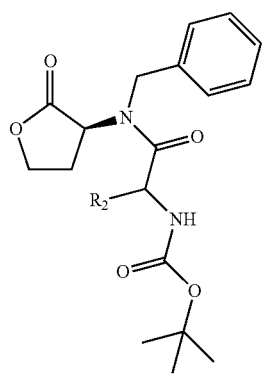
44

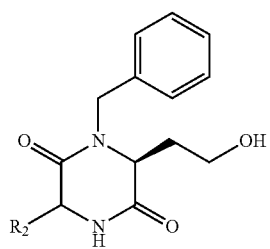
45

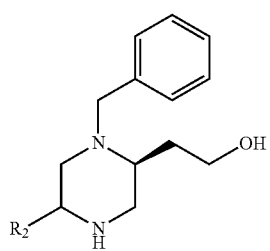
46

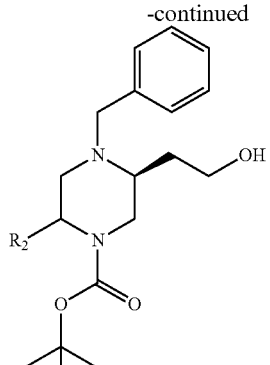
47

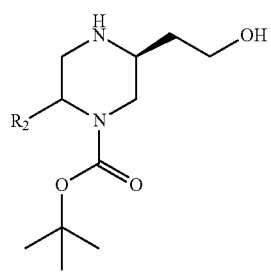
48

Scheme 10, step A depicts a reductive amination between compound (42) and benzaldehyde in a suitable solvent such as DCM with a suitable reducing agent such as sodium tri acetoxyborohydride to give compound (43). Step B shows the amide coupling between compound (43) and a boc-protected amino acid using propylphosphonic anhydride with a suitable base such as TEA in a solvent such as DCM to give compound (44). Step C depicts the acidic deprotection and rearrangement of compound (44) using TFA in a solvent such as DCM to give compound (45). Step D shows the global amide reduction of compound (45) using a reducing agent such as lithium aluminum hydride in a solvent such as THF to give compound (46). Step E depicts the protection of compound (46) using di-tert-butyl dicarbonate in aqueous sodium bicarbonate to give compound (47). Step F shows the deprotection of compound (47) by means of hydrogenation to give compound (48).

Scheme 11

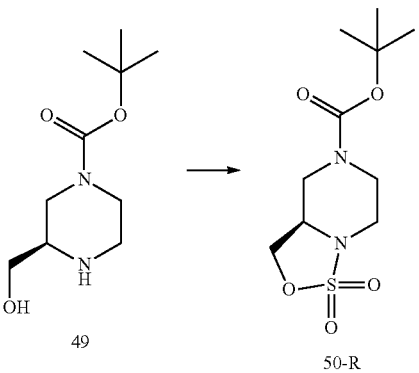

Scheme 11 shows the cyclization of compound (49) using thionyl chloride and imidazole in a solvent such as DCM at −78° C. followed by treatment with sodium periodate and ruthenium (III) chloride in ACN to give compound (50-R). The S enantiomer (50-S) is synthesized using the same conditions.

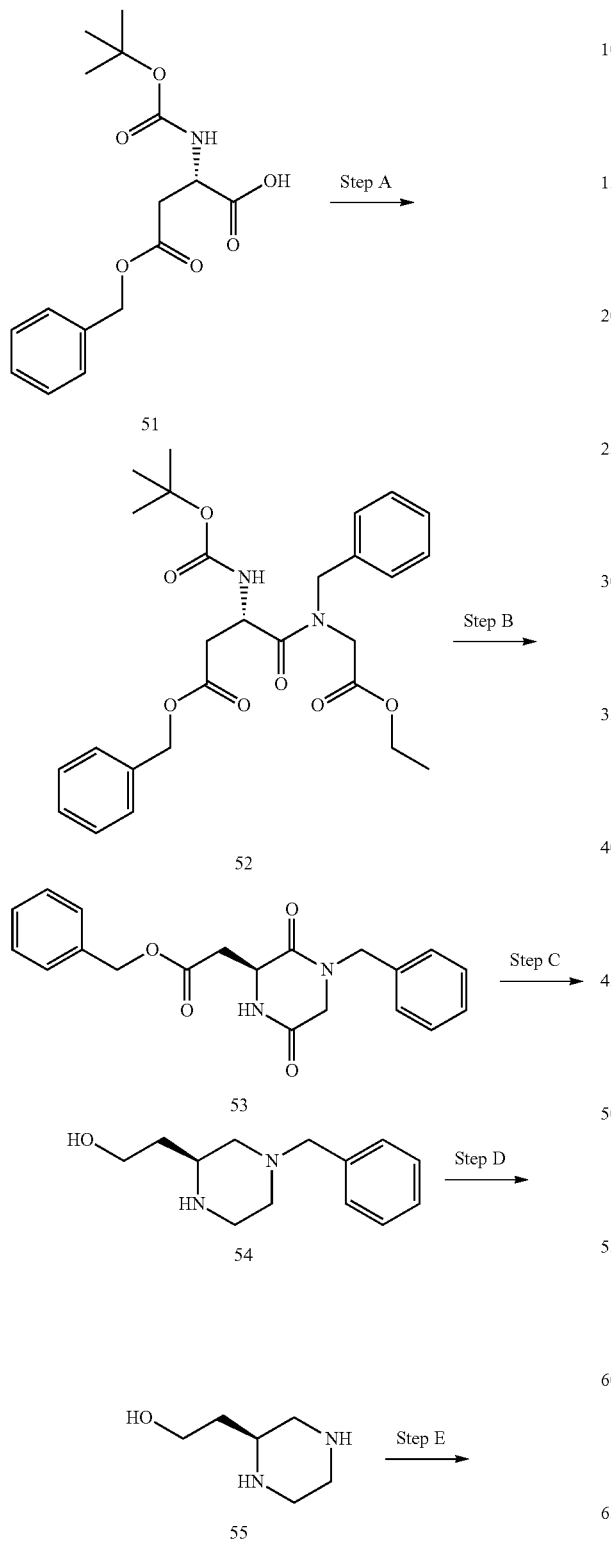

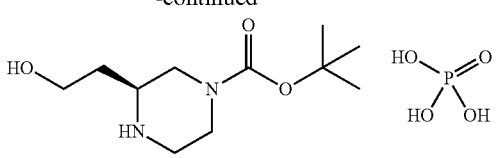

In Scheme 12, step A an amide coupling is shown between compound (51) and benzylglycine ethyl ester using a suitable coupling agent such as N,N'-dicyclohexylcarbodiimide in solvent such as DCM to give compound (52). Step B depicts the cyclization of compound (52) to compound (53) using an acid such as TFA in a solvent such as DCM. Step C depicts the global amide reduction and deprotection of compound (53) with a reducing agent such as lithium aluminum hydride in a solvent such as THF to give compound (54). Step D shows the hydrogenation of compound (54) to compound (55) using a suitable catalyst such as Pd(OH)$_2$ in a solvent such as MeOH. Step E depicts the di-tert-butyl dicarbonate protection of compound (55) and subsequent salt formation with phosphoric acid to give compound (56).

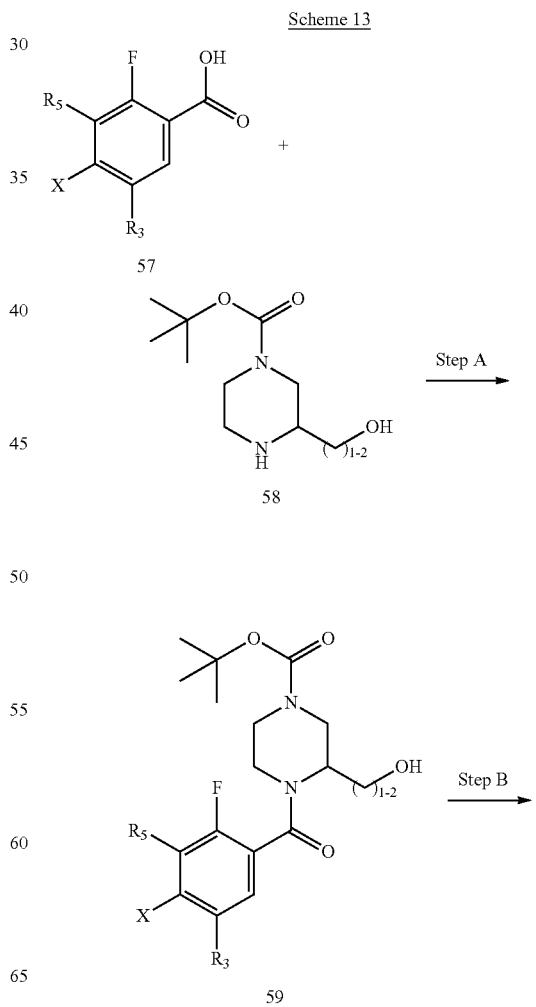

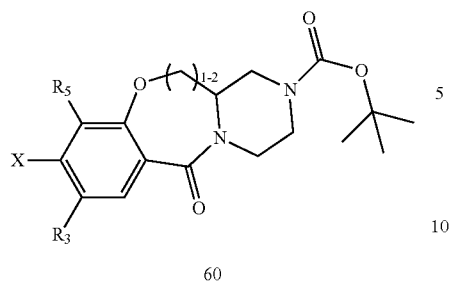

60

In Scheme 13, compound (57) represents benzoic acids from Schemes 6-9 as well as commercially available benzoic acids. The amide coupling between compound (57) and compound (58) using HATU and an appropriate base such as DIEA in a solvent such as THF to give compound (59) is shown in step A. Alternatively, the amide coupling is performed using 2-chloro-4,6-dimethoxy-1,3,5-triazine and an appropriate base such as 4-methylmorpholine in a solvent such as THF. One skilled in the art will recognize that there are a variety of conditions with which to perform an amide coupling. Step B depicts the intramolecular cyclization of compound (59) to compound (60) using an appropriate base such as sodium hydride in a solvent such as DMF.

Scheme 14

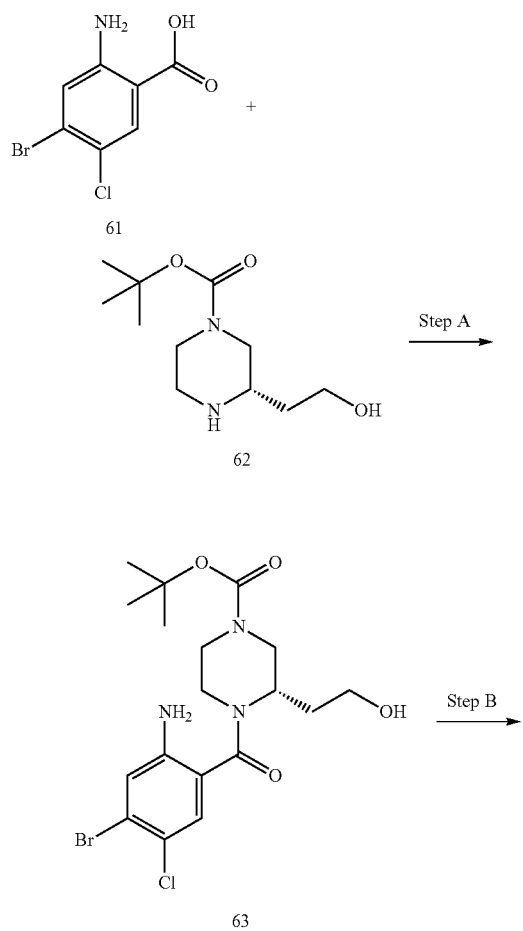

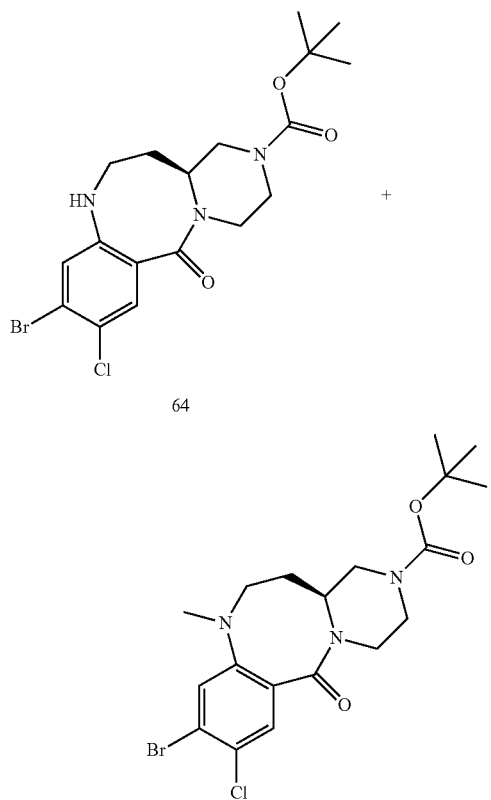

Scheme 14, step A is performed in a manner essentially analogous to the method in step A of Scheme 13 to give compound (63). Step B consists of the cyclization of compound (63) in a manner essentially analogous to the method in step B of Scheme 13 followed by methylation with methyl iodide. Compounds (64) and (65) are recovered after this step.

Scheme 15

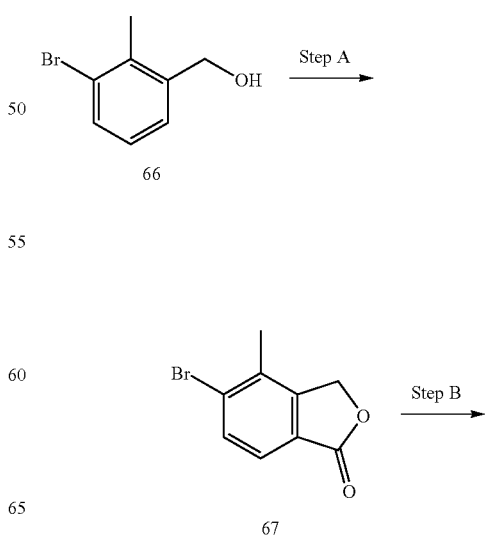

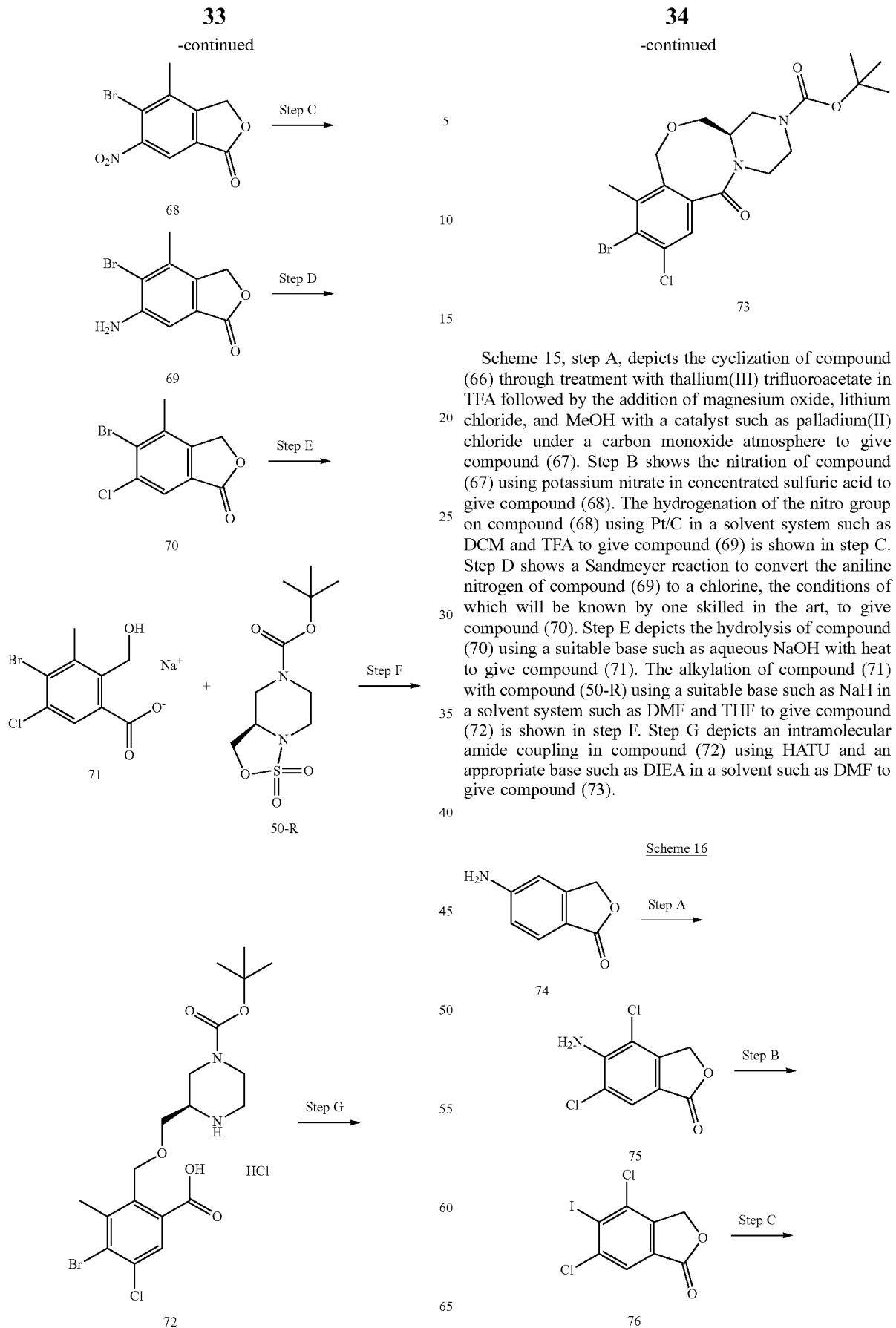

Scheme 15, step A, depicts the cyclization of compound (66) through treatment with thallium(III) trifluoroacetate in TFA followed by the addition of magnesium oxide, lithium chloride, and MeOH with a catalyst such as palladium(II) chloride under a carbon monoxide atmosphere to give compound (67). Step B shows the nitration of compound (67) using potassium nitrate in concentrated sulfuric acid to give compound (68). The hydrogenation of the nitro group on compound (68) using Pt/C in a solvent system such as DCM and TFA to give compound (69) is shown in step C. Step D shows a Sandmeyer reaction to convert the aniline nitrogen of compound (69) to a chlorine, the conditions of which will be known by one skilled in the art, to give compound (70). Step E depicts the hydrolysis of compound (70) using a suitable base such as aqueous NaOH with heat to give compound (71). The alkylation of compound (71) with compound (50-R) using a suitable base such as NaH in a solvent system such as DMF and THF to give compound (72) is shown in step F. Step G depicts an intramolecular amide coupling in compound (72) using HATU and an appropriate base such as DIEA in a solvent such as DMF to give compound (73).

35

-continued

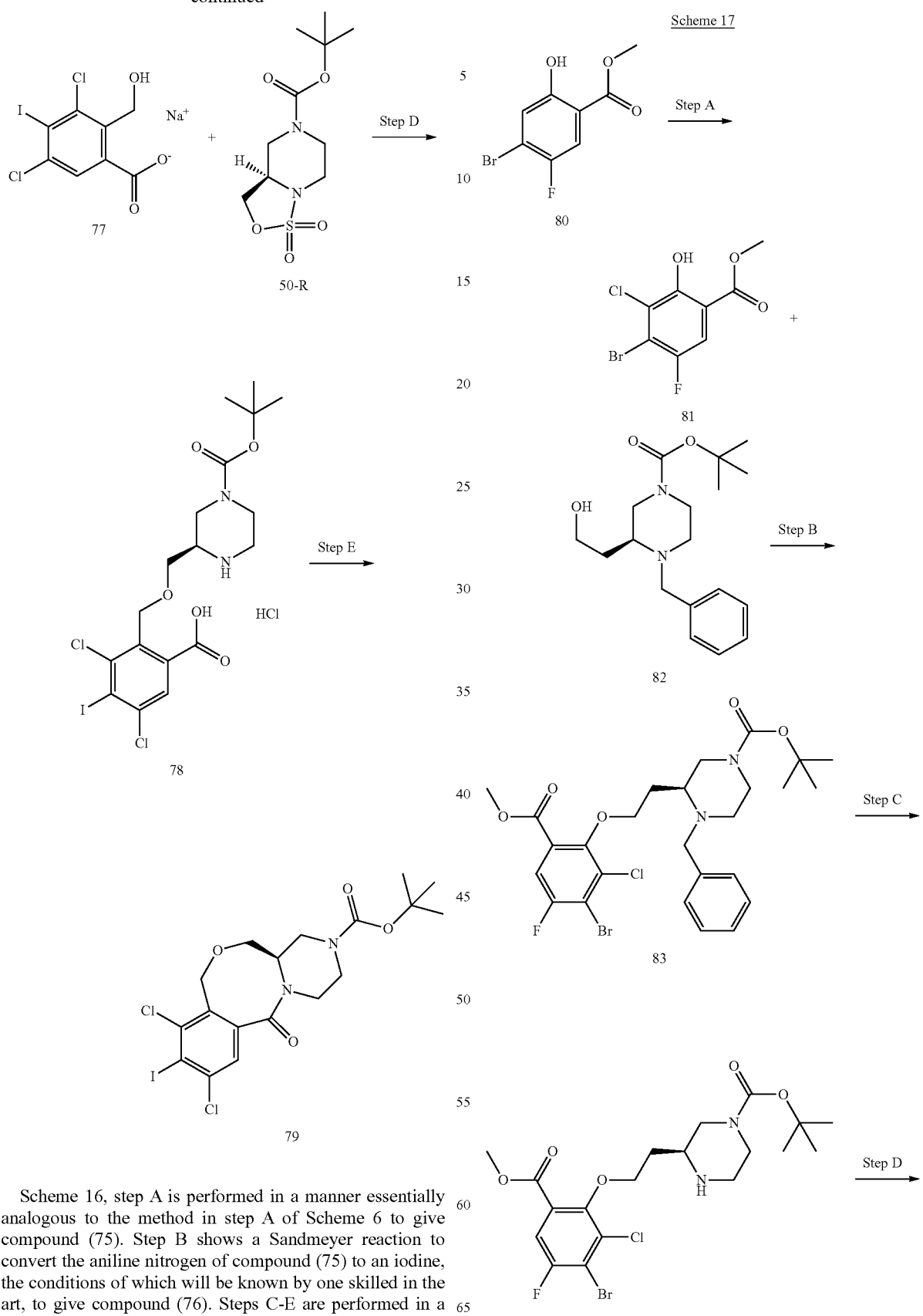

Scheme 17

Scheme 16, step A is performed in a manner essentially analogous to the method in step A of Scheme 6 to give compound (75). Step B shows a Sandmeyer reaction to convert the aniline nitrogen of compound (75) to an iodine, the conditions of which will be known by one skilled in the art, to give compound (76). Steps C-E are performed in a manner essentially analogous to the method in steps E-G of Scheme 15 to give compounds (77-79).

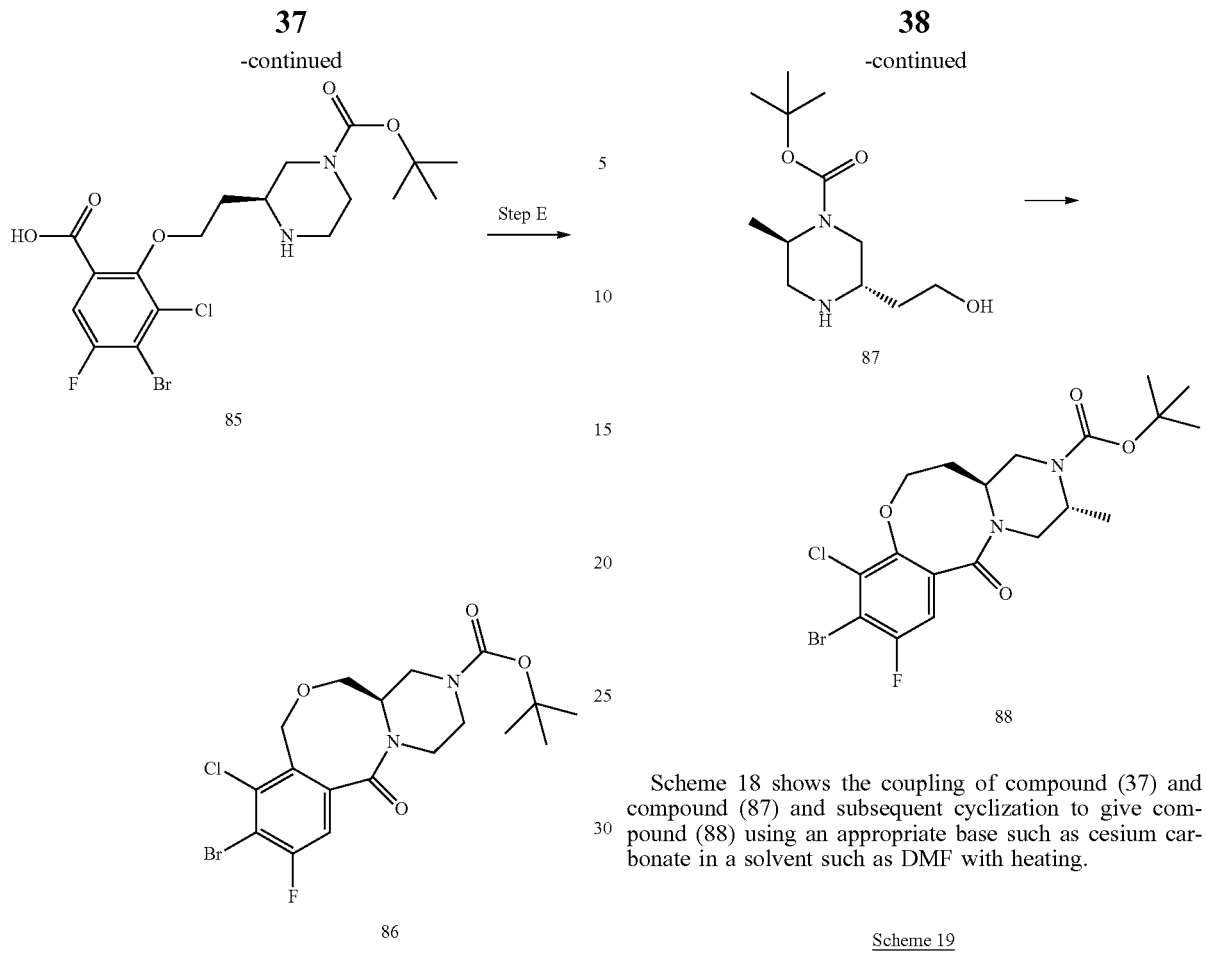

Scheme 18 shows the coupling of compound (37) and compound (87) and subsequent cyclization to give compound (88) using an appropriate base such as cesium carbonate in a solvent such as DMF with heating.

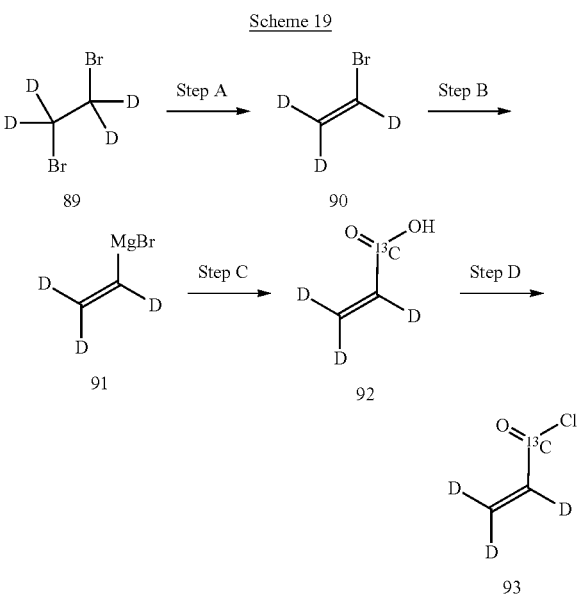

Scheme 17, step A depicts the chlorination of compound (80) with an appropriate chlorinating agent such as NCS in an appropriate solvent such as acetic acid with heating to give compound (81). Step B depicts a Mitsunobu reaction between compounds (81) and (82) using triphenyl phosphine and diisopropyl azodicarboxylate in a solvent such as THF to give compound (83). Step C shows the debenzylation of compound (83) using diisopropyl amine and 1-chloroethyl chloroformate in an appropriate solvent such as DCM to give compound (84). Step D depicts the basic hydrolysis of the ester on compound (84) using an appropriate base such as lithium hydroxide in a solvent system such as THF and water to give compound (85). The intramolecular amide coupling of compound (85) using propylphosphonic anhydride with a suitable base such as TEA in a solvent such as DCM to give compound (86) is depicted in step E.

Scheme 18

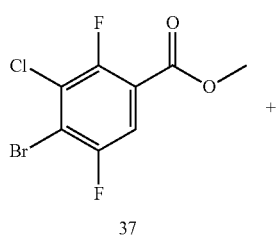

37

Scheme 19, step A shows the conversion of compound (89) to compound (90) through treatment with a suitable base such as KOH in a solvent system such as deuterated EtOH in $D_2O$. Step B depicts a Grignard reaction of compound (90) with magnesium in a solvent such as THF to give compound (91). The carboxylation of compound (91) with $^{13}CO_2$ in a solvent such as THF to give compound (92) is shown in step C. Step D shows the reaction of compound (92) with oxalyl chloride in a solvent such as DCM with catalytic DMF to give compound (93).

Scheme 20

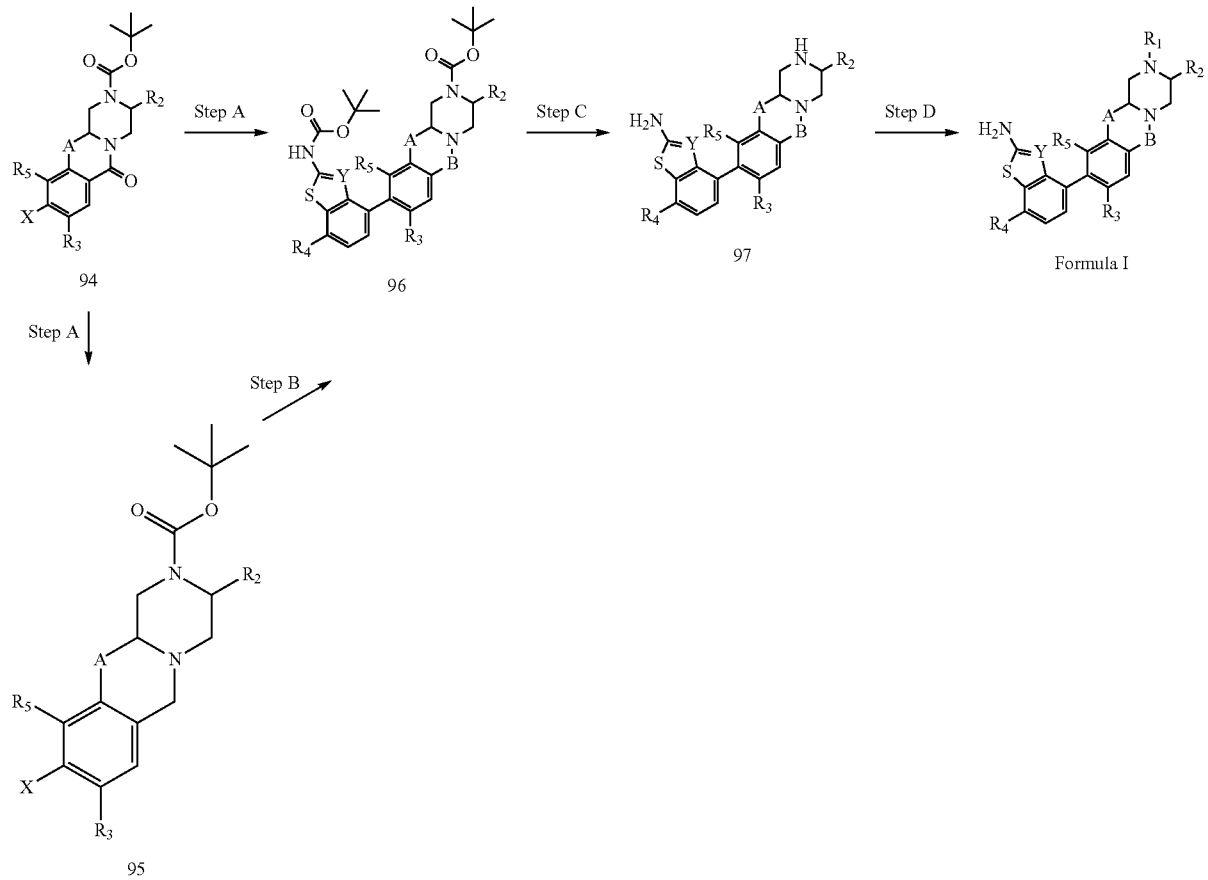

In Scheme 20, compound (94) represents the tricyclic cores described in Schemes 13-18. In step A, the amide in compound (94) is reduced using a suitable reducing agent such as borane dimethyl sulfide complex in THF to give compound (95). Compound (94) and compound (95) can both undergo a Suzuki cross-coupling with boronates as described in Schemes 1-5 using a suitable catalyst such as 1,1′-bis(di-tert-butylphosphino)ferrocene palladium dichloride with a suitable base such as potassium phosphate tribasic in a solvent system such as 1,4-dioxane and water with heating to give compound (96). This coupling could alternatively be performed using a suitable catalyst such as DPEPhosPdCl$_2$ with a base such as cesium carbonate in a solvent such as toluene with heating. One skilled in the art will recognize that there are many catalyst, base, and solvent combinations that can be utilized to perform this type of transformation. Step C shows the acidic deprotection of compound (96) with an acid such as TFA in a solvent such as DCM to give compound (97). Step D shows a coupling between compound (97) and a partner to give compounds of Formula I. The partner can be an acid chloride, a carboxylic acid, or cyanogen bromide. In cases with an acid chloride, a suitable base such as TEA or DIEA is used in a solvent such as DCM. The acid chloride can also be used with potassium carbonate as the base in a biphasic solvent system such as EtOAc, THF, and water. In cases where the partner is a carboxylic acid, the conditions include a suitable coupling reagent such as propylphosphonic anhydride with a suitable base such as DIEA in a solvent such as DMF. If the partner is cyanogen bromide, a suitable base such as aqueous NaOH is utilized in a solvent such as DCM.

PREPARATIONS AND EXAMPLES

The following Preparations and Examples further illustrate the invention and represent typical synthesis of the compounds of the invention but should not be construed to limit the scope of the invention in any way. The reagents and starting materials are readily available or may be readily synthesized either by known procedures or by employing various modifications, which may be made by one of ordinary skill in the art.

Compounds can be characterized by liquid chromatograph-electrospray mass spectrometry (LC-ES/MS) performed on an Agilent HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C-18 2.1× 50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: WATERS™ XTERRA® MS C-18 columns 2.1×50 mm, 3.5 m; gradient: 5% of solvent A for 0.25 min, gradient

Preparation 1
1,3-Dibromo-2-(bromomethyl)benzene

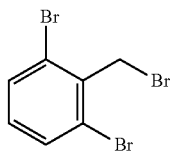

NBS (35.0 g, 195 mmol) is added to a solution of 2,6-dibromotoluene (50.0 g, 194 mmol) in carbon tetrachloride (500 mL). The mixture is heated to 80° C. and AIBN (3.20 g, 19.1 mmol) is added. The mixture is refluxed for 16 hours. After this time, the mixture is cooled to ambient temperature and filtered. The filtrate is diluted with EtOAc and washed with water, saturated aqueous sodium bicarbonate solution, and saturated aqueous sodium chloride solution. The organics are dried over magnesium sulfate, filtered, and concentrated in vacuo. The resulting residue is dried under high vacuum to give the title compound (67.5 g, 84%). $^1$H NMR (CDCl$_3$) δ 7.58 (2H, d), 7.04 (1H, t), 4.86 (2H, s).

Preparation 2
(2,6-Dibromophenyl)methanol

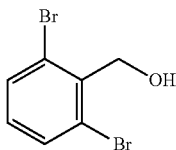

Sodium borohydride (7.83 g, 207 mmol) is added in three portions at 10 minute intervals to a 0° C. stirring solution of 2,6-dibromobenzaldehyde (148.7 g, 552.3 mmol) in EtOH (1.4 L). After the final addition, the mixture is stirred for 30 minutes before carefully quenching with saturated aqueous NH$_4$Cl solution (600 mL). DCM (1.75 L) and water (200 mL) are added and the layers separated. The aqueous layer is extracted an additional time with DCM. The combined organics are dried over sodium sulfate and filtered through a pad of silica rinsing through with EtOAc (2×500 mL). The filtrate is concentrated in vacuo, taken up in toluene, and concentrated in vacuo again to give the title compound as a white solid (148.7 g, 99%). $^1$H NMR (DMSO-d6) δ 7.66 (2H, d), 7.17 (1H, t), 5.20 (1H, t), 4.74 (2H, d).

Preparation 3
1,3-Dibromo-2-(chloromethyl)benzene

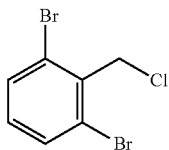

To a 0° C. solution of (2,6-dibromophenyl)methanol (199.3 g, 749.4 mmol) in DCM (1.5 L) treated with DMF (0.5 mL) is added thionyl chloride (160 mL, 2196 mmol) dropwise over 1 hour. After this time, the mixture is allowed to warm to ambient temperature and then heated to 50° C. overnight. The heat is removed and the reaction is cooled to 0° C. before carefully quenching with water (500 mL). The mixture is diluted with DCM and the layers are separated. The organics are washed with saturated aqueous sodium chloride solution, water, and again with saturated aqueous sodium chloride solution. The organics are dried over sodium sulfate, filtered, and concentrated in vacuo to give the title product as a white solid (206.98 g, 95%). $^1$H NMR (DMSO-d6) δ 7.75 (2H, d), 7.26 (1H, t), 4.95 (2H, s).

Preparation 4
2-(2,6-Dibromophenyl)acetonitrile

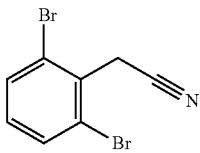

A mixture of 1,3-dibromo-2-(bromomethyl)benzene (57.0 g, 137 mmol) and potassium cyanide (28.0 g, 417 mmol) in EtOH (350 mL) and water (90 mL) is refluxed for 5 hours. The mixture is then cooled to ambient temperature and concentrated in vacuo. The residue is dissolved in EtOAc and washed with saturated sodium bicarbonate solution. The aqueous phase is extracted with EtOAc. The combined organic extracts are washed with water and saturated aqueous sodium chloride solution, dried over magnesium sulfate, filtered, and concentrated in vacuo. The resulting residue is purified by silica gel flash chromatography, eluting with 10-100% DCM/hexane to give the title compound (34.5 g, 87%). $^1$H NMR (CDCl$_3$) δ 7.62 (2H, d), 7.12 (1H, t), 4.14 (2H, s).

Alternate Preparation 4

Potassium cyanide (142.2 g, 2183.5 mmol) is added to a solution of 1,3-dibromo-2-(chloromethyl)benzene (206.98 g, 727.83 mmol) in DMSO (600 mL) and stirred at ambient temperature for 2 days. After this time, the mixture is poured into ice water and stirred for 2 hours where a white precipitate is formed. The precipitate is filtered and washed three times with water before drying in a vacuum oven. The resulting solid is purified by silica gel column chromatography eluting with 10-70% DCM/hexanes to give the title compound as a white solid (189.23 g, 94%). $^1$H NMR (DMSO-d6) δ 7.78 (2H, d), 7.28 (1H, t), 4.22 (2H, s).

--- from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparative reversed phase chromatography is performed on an Agilent 1200 LC-ES/MS equipped with a Mass Selective Detector mass spectrometer and a Leap autosampler/fraction collector. High pH methods are run on a 75×30 mm PHENOMENEX® GEMINI®-NX, 5 µm particle size column with a 10×20 mm guard. Flow rate of 85 mL/min. Eluent is 10 mM ammonium bicarbonate (pH 10) in ACN.

Preparation 5
Ethyl N-(4-bromo-3-cyano-benzothiophen-2-yl)carbamate

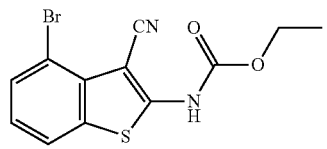

A solution of 2-(2,6-dibromophenyl)acetonitrile (20.0 g, 71.3 mmol) in DMF (200 mL) is cooled to 0° C. Sodium hydride (60 mass % in paraffin oil) (2.85 g, 71.3 mmol) is added in portions. After addition, the mixture is stirred at 0° C. for 10 minutes, then ethoxycarbonyl isothiocyanate (8.60 mL, 71.4 mmol) is added dropwise at 0-5° C. After addition, the mixture is stirred at ambient temperature for 1 hour then heated at 100° C. for 4 hours. After this time, the solvent is evaporated in vacuo. The residue is stirred in a mixture of EtOAc and saturated sodium bicarbonate solution. The resulting precipitate is collected by filtration, washed with water, and dried in a vacuum oven at 60-65° C. overnight to give the title compound (10.5 g, 45%). ES/MS m/z ($^{79}$Br/$^{81}$Br) 322.8/324.8 [M−H]$^−$.

Alternate Preparation 5

Sodium hydride (60 mass % in paraffin oil) (24.85 g, 621.3 mmol) is suspended in DMF (500 mL) and cooled to 0° C. To the cold suspension is added in a dropwise fashion a solution of 2-(2,6-dibromophenyl)acetonitrile (169.14 g, 615.19 mmol) in DMF (600 mL) over 1 hour such that the temperature does not rise over 7° C. After 30 minutes, ethoxycarbonyl isothiocyanate (77.81 mL, 646.0 mmol) is added over 30 minutes while still at 0° C. The mixture is stirred at 0° C. for 10 minutes before removing from the ice bath and stirring for an additional 20 minutes. After this time, L-proline (14.16 g, 123.0 mmol) and cuprous iodide (11.71 g, 61.49 mmol) are added and the mixture is heated to 65° C. for 4.5 hours. The mixture is treated with 0.5M aqueous EDTA (4 L) diluted with EtOAc (1.6 L) and stirred vigorously overnight. After this time, the resulting cloudy slurry is filtered and the collected solid is washed with water and EtOAc. The solid is pulled dry on vacuum for 1.5 hours then dried in a vacuum oven for 2 additional hours to give the title compound as a white solid (187.24 g, 77%). $^1$H NMR (DMSO-d6) δ 11.76 (1H, s), 8.01 (1H, d), 7.65 (1H, d), 7.27 (1H, t), 4.90 (2H, q), 1.31 (3H, t).

Preparation 6
2-Amino-4-bromo-benzothiophene-3-carbonitrile

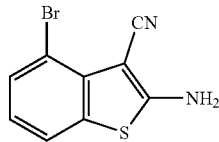

5N NaOH (765 mL, 3825 mmol) is added to a solution of ethyl N-(4-bromo cyano-benzothiophen-2-yl)carbamate (155 g, 476.6 mmol) in DMSO (480 mL). The mixture is heated to 125° C. overnight. After this time, the heat is removed and the reaction is poured into ice water (4.2 L) and stirred vigorously for 10 minutes. A precipitate is formed which is filtered, washed with water, and dried in a vacuum oven for 2 days to give the title product as a yellow solid (73.6 g, 61%). $^1$H NMR (DMSO-d6) δ 7.96 (2H, s), 7.70 (1H, d), 7.46 (1H, d), 7.02 (1H, t).

Preparation 7
tert-Butyl N-(4-bromo-3-cyano-benzothiophen-2-yl)carbamate

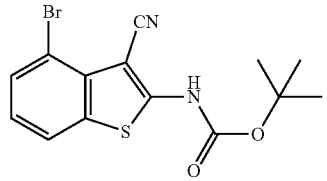

A solution of 2-amino-4-bromo-benzothiophene-3-carbonitrile (20 g, 79.2 mmol), DIEA (21 mL, 120 mmol), and DMAP (800 mg, 6.55 mmol) in THF (270 mL) and DMF (40 mL) is treated with di-tert-butyldicarbonate (19.6 g, 87.1 mmol). The mixture is stirred under nitrogen at ambient temperature for 18 hours. The reaction mixture is diluted with water, sodium bicarbonate solution, and EtOAc, then stirred for 10 minutes. The resulting precipitate is collected by filtration, washed with cold EtOAc, and dried in a vacuum oven at 60° C. overnight to afford the title compound as a beige solid (10.8 g, 38.6%). The filtrate is further extracted twice with EtOAc. The combined organic extracts are washed with water and saturated aqueous sodium chloride solution, dried over magnesium sulfate, filtered, and concentrated in vacuo. The resulting residue is purified by silica gel flash chromatography, eluting with 20-100% DCM/hexane to afford additional compound (12.5 g, 45%) giving a total yield of 23.3 g (83%). ES/MS m/z ($^{79}$Br/$^{81}$Br) 351/353 [M−H]$^−$.

Alternate Preparation 7

DIEA (77 mL, 441 mmol) and DMAP (2 g, 16 mmol) are added to a solution of 2-amino-4-bromo-benzothiophene-3-carbonitrile (74.5 g, 294 mmol) in THF (2 L) followed by addition of di-tert-butyl dicarbonate (73.1 g, 325 mmol). The mixture is stirred at ambient temperature overnight. After this time, the mixture is diluted with water, EtOAc, and saturated aqueous sodium bicarbonate solution which is then filtered to provide an off-white solid. This solid is washed with water and EtOAc then dried overnight to give the title product (32 g, 31%). The filtrate layers are then separated and the aqueous is extracted twice with EtOAc. The combined organics are washed with saturated aqueous sodium chloride, dried over sodium sulfate, filtered, and concentrated in vacuo. The resulting residue is taken up in DCM (260 mL), sonicated, diluted further with hexanes (275 mL), sonicated, triturated, and filtered to give additional title product (60.5 g, 58%) and a combined yield of 92.5 g (89%). ES/MS m/z ($^{79}$Br/$^{81}$Br) 351/353 [M−H]$^−$.

Preparation 8
tert-Butyl N-[3-cyano-4-(4,4,5,5-tetramethyl-1,3,2-dioxaborolan-2-yl)benzothiophen-2-yl] carbamate

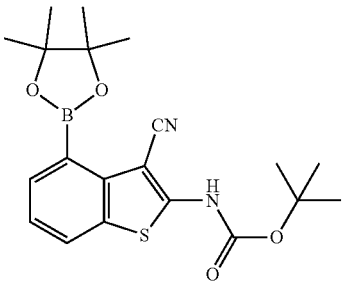

A solution of tert-butyl N-(4-bromo-3-cyano-benzothiophen-2-yl)carbamate (10.90 g, 30.7 mmol), bis(pinacolato)diboron (23.50 g, 92.54 mmol), and potassium acetate (9.05 g, 92.2 mmol) in 1,4-dioxane (150 mL) is sparged with nitrogen at 50° C. for 30 minutes. The flask is charged with 1,1'-bis(diisopropylphosphino)ferrocene (2.25 g, 5.38 mmol) and palladium acetate (0.700 g, 3.12 mmol) and then heated at 100° C. under nitrogen. After 2 hours, the mixture is cooled to ambient temperature, diluted with EtOAc, filtered through diatomaceous earth, and washed with EtOAc. The filtrate is treated with silica gel (150 g), concentrated to dryness, and then loaded into a cartridge. The crude is purified by silica gel flash chromatography, eluting with 0-50% DCM/hexane to give the title compound (9.15 g, 67%). ES/MS m/z: 399.2 (M−H).

Alternate Preparation 8

1,4-Dioxane (500 mL) is heated to reflux while sparging with nitrogen for 1 hour. The temperature is then reduced to 80° C. while continuing to sparge with nitrogen. At this temperature, tert-butyl N-(4-bromo-3-cyano-benzothiophen-2-yl)carbamate (32 g, 90.59 mmol), bis(pinacolato)diboron (60 g, 236 mmol), potassium acetate (26.67 g, 271.8 mmol), and finally palladium acetate (2.03 g, 9.04 mmol) and bis(2-diphenylphosphinophenyl)ether (8.54 g, 15.9 mmol) are added. The mixture is heated at 100° C. for three hours. After this time, the heat is removed and the mixture is diluted with EtOAc, filtered through diatomaceous earth, and concentrated in vacuo. The resulting residue is dissolved in DCM, treated with 200 g of silica, and concentrated in vacuo. This silica is placed in a pre-column, and the material is purified via silica gel chromatography eluting with 10-95% DCM and a premixed 95% DCM/EtOAc solution. The resulting fractions are separated based on relative purity. Each set is separately concentrated in vacuo, sonicated in heptanes, triturated, filtered, and rinsed with heptanes. The resulting solids are dried overnight, then combined to give the title compound (23.86 g, 65%). $^1$H NMR (DMSO-d6) δ 11.32 (1H, s), 8.02 (1H, d), 7.59 (1H, d), 7.34 (1H, t), 1.53 (9H, s), 1.37 (12H, s).

Preparation 9
6-Bromo-2,3-difluorobenzenemethanol

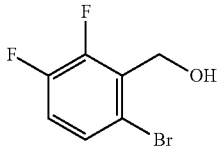

6-Bromo-2,3-difluorobenzaldehyde (20.0 g, 88.7 mmol) is dissolved in MeOH (250 mL) and sodium borohydride (6.70 g, 177 mmol) is added in portions. After the exothermic reaction is cooled down to ambient temperature (~1 hour), the reaction mixture is poured into saturated ammonium chloride solution and extracted three times with DCM. The combined organic extracts are washed with water and saturated aqueous sodium chloride solution, dried over magnesium sulfate, filtered, and concentrated in vacuo. The residue is dried under high vacuum overnight to give the title compound as a white solid (19.5 g, 97%). $^1$H NMR (CDCl$_3$) δ 7.37 (1H, m), 7.07 (1H, m), 4.88 (2H, m), 2.13 (1H, m).

Preparation 10
(6-Bromo-2,3-difluorophenyl)methyl methanesulfonate

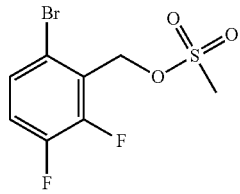

6-Bromo-2,3-difluorobenzenemethanol (19.5 g, 85.7 mmol) is dissolved in THF (200 mL) and DIEA (18.0 mL, 103 mmol) is added. The mixture is cooled to 0° C. and then treated with methanesulfonic anhydride (17.1 g, 94.2 mmol). After stirring at ambient temperature for 18 hours, the mixture is diluted with EtOAc:methyl tert-butyl ether (1:1) and washed with cold water. The layers are separated and the aqueous is extracted twice with EtOAc:methyl tert-butyl ether (1:1). The combined organics are washed with water and saturated aqueous sodium chloride solution, dried over magnesium sulfate and potassium carbonate, filtered, and concentrated in vacuo to give the title compound as a yellow oil (26.0 g, 99+%). $^1$H NMR (CDCl$_3$) d 7.44 (1H, m), 7.18 (1H, m), 5.43 (2H, d), 3.12 (3H, s).

Preparation 11
2-(6-Bromo-2,3-difluoro-phenyl)acetonitrile

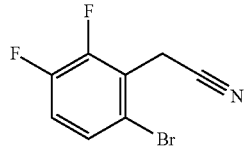

A mixture of (6-bromo-2,3-difluorophenyl)methyl methanesulfonate (26.0 g, 82.0 mmol) and potassium cyanide (6.06 g, 90.3 mmol) in EtOH (200 mL) and water (40.0 mL) is refluxed for 30 minutes and then cooled to ambient temperature. The solvent is removed in vacuo and the residue is suspended in DCM. The mixture is washed with water, saturated sodium bicarbonate solution, and saturated aqueous sodium chloride solution. The organics are dried over magnesium sulfate, filtered, and concentrated in vacuo. The crude product is purified by silica gel flash column chromatography, eluting with 10-100% DCM/hexane to give the title compound (17.9 g, 94%). $^1$H NMR (CDCl$_3$) δ 7.44 (1H, m), 7.15 (1H, m), 3.91 (2H, d).

Preparation 12

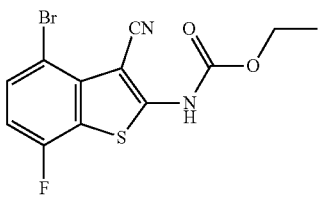

Ethyl N-(4-bromo-3-cyano-7-fluoro-
benzothiophen-2-yl)carbamate

A solution of 2-(6-bromo-2,3-difluoro-phenyl)acetonitrile (17.9 g, 77.2 mmol) in DMF (200 mL) is cooled in an ice bath and then treated with potassium tert-butoxide (9.30 g, 81.2 mmol) in portions. After addition, the mixture is stirred for 10 minutes (the reaction turns deep red) and ethoxycarbonyl isothiocyanate (9.80 mL, 81.4 mmol) is added dropwise. The reaction mixture is stirred at ambient temperature for 1 hour, and then heated at 100° C. for 30 minutes. The mixture is then cooled in an ice bath for 10 minutes and water (500 mL) is added slowly with stirring. The resultant precipitate is collected by filtration, rinsed with water and hexanes, and air dried. The solid is further dried in a vacuum oven at 60° C. overnight to give the title compound (24.5 g, 84%). ES/MS m/z ($^{79}$Br/$^{81}$Br) 340.8/342.8 [M−H]$^−$.

Preparation 13

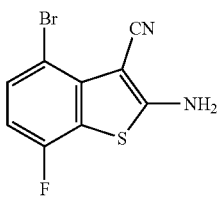

2-Amino-4-bromo-7-fluoro-benzothiophene-3-carbonitrile

A mixture of ethyl N-(4-bromo-3-cyano-7-fluoro-benzothiophen-2-yl)carbamate (24.5 g, 71.4 mmol), DMSO (100 mL), and 5N NaOH (80.0 mL, 400 mmol) is refluxed for 4 hours. The mixture is cooled to ambient temperature and treated with cold water while stirring vigorously. The resultant precipitate is collected by filtration, washed with water, and dried in a vacuum oven at 65° C. overnight to give the title compound (15.5 g, 80%). ES/MS m/z ($^{79}$Br/$^{81}$Br) 268.8/270.8 [M−H]$^−$.

Preparation 14

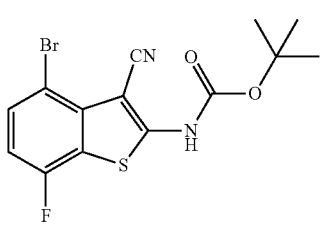

tert-Butyl N-(4-bromo-3-cyano-7-fluoro-
benzothiophen-2-yl)carbamate

The title compound is prepared from 2-amino-4-bromo-7-fluoro-benzothiophene-3-carbonitrile in a manner essentially analogous to the method of preparation 7. ES/MS m/z ($^{79}$Br/$^{81}$Br) 314.8/316.8 [M−t-Bu+H]$^+$.

Preparation 15

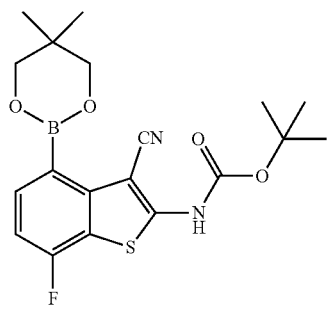

tert-Butyl N-[3-cyano-4-(5,5-dimethyl-1,3,2-
dioxaborinan-2-yl)-7-fluoro-benzothiophen-2-yl]carbamate tert-Butyl N-(4-bromo-3-cyano-7-fluoro-benzothiophen-2-yl)carbamate (16.0 g, 41.4 mmol) and bis(neopentylglycolato)diboron (37.0 g, 157 mmol) are dissolved in 1,4-dioxane (300 mL) under nitrogen. Potassium acetate (12.2 g, 124 mmol) is added, and the mixture is sparged with nitrogen for 1 hour at 50° C. DPEPhosPdCl$_2$ (3.0 g, 4.2 mmol) is added, and the flask is heated at 95° C. for 1 hour. The mixture is then cooled to ambient temperature, concentrated in vacuo to ~100 mL, diluted with heptane (200 mL), stirred for 10 minutes, and then filtered through diatomaceous earth rinsing with heptane and heptane:methyl tert-butyl ether (1:1). The filtrate is concentrated, dissolved in minimum DCM, and filtered through a pad of silica gel rinsing with EtOAc:heptane (1:1). The filtrate is washed with saturated ammonium chloride solution and saturated aqueous sodium chloride solution. The organics are dried over magnesium sulfate, filtered, and concentrated in vacuo. The residue is purified by silica gel flash column chromatography, eluting with 5-50% (20% acetone in DCM)/hexane to give the title compound (13.0 g, 78%). $^1$H NMR (DMSO-d6) δ 11.6 (1H, s), 7.61 (1H, m), 7.20 (1H, m), 3.78 (4H, s), 1.54 (9H, s), 1.03 (6H, s).

Preparation 16

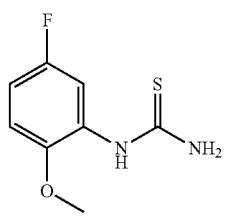

(5-Fluoro-2-methoxy-phenyl)thiourea

Benzoyl isothiocyanate (110 g, 671 mmol) and THF (875 mL) are combined and cooled to 5° C. under nitrogen. 5-Fluoro-2-methoxyaniline (83.2 mL, 705 mmol) is added dropwise while maintaining the internal reaction temperature below 10° C. The mixture is warmed to ambient temperature and stirred for 30 minutes. 5N NaOH (161 mL, 805 mmol) and water (200 mL) are added and the mixture is heated at reflux for 3.5 hours. After this time, water (500 mL) and isopropyl acetate (800 mL) are added and the mixture is cooled to ambient temperature. Concentrated aqueous HCl is added to adjust the pH to ~9-10. The layers are separated. The organic layer is dried over anhydrous magnesium sulfate, filtered, and concentrated in vacuo. EtOAc (360 mL) and hexanes (840 mL) are added to the residue and the mixture is refluxed for five minutes. After this time, the mixture is cooled to −20° C. and allowed to sit overnight. The resulting solid is filtered off and the collected solid is washed with cold hexanes to give the title compound as a colorless solid (118 g, 88%). ES/MS m/z: 201 (M+H).

Preparation 17

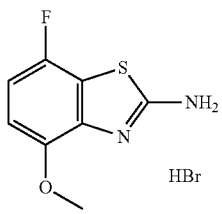

7-Fluoro-4-methoxy-1,3-benzothiazol-2-amine hydrogen bromide

A solution of (5-fluoro-2-methoxy-phenyl)thiourea (118 g, 571 mmol) and CHCl$_3$ (2 L) is cooled to 5° C. under nitrogen. Bromine (30.1 mL, 582 mmol) is added dropwise while maintaining the internal reaction temperature below 7° C. The mixture is stirred at 0° C. for 30 minutes before heating at reflux for 2.25 hours. After this time, the mixture is cooled to −20° C. and allowed to sit overnight. The resulting solids are filtered off and washed with cold hexanes to give the title compound as a yellow solid (141 g, 89%). ES/MS m/z: 199 (M+H).

Preparation 18

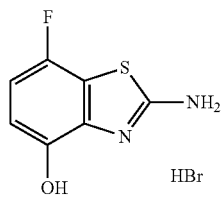

2-Amino-7-fluoro-1,3-benzothiazol-4-ol hydrogen bromide

BBr$_3$ (150 mL, 1589 mmol) is added via a cannula to DCM (1.5 L) at 0° C. under nitrogen. 7-Fluoro-4-methoxy-1,3-benzothiazol-2-amine hydrogen bromide (141 g, 506 mmol) is added portion wise over 15 minutes and the reaction mixture allowed to slowly warm to ambient temperature and with stirring overnight. The mixture is cooled to 0° C. and quenched carefully with MeOH while maintaining the internal temperature below 10° C. While quenching, the gas output is bubbled into cold 5N NaOH. The resulting solid is filtered and washed with cold DCM to give the title compound as a colorless solid (117 g, 87%). ES/MS m/z: 185 (M+H).

Preparation 19

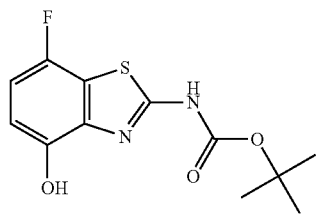

tert-Butyl (7-fluoro-4-hydroxy-1,3-benzothiazol-2-yl)carbamate

2-Amino-7-fluoro-1,3-benzothiazol-4-ol hydrogen bromide (117 g, 441 mmol) in 1,4-dioxane (1.5 L) is cooled to 10° C. TEA (129 mL, 926 mmol) is added while maintaining the internal reaction temperature below 15° C. DMAP (2.7 g, 22 mmol) and di-tert-butyl dicarbonate (228 g, 1014 mmol) are added and the reaction mixture is slowly warmed to ambient temperature and stirred for two days. The mixture is diluted with water, EtOAc, and saturated aqueous sodium chloride and the layers are separated. The organic layer is concentrated in vacuo. MeOH (900 mL) and NaOMe (5M in MeOH, 132 mL) are added and the mixture is stirred at ambient temperature overnight. Additional NaOMe (5M in MeOH, 10 mL) is added and the mixture is stirred at ambient temperature for three hours before concentrating in vacuo. Water and EtOAc are added and the layers separated. The organic layer is dried over anhydrous magnesium sulfate, filtered, and concentrated in vacuo until solids form. Hexanes are added and the resulting solids are filtered and washed with hexanes to give the title compound as a light tan solid (97.2 g, 78%). ES/MS m/z: 283 (M−H).

Preparation 20

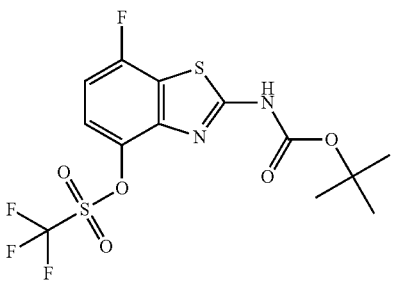

2-[(tert-Butoxycarbonyl)amino]-7-fluoro-1,3-benzothiazol-4-yl trifluoromethanesulfonate tert-Butyl (7-fluoro-4-hydroxy-1,3-benzothiazol-2-yl) carbamate (116 g, 407 mmol), DCM (1.4 L), and pyridine (66 mL, 814 mmol) are combined and cooled to 5° C. under nitrogen. Trifluoromethansulfonic anhydride (83 mL, 488 mmol) is added dropwise while maintaining the internal reaction temperature below 10° C. The mixture is diluted with water and the layers are separated. The organic layer is washed with 10% aqueous citric acid. The organic layer is dried over anhydrous magnesium sulfate, filtered, and concentrated in vacuo. The resulting residue is purified by normal phase chromatography, eluting with a 25-28% B in A gradient (A: hexanes, B: 25% DCM in EtOAc), to give the title compound as a yellow solid (123 g, 73%). ES/MS m/z: 415 (M−H).

Preparation 21

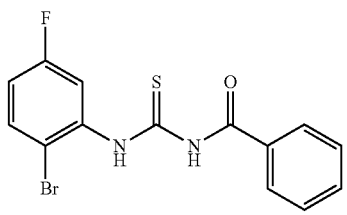

N-[(2-Bromo-5-fluoro-phenyl)carbamothioyl]benzamide

A solution of 2-bromo-5-fluoroaniline (250 g, 1289.4 mmol) in THF (400 mL) is stirred with an overhead mechanical stirrer. Benzoyl isothiocyanate (130 g, 780.6 mmol) in THF (800 mL) is added over 30 minutes using an addition funnel. A water bath is used to keep internal temperature below 30° C. during the addition. After 1.5 hours, the reaction mixture is poured equally into three 4-liter flasks containing water (3 L). The resulting solids were vacuum filtered through a sintered glass funnel. The solids were rinsed with deionized water (8 L) and air dried under vacuum to give the title compound as a tan colored solid (456 g, 99+%). ES/MS m/z ($^{79}$Br/$^{81}$Br) 353/355 [M−H]$^-$.

Preparation 22

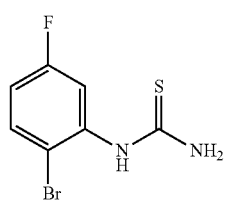

(2-Bromo-5-fluoro-phenyl)thiourea

To a suspension of N-[(2-bromo-5-fluoro-phenyl)carbamothioyl]benzamide (1600 g, 4.53 mol), THF (6 L), and MeOH (1.6 L) is added aqueous 5N NaOH (1 L). After 18 hours of stirring at ambient temperature, the reaction mixture is filtered through a pad of diatomaceous earth to remove black particulates. The pad was rinsed with THF/MeOH then 100% MeOH. The solvent is removed in vacuo to obtain a tan solid. Ice water (4 L) is added to the solid and with the use of an overhead stirrer, 5N HCl (~300 mL) is added in 100 mL portions to adjust the pH to 7. Additional ice water is added, and the mixture is stirred for ~1 hour. Water (4 L) is added and the suspension is filtered through a large sintered glass funnel under vacuum. The solids are rinsed with deionized water and after most of the water is removed, the solids are rinsed with hexanes (8 L), and air dried. The solids are placed in a vacuum oven at 50° C. for 24 hours to give the title compound as an off-white solid (1035 g, 92%). ES/MS m/z ($^{79}$Br/$^{81}$Br) 249/251 [M−H]$^-$.

Preparation 23

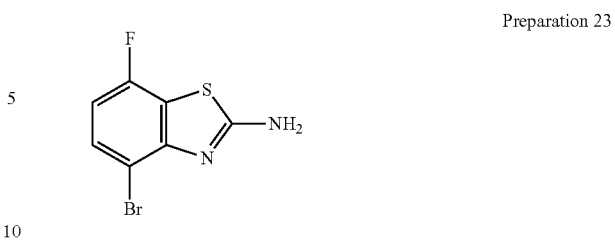

4-Bromo-7-fluoro-1,3-benzothiazol-2-amine

Sulfuric acid (350 mL), cooled with an ice/sodium chloride bath, is stirred with an overhead mechanical stirrer. (2-Bromo-5-fluoro-phenyl)thiourea (130.5 g, 523.9 mmol) is added in portions over a 5 minute period. After ten minutes, the internal temperature reached ~1° C. Under nitrogen, pyridinium tribromide (185 g, 549.53 mmol) is added in 8 portions over a period of ~15 minutes while maintaining the internal temperature below 5° C. The vapor generated is bubbled through a NaOH trap cooled in ice. After stirring at ~0° C. for 75 minutes, the reaction is warmed to ambient temperature. The reaction is then heated to an initial internal temperature of 50° C. then gradually heated to 59° C. After 1.5 hours, the reaction is cooled to ambient temperature. The reaction mixture is poured into a large flask containing ice. The pH is carefully adjusted to ~7 with 18.9N NaOH (620 mL). The solids are filtered through a sintered glass funnel and rinsed with deionized water until the filtrate pH matched that of deionized water. The solid is air dried then placed in a vacuum oven at ~50° C. for 24 hours to give the title compound as a tan solid (129.3 g, 99+%). ES/MS m/z ($^{79}$Br/$^{81}$Br) 247/249 [M+H]$^+$.

Preparation 24

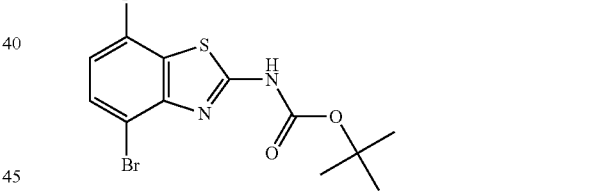

tert-Butyl N-(4-bromo-7-fluoro-1,3-benzothiazol-2-yl)carbamate

To a stirred suspension of 4-bromo-7-fluoro-1,3-benzothiazol-2-amine (370.6 g, 1500 mmol) and DMAP (36.6 g, 300 mmol) in DCM (1500 mL) is added portionwise a solution of di-tert-butyl dicarbonate (388 g, 1724 mmol) dissolved in DCM (150 ml) via addition funnel at such a rate as to control for gas evolution. The reaction mixture is stirred at ambient temperature for 1 hour and then an additional portion of di-tert-butyl dicarbonate (5.0 g, 23 mmol) is added. The reaction mixture is stirred at ambient temperature for 30 minutes and then 10% aqueous citric acid (800 mL) is added and the layers are separated. The aqueous layer is extracted twice with DCM and the combined organic extracts are washed once with saturated aqueous sodium bicarbonate solution. The organic layer is concentrated in vacuo and to the residue is added DCM (200 mL) and hexanes (1800 mL). The acquired slurry is filtered, air-dried, and the collected solid is reserved. The filtrate is concentrated in vacuo and to the residue is added MeOH (500 mL) and sodium methoxide (20 mL, 5N in MeOH, 100 mmol). The mixture is concentrated in vacuo at 45° C. To the residue is added MeOH (500 mL) and 5N NaOH (100 mL, 500 mmol). The mixture is concentrated in vacuo at 45° C. To the residue is added water and DCM and the layers are separated. The aqueous layer is extracted once with DCM. The organics are dried over anhydrous magnesium sulfate, filtered, and concentrated in vacuo. To the residue is added 100 mL DCM and 900 mL hexanes, the resulting solid is slurried, filtered, air dried, and combined with the initially acquired solid to give the title compound as an off-white solid (489.55 g, 94%). ES/MS m/z ($^{79}$Br/$^{81}$Br) 290.8/292.8 [M−t-Bu+H]$^+$.

Preparation 25

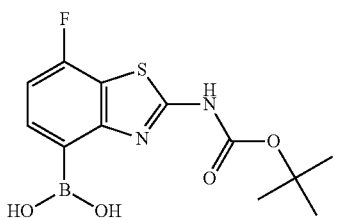

[2-(tert-Butoxycarbonylamino)-7-fluoro-1,3-benzothiazol-4-yl]boronic acid

2-[(tert-Butoxycarbonyl)amino]-7-fluoro-1,3-benzothiazol-4-yl trifluoromethanesulfonate (20.0 g, 48.1 mmol), potassium acetate (14.2 g, 144 mmol), bis(pinacolato)diboron (97.7 g, 385 mmol), tetrakis(triphenylphosphine)palladium(0) (5.55 g, 4.8 mmol) and 1,4-dioxane (240 mL) are combined and sparged with nitrogen for ten minutes. The mixture is heated at 80° C. overnight before cooling to ambient temperature and diluting with water and EtOAc. The layers are separated. The organic layer is dried over anhydrous magnesium sulfate, filtered, and concentrated in vacuo. Acetone (500 mL), water (500 mL), and ammonium acetate (112 g, 1443 mmol) are added. This is followed by the addition of NaIO$_4$ (309 g, 1443 mmol), while maintaining the internal reaction temperature between 18-23° C. The mixture is stirred vigorously at ambient temperature overnight. After this time, EtOAc is added. The mixture is stirred for 30 minutes, filtered through diatomaceous earth, and the layers are separated. The organic layer is concentrated in vacuo. The aqueous layer is diluted with saturated aqueous sodium chloride solution and extracted twice with EtOAc. These organic extracts are combined with the previously concentrated organic layer. The combined extracts are washed with water, saturated aqueous sodium chloride solution, water, and saturated aqueous sodium bicarbonate solution. The organic layer is dried over anhydrous magnesium sulfate, filtered, and concentrated in vacuo. The residue is slurried in hexanes with a small amount of DCM. The resulting solids are filtered and washed with hexanes to give the title compound as a tan solid (13.4 g, 89%). ES/MS m/z: 313 (M+H).

Alternate Preparation 25

To a suspension of sodium hydride (60% in paraffin oil) (34.6 g, 865 mmol) in THF (2000 mL) at an internal temperature of −17° C. is added a solution of tort-butyl N-(4-bromo-7-fluoro-1,3-benzothiazol-2-yl)carbamate (250.18 g, 720.6 mmol) dissolved in THF (500 mL) over 15 minutes maintaining the internal temperature at −10° C. to −15° C. over the course of the addition. After the addition, the mixture is stirred at −10° C. to −15° C. for 15 minutes at which point gas evolution ceased. The reaction mixture is cooled to an internal temperature of −65° C. and then n-butyllithium (350 mL, 2.5M in hexanes, 875 mmol) is added dropwise via addition funnel over 30 minutes at such a rate to maintain the internal temperature at −60° C. to −65° C. After the addition, the reaction mixture is stirred at this temperature for 20 minutes and then triisopropyl borate (416 ml, 1800 mmol) is added dropwise over 15 minutes maintaining an internal temperature below −60° C. The reaction mixture is allowed to slowly warm to an internal temperature of 0° C. over 5 hours 45 minutes and then saturated aqueous ammonium chloride solution (400 mL) is added carefully to control for gas evolution. To the mixture is added water (400 mL) and EtOAc (400 mL) and the layers are separated. To the aqueous layer is added enough 1N aqueous HCl to bring the pH to 3-4 and then the aqueous layer is extracted twice with EtOAc. The combined organic extracts are dried over anhydrous magnesium sulfate, filtered, and concentrated in vacuo. To the residue is added n-heptane (500 mL) and the mixture is concentrated in vacuo at 55° C. To the residue is added an additional portion of n-heptane (500 mL) and the mixture is concentrated in vacuo at 55° C. To the solid residue is added 200 mL DCM and 1800 mL hexanes and the mixture is slurried. The solid is filtered, washed with hexanes, and air dried to give the title compound as an off-white solid (217.2 g, 94%). ES/MS m/z: 313 (M+H).

Preparation 26

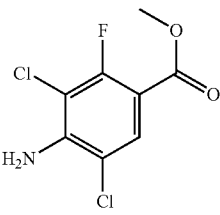

Methyl 4-amino-3,5-dichloro-2-fluoro-benzoate

Methyl 4-amino-2-fluoro-benzoate (27.0 g, 160 mmol) and NCS (46.3 g, 336 mmol) are dissolved in DMF (300 mL) and heated at 80° C. After 40 minutes, the reaction mixture is poured over ice water and extracted twice with EtOAc. The combined organic extracts are washed once with 5N NaOH, twice with 0.2N aqueous LiCl, dried over anhydrous magnesium sulfate, filtered, and concentrated in vacuo to give the title compound (37.0 g, 97%). ES/MS m/z ($^{35}$Cl/$^{37}$Cl) 238/240 [M+H]$^+$.

TABLE 1

Compounds synthesized in a manner essentially analogous to that of Preparation 26

| Preparation | Structure | Compound Name | NMR |
|---|---|---|---|
| 27 | 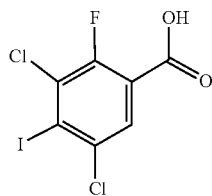 | 4-Amino-5-chloro-2,3-difluoro-benzoic acid | $^1$H NMR (DMSO-d6) d 12.96 (s, 1H), 7.54 (dd, J = 2.1, 6.9 Hz, 1H), 6.56 (bs, 2H) |
| 28 | 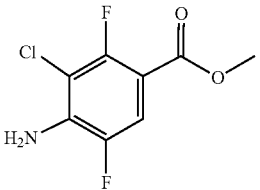 | Methyl 4-amino-5-chloro-2-fluoro-3-methyl-benzoate | $^1$H NMR (CDCl$_3$) d 7.80 (d, J = 7.2 Hz, 1H), 4.56 (bs, 2H), 3.16 (s, 3H), 2.14 (d, 3H) |

Preparation 29

3,5-Dichloro-2-fluoro-4-iodo-benzoic acid

Cuprous iodide (10.0 g, 51.5 mmol), ACN (128 mL) and tert-butyl nitrite (13.6 mL, 103 mmol) are combined and the mixture is heated at 50° C. for 30 minutes and then to the mixture is added methyl 4-amino-3,5-dichloro-2-fluoro-benzoate (6.11 g, 25.7 mmol). Gas evolution is noted. After 1 hour 40 minutes at 50° C. the solvent is removed in vacuo. Water, EtOAc, and 1N aqueous HCl are added. The aqueous layer is extracted twice with EtOAc. The combined organic extracts are washed with aqueous sodium bisulfite, dried over anhydrous magnesium sulfate, filtered, and concentrated in vacuo. The crude mixture is purified by silica gel flash chromatography eluting with 3-5% EtOAc in hexanes. The cleanest fractions are combined and concentrated in vacuo to give the methyl ester intermediate (5.85 g, 65%).

To methyl 3,5-dichloro-2-fluoro-4-iodo-benzoate (5.85 g, 16.8 mmol) is added MeOH (170 mL) and 1N aqueous NaOH (17 mL). In the course of stirring at ambient temperature over 40 minutes, the material is fully dissolved. The MeOH is removed in vacuo. To the residue is added EtOAc and 1N aqueous HCl. The aqueous layer is extracted twice with EtOAc and the combined organic extracts are dried over anhydrous magnesium sulfate, filtered, and concentrated in vacuo to give the title compound (5.56 g, 99%): $^1$H NMR (CDCl$_3$) d 8.063-8.08 (d, 1H, J=6.34 Hz).

Preparation 30

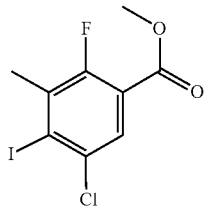

Methyl 5-chloro-2-fluoro-4-iodo-3-methyl-benzoate

Methyl 4-amino-5-chloro-2-fluoro-3-methyl-benzoate (14.8 g, 68.0 mmol) in ACN (100 mL) is added to a stirring mixture of cuprous iodide (15.7 g, 82.4 mmol), ACN (100 mL) and tert-butyl nitrite (12.3 mL, 103 mmol). The mixture is heated under N$_2$ at 40° C. for 18 hours. The mixture is concentrated in vacuo to half of the original volume, diluted with EtOAc, and filtered twice through diatomaceous earth. The collected filtrate is concentrated in vacuo. The crude mixture is purified by silica gel flash chromatography eluting with EtOAc in hexanes. The cleanest fractions are combined and concentrated in vacuo to give the title compound (22.46 g, 52.8%). $^1$H NMR (CDCl$_3$) d 7.91 (d, J=6.6 Hz, 1H), 3.95 (s, 3H), 2.53 (d, J=3.1 Hz, 3H).

Preparation 31

Methyl 4-amino-3-chloro-2,5-difluoro-benzoate

To a solution of methyl 4-amino-2,5-difluorobenzoate (25 g, 127 mmol) in DMF (100 mL) is added NCS (19.9 g, 146 mmol) at ambient temperature and then the mixture is heated at 45° C. for 18 hours. The reaction mixture is poured into a mixture of water (1.5 L) and diethyl ether (1.2 L), and the layers are separated. The aqueous layer is extracted with diethyl ether (1 L). The combined organic extracts are washed with cold 1N aqueous NaOH, water, and saturated aqueous sodium chloride solution. The organics are dried over anhydrous sodium sulfate, filtered, and concentrated in vacuo. The residue is purified by silica gel flash column chromatography, eluting with 10-30% (75% EtOAc in DCM)/hexane to give the title compound (24.5 g, 87%). ES/MS m/z: 222.2 (M+H).

Preparation 32

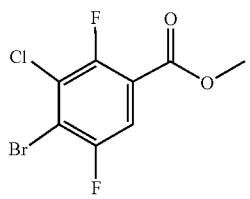

Methyl 4-bromo-3-chloro-2,5-difluoro-benzoate

Methyl 4-amino-3-chloro-2,5-difluoro-benzoate (24.5 g, 111 mmol) in ACN (100 mL) is added to a cold mixture of cupric bromide (6.2 g, 28 mmol) and tert-butyl nitrite (20 mL, 168 mmol) in ACN (100 mL). The green colored mixture is warmed up to ambient temperature over 18 hours. The reaction mixture is then diluted with ACN, filtered through a pad of diatomaceous earth, and rinsed with DCM. The filtrate is concentrated and diluted with DCM, filtered again through diatomaceous earth, and rinsed with DCM. The filtrate is washed with water, saturated ammonium chloride solution (2×), saturated aqueous sodium chloride solution (2×), dried over sodium sulfate, filtered, and concentrated in vacuo. The residue is purified by silica gel flash column chromatography, eluting with 0-50% (10% EtOAc in DCM)/hexane to give the title compound (23.5 g, 70%). $^1$H NMR (CDCl$_3$) δ 7.68 (1H, m), 3.99 (3H, s).

TABLE 2

Compound synthesized in a manner essentially analogous to that of Preparation 32

| Preparation | Structure | Compound Name | NMR |
|---|---|---|---|
| 33 | 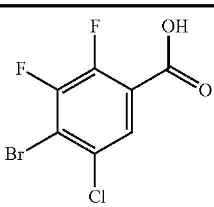 | 4-Bromo-5-chloro-2,3-difluoro-benzoic acid | $^1$H NMR (DMSO-d6) d 7.89 (dd, J = 2.2, 6.2 Hz, 1H) |

Preparation 34

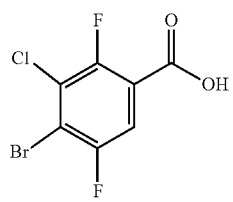

4-Bromo-3-chloro-2,5-difluoro-benzoic acid

To a solution of methyl 4-bromo-3-chloro-2,5-difluoro-benzoate (10.8 g, 37.8 mmol) in THF (100 mL) is added MeOH (50 mL). The homogeneous solution is cooled in an ice bath and 2N NaOH (60 mL, 120 mmol) is added dropwise. After addition, the mixture is stirred at ambient temperature for 30 minutes. The organic solvent is removed in vacuo. The aqueous is ice chilled and pH is adjusted to ~2.0 with 5N HCl (24 mL). The aqueous is extracted with EtOAc (3×). The combined organic extracts are washed with saturated aqueous sodium chloride solution, dried over magnesium sulfate, filtered, and concentrated in vacuo. The resulting residue is dried in a vacuum oven at 60° C. overnight to give the title compound (10.3 g, 99%). $^1$H NMR (DMSO-d6) δ 7.81 (dd, J=6.0, 8.6 Hz, 1H).

TABLE 3

Compound synthesized in a manner essentially analogous to that of Preparation 34

| Preparation | Structure | Compound Name | NMR |
|---|---|---|---|
| 35 | 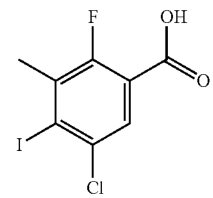 | 5-Chloro-2-fluoro-4-iodo-3-methyl-benzoic acid | $^1$H NMR (DMSO-d6) d 13.62 (s, 1H), 7.84 (d, J = 6.7 Hz, 1H), 2.45 (d, 3H). |

Preparation 36

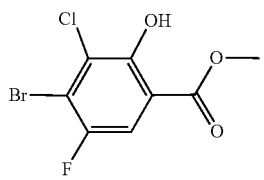

Methyl 4-bromo-3-chloro-5-fluoro-2-hydroxy-benzoate

To a solution of methyl 4-bromo-5-fluoro-2-hydroxy-benzoate (9 g, 34.3 mmol) in acetic acid (70 mL) is added NCS (14 g, 104.8 mmol) and the mixture is heated to 55° C. After 18 hours, additional NCS (5.5 g, 37.7 mmol) is added and the mixture is stirred for 24 hours at 55° C. The reaction is then cooled to ambient temperature and the excess acetic acid is removed in vacuo. The residue is purified by silica gel flash column chromatography, eluting with 100% DCM to give the title compound as a solid (7.1 g, 73%). ES/MS m/z ($^{79}$Br/$^{81}$Br) 281/283 [M–H]$^-$.

Preparation 37

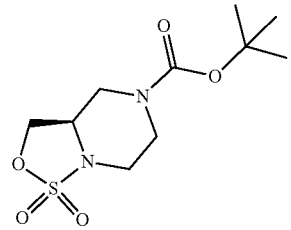

tert-Butyl (3aR)-1,1-dioxo-3a,4,6,7-tetrahydro-3H-oxathiazolo[3,4-a]pyrazine-5-carboxylate To a suspension of imidazole (24.9 g, 362 mmol) in DCM (181 mL) at 0° C. is added thionyl chloride (8.0 mL, 110 mmol) dropwise. The mixture is stirred at 0° C. for 5 minutes and at ambient temperature for 1 hour. The mixture is cooled to −78° C. and a solution of tort-butyl (3R)-3-(hydroxymethyl)piperazine-1-carboxylate (8.00 g, 36.2 mmol) in DCM (181 mL) is added dropwise over 45 minutes. The mixture is warmed to ambient temperature and stirred for 2.5 days. The reaction is quenched with saturated aqueous ammonium chloride and diluted with water and DCM. The layers are separated, and the aqueous layer is extracted again with DCM. The combined organic layers are washed with saturated aqueous sodium chloride, dried over sodium sulfate, filtered, and concentrated in vacuo to give an amber syrup. To a solution of the syrup in acetonitrile (282 mL) at 0° C. is added a solution of sodium periodate (10.2 g, 47.6 mmol) in water (92 mL). Ruthenium(III) chloride (76 mg, 0.37 mmol) is added. The resulting suspension is stirred at 0° C. for 5 minutes and at ambient temperature for 5 hours. The reaction is quenched with saturated aqueous ammonium chloride and diluted with water and EtOAc. The layers are separated, and the aqueous layer is extracted again with EtOAc. The combined organic layers are washed with saturated aqueous sodium chloride, dried over sodium sulfate, and filtered through filter paper and then through a short plug of silica gel. The filtrate is concentrated in vacuo. To the residue is added DCM, and the mixture is concentrated in vacuo and placed under vacuum overnight to give the title compound as a tan solid (9.39 g, 93%). $^1$H NMR (CDCl$_3$) δ 4.63 (1H, dd), 4.23 (1H, t), 4.23 (1H, br s), 4.07 (1H, br s), 3.64 (1H, m), 3.45 (1H, d), 3.13 (1H, m), 2.96 (2H, td), 1.47 (9H, s).

TABLE 4

Compounds synthesized in a manner
essentially analogous to that of Preparation 37

| Preparation | Structure | Compound Name | $^1$H NMR (CDCl$_3$) |
|---|---|---|---|
| 38 | 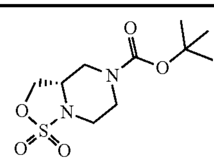 | tert-Butyl (3aS)-1,1-dioxo-3a,4,6,7-tetrahydro-3H-oxathiazolo[3,4-a]pyrazine-5-carboxylate | 4.63 (1H, dd), 4.23 (1H, t), 4.23 (1H, br s), 4.07 (1H, br s), 3.64 (1H, m), 3.45 (1H, d), 3.13 (1H, m), 2.96 (2H, td), 1.47 (9H, s) |

Preparation 39

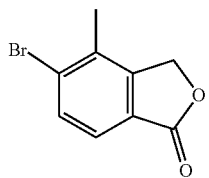

5-Bromo-4-methyl-3H-
isobenzofuran-1-one

To a suspension of (3-bromo-2-methylphenyl)methanol (15.0 g, 73.1 mmol) in TFA (75 mL) is added thallium(III) trifluoroacetate (41.8 g 73.1 mmol). Additional TFA (25 mL) is used to rinse the thallium(III) trifluoroacetate into the reaction vessel. The mixture is stirred under nitrogen at ambient temperature overnight and concentrated in vacuo and dried under vacuum to provide a light tan solid. The solid is placed under nitrogen and combined with magnesium oxide (6.01 g, 149 mmol), lithium chloride (6.32 g, 149 mmol), and MeOH (300 mL). Palladium(II) chloride (1.32 g, 7.38 mmol) is added. The mixture is purged five times with carbon monoxide and placed under a carbon monoxide atmosphere (balloon pressure). The mixture is stirred at ambient temperature for 2 hours and palladium(II) chloride (262 mg, 1.46 mmol) and magnesium oxide (1.18 g, 29.2 mmol) are added. The mixture is purged three times with carbon monoxide and placed under a carbon monoxide atmosphere (balloon pressure). The mixture is stirred at ambient temperature for 30 minutes and palladium(II) chloride (262 mg, 1.46 mmol) and magnesium oxide (1.18 g, 29.2 mmol) are added. The mixture is purged four times with carbon monoxide and placed under a carbon monoxide atmosphere (balloon pressure). The mixture is stirred at ambient temperature for 1.5 hours and palladium(II) chloride (327 mg, 1.83 mmol) and magnesium oxide (1.77 g, 43.9 mmol) are added. The mixture is purged with carbon monoxide and placed under a carbon monoxide atmosphere (balloon pressure). The mixture is stirred at ambient temperature for 1.5 hours, filtered through diatomaceous earth, and washed through the diatomaceous earth with EtOAc. The filtrate is concentrated in vacuo to give a residue. The crude product is purified by silica gel flash chromatography eluting with 0-30% EtOAc/hexanes. The product-containing fractions are concentrated in vacuo to give the title compound as a white solid (14.48 g, 70%). ES/MS m/z ($^{79}$Br/$^{81}$Br) 227.0/229.0 [M+H]$^+$.

Preparation 40

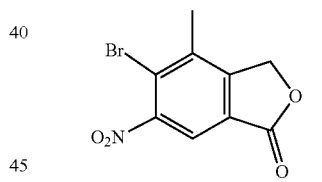

5-Bromo-4-methyl-6-nitro-3H-
isobenzofuran-1-one

A solution of 5-bromo-4-methyl-3H-isobenzofuran-1-one (14.4 g, 50.7 mmol, 80% purity) in concentrated sulfuric acid (160 mL) is cooled to −5° C. and potassium nitrate (9.62 g, 95.2 mmol) is added. The mixture is stirred under nitrogen for 2.5 hours and ice (750 g) is added with stirring. The mixture is extracted three times with EtOAc. The combined organic layers are washed with saturated aqueous sodium chloride, dried over sodium sulfate, filtered, and concentrated in vacuo. The crude material is purified by silica gel flash chromatography eluting with 10-70% EtOAc/hexanes. The product-containing fractions are concentrated in vacuo to give the title compound as an off-white to yellow/orange solid (11.98 g, 87%). ES/MS m/z ($^{79}$Br/$^{81}$Br) 289.0/291.0 [M+H]$^+$.

Preparation 41

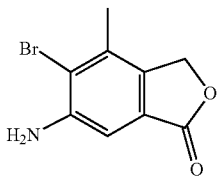

6-Amino-5-bromo-4-methyl-
3H-isobenzofuran-1-one

To a pressure flask are added 5-bromo-4-methyl-6-nitro-3H-isobenzofuran one (11.98 g, 44.04 mmol), DCM (1000 mL), TFA (300 mL, 4 mol), and platinum (5% on carbon, sulfided, 3.00 g, 0.769 mmol). The mixture is purged with hydrogen and pressurized to 45 PSI for 1.25 hours. The reaction mixture is filtered through diatomaceous earth and washed through with DCM. The filtrate is concentrated in vacuo to give a residue. The residue is dried under vacuum and purified by silica gel flash chromatography eluting with 10-60% EtOAc/DCM. The product-containing fractions are concentrated in vacuo to give the title compound as a peach-colored solid (9.86 g, 96%). ES/MS m/z ($^{79}$Br/$^{81}$Br) 242.0/244.0 [M+H]$^+$.

Preparation 42

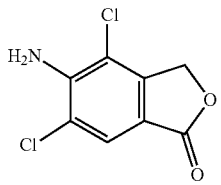

5-Amino-4,6-dichloro-3H-
isobenzofuran-1-one

To a solution of 5-amino-3H-isobenzofuran-1-one (10.44 g, 68.60 mmol) in DMF (100 mL) at ambient temperature is added NCS (20.56 g, 150.9 mmol). The mixture is stirred at 50° C. for 2.5 hours and at ambient temperature overnight. The mixture is poured into water (1 L) and the precipitate is filtered out with a filter frit, washed twice with water and then with diethyl ether, and dried by drawing air through the frit. The precipitate is taken up in EtOAc, dried over sodium sulfate, filtered, and concentrated in vacuo to give the title compound as a yellowish-orange solid (14.27 g, 93%). ES/MS m/z ($^{35}$Cl/$^{37}$Cl) 218.2/220.0 [M+H]$^+$.

Preparation 43

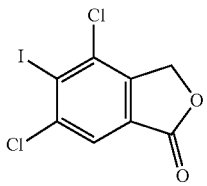

4,6-Dichloro-5-iodo-3H-
isobenzofuran-1-one

To a suspension of 5-amino-4,6-dichloro-3H-isobenzofuran-1-one (8.00 g, 35.6 mmol) in acetonitrile (237 mL) at −15° C. is added concentrated sulfuric acid (6.5 mL, 120 mmol) dropwise. A solution of sodium nitrite (4.96 g, 71.2 mmol) in water (36 mL) is added slowly. The mixture is stirred at 0° C. for 30 minutes. A solution of potassium iodide (23.6 g, 142 mmol) in water (36 mL) is added dropwise. The mixture is stirred at 0° C. for 15 minutes and at ambient temperature for 30 minutes. The mixture is diluted with saturated aqueous sodium sulfite and partially concentrated under vacuum to remove most of the acetonitrile. The mixture is diluted with EtOAc and the layers are separated. The organic layer is washed with saturated aqueous sodium chloride, dried over sodium sulfate, filtered, and concentrated in vacuo. The crude material is purified by silica gel flash chromatography eluting with 0-25% EtOAc/hexanes. The impure product-containing fractions are concentrated in vacuo and further purified by silica gel flash chromatography eluting with 100% DCM. The pure product-containing fractions from both chromatographic purifications are combined, concentrated in vacuo, and placed under vacuum overnight to give the title compound as a pale yellow solid (6.62 g, 51%). $^1$H NMR (CDCl$_3$) d 7.89 (1H, s), 5.25 (2H, s).

Preparation 44

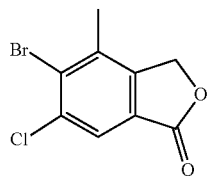

5-Bromo-6-chloro-4-methyl-
3H-isobenzofuran-1-one

To a suspension of cupric chloride (5.85 g, 43.5 mmol) in acetonitrile (150 mL) in a cool water bath is added tert-butyl nitrite (12.9 mL, 108 mmol) over 5 minutes. The mixture is stirred for 10 minutes and the cool water bath is removed. The mixture is stirred under nitrogen for another 25 minutes. A solution of 6-amino-5-bromo-4-methyl-3H-isobenzofuran-1-one (8.73 g, 36.1 mmol) in acetonitrile (550 mL) is added dropwise and the mixture is stirred under nitrogen for 1.5 hours. The mixture is partially concentrated in vacuo to reduce the volume to about 275 mL. The mixture is diluted with saturated aqueous sodium chloride (300 mL) and 1M HCl (500 mL) and extracted twice with EtOAc. The combined organic layers are washed twice with saturated aqueous sodium bicarbonate, washed twice with saturated aqueous sodium chloride, dried over sodium sulfate, filtered, and concentrated in vacuo. The crude material is purified by silica gel flash chromatography eluting with 5-30% EtOAc/DCM. The product-containing fractions are concentrated in vacuo to give the title compound as a pale yellow solid (9.03 g, 96%). ES/MS m/z ($^{79}$Br/$^{81}$Br) 278.0/280.0 [M+H]$^+$.

Preparation 45

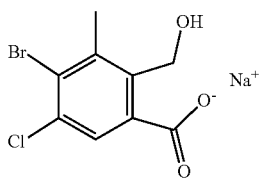

Sodium 4-bromo-5-chloro-2-(hydroxymethyl)-3-methyl-benzoate

Into a screw top vial with a stir bar are added 5-bromo-6-chloro-4-methyl-3H-isobenzofuran-1-one (2.459 g, 8.557 mmol) and 1M NaOH (9.4 mL, 9.4 mmol). The vial is capped and heated at 100° C. for 2 hours. The reaction mixture is cooled to ambient temperature and transferred to a 1 L flask. Toluene (100 mL) is added and the mixture is concentrated in vacuo and placed under vacuum for 3 days to give the title compound as a tan solid (2.81 g, 99+%). ES/MS m/z ($^{79}$Br/$^{81}$Br) 276.8/278.8 [M−H]$^{−}$.

TABLE 5

Compounds synthesized in a manner essentially analogous to that of Preparation 45

| Preparation | Structure | Compound Name | ES/MS m/z (M + H) |
|---|---|---|---|
| 46 | ![structure] | Sodium 3,5-dichloro-2-(hydroxymethyl)-4-iodo-benzoate | 344.8/346.8 |

Preparation 47

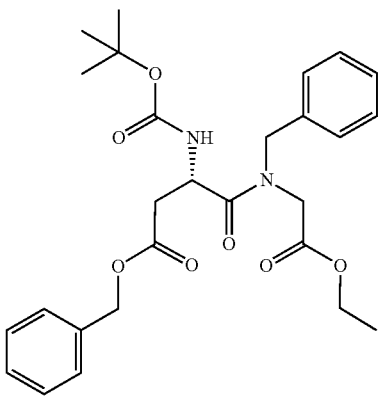

Benzyl (3S)-4-[benzyl-(2-ethoxy-2-oxo-ethyl)amino]-3-(tert-butoxycarbonylamino)-4-oxo-butanoate Boc-L-Aspartic acid 4-benzyl ester (114 g, 352.6 mmol) is added to a reaction vessel. DCM (950 mL) and N,N'-dicyclohexylcarbodiimide (74.5 g, 361 mmol) are added, and the mixture cooled to 10-20° C. Benzylglycine ethyl ester (68.2 g, 353 mmol) is added dropwise, keeping the temperature below 20° C. The mixture is stirred at 10-20° C. for 17 hours, then filtered and concentrated in vacuo. MTBE (230 mL) is added and the mixture stirred for 0.5 hours. The mixture is filtered and concentrated in vacuo to give the title compound as an oil (174.4 g, 99%).

Preparation 48

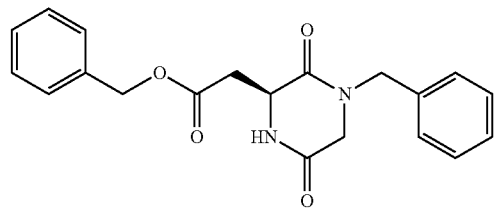

Benzyl 2-[(2S)-4-benzyl-3,6-dioxo-piperazin-2-yl]acetate

Benzyl (3S)-4-[benzyl-(2-ethoxy-2-oxo-ethyl)amino]-3-(tert-butoxycarbonylamino)-4-oxo-butanoate (174.4 g, 349.8 mmol) is added to a reaction vessel along with DCM (500 mL) and TFA (230 mL). The mixture is stirred at 15-20° C. for 16 hours, then concentrated in vacuo to dryness. The residue is dissolved in isopropanol (500 mL) and heated to 80° C. for 1 hour. The mixture is concentrated in vacuo, then diluted with water (230 mL). The mixture is neutralized with 15% NaOH in water to pH 8-9 (109 g of 15% aq NaOH is used). The mixture is filtered and rinsed with water (2×100 mL). The solids are dried under vacuum at 50-55° C. for 2 days to give the title compound as a solid (95.9 g, 78%). $^{1}$H NMR (CDCl$_{3}$) δ 7.44-7.29 (m, 8H), 7.32-7.23 (m, 2H), 6.91 (br s, 1H), 5.18 (d, J=12.1 Hz, 1H), 5.14 (d, J=12.2 Hz, 1H), 4.64 (d, J=14.5 Hz, 1H), 4.54 (d, J=14.5 Hz, 1H), 4.44 (br d, J=7.9 Hz, 1H), 3.88 (d, J=17.7 Hz, 1H), 3.82 (d, J=17.7 Hz, 1H), 3.15 (dd, J=17.5, 3.4 Hz, 1H), 2.93 (dd, J=17.5, 8.3 Hz, 1H).

Preparation 49

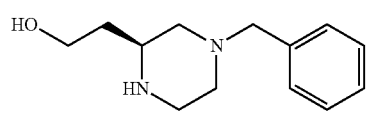

2-[(2S)-4-Benzylpiperazin-2-yl]ethanol

Lithium aluminum hydride (13 g, 342.5 mmol) is added to a reaction vessel along with THF (200 mL). The mixture is cooled to −5-0° C. Benzyl 2-[(2S)-4-benzyl-3,6-dioxo-piperazin-2-yl]acetate (50 g, 141.9 mmol) is added to a second vessel along with THF (400 mL). The solution of benzyl 2-[(2S)-4-benzyl-3,6-dioxo-piperazin-2-yl]acetate is added slowly to the lithium aluminum hydride solution, keeping the temperature between −5 and 0° C. The reaction mixture is heated to 60-65° C. and stirred for 2 hours. The mixture is cooled to 20-30° C. and stirred for 16 hours. Water (13 g) is added, then 4% NaOH in water (52 g) is added. The mixture is stirred for 1 hour, filtered, and concentrated in vacuo. Isopropyl acetate (200 mL) and 2M HCl (150 g) are added. The layers are separated and the aqueous layer is washed again with isopropyl acetate (100 mL). The aqueous layer is adjusted to pH 11-12 with NaOH, and DCM (150 mL) is added. The layers are separated and the organic layer is washed with water (100 mL). The layers are separated and the organic layer is concentrated in vacuo to give the title compound as a solid (20.1 g, 64%).

$^1$H NMR (CDCl$_3$) δ 7.44-7.20 (m, 5H), 3.81 (t, J=5.2 Hz, 2H), 3.50 (s, 2H), 3.08-2.93 (m, 2H), 2.93-2.82 (m, 1H), 2.76 (d, J=11.5 Hz, 2H), 2.02 (td, J=11.1, 3.3 Hz, 1H), 1.85 (t, J=10.4 Hz, 1H), 1.67-1.52 (m, 2H).

Preparation 50

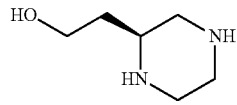

2-[(2S)-Piperazin-2-yl]ethanol

2-[(2S)-4-Benzylpiperazin-2-yl]ethanol (20 g, 91 mmol) is added to an H$_2$-flushed reaction vessel. MeOH (200 mL) is added and Pd(OH)$_2$ (2 g) is added. The mixture is flushed with H$_2$, then pressurized to 45 psi H$_2$. The mixture is heated to 50° C. and stirred for 44 hours. The reaction mixture is filtered and concentrated in vacuo to give the title compound as an oil (12.7 g, 99+%). $^1$H NMR (CDCl$_3$) δ 3.84-3.65 (m, 2H), 3.44 (s, 1H), 2.99-2.83 (m, 4H), 2.78 (td, J=11.6, 2.5 Hz, 1H), 2.68 (td, J=11.4, 2.8 Hz, 1H), 2.54-2.42 (m, 1H), 1.65-1.43 (m, 2H).

Preparation 51

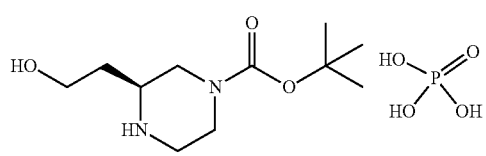

tert-Butyl (3S)-3-(2-hydroxyethyl)piperazine-1-carboxylate; phosphoric acid

2-[(2S)-Piperazin-2-yl]ethanol (9.2 g, 70.4 mmol) is added to a reaction vessel, along with MeOH (83 mL) and water (9 mL). The mixture is stirred for 0.5 hours at 15° C. Di-tert-butyl dicarbonate (15.4 g, 70.6 mmol) is added to a second vessel, along with MeOH (92 mL). The di-tert-butyl dicarbonate solution is added to the 2-[(2S)-piperazin-2-yl] ethanol solution over 0.5 hours, keeping the temperature below 15° C. The mixture is stirred for 2 hours at 15° C. Phosphoric acid (85% strength, 8.11 g, 70.4 mmol) and EtOH are combined in a separate vessel, and the phosphoric acid solution is added to the reaction mixture over 30 minutes. The mixture is stirred for 20 minutes at 15° C., then cooled to −5° C. over 3 hours. The mixture is stirred at −5° C. for 1 hour, filtered and washed with EtOH, then dried at 50° C. for 4 hours to give the title compound as a solid (5.82 g, 25%). $^1$H NMR (D$_2$O) δ 4.11-4.03 (m, 1H), 4.00 (br s, 1H), 3.75-3.62 (m, 2H), 3.43-3.30 (m, 2H), 3.30-3.18 (m, 1H), 3.17-2.95 (m, 2H), 1.86-1.78 (m, 2H), 1.38 (s, 9H).

Preparation 52

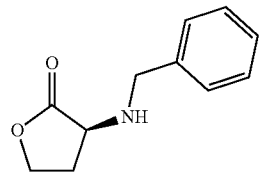

(3S)-3-(Benzylamino)tetrahydrofuran-2-one

A suspension L-homoserine lactone hydrochloride (100 g, 726.93 mmol, 4 Å powdered molecular sieves (178 g), and benzaldehyde (57 mL, 561.3 mmol) in DCM (2500 mL) is stirred overnight under nitrogen at 35° C. After this time, the heating is removed and the mixture is cooled to 20° C. Sodium triacetoxyborohydride (208 g, 981.41 mmol) is added to the mixture which is then allowed to warm to ambient temperature after 20 minutes and stirred for 2 hours. After this time, the mixture is cooled to −10° C. and carefully quenched with saturated aqueous sodium bicarbonate solution (400 mL). The pH is adjusted to 8 with saturated aqueous sodium bicarbonate solution and solid sodium bicarbonate. The mixture is filtered through a pad of diatomaceous earth and rinsed through with DCM. The layers are separated and the aqueous is extracted an additional time with DCM (1 L). The combined organics are dried over sodium sulfate, filtered, and concentrated in vacuo to give the title compound as a clear oil (87 g, 66.5%, 81 mass %). ES/MS m/z: 192.2 (M+H). For further analytical work, a sample of the title compound (1 g) is purified by silica gel flash chromatography eluting with 10-50% EtOAc/DCM to give 422 mg of purified title compound. This material is analyzed using Chiralpak® IC, 4.6×150 mm, 10% IPA (0.2% IPAm)/CO$_2$, 5 mL/min, 225 nm showing >98% e.e.

Preparation 53

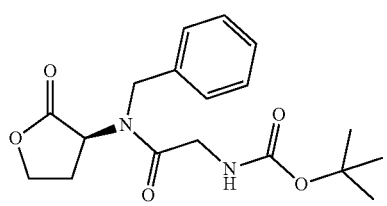

tert-Butyl N-[2-[benzyl-[(3S)-2-oxotetrahydrofuran-3-yl]amino]-2-oxo-ethyl]carbamate A mixture of (3S)-3-(benzylamino)tetrahydrofuran-2-one (86 g, 364.27 mmol, 81 mass %), boc-Gly-OH (97 g, 553.71 mmol), and TEA (103 mL, 739 mmol) in DCM (700 mL) is cooled to −5° C. Propylphosphonic anhydride (50 mass % in EtOAc) (430 mL, 737 mmol) is added dropwise over one hour to the mixture while keeping the internal temperature ~10° C. Upon addition, the mixture is allowed to warm to ambient temperature. After seven hours, the mixture is cooled to 10° C. and additional boc-Gly-OH (3.1 g, 18 mmol), TEA (5 mL, 35.9 mmol), and propylphosphonic anhydride (50 mass % in EtOAc) (22 mL, 37.7 mmol) are added. The mixture is warmed to ambient temperature and stirred overnight. After this time, the mixture is cooled to 8° C. and additional boc-Gly-OH (9.6 g, 55 mmol), TEA (10 mL, 71.7 mmol), and propylphosphonic anhydride (50 mass % in EtOAc) (42 mL, 71.9 mmol) are added. The mixture is warmed to ambient temperature and stirred for ~7 hours. After this time, the mixture is poured over ice and quenched carefully with saturated aqueous sodium bicarbonate solution (1 L). The pH is adjusted to 8 with solid sodium bicarbonate and the layers are separated. The aqueous is extracted twice more with DCM. The combined organics are washed with saturated aqueous sodium chloride solution (500 mL). The organic layer is filtered through a pad of diatomaceous earth and sodium sulfate. The organics are concentrated in vacuo to a volume of 1 L and washed twice with saturated aqueous sodium chloride solution. The organics are dried over magnesium sulfate, filtered, and concentrated in vacuo to give the title compound to be used without further purification (194 g, 53.5%, 35 mass %). ES/MS m/z: 249.0 (M−t-Bu+H)

TABLE 6

Compounds synthesized in a manner essentially analogous to that of Preparation 53

| Preparation | Structure | Compound Name | ES/MS m/z (M + H) |
|---|---|---|---|
| 54 | 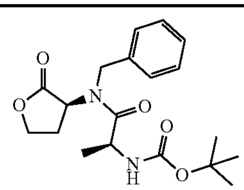 | tert-Butyl N-[(1S)-2-[benzyl-[(3S)-2-oxotetrahydrofuran-3-yl]amino]-1-methyl-2-oxo-ethyl]carbamate | 263.0 |
| 55 | 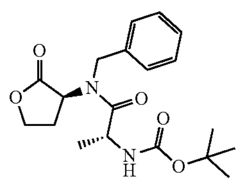 [SMILES: C[C@@H](NC(=O)OC(C)(C)C)C(=O)N(Cc1ccccc1)[C@H]1CCOC1=O] | tert-Butyl N-[(1R)-2-[benzyl-[(3S)-2-oxotetrahydrofuran-3-yl]amino]-1-methyl-2-oxo-ethyl]carbamate | 263.0 |

Preparation 56

(6S)-1-Benzyl-6-(2-hydroxyethyl)piperazine-2,5-dione

TFA (100 mL, 1310 mmol) is added to a mixture of tert-butyl N-[2-[benzyl-[(3S)-2-oxotetrahydrofuran-3-yl]amino]-2-oxo-ethyl]carbamate (194 g, 194.9 mmol, 35 mass %) in DCM (500 mL). The mixture is stirred at ambient temperature overnight. After this time, additional TFA (50 mL, 653 mmol) is added and the mixture is stirred at ambient temperature. After two hours, additional TFA (50 mL, 653 mmol) is added and the mixture is stirred at ambient temperature overnight. After this time, the mixture is concentrated in vacuo. The resulting residue is diluted with water (600 mL) and washed twice with diethyl ether. The pH is adjusted to 7 with 1N aqueous NaOH solution and further adjusted to pH 12 with 5N aqueous NaOH solution. MeOH mL) is added and the mixture is stirred at ambient temperature. Additional 5N aqueous NaOH solution is added to the mixture at five minute intervals to readjust the pH to 12. Overall, the mixture is stirred at pH 12 for 35 minutes. After this time, the pH is adjusted to 8 with 10% aqueous HCl solution and extracted with DCM (5×1 L). The aqueous pH is then adjusted to 5 with 10% aqueous HCl solution and again extracted with DCM (1 L). The combined organics are dried over sodium sulfate, filtered, and concentrated in vacuo to give the title compound as a light tan solid (17 g, 33.4%). Additional extractions of the aqueous are performed with alternating 25% WA/chloroform and DCM until the title product is removed from the aqueous according to LC/MS. To the combined organics is added WA (150 mL). The organics are washed with saturated aqueous sodium chloride solution twice, dried over sodium sulfate and magnesium sulfate, filtered, and concentrated in vacuo to give additional title compound (17.2 g, 35.5%) for an overall yield of 34.2 g (68.9%). ES/MS m/z: 249.0 (M+H)

TABLE 7

Compounds synthesized in a manner essentially analogous to that of Preparation 56

| Preparation | Structure | Compound Name | ES/MS m/z (M + H) |
|---|---|---|---|
| 57 | 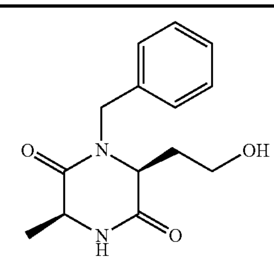 | (3S,6S)-1-benzyl-6-(2-hydroxyethyl)-3-methyl-piperazine-2,5-dione | 263.0 |
| 58 | 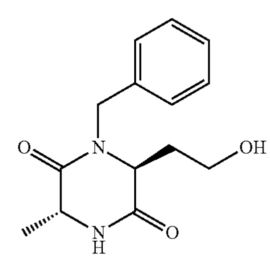 [SMILES: C[C@H]1NC(=O)[C@H](CCO)N(Cc2ccccc2)C1=O] | (3R,6S)-1-benzyl-6-(2-hydroxyethyl)-3-methyl-piperazine-2,5-dione | 263.0 |

Preparation 59

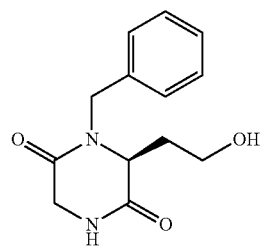

2-[(2S)-1-Benzylpiperazin-2-yl]ethanol

To a 45° C. solution of 2M lithium aluminum hydride in THF (131 mL, 262 mmol) is added a solution of (6S)-1-benzyl-6-(2-hydroxyethyl)piperazine-2,5-dione (34 g, 131.5 mmol) in THF (200 mL) in a dropwise fashion. After addition, the mixture is heated to 60° C. After ~3.5 hours, additional 2M lithium aluminum hydride in THF (33 mL, 66 mmol) is added and the mixture is stirred at 60° C. After an hour, additional 2M lithium aluminum hydride in THF (131 mL, 262 mmol) is added and the mixture is stirred at 60° C. overnight. After this time, 2M lithium aluminum hydride in THF (6 mL, 12 mmol) is added and the mixture is stirred at 60° C. After four hours, 2M lithium aluminum hydride in THF (6 mL, 12 mmol) is added and the mixture is stirred for two hours at 60° C. The heat is removed and the mixture is cooled to 10° C. Water (16 mL) is added dropwise, followed by dropwise addition of 3.75M aqueous NaOH (16 mL) then THF (300 mL). Water (48 mL) is added and the resulting mixture is stirred overnight at ambient temperature. After this time, the mixture is filtered through a pad of diatomaceous earth and rinsed through with EtOAc. The filtrate is concentrated in vacuo to give the title compound (28.8 g, 67.6%, 68 mass %). ES/MS m/z: 221.0 (M+H)

TABLE 8

Compounds synthesized in a manner essentially analogous to that of Preparation 59

| Preparation | Structure | Compound Name | ES/MS m/z (M + H) |
| --- | --- | --- | --- |
| 60 | ![structure] | 2-[(2S,5S)-1-Benzyl-5-methyl-piperazin-2-yl]ethanol | 235.0 |
| 61 | ![structure] | 2-[(2S,5R)-1-Benzyl-5-methyl-piperazin-2-yl]ethanol | 235.0 |

Preparation 62

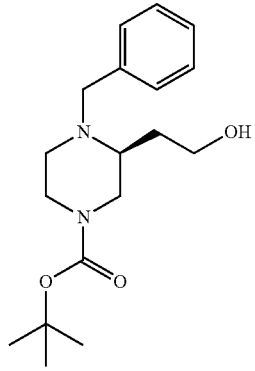

tert-Butyl (3S)-4-benzyl-3-(2-hydroxyethyl)piperazine-1-carboxylate

Sodium bicarbonate (80 g, 952 mmol) in water (500 mL) is added to 2-[(2S)-1-benzylpiperazin-2-yl]ethanol (28 g, 86.43 mmol) in 1,4-dioxane (500 mL) at ambient temperature. Di-tert-butyl dicarbonate (26.6 g, 122 mmol) is added and the mixture is stirred at ambient temperature for 20 minutes. After this time, ice (400 mL), water (200 mL), and EtOAc (1 L) are added and the layers separated. The aqueous is extracted once more with EtOAc (1 L). The combined organics are washed with water (250 mL) and saturated aqueous sodium chloride solution (250 mL), dried over sodium sulfate, filtered, and concentrated in vacuo. The resulting oil is purified by silica gel flash chromatography eluting with 10-70% EtOAc/hexanes to give the title compound (20.79 g, 74%). ES/MS m/z: 321.2 (M+H) This material is analyzed using Chiralpak® IC, 4.6×150 mm, 15% IPA (0.2% IPAm)/CO₂, 5 mL/min, 225 nm showing 96% e.e.

TABLE 9

Compounds synthesized in a manner essentially analogous to that of Preparation 62

| Preparation | Structure | Compound Name | ES/MS m/z (M + H) |
| --- | --- | --- | --- |
| 63 | ![structure] | tert-Butyl (2S,5S)-4-benzyl-5-(2-hydroxyethyl)-2-methyl-piperazine-1-carboxylate | 335.0 |

TABLE 9-continued

Compounds synthesized in a manner essentially analogous to that of Preparation 62

| Preparation | Structure | Compound Name | ES/MS m/z (M + H) |
|---|---|---|---|
| 64 | 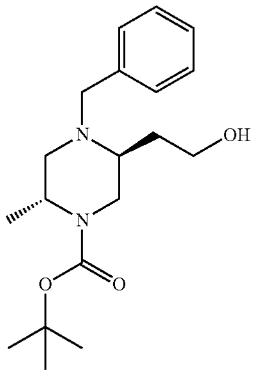 [SMILES: C[C@@H]1CN(Cc2ccccc2)[C@@H](CCO)CN1C(=O)OC(C)(C)C] | tert-Butyl (2R,5S)-4-benzyl-5-(2-hydroxyethyl)-2-methyl-piperazine-1-carboxylate | 335.0 |

TABLE 10

Compounds synthesized in a manner essentially analogous to that of Preparation 65

| Preparation | Structure | Compound Name | ES/MS m/z (M + H) |
|---|---|---|---|
| 66 | 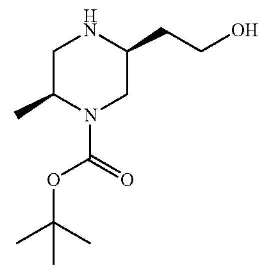 [SMILES: C[C@H]1CN[C@@H](CCO)CN1C(=O)OC(C)(C)C] | tert-Butyl (2S,5S)-5-(2-hydroxyethyl)-2-methyl-piperazine-1-carboxylate | 245.0 |
| 67 | 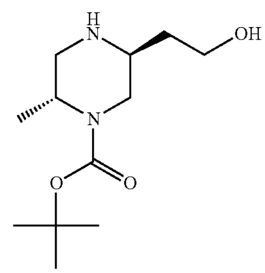 [SMILES: C[C@@H]1CN[C@@H](CCO)CN1C(=O)OC(C)(C)C] | tert-Butyl (2R,5S)-5-(2-hydroxyethyl)-2-methyl-piperazine-1-carboxylate | 245.0 |

Preparation 65

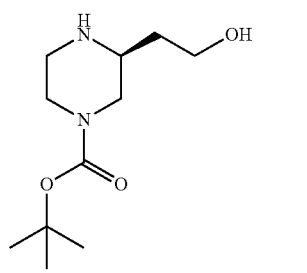

tert-Butyl (3S)-3-(2-hydroxyethyl)piperazine-1-carboxylate

20% Pd(OH)$_2$ on carbon (24.39 g, 176.4 mmol) is added to a vessel which is purged with nitrogen. EtOH (620 mL) is added to the vessel followed by tert-butyl (3S)-4-benzyl-3-(2-hydroxyethyl)piperazine-1-carboxylate (61.93 g, 193.3 mmol) and EtOH (620 mL). The vessel is sealed, purged with nitrogen, purged with hydrogen, and pressurized under hydrogen (60 psi). The vessel is placed on a Parr shaker for 15 hours at ambient temperature. After this time, the reaction mixture is filtered and concentrated in vacuo to give the title compound (42.74 g, 98%). ES/MS m/z 231.0: (M+H).

Preparation 68

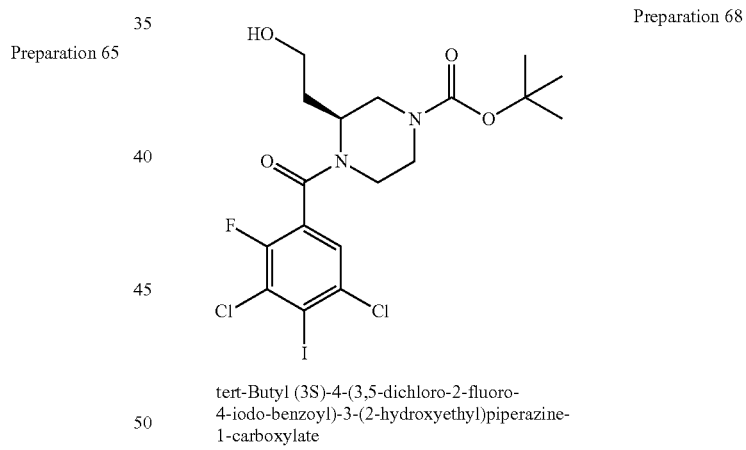

tert-Butyl (3S)-4-(3,5-dichloro-2-fluoro-4-iodo-benzoyl)-3-(2-hydroxyethyl)piperazine-1-carboxylate 3,5-Dichloro-2-fluoro-4-iodo-benzoic acid (0.80 g, 2.4 mmol) is added to DIEA (2 mL, 11.5 mmol) in THF (22 mL) followed by HATU (0.84 g, 2.2 mmol) and stirred for 1 hour. tert-Butyl (3S)-3-(2-hydroxyethyl)piperazine-1-carboxylate (0.50 g, 2.2 mmol) is then added and the reaction mixture is refluxed overnight. After this time, 5N NaOH is added and the reaction is stirred for 1 hour. EtOAc and water are added. The aqueous layer is extracted two times with EtOAc. The combined organic extracts are dried over anhydrous magnesium sulfate, filtered, and concentrated in vacuo. The crude mixture is purified by silica gel flash chromatography eluting with EtOAc: hexane (30:70) to give the title compound (0.858 g, 72%). ES/MS m/z ($^{35}$Cl/$^{37}$Cl) 491/493 [M−t-Bu+H]$^+$.

TABLE 11

Compounds synthesized in a manner essentially analogous to that of Preparation 68.

| Preparation | Structure | Compound Name | ES/MS m/z (M + H) |
|---|---|---|---|
| 69 | 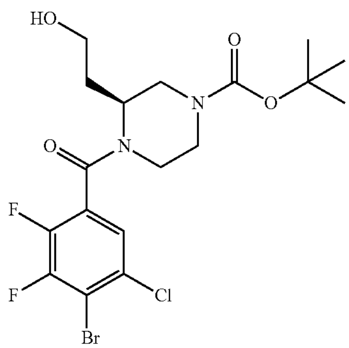 [SMILES: CC(C)(C)OC(=O)N1CCN(C(=O)c2cc(Cl)c(Br)c(F)c2F)[C@@H](CCO)C1] | tert-Butyl (3S)-4-(4-bromo-5-chloro-2,3-difluoro-benzoyl)-3-(2-hydroxyethyl)piperazine-1-carboxylate | 427.0/429.0 |
| 70 | 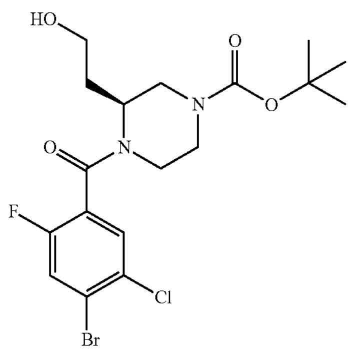 [SMILES: CC(C)(C)OC(=O)N1CCN(C(=O)c2cc(Cl)c(Br)cc2F)[C@@H](CCO)C1] | tert-Butyl (3S)-4-(4-bromo-5-chloro-2-fluoro-benzoyl)-3-(2-hydroxyethyl)piperazine-1-carboxylate | 408.8/410.8 |
| 71 | 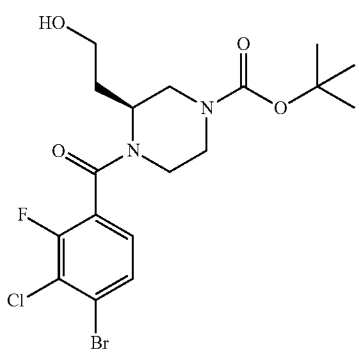 [SMILES: CC(C)(C)OC(=O)N1CCN(C(=O)c2ccc(Br)c(Cl)c2F)[C@@H](CCO)C1] | tert-Butyl (3S)-4-(4-bromo-3-chloro-2-fluoro-benzoyl)-3-(2-hydroxyethyl)piperazine-1-carboxylate | 408.9/411.0 |
| 72 | 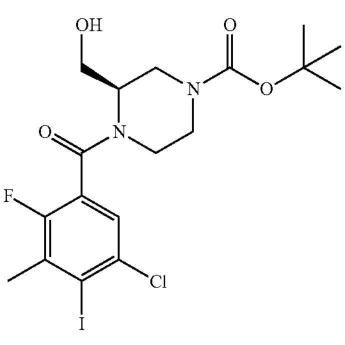 [SMILES: Cc1c(F)c(C(=O)N2CCN(C(=O)OC(C)(C)C)C[C@@H]2CO)cc(Cl)c1I] | tert-Butyl (3R)-4-(5-3chloro-2-fluoro-4-iodo-5-methyl-benzoyl)-3-(hydroxymethyl)piperazine-1-carboxylate | 457.0/459.2 |

TABLE 11-continued

Compounds synthesized in a manner essentially analogous to that of Preparation 68.

| Preparation | Structure | Compound Name | ES/MS m/z (M + H) |
|---|---|---|---|
| 73 | 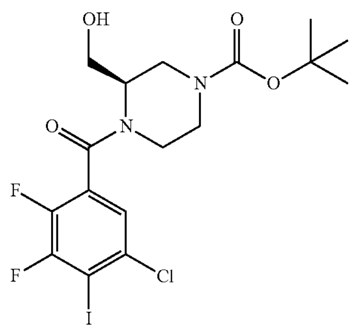 [SMILES: CC(C)(C)OC(=O)N1CCN(C(=O)c2cc(Cl)c(I)c(F)c2F)[C@@H](CO)C1] | tert-Butyl (3R)-4-(5-chloro-2,3-difluoro-4-iodo-benzoyl)-3-(hydroxymethyl)piperazine-1-carboxylate | 461.0/463.0 |
| 74 | 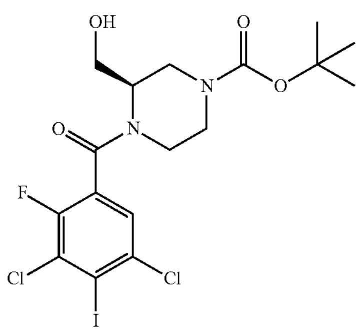 [SMILES: CC(C)(C)OC(=O)N1CCN(C(=O)c2cc(Cl)c(I)c(Cl)c2F)[C@@H](CO)C1] | tert-Butyl (3R)-4-(3,5-dichloro-2-fluoro-4-iodo-benzoyl)-3-(hydroxymethyl)piperazine-1-carboxylate | 476.8/478.8 |
| 75 | 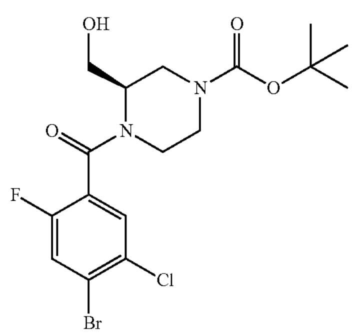 [SMILES: CC(C)(C)OC(=O)N1CCN(C(=O)c2cc(Cl)c(Br)cc2F)[C@@H](CO)C1] | tert-Butyl (3R)-4-(4-bromo-5-chloro-2-fluoro-benzoyl)-3-(hydroxymethyl)piperazine-1-carboxylate | 394.8/396.8 |
| 76 | 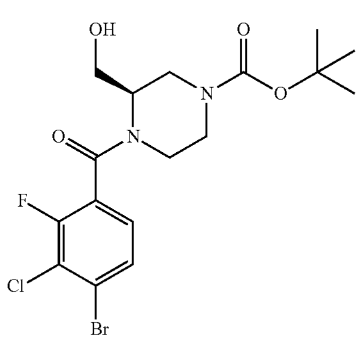 [SMILES: CC(C)(C)OC(=O)N1CCN(C(=O)c2ccc(Br)c(Cl)c2F)[C@@H](CO)C1] | tert-Butyl (3R)-4-(4-bromo-3-chloro-2-fluoro-benzoyl)-3-(hydroxymethyl)piperazine-1-carboxylate | 394.8/396.8 |

TABLE 11-continued

Compounds synthesized in a manner essentially analogous to that of Preparation 68.

| Preparation | Structure | Compound Name | ES/MS m/z (M + H) |
|---|---|---|---|
| 77 | 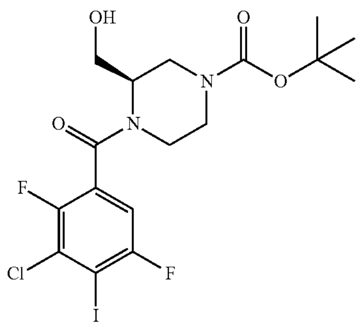 [SMILES: CC(C)(C)OC(=O)N1CCN(C(=O)c2cc(F)c(I)c(Cl)c2F)[C@@H](CO)C1] | tert-Butyl (3R)-4-(3-chloro-2,5-difluoro-4-iodo-benzoyl)-3-(hydroxymethyl)piperazine-1-carboxylate | 461.0/463.0 |
| 78 | 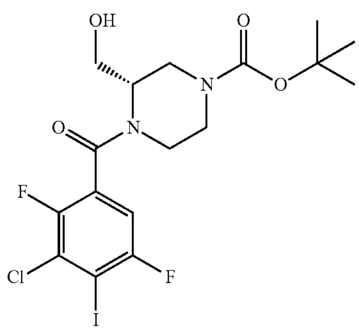 [SMILES: CC(C)(C)OC(=O)N1CCN(C(=O)c2cc(F)c(I)c(Cl)c2F)[C@H](CO)C1] | tert-Butyl (3S)-4-(3-chloro-2,5-difluoro-4-iodo-benzoyl)-3-(hydroxymethyl)piperazine-1-carboxylate | 461.2/463.0 |
| 79 | 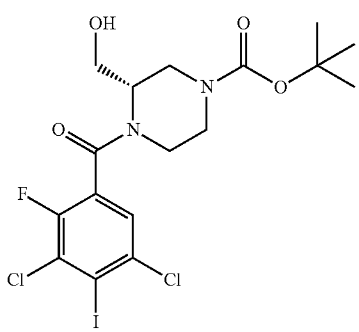 [SMILES: CC(C)(C)OC(=O)N1CCN(C(=O)c2cc(Cl)c(I)c(Cl)c2F)[C@H](CO)C1] | tert-butyl (3S)-4-(3,5-dichloro-2-fluoro-4-iodo-benzoyl)-3-(hydroxymethyl)piperazine-1-carboxylate | 477.0/478.9 |
| 80 | 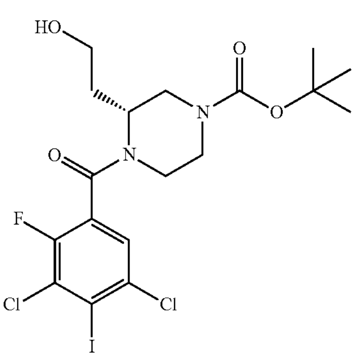 [SMILES: CC(C)(C)OC(=O)N1CCN(C(=O)c2cc(Cl)c(I)c(Cl)c2F)[C@H](CCO)C1] | tert-butyl (3R)-4-(3,5-dichloro-2-fluoro-4-iodo-benzoyl)-3-(2-hydroxyethyl)piperazine-1-carboxylate | 490.9/492.8 |

TABLE 11-continued

Compounds synthesized in a manner essentially analogous to that of Preparation 68.

| Preparation | Structure | Compound Name | ES/MS m/z (M + H) |
|---|---|---|---|
| 81 | 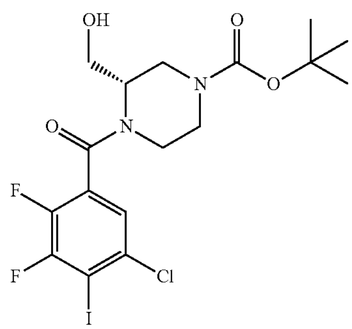 [SMILES: CC(C)(C)OC(=O)N1CCN(C(=O)c2cc(Cl)c(I)c(F)c2F)[C@H](CO)C1] | tert-butyl (3S)-4-(5-chloro-2,3-difluoro-4-iodo-benzoyl)-3-(hydroxymethyl)piperazine-1-carboxylate | 461.0/463.0 |
| 82 | 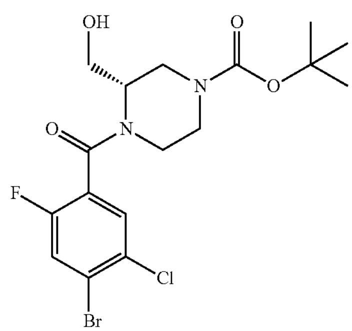 [SMILES: CC(C)(C)OC(=O)N1CCN(C(=O)c2cc(Cl)c(Br)cc2F)[C@H](CO)C1] | tert-butyl (3S)-4-(4-bromo-5-chloro-2-fluoro-benzoyl)-3-(hydroxymethyl)piperazine-1-carboxylate | 394.8/396.8 |
| 83 | 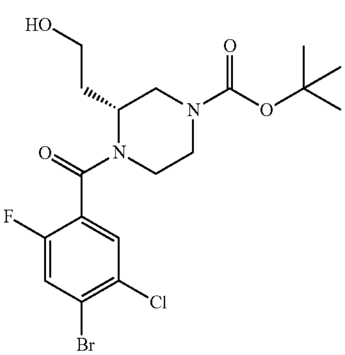 [SMILES: CC(C)(C)OC(=O)N1CCN(C(=O)c2cc(Cl)c(Br)cc2F)[C@H](CCO)C1] | tert-butyl (3R)-4-(4-bromo-5-chloro-2-fluoro-benzoyl)-3-(2-hydroxyethyl)piperazine-1-carboxylate | 408.8/410.8 |
| 84 | 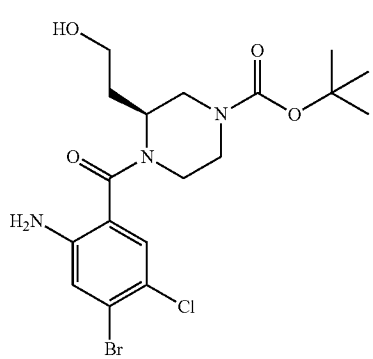 [SMILES: CC(C)(C)OC(=O)N1CCN(C(=O)c2cc(Cl)c(Br)cc2N)[C@@H](CCO)C1] | tert-Butyl (3S)-4-(2-amino-4-bromo-5-chloro-benzoyl)-3-(2-hydroxyethyl)piperazine-1-carboxylate | 406.0/408.0 |

Preparation 85

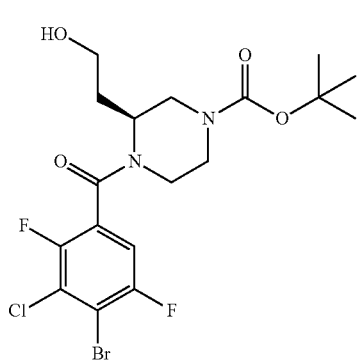

tert-Butyl (3S)-4-(4-bromo-3-chloro-2,5-
difluoro-benzoyl)-3-(2-hydroxyethyl)piperazine-
1-carboxylate A solution of 4-bromo-3-chloro-2,5-difluoro-benzoic acid (10.2 g, 37.6 mmol) and 4-methylmorpholine (7.50 mL, 68.0 mmol) in THF (200 mL) is cooled to 0° C. in an ice bath and treated with 2-chloro-4,6-dimethoxy-1,3,5-triazine (9.10 g, 50.8 mmol). The mixture is stirred in ice bath for 30 minutes, and then tert-butyl (3S)-3-(2-hydroxyethyl)piperazine-1-carboxylate (0.93M in THF, 40.0 mL, 37.2 mmol) is added dropwise via a dropping funnel. After 1 hour at 0° C., 5N NaOH (35.0 mL, 180 mmol) is added and the mixture is stirred at ambient temperature for 30 minutes. The mixture is diluted with EtOAc, treated with saturated sodium bicarbonate solution, and stirred for 15 minutes. The organic phase is separated, washed with saturated aqueous sodium chloride solution, dried over magnesium sulfate, filtered, and concentrated in vacuo. The residue is purified by silica gel flash column chromatography, eluting with 0-90% (20% acetone in DCM)/hexane to give the title compound (16.0 g, 88%). ES/MS m/z ($^{79}$Br/$^{81}$Br) 427/429 [M−t-Bu+H]$^+$.

Preparation 87

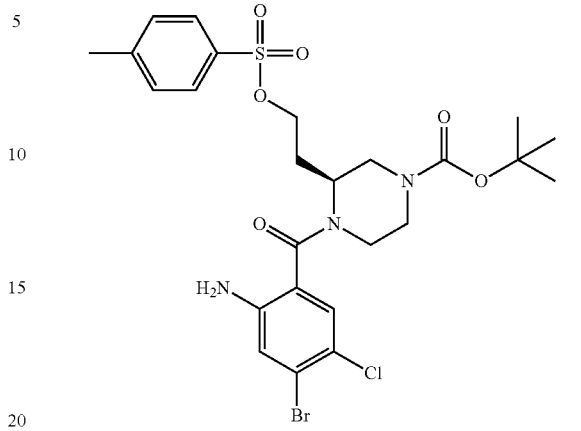

tert-Butyl (3S)-4-(2-amino-4-bromo-5-chloro-benzoyl)-3-[2-(p-
tolylsulfonyloxy)ethyl]piperazine-1-carboxylate To a 0° C. solution of tert-butyl (3S)-4-(2-amino-4-bromo-5-chloro-benzoyl)-3-(2-hydroxyethyl)piperazine-1-carboxylate (1 g, 2.16 mmol) and TEA (1 mL, 7.14 mmol) in DCM (25 mL) is added DMAP (45 mg, 0.36 mmol) and p-toluenesulfonyl chloride (469 mg, 2.39 mmol). The reaction mixture is stirred at 0° C. for 15 minutes before allowing to warm to ambient temperature. Additional p-toluenesulfonyl chloride (122 mg, 0.62 mmol) is added after 3 hours. After 1 hour, the reaction is diluted with DCM and washed with saturated aqueous sodium bicarbonate solution. The organics are washed with saturated aqueous sodium chloride, dried over sodium sulfate, and concentrated in vacuo. The resulting residue is purified by silica gel flash chromatography to give the title compound (473 mg, 35%). ES/MS m/z ($^{79}$Br/$^{81}$Br) 616.0/618.0 [M+H]$^+$

TABLE 12

Compound synthesized in a manner essentially analogous to that of Preparation 85

| Preparation | Structure | Compound Name | ES/MS m/z (M + H) |
|---|---|---|---|
| 86 | 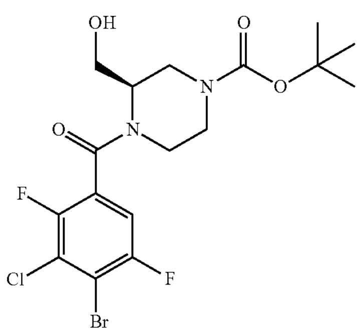 [SMILES: CC(C)(C)OC(=O)N1CCN(C(=O)c2cc(F)c(Br)c(Cl)c2F)[C@@H](CO)C1] | tert-Butyl (3R)-4-(4-bromo-3-chioro-2,5-difluoro-benzoyl)-3-(hydroxymethyl)piperazine-1-carboxylate | 412.8/414.8 |

Preparation 88

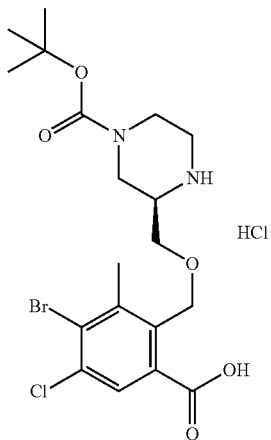

4-Bromo-2-[[(2R)-4-tert-butoxycarbonylpiperazin-2-yl]methoxymethyl]-5-chloro-3-methyl-benzoic acid hydrochloride To sodium 4-bromo-5-chloro-2-(hydroxymethyl)-3-methyl-benzoate (2.05 g, 6.39 mmol) in a 250 mL flask is added toluene (50 mL) and the mixture is concentrated in vacuo. The residue is dissolved in DMF (21 mL) and THF (11 mL) and cooled to 0° C. Sodium hydride (60 mass % in paraffin oil) (511 mg, 12.8 mmol) is added. After addition, the mixture is stirred at 0° C. for 10 minutes. To tert-butyl (3aR)-1,1-dioxo-3a,4,6,7-tetrahydro-3H-oxathiazolo[3,4-a]pyrazine-5-carboxylate (1.96 g, 7.04 mmol) in a second flask is added toluene (20 mL) and the mixture is concentrated in vacuo. The residue is dissolved in THF (11 mL) and added dropwise to the contents of the first flask at 0° C. The mixture is warmed to ambient temperature and stirred for 1.5 hours. 5M HCl (7 mL) is added slowly and the mixture is stirred at ambient temperature for 5 minutes and then quenched with saturated aqueous sodium bicarbonate. The pH is lowered to pH 2 by the slow addition of 5M HCl, and the mixture is diluted with EtOAc. The layers are separated, and the aqueous layer is extracted three times with EtOAc. The combined organic layers are dried over sodium sulfate, filtered, and concentrated in vacuo. The residue is dissolved in THF (40 mL) and 5M HCl (6 mL) is added. The mixture is stirred at ambient temperature for 20 minutes. The mixture is diluted with saturated aqueous sodium chloride and EtOAc and the layers are separated. The organic layer is dried over sodium sulfate, filtered, and concentrated in vacuo, and placed under vacuum for 2 hours to give the title compound as a tan solid (4.27 g, 73%). ES/MS m/z ($^{79}$Br/$^{81}$Br) 477.2/479.2 [M+H]$^+$.

TABLE 13

Compounds synthesized in a manner essentially analogous to that of Preparation 88

| Preparation | Structure | Compound Name | ES/MS m/z (M + H) |
|---|---|---|---|
| 89 | 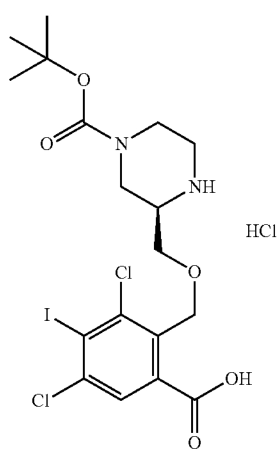 [SMILES: CC(C)(C)OC(=O)N1CCN[C@@H](COCc2c(C(=O)O)cc(Cl)c(I)c2Cl)C1 ; Cl] | 2-[[(2R)-4-tert-Butoxycarbonylpiperazin-2-yl]methoxymethyl]-3,5-dichloro-4-iodo-benzoic acid hydrochloride | 545.2/547.2 |

TABLE 13-continued

Compounds synthesized in a manner essentially analogous to that of Preparation 88

| Preparation | Structure | Compound Name | ES/MS m/z (M + H) |
|---|---|---|---|
| 90 | 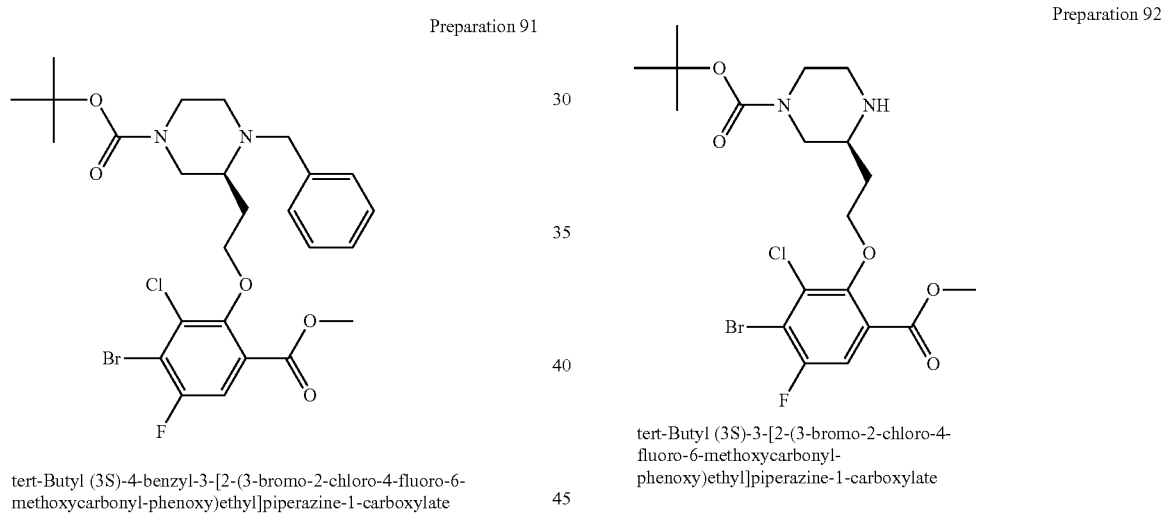 | 2-[[(2S)-4-tert-Butoxycarbonylpiperazin-2-yl]methoxymethyl]-3,5-dichloro-4-iodo-benzoic acid hydrochloride | 545.0/547.2 |

Preparation 91 tert-Butyl (3S)-4-benzyl-3-[2-(3-bromo-2-chloro-4-fluoro-6-methoxycarbonyl-phenoxy)ethyl]piperazine-1-carboxylate Preparation 92 tert-Butyl (3S)-3-[2-(3-bromo-2-chloro-4-fluoro-6-methoxycarbonyl-phenoxy)ethyl]piperazine-1-carboxylate A solution of methyl 4-bromo-3-chloro-5-fluoro-2-hydroxy-benzoate (3.0 g, 11.0 mmol), triphenyl phosphine (4.19 g, 16.0 mmol), and tert-butyl (3 S)-4-benzyl-3-(2-hydroxyethyl)piperazine-1-carboxylate (12 mL, 1.039M in THF) in THF (~50 mL) is cooled to 0° C. for 10 minutes. Diisopropyl azodicarboxylate (3.1 mL, 16 mmol) is added dropwise and the mixture is allowed to warm to ambient temperature. After the alcohol starting material is consumed, ice is added, and the reaction is diluted with EtOAc. The mixture is washed twice with saturated aqueous sodium chloride solution and the organic layer is dried over sodium sulfate, filtered, and concentrated in vacuo to an amber colored oil. The residue is purified by silica gel column chromatography, eluting with 0-10% EtOAc/hexanes to give the title compound (6.2 g, 99+%). An analytical sample ~95% purity is obtained by silica gel column chromatography, eluting with 25-50% (1:1 EtOAc:DCM)/hexanes to give the title compound as a colorless oil. ES/MS m/z ($^{79}$Br/$^{81}$Br) 585/587 [M+H]$^+$.

To a solution of tert-butyl (3S)-4-benzyl-3-[2-(3-bromo-2-chloro-4-fluoro-6-methoxycarbonyl-phenoxy)ethyl]piperazine-1-carboxylate (7.0 g, 11.35 mmol) in DCM (75 mL) is added N,N-diisopropylamine (5.94 mL, 34.1 mmol). The solution is cooled in an ice bath and 1-chloroethyl chloroformate (3.7 mL, 34 mmol) is added dropwise. After addition, the ice bath is removed, and the reaction is stirred at ambient temperature for 18 hours. Additional 1-chloroethyl chloroformate (2 mL, 17 mmol) and N,N-diisopropylamine (3 mL, 17 mmol) is added dropwise at ambient temperature and after 7 hours, more 1-chloroethyl chloroformate (0.60 mL, 5.67 mmol) and N,N-diisopropylamine (1 mL, 5.67 mmol) are added to consume the remaining starting material. The reaction mixture is concentrated in vacuo. To the residue is added toluene and the mixture is concentrated (repeat 2×). The resulting semisolid is diluted with MeOH (100 mL) and is stirred at ambient temperature until the product formation is completed. The solvent is removed in vacuo to give an amber colored residue. The residue is purified by silica gel column chromatography eluting with 0-10% MeOH/DCM to give the title compound as a solid (5.11 g, 91%). ES/MS m/z ($^{79}$Br/$^{81}$Br) 495/497 [M+H]$^+$.

Preparation 93

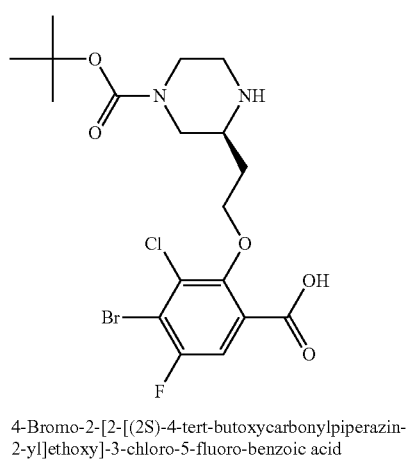

4-Bromo-2-[2-[(2S)-4-tert-butoxycarbonylpiperazin-2-yl]ethoxy]-3-chloro-5-fluoro-benzoic acid Preparation 94

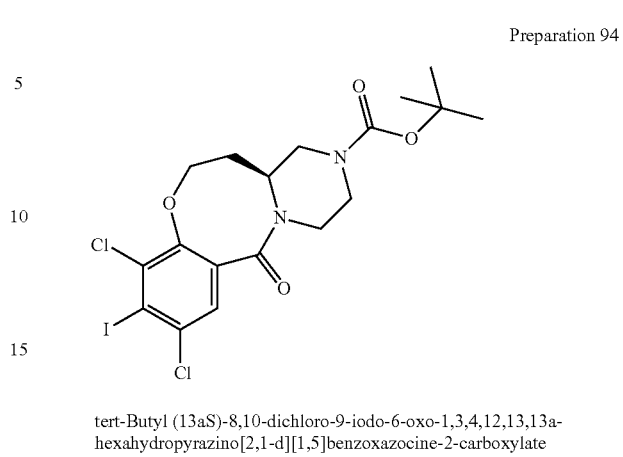

tert-Butyl (13aS)-8,10-dichloro-9-iodo-6-oxo-1,3,4,12,13,13a-hexahydropyrazino[2,1-d][1,5]benzoxazocine-2-carboxylate A solution of tert-butyl (3 S)-3-[2-(3-bromo-2-chloro-4-fluoro-6-methoxycarbonyl-phenoxy)ethyl]piperazine-1-carboxylate (5 g, 10.08 mmol) in THF (100 mL) and MeOH (12 mL) is cooled with an ice bath. An aqueous solution of lithium hydroxide (6.5 mL, 6.25M) and deionized water (10 mL) are added. The ice bath is removed and the mixture is stirred at ambient temperature. After 3 hours, ice is added to the reaction mixture and the pH is adjusted between 5-6 with 10% citric acid (12 mL). Saturated aqueous sodium chloride solution (100 mL) is added and the mixture is diluted with EtOAc (400 mL) and the layers are separated. The aqueous layer is extracted again with EtOAc (300 mL) and the combined organics are dried over sodium sulfate, filtered, and concentrated in vacuo to give the title compound as a solid (4.83 g, 98%). ES/MS m/z ($^{79}$Br/$^{81}$Br) 481/483 [M+H]$^+$.

tert-Butyl (3S)-4-(3,5-dichloro-2-fluoro-4-iodo-benzoyl)-3-(2-hydroxyethyl)piperazine-1-carboxylate (4.438 g, 8.110 mmol) in DMF (100 mL) is cooled to 0° C. and then to the solution is added solid sodium hydride (60 mass % in paraffin oil) (0.81 g, 20 mmol). After 1 hour at 0° C., the reaction mixture is quenched with saturated aqueous sodium bicarbonate solution. Water and EtOAc are added. The aqueous layer is extracted two times with EtOAc. The combined organic extracts are washed twice with 0.2 M aqueous lithium chloride, dried over anhydrous magnesium sulfate, filtered, and concentrated in vacuo. The crude mixture is purified by silica gel flash chromatography eluting with 30-50% EtOAc/hexane to give the title compound (3.394 g, 79%). ES/MS m/z ($^{35}$Cl/$^{37}$Cl) 471/473 [M−t-Bu+H]$^+$.

TABLE 14

Compounds synthesized in a manner essentially analogous to that of Preparation 94

| Preparation | Structure | Compound Name | ES/MS m/z (M + H) |
|---|---|---|---|
| 95 | 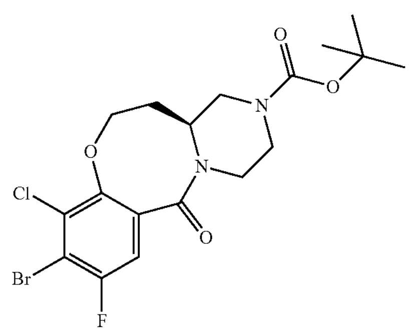 [SMILES: CC(C)(C)OC(=O)N1CCN2C(=O)c3cc(F)c(Br)c(Cl)c3OCC[C@H]2C1] | tert-Butyl (13aS)-9-bromo-10-chloro-8-fluoro-6-oxo-1,3,4,12,13,13a-hexahydropyrazino[2,1-d][1,5]benzoxazocine-2-carboxylate | 407.0/409.0 |

TABLE 14-continued

Compounds synthesized in a manner essentially analogous to that of Preparation 94

| Preparation | Structure | Compound Name | ES/MS m/z (M + H) |
|---|---|---|---|
| 96 | 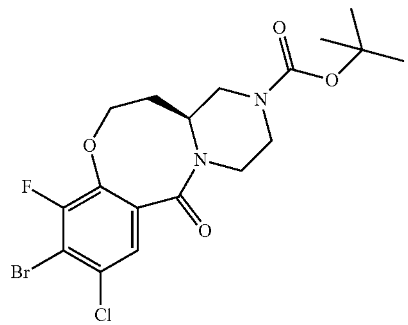 [SMILES: CC(C)(C)OC(=O)N1CCN2C(=O)c3cc(Cl)c(Br)c(F)c3OCC[C@H]2C1] | tert-Butyl (13aS)-9-bromo-8-chloro-10-fluoro-6-oxo-1,3,4,12,13,13a-hexahydropyrazino[2,1-d][1,5]benzoxazocine-2-carboxylate | 406.9/409.0 |
| 97 | 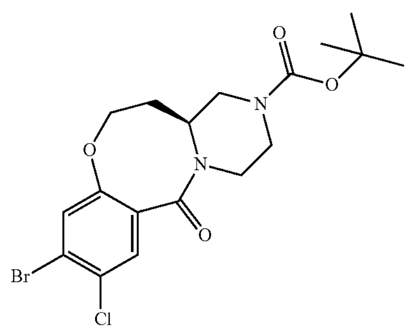 [SMILES: CC(C)(C)OC(=O)N1CCN2C(=O)c3cc(Cl)c(Br)cc3OCC[C@H]2C1] | tert-Butyl (13aS)-9-bromo-8-chloro-6-oxo-1,3,4,12,13,13a-hexahydropyrazino[2,1-d][1,5]benzoxazocine-2-carboxylate | 388.8/390.8 |
| 98 | 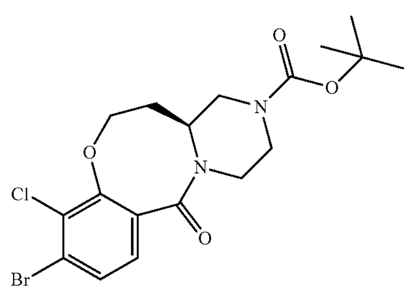 [SMILES: CC(C)(C)OC(=O)N1CCN2C(=O)c3ccc(Br)c(Cl)c3OCC[C@H]2C1] | tert-Butyl (13aS)-9-bromo-10-chloro-6-oxo-1,3,4,12,13,13a-hexahydropyrazino[2,1-d][1,5]benzoxazocine-2-carboxylate | 389.0/391.0 |
| 99 | 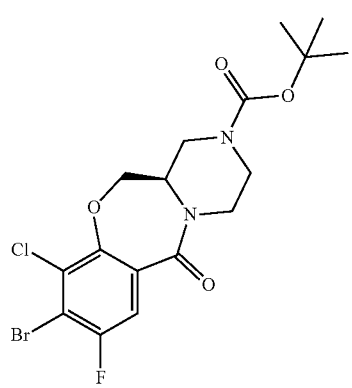 [SMILES: CC(C)(C)OC(=O)N1CCN2C(=O)c3cc(F)c(Br)c(Cl)c3OC[C@H]2C1] | tert-Butyl (4aR)-8-bromo-7-chloro-9-fluoro-11-oxo-2,4,4a,5-tetrahydro-1H-pyrazino[2,1-c][1,4]benzoxazepine-3-carboxylate | 393.0/395.0 |

TABLE 14-continued

Compounds synthesized in a manner essentially analogous to that of Preparation 94

| Preparation | Structure | Compound Name | ES/MS m/z (M + H) |
| --- | --- | --- | --- |
| 100 | 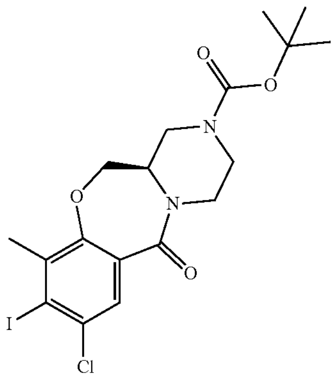 [SMILES: Cc1c(I)c(Cl)cc2c1OC[C@H]1CN(C(=O)OC(C)(C)C)CCN1C2=O] | tert-Butyl (4aR)-7-chloro-8-iodo-7-methyl-11-oxo-2,4,4a,5-tetrahydro-1H-pyrazino[2,1-c][1,4]benzoxazepine-3-carboxylate | 9437.0 |
| 101 | 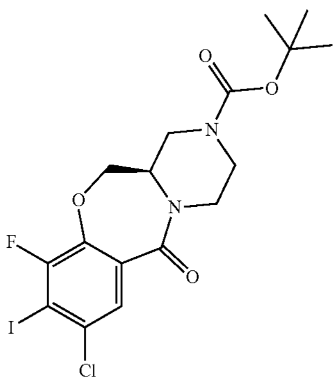 [SMILES: CC(C)(C)OC(=O)N1CCN2C(=O)c3cc(Cl)c(I)c(F)c3OC[C@H]2C1] | tert-Butyl (4aR)-9-chloro-7-fluoro-8-iodo-11-oxo-2,4,4a,5-tetrahydro-1H-pyrazino[2,1-c][1,4]benzoxazepine-3-carboxylate | 441.0/443.0 |
| 102 | 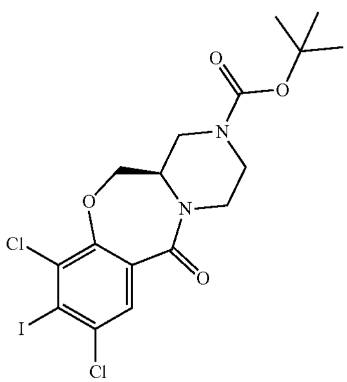 [SMILES: CC(C)(C)OC(=O)N1CCN2C(=O)c3cc(Cl)c(I)c(Cl)c3OC[C@H]2C1] | tert-Butyl (4aR)-7,9-dichloro-8-iodo-11-oxo-2,4,4a,5-tetrahydro-1H-pyrazino[2,1-c][1,4]benzoxazepine-3-carboxylate | 456.8/458.8 |
| 103 | 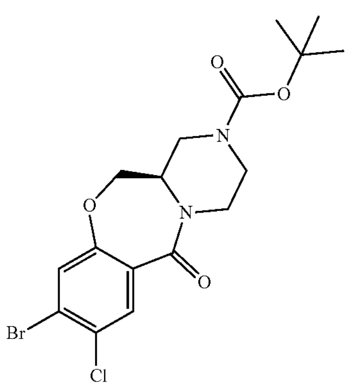 [SMILES: CC(C)(C)OC(=O)N1CCN2C(=O)c3cc(Cl)c(Br)cc3OC[C@H]2C1] | tert-Butyl (4aR)-8-bromo-9-chloro-11-oxo-2,4,4a,5-tetrahydro-1H-pyrazino[2,1-c][1,4]benzoxazepine-3-carboxylate | 374.8/376.8 |

TABLE 14-continued

Compounds synthesized in a manner essentially analogous to that of Preparation 94

| Preparation | Structure | Compound Name | ES/MS m/z (M + H) |
|---|---|---|---|
| 104 | 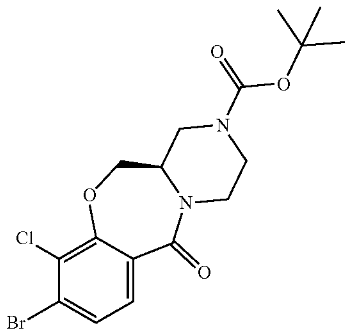 [SMILES: CC(C)(C)OC(=O)N1CCN2C(=O)c3ccc(Br)c(Cl)c3OC[C@H]2C1] | tert-Butyl (4aR)-8-bromo-7-chloro-11-oxo-2,4,4a,5-tetrahydro-1H-pyrazino[2,1-c][1,4]benzoxazepine-3-carboxylate | 374.8/376.8 |
| 105 | 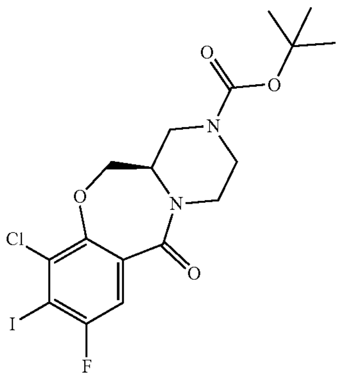 [SMILES: CC(C)(C)OC(=O)N1CCN2C(=O)c3cc(F)c(I)c(Cl)c3OC[C@H]2C1] | tert-Butyl (4aR)-7-chloro-9-fluoro-8-iodo-11-oxo-2,4,4a,5-tetrahydro-1H-pyrazino[2,1-c][1,4]benzoxazepine-3-carboxylate | 441.0/443.0 |
| 106 | 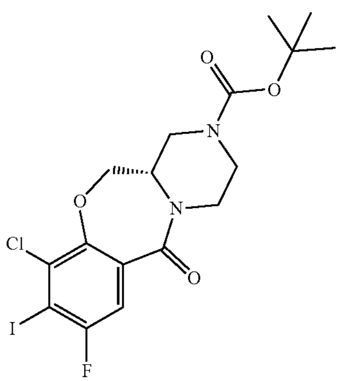 [SMILES: CC(C)(C)OC(=O)N1CCN2C(=O)c3cc(F)c(I)c(Cl)c3OC[C@@H]2C1] | tert-Butyl (4aS)-7-chloro-9-fluoro-8-iodo-11-oxo-2,4,4a,5-tetrahydro-1H-pyrazino[2,1-c][1,4]benzoxazepine-3-carboxylate | 441.0/443.0 |
| 107 | 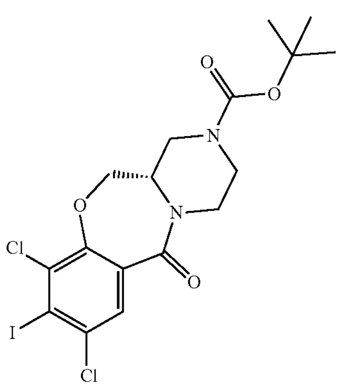 [SMILES: CC(C)(C)OC(=O)N1CCN2C(=O)c3cc(Cl)c(I)c(Cl)c3OC[C@@H]2C1] | tert-Butyl (4aS)-7,9-dichloro-8-iodo-11-oxo-2,4,4a,5-tetrahydro-1H-pyrazino[2,1-c][1,4]benzoxazepine-3-carboxylate | 456.9/458.9 |

TABLE 14-continued

Compounds synthesized in a manner essentially analogous to that of Preparation 94

| Preparation | Structure | Compound Name | ES/MS m/z (M + H) |
|---|---|---|---|
| 108 | 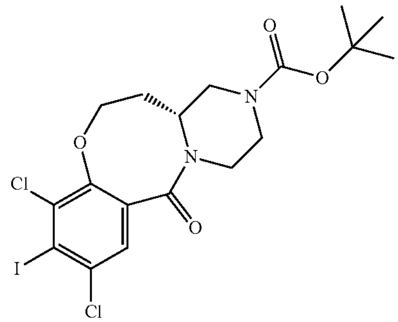 [SMILES: CC(C)(C)OC(=O)N1CCN2C(=O)c3cc(Cl)c(I)c(Cl)c3OCC[C@@H]2C1] | ter-Butyl (13aR)-8,10-dichloro-9-iodo-6-oxo-1,3,4,12,13,13a-hexahydropyrazino[2,1-d][1,5]benzoxazocine-2-carboxylate | 470.8/472.8 |
| 109 | 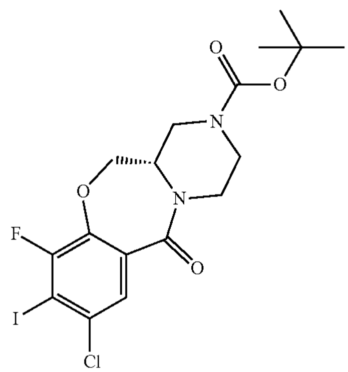 [SMILES: CC(C)(C)OC(=O)N1CCN2C(=O)c3cc(Cl)c(I)c(F)c3OC[C@@H]2C1] | tert-Butyl (4aS)-9-chloro-7-fluoro-8-iodo-11-oxo-2,4,4a,5-tetrahydro-1H-pyrazino[2,1-c][1,4]benzoxazepine-3-carboxylate | 441.0/443.0 |
| 110 | 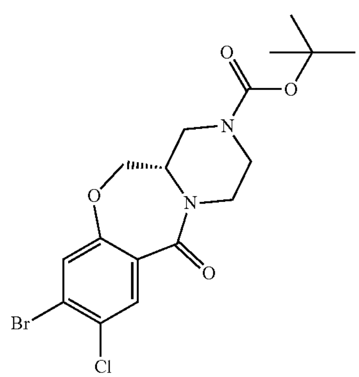 [SMILES: CC(C)(C)OC(=O)N1CCN2C(=O)c3cc(Cl)c(Br)cc3OC[C@@H]2C1] | tert-Butyl (4aS)-8-bromo-9-chloro-11-oxo-2,4,4a,5-tetrahydro-1H-pyrazino[2,1-c][1,4]benzoxazepine-3-carboxylate | 374.8/376.8 |
| 111 | 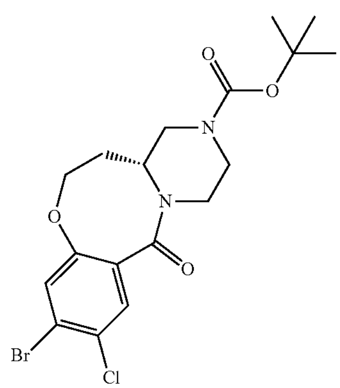 [SMILES: CC(C)(C)OC(=O)N1CCN2C(=O)c3cc(Cl)c(Br)cc3OCC[C@@H]2C1] | tert-Butyl (13aR)-9-bromo-8-chloro-6-oxo-1,3,4,12,13,13a-hexahydropyrazino[2,1-d][1,5]benzoxazocine-2-carboxylate | 388.8/390.8 |

TABLE 14-continued

Compounds synthesized in a manner essentially analogous to that of Preparation 94

| Preparation | Structure | Compound Name | ES/MS m/z (M + H) |
|---|---|---|---|
| 112 | 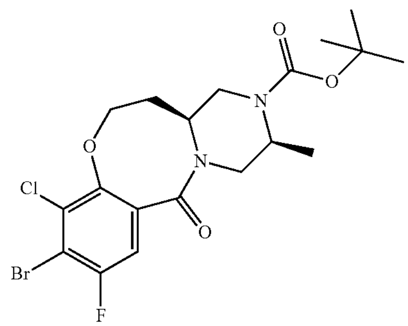 [SMILES: C[C@H]1CN2C(=O)c3cc(F)c(Br)c(Cl)c3OCC[C@H]2CN1C(=O)OC(C)(C)C] | tert-Butyl (3S,13aS)-9-bromo-10-chloro-8-fluoro-3-methyl-6-oxo-1,3,4,12,13,13a-hexahydropyrazino[2,1-d][1,5]benzoxazocine-2-carboxylate | 421.0/423.0 |

Preparation 113 tert-Butyl (13aS)-9-bromo-8-chloro-11-methyl-6-oxo-1,3,4,12,13,13a-hexahydropyrazino[2,1-d][1,5]benzodiazocine-2-carboxylate and tert-Butyl (13aS)-9-bromo-8-chloro-6-oxo-3,4,11,12,13,13a-hexahydro-1H-pyrazino [2,1-d][1,5]benzodiazocine-2-carboxylate tert-Butyl (3S)-4-(2-amino-4-bromo-5-chloro-benzoyl)-3-[2-(p-tolylsulfonyloxy)ethyl]piperazine-1-carboxylate (473 mg, 0.767 mmol) in DMF (15 mL) is cooled to 0° C. and then to the solution is added solid sodium hydride (60 mass % in paraffin oil) (49 mg, 1.225 mmol). The reaction mixture is stirred at 0° C. for 2 hours before allowing to warm to ambient temperature and stir for an additional 2 hours. After this time, the reaction mixture is cooled to −78° C. and methyl iodide (50 µL, 0.803 mmol) is added. After 30 minutes, the reaction mixture is warmed to 0° C. and stirred for 18 hours and warms to ambient temperature. The mixture is cooled back down to 0° C. and additional methyl iodide (50 µL, 0.803 mmol) is added. After 1 hour, no additional methylation is observed, the reaction mixture is warmed to ambient temperature and triethylamine (100 µL, 0.717 mmol) is added. After another 1 hour, the reaction mixture is quenched with water, diluted with saturated aqueous NH₄Cl solution and EtOAc. The layers are separated and the aqueous is extracted twice more with EtOAc. The combined organics are washed with saturated aqueous sodium chloride solution, dried over sodium sulfate, and concentrated in vacuo. The resulting solid is triturated with ACN and dried under vacuum without any further purification to give a mixture of the title compounds (3:2 NH to NMe, 345 mg, 99+%). ES/MS m/z ($^{79}$Br/$^{81}$Br) 444.0/446.0 [M+H]⁺ and 458.0/460.0 [M+H]⁺.

Preparation 114 tert-Butyl (13aR)-9-bromo-8-chloro-10-methyl-6-oxo-1,3,4,11,13,13a-hexahydropyrazino[2,1-d][2,5]benzoxazocine-2-carboxylate A solution of 4-bromo-2-[[(2R)-4-tert-butoxycarbonylpiperazin-yl]methoxymethyl]-5-chloro-3-methyl-benzoic acid hydrochloride (500 mg, 0.749 mmol) and DIEA (0.39 mL, 2.2 mmol) in DMF (3.7 mL) is added dropwise to a solution of HATU (581 mg, 1.50 mmol) in DMF (3.7 mL) at 0° C. The mixture is stirred at 0° C. for 1 hour and at ambient temperature for 30 minutes. In a separate flask, a solution of 4-bromo-2-[[(2R)-4-tert-butoxycarbonylpiperazin-2-yl]methoxymethyl]-5-chloro-3-methyl-benzoic acid hydrochloride (2.62 g, 3.92 mmol, 77% purity) and DIEA (2.1 mL, 12 mmol) in DMF (20 mL) is added dropwise to a solution of HATU (3.04 g, 7.84 mmol) in DMF (20 mL) at 0° C. The mixture is stirred at 0° C. for 1 hour and at ambient temperature for 30 minutes. The two reaction mixtures are combined, diluted with EtOAc, and washed with 0.5M HCl, water, saturated aqueous sodium bicarbonate, and saturated aqueous sodium chloride. The organic layer is dried over sodium sulfate, filtered, and concentrated in vacuo. The crude material is purified by silica gel flash chromatography eluting with 0-65% EtOAc/hexanes. The pure fractions are concentrated in vacuo. To the residue is added DCM and the mixture is concentrated in vacuo and placed under vacuum for 3 hours to give the title compound as a white solid (1.95 g, 86%). ES/MS m/z ($^{79}$Br/$^{81}$Br) 459/461 [M+H]$^+$.

TABLE 15

Compounds synthesized in a manner essentially analogous to that of Preparation 114

| Preparation | Structure | Compound Name | ES/MS m/z (M + H) |
|---|---|---|---|
| 115 | 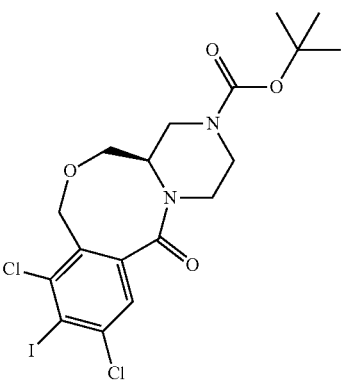 [SMILES: CC(C)(C)OC(=O)N1CCN2C(=O)c3cc(Cl)c(I)c(Cl)c3COC[C@H]2C1] | tert-Butyl (13aR)-8,10-dichloro-9-iodo-6-oxo-1,3,4,11,13,13a-hexahydropyrazino[2,1-d][2,5]benzoxazocine-2-carboxylate | 527.2/529.0 |
| 116 | 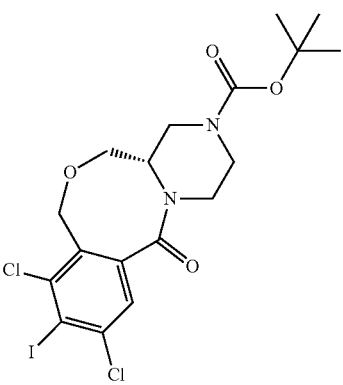 [SMILES: CC(C)(C)OC(=O)N1CCN2C(=O)c3cc(Cl)c(I)c(Cl)c3COC[C@@H]2C1] | tert-Butyl (13aS)-8,10-dichloro-9-iodo-6-oxo-1,3,4,11,13,13a-hexahydropyrazino[2,1-d][2,5]benzoxazocine-2-carboxylate | 471.0/473.0 |

Preparation 117

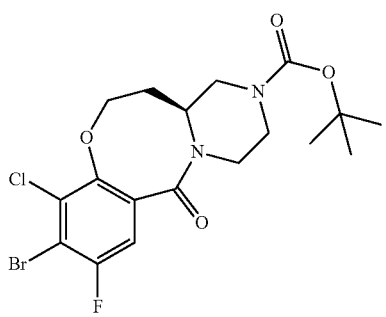

tert-Butyl (13aS)-9-bromo-10-chloro-8-fluoro-6-oxo-1,3,4,12,13,13a-hexahydropyrazino[2,1-d][1,5]benzoxazocine-2-carboxylate To a solution of 4-bromo-2-[2-[(2S)-4-tert-butoxycarbonylpiperazin-2-yl]ethoxy]-3-chloro-5-fluoro-benzoic acid (4.8 g, 10 mmol) in DCM (50 mL), cooled with an ice bath, is added TEA (2.8 mL, 20 mmol). Propylphosphonic anhydride (11 mL, 18.8 mmol, 50 mass % in EtOAc) is added dropwise. After addition, the mixture is stirred for 10 minutes. DCM (250 mL) and saturated ammonium chloride solution (100 mL) are added. The aqueous layer is removed and extracted with DCM (100 mL) and the combined organic layers are washed with saturated aqueous sodium chloride solution (100 mL), dried over sodium sulfate, and filtered. The filtrate is treated with activated charcoal (3.5 g) and stirred for 10 minutes. The mixture is filtered through a pad of diatomaceous earth and concentrated in vacuo to an oil. Chloroform is added and concentrated in vacuo (repeat 2×) to give the title compound as a solid (4.64 g, 99%). ES/MS m/z ($^{79}$Br/$^{81}$Br) 407/409 [M−t-Bu+H]$^+$.

Preparation 118

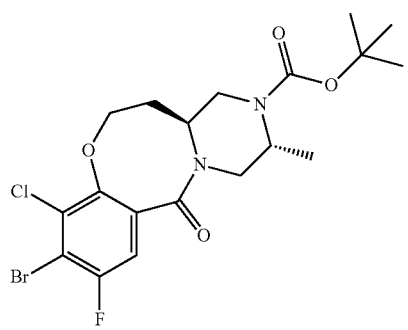

tert-Butyl (3R, 13aS)-9-bromo-10-chloro-8-fluoro-3-methyl-6-oxo-1,3,4,12,13,13a-hexahydropyrazino[2,1-d][1,5]benzoxazocine-2-carboxylate A solution of methyl 4-bromo-3-chloro-2,5-difluoro-benzoate (1.00 g, 3.50 mmol) and tert-butyl (2R,5S)-5-(2-hydroxyethyl)-2-methyl-piperazine-1-carboxylate (1.07 g, 4.38 mmol) in DMF (17.5 mL) is cooled with an ice bath. Cesium carbonate (2.31 g, 7.01 mmol) is added. The reaction is allowed to slowly warm to ambient temperature overnight. After 18 hours, the reaction is heated to 80° C. for 24 hours. After cooling to room temperature, half saturated aqueous sodium chloride solution (50 mL) is added and the mixture is diluted with EtOAc (100 mL) and the layers are separated. The aqueous layer is extracted two more times with EtOAc (50 mL) and the combined organics are washed with water (2×50 mL), saturated aqueous sodium chloride solution (50 mL), and then dried over sodium sulfate, filtered, and concentrated in vacuo. The crude material is purified by silica gel flash chromatography eluting with 0-100% MTBE/hexane to give the title compound as a solid (690 mg, 41%). ES/MS m/z ($^{79}$Br/$^{81}$Br) 476.0/478.0 [M+H]$^+$.

Preparation 119

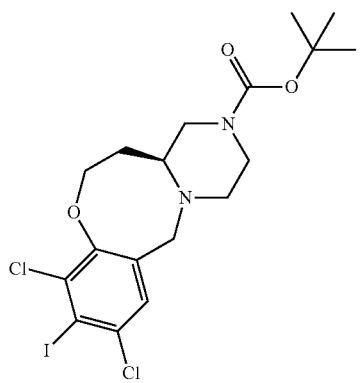

tert-Butyl (13aS)-8,10-dichloro-9-iodo-3,4,6,12,13,13a-hexahydro-1H-pyrazino[2,1-d][1,5]benzoxazocine-2-carboxylate 1M Borane dimethyl sulfide complex in THF (2 mL, 2 mmol) is added to a stirring mixture of tort-butyl (13aS)-8,10-dichloro-9-iodo-6-oxo-1,3,4,12,13,13a-hexahydropyrazino[2,1-d][1,5]benzoxazocine-2-carboxylate (1.0 g, 1.9 mmol) in THF (20 mL) and heated to reflux for 18 hours. After this time, additional 1M borane dimethyl sulfide complex in THF (2 mL, 2 mmol) is added to the mixture and stirred at reflux for an additional 5 hours. The mixture is cooled to ambient temperature, carefully quenched with MeOH, and concentrated in vacuo. The residue is purified by silica gel flash column chromatography, eluting with 30-70% EtOAc/hexane to give the title compound (900 mg, 90%). ES/MS m/z ($^{35}$Cl/$^{37}$Cl) 512.8/514.8 [M+H]$^{+-}$.

TABLE 16

Compounds synthesized in a manner essentially analogous to that of Preparation 119

| Preparation | Structure | Compound Name | ES/MS m/z (M + H) |
|---|---|---|---|
| 120 | 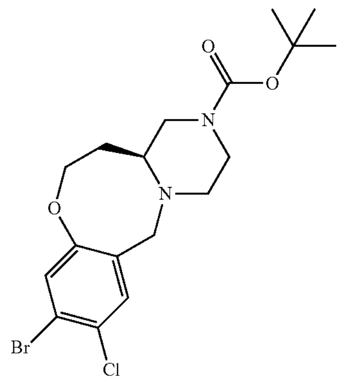 [SMILES: CC(C)(C)OC(=O)N1CCN2Cc3cc(Cl)c(Br)cc3OCC[C@H]2C1] | tert-Butyl (13aS)-9-bromo-8-chloro-3,4,6,12,13,13a-hexahydro-1H-pyrazino[2,1-d][1,5]benzoxazocine-2-carboxylate | 430.9/433.0 |
| 121 | 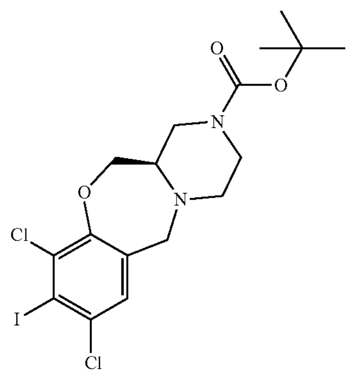 [SMILES: CC(C)(C)OC(=O)N1CCN2Cc3cc(Cl)c(I)c(Cl)c3OC[C@H]2C1] | tert-Butyl (4aR)-7,9-dichloro-8-iodo-1,2,4,4a,5,11-hexahydropyrazino[2,1-c][1,4]benzoxazepine-3-carboxylate | 498.8/500.8 |
| 122 | 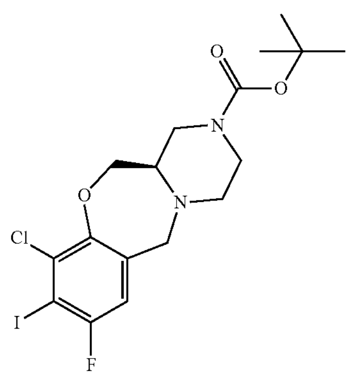 [SMILES: CC(C)(C)OC(=O)N1CCN2Cc3cc(F)c(I)c(Cl)c3OC[C@H]2C1] | tert-Butyl (4aR)-7-chloro-9-fluoro-8-iodo-1,2,4,4a,5,11-hexahydropyrazino[2,1-c][1,4]benzoxazepine-3-carboxylate | 483.2/485.2 |
| 123 | 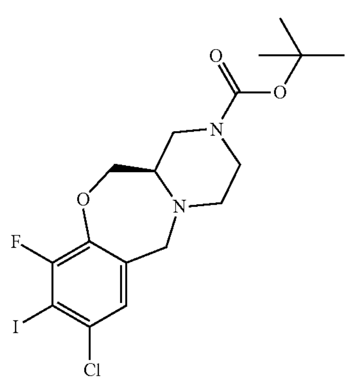 [SMILES: CC(C)(C)OC(=O)N1CCN2Cc3cc(Cl)c(I)c(F)c3OC[C@H]2C1] | tert-Butyl (4aR)-9-chloro-7-fluoro-8-iodo-1,2,4,4a,5,11-hexahydropyrazino[2,1-c][1,4]benzoxazepine-3-carboxylate | 483.0/485.0 |

TABLE 16-continued

Compounds synthesized in a manner essentially analogous to that of Preparation 119

| Preparation | Structure | Compound Name | ES/MS m/z (M + H) |
|---|---|---|---|
| 124 | 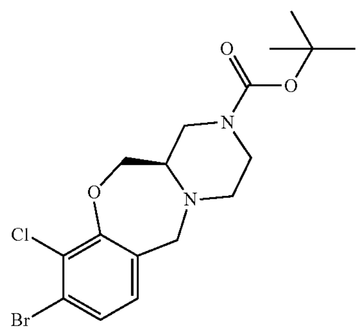 [SMILES: CC(C)(C)OC(=O)N1CCN2Cc3ccc(Br)c(Cl)c3OC[C@H]2C1] | tert-Butyl (4aR)-8-bromo-7-chloro-1,2,4,4a,5,11-hexahydropyrazino[2,1-c][1,4]benzoxazepine-3-carboxylate | 417.0/419.0 |
| 125 | 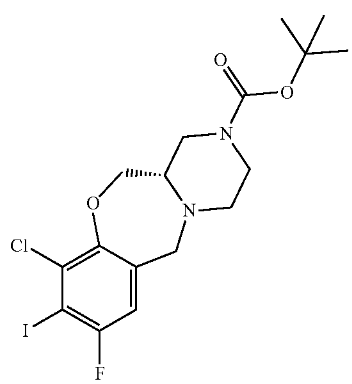 [SMILES: CC(C)(C)OC(=O)N1CCN2Cc3cc(F)c(I)c(Cl)c3OC[C@@H]2C1] | tert-Butyl (4aS)-7-chloro-9-fluoro-8-iodo-1,2,4,4a,5,11-hexahydropyrazino[2,1-c][1,4]benzoxazepine-3-carboxylate | 483.2/485.2 |
| 126 | 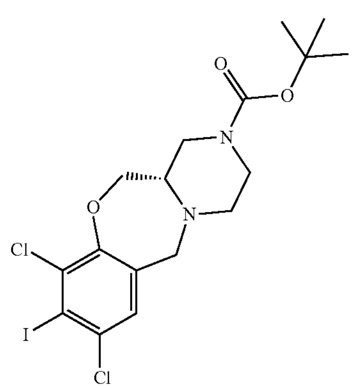 [SMILES: CC(C)(C)OC(=O)N1CCN2Cc3cc(Cl)c(I)c(Cl)c3OC[C@@H]2C1] | tert-Butyl (4aS)-7,9-dichloro-8-iodo-11-oxo-2,4,4a,5-tetrahydro-1H-pyrazino[2,1-c][1,4]benzoxazepine-3-carboxylate | 499.0/501.0 |
| 127 | 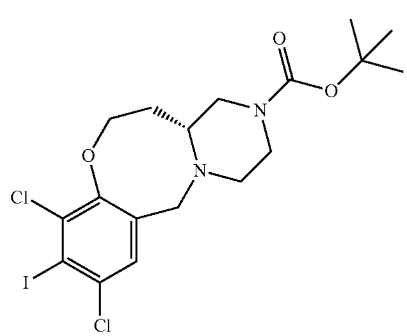 [SMILES: CC(C)(C)OC(=O)N1CCN2Cc3cc(Cl)c(I)c(Cl)c3OCC[C@@H]2C1] | tert-Butyl (13aR)-8,10-dichloro-9-iodo-3,4,6,12,13,13a-hexahydro-1H-pyrazino[2,1-d][1,5]benzoxazocine-2-carboxylate | 512.9/514.8 |

TABLE 16-continued

Compounds synthesized in a manner essentially analogous to that of Preparation 119

| Preparation | Structure | Compound Name | ES/MS m/z (M + H) |
|---|---|---|---|
| 128 | 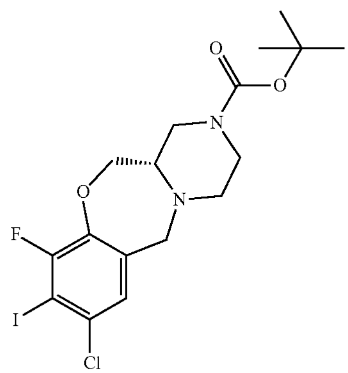 [SMILES: CC(C)(C)OC(=O)N1CCN2Cc3cc(Cl)c(I)c(F)c3OC[C@@H]2C1] | tert-Butyl (4aS)-9-chloro-7-fluoro-8-iodo-1,2,4,4a,5,11-hexahydropyrazino[2,1-c][1,4]benzoxazepine-3-carboxylate | 483.0/485.0 |
| 129 | 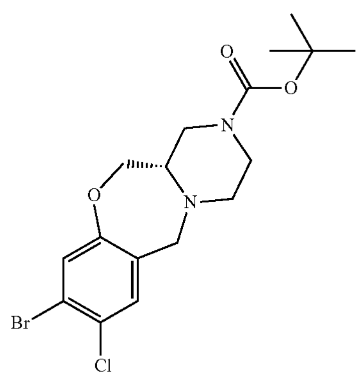 [SMILES: CC(C)(C)OC(=O)N1CCN2Cc3cc(Cl)c(Br)cc3OC[C@@H]2C1] | tert-Butyl (4aS)-8-bromo-9-chloro-1,2,4,4a,5,11-hexahydropyrazino[2,1-c][1,4]benzoxazepine-3-carboxylate | 416.8/419.0 |
| 130 | 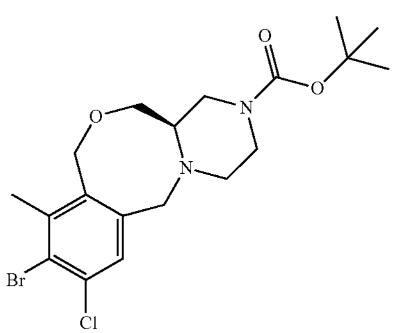 [SMILES: Cc1c(Br)c(Cl)cc2c1COC[C@H]1CN(C(=O)OC(C)(C)C)CCN1C2] | tert-Butyl (13aR)-9-bromo-8-chloro-10-methyl-3,4,6,11,13,13a-hexahydro-1H-pyrazino[2,1-d][2,5]benzoxazocine-2-carboxylate | 445.2/447.2 |
| 131 | 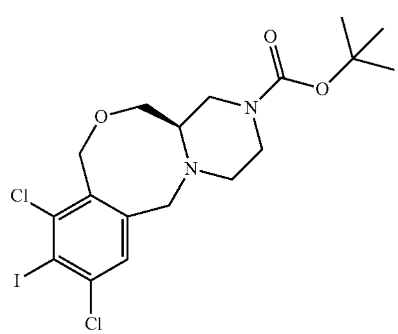 [SMILES: CC(C)(C)OC(=O)N1CCN2Cc3cc(Cl)c(I)c(Cl)c3COC[C@H]2C1] | tert-Butyl (13aR)-8,10-dichloro-9-iodo-3,4,6,11,13,13a-hexahydro-1H-pyrazino[2,1-d][2,5]benzoxazocine-2-carboxylate | 513.2/515.2 |

Preparation 132

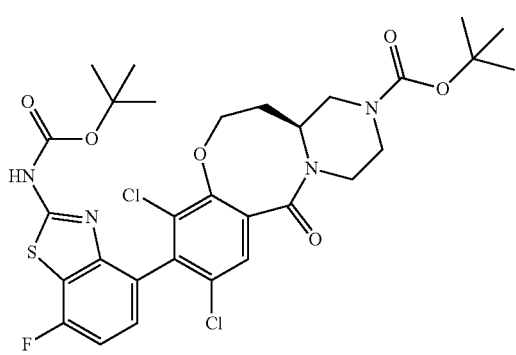

tert-Butyl (13aS)-9-[2-(tert-butoxycarbonylamino)-7-fluoro-1,3-benzothiazol-4-yl]-8,10-dichloro-6-oxo-1,3,4,12,13,13a-hexahydropyrazino[2,1-d][1,5]benzoxazocine-2-carboxylate Into a screw top sealable tube with a stir bar is added tert-butyl (13aS)-8,10-dichloro-9-iodo-6-oxo-1,3,4,12,13,13a-hexahydropyrazino[2,1-d][1,5]benzoxazocine-2-carboxylate (750 mg, 1.423 mmol), [2-(tert-butoxycarbonylamino)-7-fluoro-1,3-benzothiazol-4-yl]boronic acid (650 mg, 2.083 mmol), potassium phosphate tribasic (450 mg, 2.12 mmol), and 1,1'-bis(di-tert-butylphosphino)ferrocene palladium dichloride (100 mg, 0.15 mmol). Previously mixed and degassed 1,4-dioxane (15 mL) and water (5 mL) are added and the mixture is purged with nitrogen for 20 minutes. The tube is capped and heated at 80° C. for 1 hour. The contents of the reaction mixture are then poured over water, saturated aqueous sodium chloride solution, and EtOAc. The layers are separated, and the aqueous layer is extracted once with EtOAc. The combined organic extracts are dried over anhydrous magnesium sulfate, filtered, and concentrated in vacuo. The crude material is purified by silica gel flash chromatography eluting with 30-70% EtOAc/hexane to give the title compound (724 mg, 76%). ES/MS m/z ($^{35}$Cl/$^{37}$Cl) 667/669 [M+H]$^+$. 45:55 ratio of atropisomers (LC).

TABLE 17

Compounds synthesized in a manner essentially analogous to that of Preparation 132

| Preparation | Structure | Compound Name | ES/MS m/z (M + H) |
|---|---|---|---|
| 133 | 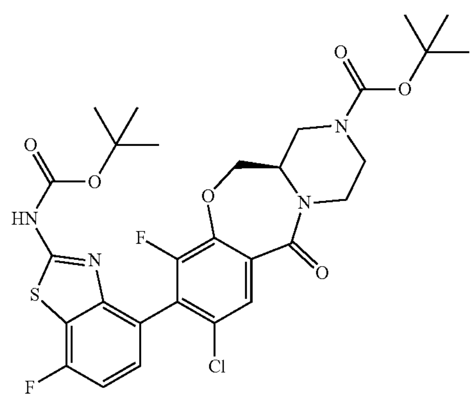 [SMILES: CC(C)(C)OC(=O)Nc1nc2c(-c3c(Cl)cc4c(c3F)OC[C@H]3CN(C(=O)OC(C)(C)C)CCN3C4=O)ccc(F)c2s1] | ter-Butyl (4aR)-8-[2-(tert-butoxycarbonylamino)-7-fluoro-1,3-benzothiazol-4-yl]-9-chloro-7-fluoro-11-oxo-2,4,4a,5-tetrahydro-1H-pyrazino[2,1-c][1,4]benzoxazepine-3-carboxylate | 537.2/539.2 |
| 134 | 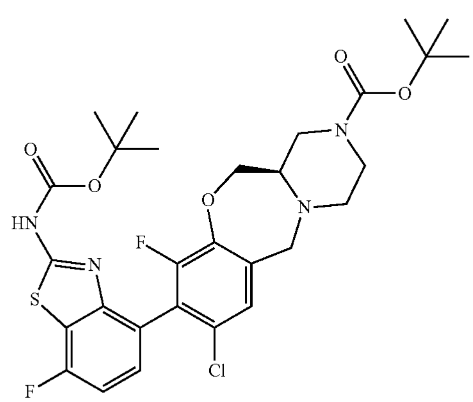 [SMILES: CC(C)(C)OC(=O)Nc1nc2c(-c3c(Cl)cc4c(c3F)OC[C@H]3CN(C(=O)OC(C)(C)C)CCN3C4)ccc(F)c2s1] | tert-Butyl (4aR)-8-[2-(tert-butoxycarbonylamino)-7-fluoro-1,3-benzothiazol-4-yl]-9-chloro-7-fluoro-1,2,4,4a,5,11-hexahydropyrazino[2,1-c][1,4]benzoxazepine-3-carboxylate | 623.2/625.2 |

TABLE 17-continued

Compounds synthesized in a manner essentially analogous to that of Preparation 132

| Preparation | Structure | Compound Name | ES/MS m/z (M + H) |
|---|---|---|---|
| 135 | 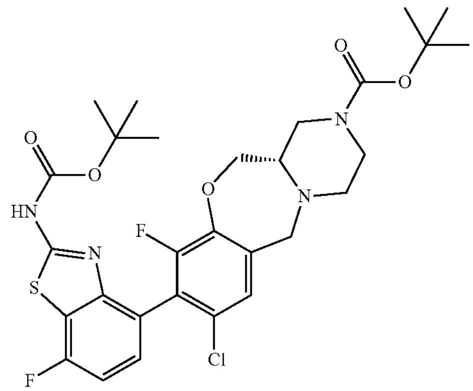 [SMILES: CC(C)(C)OC(=O)Nc1nc2c(-c3c(Cl)cc4c(c3F)OC[C@@H]3CN(C(=O)OC(C)(C)C)CCN3C4)ccc(F)c2s1] | tert-Butyl (4aS)-8-[2-(tert-butoxycarbonylamino)-7-fluoro-1,3-benzothiazol-4-yl]-9-chloro-7-fluoro-1,2,4,4a,5,11-hexahydropyrazino[2,1-c][1,4]benzoxazepine-3-carboxylate | 623.2/625.2 |
| 136 | 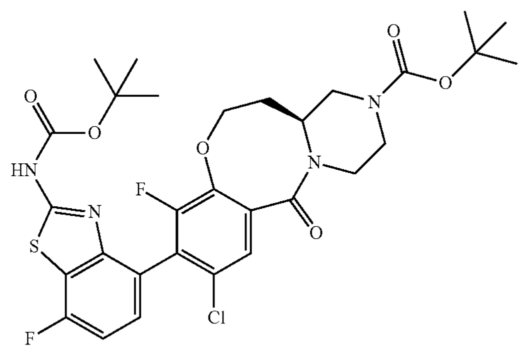 [SMILES: CC(C)(C)OC(=O)Nc1nc2c(-c3c(Cl)cc4c(c3F)OCC[C@H]3CN(C(=O)OC(C)(C)C)CCN3C4=O)ccc(F)c2s1] | tert-Butyl (13aS)-9-[2-(tert-butoxycarbonylamino)-7-fluoro-1,3-benzothiazol-4-yl]-8-chloro-10-fluoro-6-oxo-1,3,4,12,13,13a-hexahydropyrazino[2,1-d][1,5]benzoxazocine-2-carboxylate | 551.1/553.1 |
| 137 | 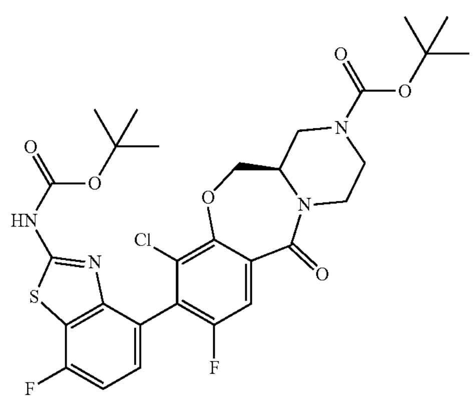 [SMILES: CC(C)(C)OC(=O)Nc1nc2c(-c3c(F)cc4c(c3Cl)OC[C@H]3CN(C(=O)OC(C)(C)C)CCN3C4=O)ccc(F)c2s1] | tert-Butyl (4aR)-8-[2-(tert-butoxycarbonylamino)-7-fluoro-1,3-benzothiazol-4-yl]-7-chloro-9-fluoro-11-oxo-2,4,4a,5-tetrahydro-H-pyrazino[2,1-c][1,4]benzoxazepine-3-carboxylate | 537.2/539.2 |
| 138 | 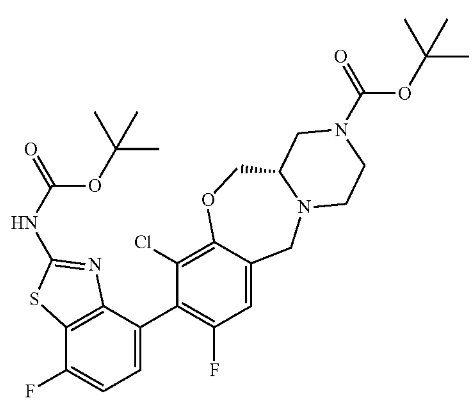 [SMILES: CC(C)(C)OC(=O)Nc1nc2c(-c3c(F)cc4c(c3Cl)OC[C@@H]3CN(C(=O)OC(C)(C)C)CCN3C4)ccc(F)c2s1] | ter-Butyl (4aS)-8-[2-(tert-butoxycarbonylamino)-7-fluoro-1,3-benzothiazol-4-yl]-7-chloro-9-fluoro-1,2,4,4a,5,11-hexahydropyrazino[2,1-c][1,4]benzoxazepine-3-carboxylate | 623.4/625.4 |

TABLE 17-continued

Compounds synthesized in a manner essentially analogous to that of Preparation 132

| Preparation | Structure | Compound Name | ES/MS m/z (M + H) |
|---|---|---|---|
| 139 | 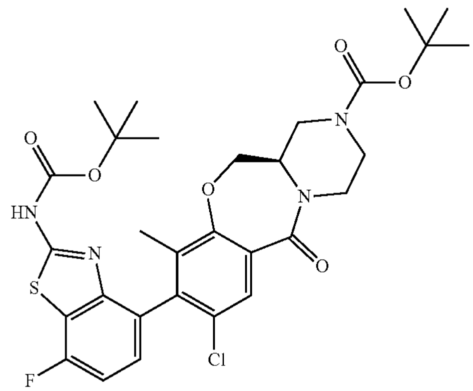 [SMILES: Cc1c2c(cc(Cl)c1-c1ccc(F)c3sc(NC(=O)OC(C)(C)C)nc13)C(=O)N1CCN(C(=O)OC(C)(C)C)C[C@@H]1CO2] | tert-Butyl (4aR)-8-[2-(tert-butoxycarbonylamino)-7-fluoro-1,3-benzothiazol-4-yl]-9-chloro-7-methyl-11-oxo-2,4,4a,5-tetrahydro-1H-pyrazino[2,1-c][1,4]benzoxazepine-3-carboxylate | 533.2/534.2 |
| 140 | 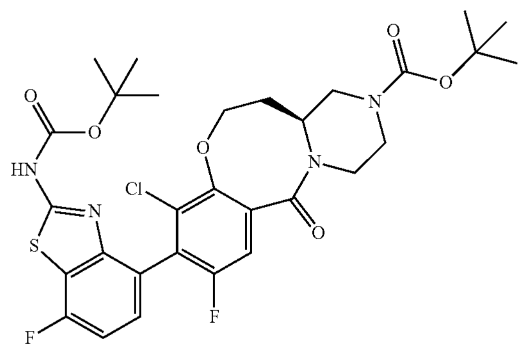 [SMILES: CC(C)(C)OC(=O)Nc1nc2c(-c3c(F)cc4c(c3Cl)OCC[C@H]3CN(C(=O)OC(C)(C)C)CCN3C4=O)ccc(F)c2s1] | tert-Butyl (13aS)-9-[2-(tert-butoxycarbonylamino)-7-fluoro-1,3-benzothiazol-4-yl]-10-chloro-8-fluoro-6-oxo-1,3,4,12,13,13a-hexahydropyrazino[2,1-d][1,5]benzoxazocine-2-carboxylate | 551.0/553.0 |
| 141 | 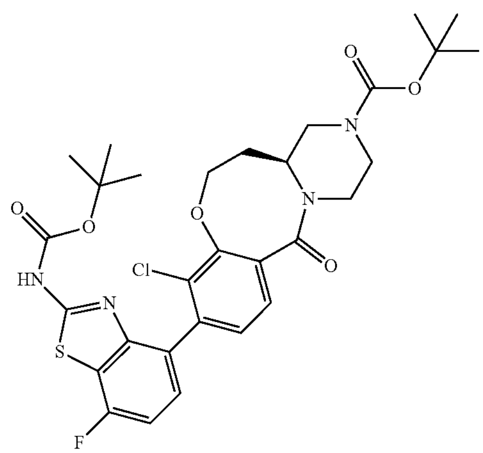 [SMILES: CC(C)(C)OC(=O)Nc1nc2c(-c3ccc4c(c3Cl)OCC[C@H]3CN(C(=O)OC(C)(C)C)CCN3C4=O)ccc(F)c2s1] | tert-Butyl (13aS)-9-[2-(tert-butoxycarbonylamino)-7-fluoro-1,3-benzothiazol-4-yl]-10-chloro-6-oxo-1,3,4,12,13,13a-hexahydropyrazino[2,1-d][1,5]benzoxazocine-2-carboxylate | 533.0/535.0 |
| 142 | 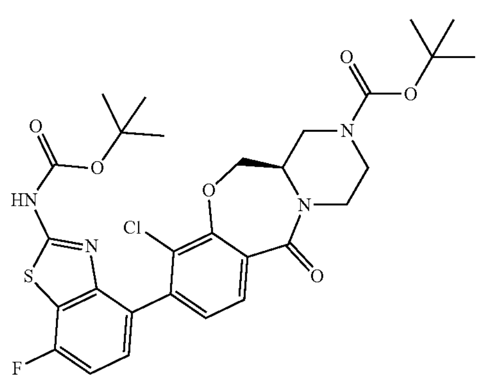 [SMILES: CC(C)(C)OC(=O)Nc1nc2c(-c3ccc4c(c3Cl)OC[C@H]3CN(C(=O)OC(C)(C)C)CCN3C4=O)ccc(F)c2s1] | tert-Butyl (4aR)-8-[2-(tert-butoxycarbonylamino)-7-fluoro-1,3-benzothiazol-4-yl]-7-chloro-11-oxo-2,4,4a,5-tetrahydro-1H-pyrazino[2,1-c][1,4]benzoxazepine-3-carboxylate | 519.0/521.0 |

TABLE 17-continued

Compounds synthesized in a manner essentially analogous to that of Preparation 132

| Preparation | Structure | Compound Name | ES/MS m/z (M + H) |
|---|---|---|---|
| 143 | 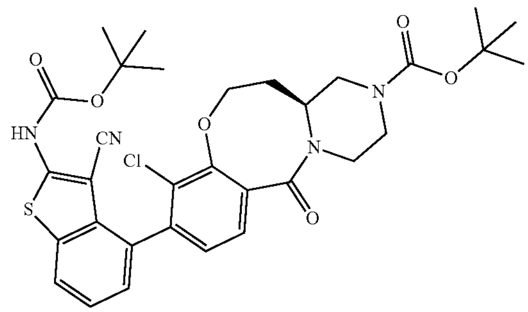 [SMILES: CC(C)(C)OC(=O)Nc1sc2cccc(-c3ccc4c(c3Cl)OCC[C@H]3CN(C(=O)OC(C)(C)C)CCN3C4=O)c2c1C#N] | tert-Butyl (13aS)-9-[2-(tert-butoxycarbonylamino)-3-cyano-benzothiophen-4-yl]-10-chloro-6-oxo-1,3,4,12,13,13a-hexahydropyrazino[2,1-d][1,5]benzoxazocine-2-carboxylate | 539.0/541.0 |
| 144 | 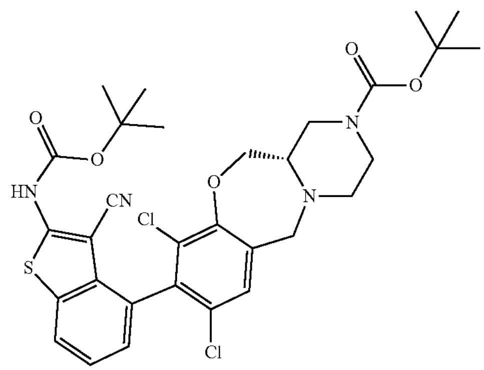 [SMILES: CC(C)(C)OC(=O)Nc1sc2cccc(-c3c(Cl)cc4c(c3Cl)OC[C@@H]3CN(C(=O)OC(C)(C)C)CCN3C4)c2c1C#N] | tert-Butyl (4aS)-8-[2-(tert-butoxycarbonylamino)-3-cyano-benzothiophen-4-yl]-7,9-dichloro-1,2,4,4a,5,11-hexahydropyrazino[2,1-c][1,4]benzoxazepine-3-carboxylate | 645.4/647.4 |
| 145 | 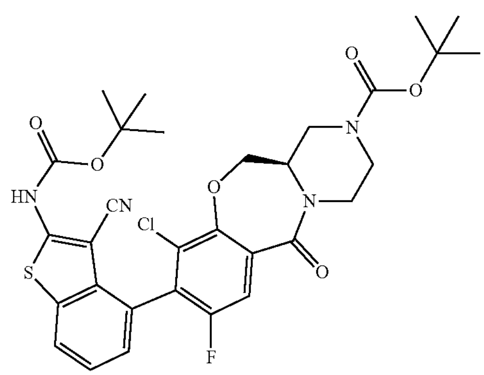 [SMILES: CC(C)(C)OC(=O)Nc1sc2cccc(-c3c(F)cc4c(c3Cl)OC[C@H]3CN(C(=O)OC(C)(C)C)CCN3C4=O)c2c1C#N] | tert-Butyl (4aR)-8-[2-(tert-butoxycarbonylamino)-3-cyano-benzothiophen-4-yl]-7-chloro-9-fluoro-11-oxo-2,4,4a,5-tetrahydro-1H-pyrazino[2,1-c][1,4]benzoxazepine-3-carboxylate | 587.2/589.2 |
| 146 | 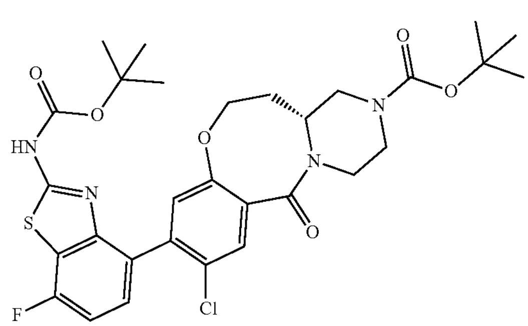 [SMILES: CC(C)(C)OC(=O)Nc1nc2c(-c3cc4c(cc3Cl)C(=O)N3CCN(C(=O)OC(C)(C)C)C[C@H]3CCO4)ccc(F)c2s1] | tert-Butyl (13aR)-9-[2-(tert-butoxycarbonylamino)-7-fluoro-1,3-benzothiazol-4-yl]-8-chloro-6-oxo-1,3,4,12,13,13a-hexahydropyrazino[2,1-d][1,5]benzoxazocine-2-carboxylate | 533.0/535.0 |

TABLE 17-continued

Compounds synthesized in a manner essentially analogous to that of Preparation 132

| Preparation | Structure | Compound Name | ES/MS m/z (M + H) |
|---|---|---|---|
| 147 | 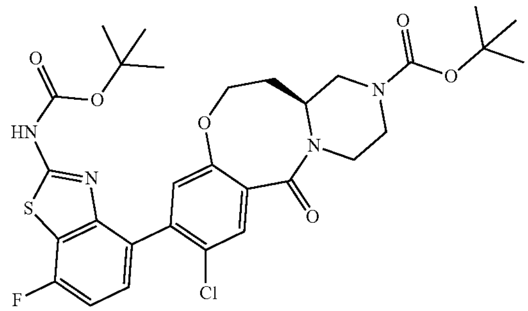 [SMILES: CC(C)(C)OC(=O)Nc1nc2c(-c3cc4c(cc3Cl)C(=O)N3CCN(C(=O)OC(C)(C)C)C[C@@H]3CCO4)ccc(F)c2s1] | tert-Butyl (13aS)-9-[2-(tert-butoxycarbonylamino)-7-fluoro-1,3-benzothiazol-4-yl]-8-chloro-6-oxo-1,3,4,12,13,13a-hexahydropyrazino[2,1-d][1,5]benzoxazocine-2-carboxylate | 533.0/535.0 |
| 148 | 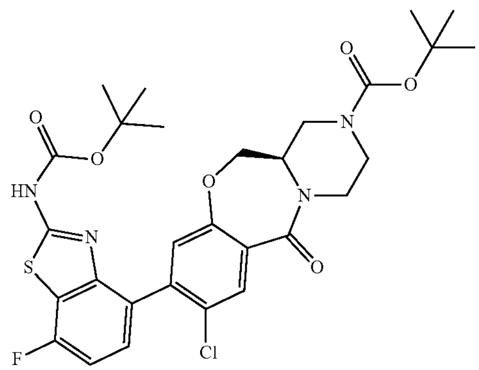 [SMILES: CC(C)(C)OC(=O)Nc1nc2c(-c3cc4c(cc3Cl)C(=O)N3CCN(C(=O)OC(C)(C)C)C[C@@H]3CO4)ccc(F)c2s1] | tert-Butyl (4aR)-8-[2-(tert-butoxycarbonylamino)-7-fluoro-1,3-benzothiazol-4-yl]-9-chloro-11-oxo-2,4,4a,5-tetrahydro-1H-pyrazino[2,1-c][1,4]benzoxazepine-3-carboxylate | 519.0/521.0 |
| 149 | 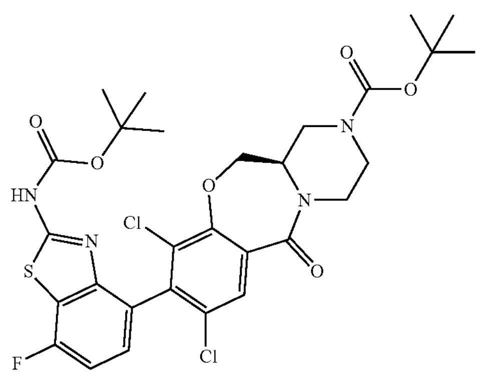 [SMILES: CC(C)(C)OC(=O)Nc1nc2c(-c3c(Cl)cc4c(c3Cl)OC[C@H]3CN(C(=O)OC(C)(C)C)CCN3C4=O)ccc(F)c2s1] | ter-Butyl (4aR)-8-[2-(tert-butoxycarbonylamino)-7-fluoro-1,3-benzothiazol-4-yl]-7,9-dichloro-11-oxo-2,4,4a,5-tetrahydro-1H-pyrazino[2,1-c][1,4]benzoxazepine-3-carboxylate | 553.0/555.0 |
| 150 | 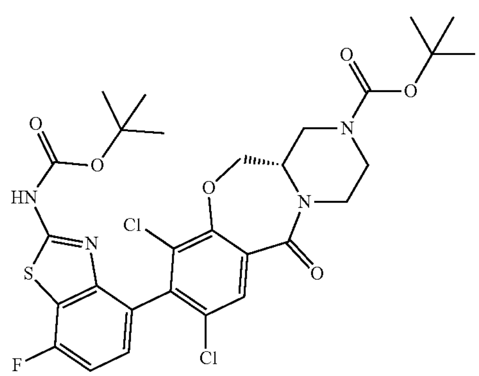 [SMILES: CC(C)(C)OC(=O)Nc1nc2c(-c3c(Cl)cc4c(c3Cl)OC[C@@H]3CN(C(=O)OC(C)(C)C)CCN3C4=O)ccc(F)c2s1] | tert-Butyl (4aS)-8-[2-(tert-butoxycarbonylamino)-7-fluoro-1,3-benzothiazol-4-yl]-7,9-dichloro-11-oxo-2,4,4a,5-tetrahydro-1H-pyrazino[2,1-c][1,4]benzoxazepine-3-carboxylate | 553.0/555.0 |

TABLE 17-continued

Compounds synthesized in a manner essentially analogous to that of Preparation 132

| Preparation | Structure | Compound Name | ES/MS m/z (M + H) |
|---|---|---|---|
| 151 | 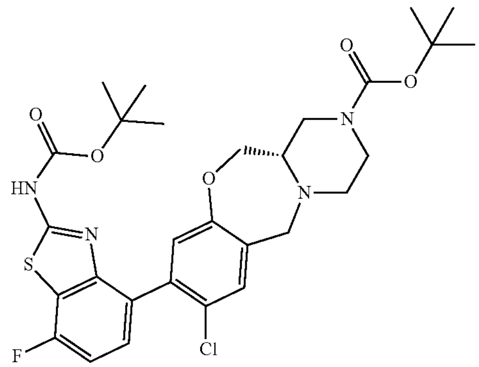 [SMILES: CC(C)(C)OC(=O)Nc1nc2c(-c3cc4c(cc3Cl)CN3CCN(C(=O)OC(C)(C)C)C[C@H]3CO4)ccc(F)c2s1] | tert-Butyl (4aS)-8-[2-(tert-butoxycarbonylamino)-7-fluoro-1,3-benzothiazol-4-yl]-9-chloro-1,2,4,4a,5,11-hexahydropyrazino[2,1-c][1,4]benzoxazepine-3-carboxylate | 605.0/607.0 |
| 152 | 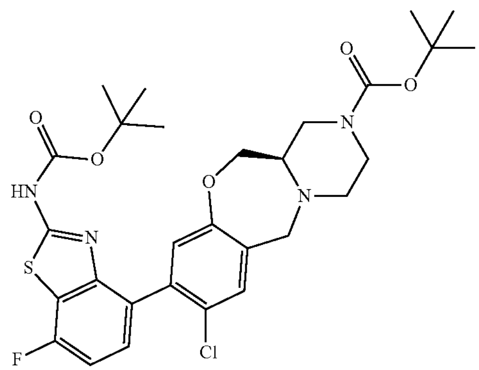 [SMILES: CC(C)(C)OC(=O)Nc1nc2c(-c3cc4c(cc3Cl)CN3CCN(C(=O)OC(C)(C)C)C[C@@H]3CO4)ccc(F)c2s1] | tert-Butyl (4aR)-8-[2-(tert-butoxycarbonylamino)-7-fluoro-1,3-benzothiazol-4-yl]-9-chloro-1,2,4,4a, 5,11-hexahydropyrazino[2,1-c][1,4]benzoxazepine-3-carboxylate | 605.0/607.0 |
| 153 | 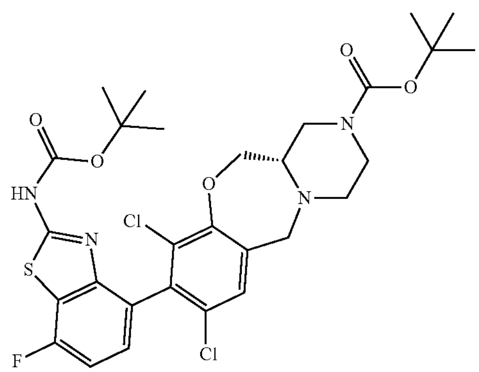 [SMILES: CC(C)(C)OC(=O)Nc1nc2c(-c3c(Cl)cc4c(c3Cl)OC[C@@H]3CN(C(=O)OC(C)(C)C)CCN3C4)ccc(F)c2s1] | tert-Butyl (4aS)-8-[2-(tert-butoxycarbonylamino)-7-fluoro-1,3-benzothiazol-4-yl]-7,9-dichloro-1,2,4,4a,5,11-hexahydropyrazino[2,1-c][1,4]benzoxazepine-3-carboxylate | 639.0/641.0 |
| 154 | 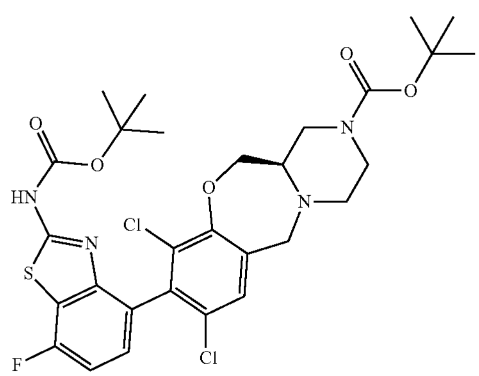 [SMILES: CC(C)(C)OC(=O)Nc1nc2c(-c3c(Cl)cc4c(c3Cl)OC[C@H]3CN(C(=O)OC(C)(C)C)CCN3C4)ccc(F)c2s1] | tert-Butyl (4aS)-8-[2-(tert-butoxycarbonylamino)-7-fluoro-1,3-benzothiazol-4-yl]-7,9-dichloro-1,2,4,4a,5,11-hexahydropyrazino[2,1-c][1,4]benzoxazepine-3-carboxylate | 639.0/641.0 |

TABLE 17-continued

Compounds synthesized in a manner essentially analogous to that of Preparation 132

| Preparation | Structure | Compound Name | ES/MS m/z (M + H) |
|---|---|---|---|
| 155 | 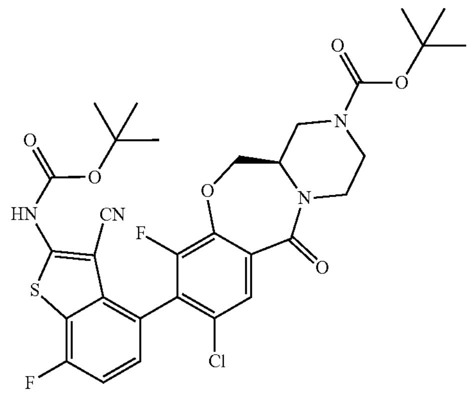 [SMILES: CC(C)(C)OC(=O)Nc1sc2c(F)ccc(-c3c(Cl)cc4c(c3F)OC[C@H]3CN(C(=O)OC(C)(C)C)CCN3C4=O)c2c1C#N] | tert-Butyl (4aR)-8-[2-(tert-butoxycarbonylamino)-3-cyano-7-fluoro-benzothiophen-4-yl]-9-chloro-7-fluoro-11-oxo-2,4,4a,5-tetrahydro-1H-pyrazino[2,1-c][1,4]benzoxazepine-3-carboxylate | 605.0/607.0 |
| 156 | 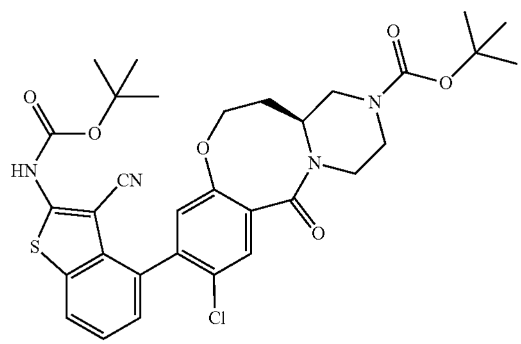 [SMILES: CC(C)(C)OC(=O)Nc1sc2cccc(-c3cc4c(cc3Cl)C(=O)N3CCN(C(=O)OC(C)(C)C)C[C@@H]3CCO4)c2c1C#N] | tert-Butyl (13aS)-9-[2-(tert-butoxycarbonylamino)-3-cyano-benzothiophen-4-yl]-8-chloro-6-oxo-1,3,4,12,13,13a-hexahydropyrazino[2,1-d][1,5]benzoxazocine-2-carboxylate | 639.2/641.2 |
| 157 | 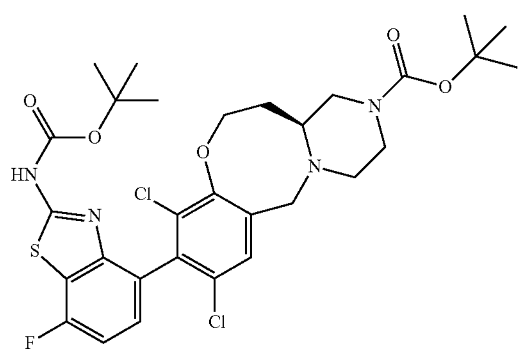 [SMILES: CC(C)(C)OC(=O)Nc1nc2c(-c3c(Cl)cc4c(c3Cl)OCC[C@H]3CN(C(=O)OC(C)(C)C)CCN3C4)ccc(F)c2s1] | ter-Butyl (13aS)-9-[2-(tert-butoxycarbonylamino)-7-fluoro-1,3-benzothiazol-4-yl]-8,10-dichloro-3,4,6,12,13,13a-hexahydro-1H-pyrazino[2,1-d][1,5]benzoxazocine-2-carboxylate | 653.0/655.2 |
| 158 | 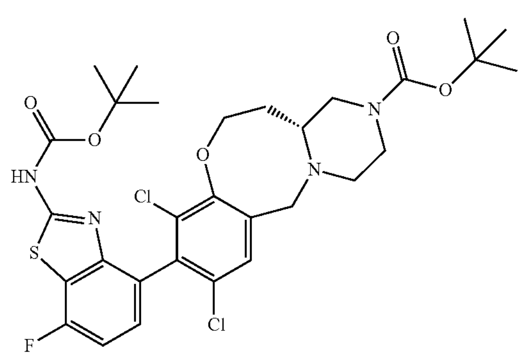 [SMILES: CC(C)(C)OC(=O)Nc1nc2c(-c3c(Cl)cc4c(c3Cl)OCC[C@@H]3CN(C(=O)OC(C)(C)C)CCN3C4)ccc(F)c2s1] | ter-Butyl (13aR)-9-[2-(tert-butoxycarbonylamino)-7-fluoro-1,3-benzothiazol-4-yl]-8,10-dichloro-3,4,6,12,13,13a-hexahydro-1H-pyrazino[2,1-d][1,5]benzoxazocine-2-carboxylate | 653.0/655.0 |

TABLE 17-continued

Compounds synthesized in a manner essentially analogous to that of Preparation 132

| Preparation | Structure | Compound Name | ES/MS m/z (M + H) |
|---|---|---|---|
| 159 | 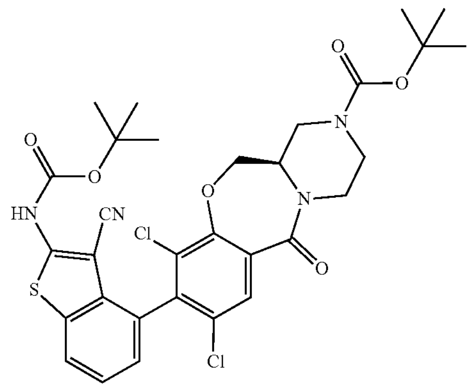 [SMILES: CC(C)(C)OC(=O)Nc1sc2cccc(-c3c(Cl)cc4c(c3Cl)OC[C@H]3CN(C(=O)OC(C)(C)C)CCN3C4=O)c2c1C#N] | tert-Butyl (4aR)-8-[2-(tert-butoxycarbonylamino)-3-cyano-benzothiophen-4-yl]-7,9-dichloro-11-oxo-2,4,4a,5-tetrahydro-1H-pyrazino[2,1-c][1,4]benzoxazepine-3-carboxylate | 603.0/605.0 |
| 160 | 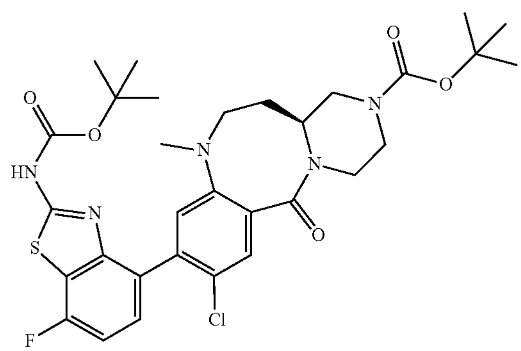 [SMILES: CN1CC[C@H]2CN(C(=O)OC(C)(C)C)CCN2C(=O)c2cc(Cl)c(-c3ccc(F)c4sc(NC(=O)OC(C)(C)C)nc34)cc21] | tert-Butyl (13aS)-9-[2-(tert-butoxycarbonylamino)-7-fluoro-1,3-benzothiazol-4-yl]-8-chloro-11-methyl-6-oxo-1,3,4,12,13,13a-hexahydropyrazino[2,1-d][1,5]benzodiazocine-2-carboxylate | 646.2/648.2 |
| 161 | 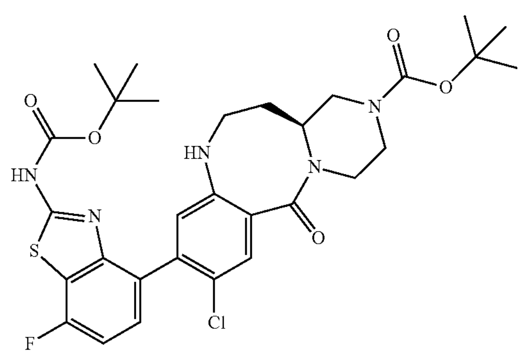 [SMILES: CC(C)(C)OC(=O)Nc1nc2c(-c3cc4c(cc3Cl)C(=O)N3CCN(C(=O)OC(C)(C)C)C[C@@H]3CCN4)ccc(F)c2s1] | tert-Butyl (13aS)-9-[2-(tert-butoxycarbonylamino)-7-fluoro-1,3-benzothiazol-4-yl]-8-chloro-6-oxo-3,4,11,12,13,13a-hexahydro-1H-pyrazino[2,1-d][1,5]benzodiazocine-2-carboxylate | 632.2/634.2 |
| 162 | 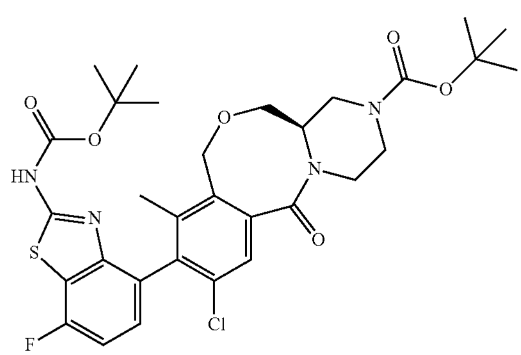 [SMILES: Cc1c2c(cc(Cl)c1-c1ccc(F)c3sc(NC(=O)OC(C)(C)C)nc13)C(=O)N1CCN(C(=O)OC(C)(C)C)C[C@@H]1COC2] | tert-Butyl (13aR)-9-[2-(tert-butoxycarbonylamino)-7-fluoro-1,3-benzothiazol-4-yl]-8-chloro-10-methyl-6-oxo-1,3,4,11,13,13a-hexahydropyrazino[2,1-d][2,5]benzoxazocine-2-carboxylate | 645.2/647.2 |

TABLE 17-continued

Compounds synthesized in a manner essentially analogous to that of Preparation 132

| Preparation | Structure | Compound Name | ES/MS m/z (M + H) |
|---|---|---|---|
| 163 | 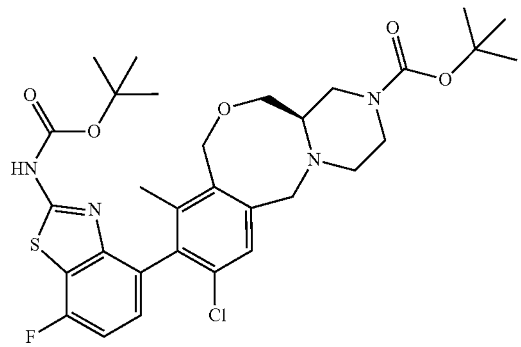 [SMILES: Cc1c2c(cc(Cl)c1-c1ccc(F)c3sc(NC(=O)OC(C)(C)C)nc13)CN1CCN(C(=O)OC(C)(C)C)C[C@@H]1COC2] | tert-Butyl (13aR)-9-[2-(tert-butoxycarbonylamino)-7-fluoro-1,3-benzothiazol-4-yl]-8-chloro-10-methyl-3,4,6,11,13,13a-hexahydro-1H-pyrazino[2,1-d][2,5]benzoxazocine-2-carboxylate | 633.4/635.4 |
| 164 | 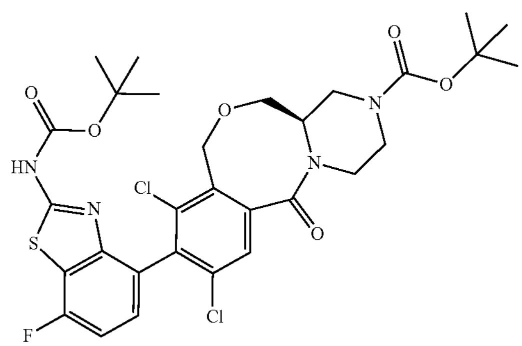 [SMILES: CC(C)(C)OC(=O)Nc1nc2c(-c3c(Cl)cc4c(c3Cl)COC[C@H]3CN(C(=O)OC(C)(C)C)CCN3C4=O)ccc(F)c2s1] | tert-Butyl (13aR)-9-[2-(tert-butoxycarbonylamino)-7-fluoro-1,3-benzothiazol-4-yl]-8,10-dichloro-6-oxo-1,3,4,11,13,13a-hexahydropyrazino[2,1-d][2,5]benzoxazocine-2-carboxylate | 665.2/667.2 |
| 165 | 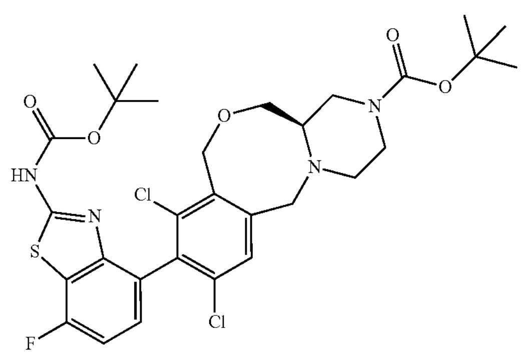 | tert-Butyl (13aR)-9-[2-(tert-butoxycarbonylamino)-7-fluoro-1,3-benzothiazol-4-yl]-8,10-dichloro-3,4,6,11,13,13a-hexahydro-1H-pyrazino[2,1-d][2,5]benzoxazocine-2-carboxylate | 653.4/655.2 |
| 166 | 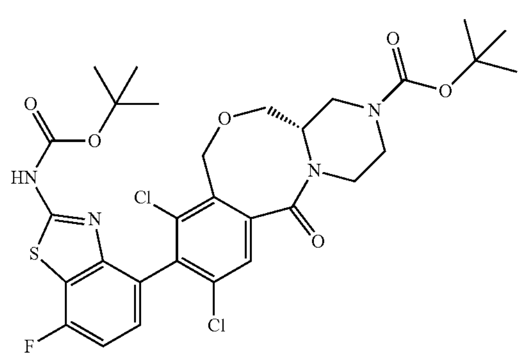 [SMILES: CC(C)(C)OC(=O)Nc1nc2c(-c3c(Cl)cc4c(c3Cl)COC[C@@H]3CN(C(=O)OC(C)(C)C)CCN3C4=O)ccc(F)c2s1] | tert-Butyl (13aS)-9-[2-(tert-butoxycarbonylamino)-7-fluoro-1,3-benzothiazol-4-yl]-8,10-dichloro-3,4,6,11,13,13a-hexahydro-1H-pyrazino[2,1-d][2,5]benzoxazocine-2-carboxylate | 665.2/667.2 |

In some cases, K$_2$CO$_3$ is used in place of K$_3$PO$_4$

Preparation 167

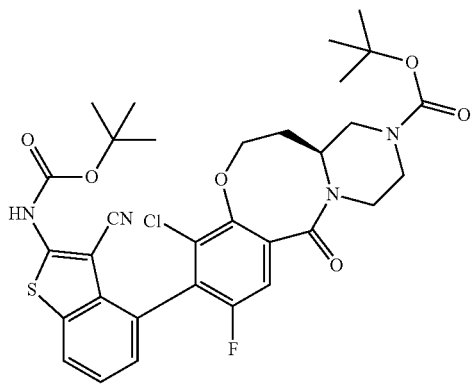

tert-Butyl (13aS)-9-[2-(tert-butoxycarbonylamino)-3-cyano-benzothiaphen-4-yl]-10-chloro-8-fluoro-6-oxo-1,3,4,12,13,13a-hexahydropyrazino[2,1-d][1,5]benzoxazocine-2-carboxylate To a sealed flask are added toluene (300 mL), tert-butyl (13aS)-9-bromo-10-chloro-8-fluoro-6-oxo-1,3,4,12,13,13a-hexahydropyrazino[2,1-d][1,5]benzoxazocine-2-carboxylate (6.20 g, 11.0 mmol), and tert-butyl N-[3-cyano-4-(4,4,5,5-tetramethyl-1,3,2-dioxaborolan-2-yl)benzothiophen-2-yl]carbamate (6.20 g, 15.5 mmol). The mixture is sparged with nitrogen for 30 minutes, and then DPEPhosPdCl$_2$ (1.20 g, 1.68 mmol) is added, followed by cesium carbonate (9.00 g, 27.6 mmol). The flask is sealed and stirred at 105° C. for 6 hours. The mixture is cooled to ambient temperature and filtered through diatomaceous earth, washed with EtOAc, and the filtrate is concentrated in vacuo. The residue is purified by silica gel flash column chromatography, eluting with 0-30% acetone/hexane. The desired diastereomer is eluded after the undesired one to give the title compound (major, 3.50 g, 49%). ES/MS m/z ($^{35}$Cl/$^{37}$Cl) 657.0/659.0 [M+H]$^+$.

TABLE 18

Compounds synthesized in a manner essentially analogous to that of Preparation 167

| Preparation | Structure | Compound Name | ES/MS m/z (M + H) |
|---|---|---|---|
| 168 | 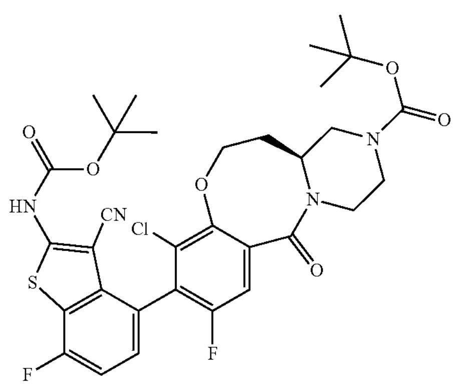 [SMILES: CC(C)(C)OC(=O)Nc1sc2c(F)ccc(-c3c(F)cc4c(c3Cl)OCC[C@H]3CN(C(=O)OC(C)(C)C)CCN3C4=O)c2c1C#N] | tert-Butyl (13aS)-9-[2-(tert-butoxycarbonylamino)-3-cyano-7-fluoro-benzothiophen-4-yl]-10-chloro-8-fluoro-6-oxo-1,3,4,12,13,13a-hexahydropyrazino[2,1-d][1,5]benzoxazocine-2-carboxylate | 675.2/677.2 |
| 169 | 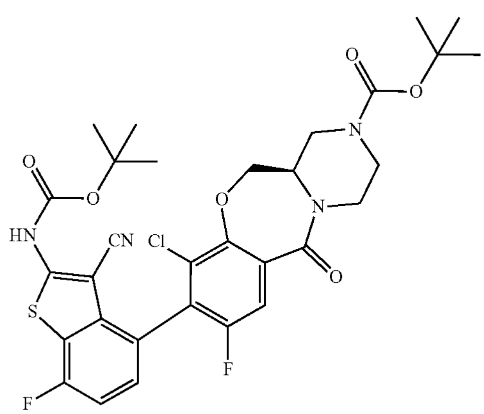 [SMILES: CC(C)(C)OC(=O)Nc1sc2c(F)ccc(-c3c(F)cc4c(c3Cl)OC[C@H]3CN(C(=O)OC(C)(C)C)CCN3C4=O)c2c1C#N] | tert-Butyl (4aR)-8-[2-(tert-butoxycarbonylamino)-3-cyano-7-fluoro-benzothiophen-4-yl]-7-chloro-9-fluoro-11-oxo-2,4,4a,5-tetrahydro-1H-pyrazino[2,1-c][1,4]benzoxazepine-3-carboxylate | 605.2/607.2 |

TABLE 18-continued

Compounds synthesized in a manner essentially analogous to that of Preparation 167

| Preparation | Structure | Compound Name | ES/MS m/z (M + H) |
|---|---|---|---|
| 170 | 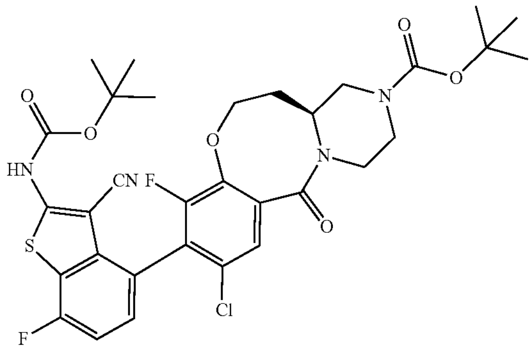 [SMILES: CC(C)(C)OC(=O)Nc1sc2c(F)ccc(-c3c(Cl)cc4c(c3F)OCC[C@H]3CN(C(=O)OC(C)(C)C)CCN3C4=O)c2c1C#N] | tert-Butyl (13aS)-9-[2-(tert-butoxycarbonylamino)-3-cyano-7-fluoro-benzothiophen-4-yl]-8-chloro-10-fluoro-6-oxo-1,3,4,12,13,13a-hexahydropyrazino[2,1-d][1,5]benzoxazocine-2-carboxylate | 675.2/677.2 |
| 171 | 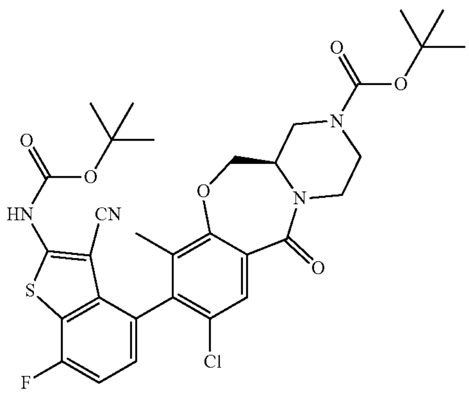 [SMILES: Cc1c2c(cc(Cl)c1-c1ccc(F)c3sc(NC(=O)OC(C)(C)C)c(C#N)c13)C(=O)N1CCN(C(=O)OC(C)(C)C)C[C@@H]1CO2] | tert-Butyl (4aR)-8-[2-(tert-butoxycarbonylamino)-7-fluoro-3-methyl-benzothiophen-4-yl]-9-chloro-7-methyl-11-oxo-2,4,4a,5-tetrahydro-1H-pyrazino[2,1-c][1,4]benzoxazepine-3-carboxylate | 601.2/603.3 |
| 172 | 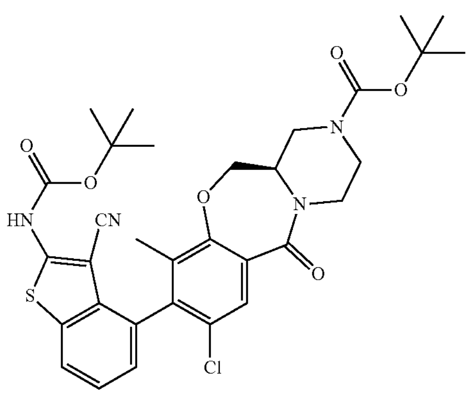 [SMILES: Cc1c2c(cc(Cl)c1-c1cccc3sc(NC(=O)OC(C)(C)C)c(C#N)c13)C(=O)N1CCN(C(=O)OC(C)(C)C)C[C@@H]1CO2] | tert-Butyl (4aR)-8-[2-(tert-butoxycarbonylamino)-3-methyl-benzothiophen-4-yl]-9-chloro-7-methyl-11-oxo-2,4,4a,5-tetrahydro-1H-pyrazino[2,1-c][1,4]benzoxazepine-3-carboxylate | 583.2/585.2 |
| 173 | 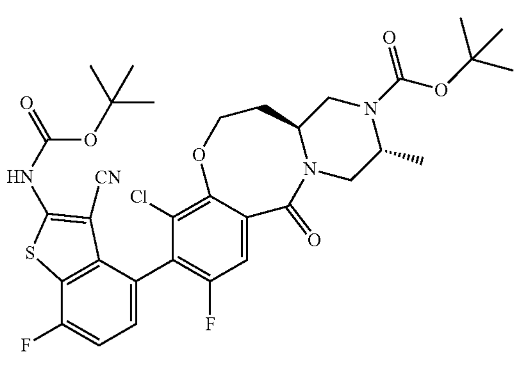 [SMILES: C[C@@H]1CN2C(=O)c3cc(F)c(-c4ccc(F)c5sc(NC(=O)OC(C)(C)C)c(C#N)c45)c(Cl)c3OCC[C@H]2CN1C(=O)OC(C)(C)C] | tert-Butyl (3R, 13 aS)-9-[2-(tert-butoxycarbonylamino)-3-cyano-7-fluoro-benzothiophen-4-yl]-10-chloro-8-fluoro-3-methyl-6-oxo-1,3,4,12,13,13a-hexahydropyrazino[2,1-d][1,5]benzoxazocine-2-carboxylate | 689.2/691.2 |

TABLE 18-continued

Compounds synthesized in a manner essentially analogous to that of Preparation 167

| Preparation | Structure | Compound Name | ES/MS m/z (M + H) |
|---|---|---|---|
| 174 | 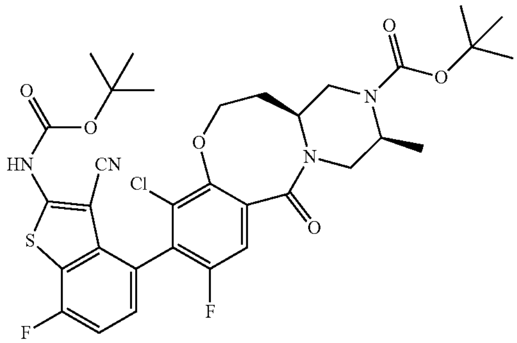 [SMILES: C[C@H]1CN2C(=O)c3cc(F)c(-c4ccc(F)c5sc(NC(=O)OC(C)(C)C)c(C#N)c45)c(Cl)c3OCC[C@H]2CN1C(=O)OC(C)(C)C] | tert-Butyl (3S,13aS)-9-[2-(tert-butoxycarbonylamino)-3-cyano-7-fluoro-benzothiophen-4-yl]-10-chloro-8-fluoro-3-methyl-6-oxo-1,3,4,12,13,13a-hexahydropyrazino[2,1-d][1,5]benzoxazocine-2-carboxylate | 633.4/635.4 |

Preparation 175

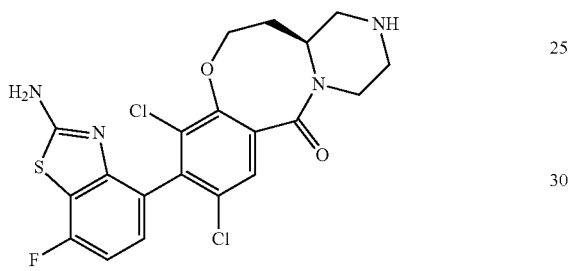

(13aS)-9-(2-Amino-7-fluoro-1,3-benzothiazol-4-yl)-8,10-dichloro-2,3,4,12,13,13a-hexahydro-1H-pyrazino[2,1-d][1,5]benzoxazocin-6-one tert-Butyl (13aS)-9-[2-(tert-butoxycarbonylamino)-7-fluoro-1,3-benzothiazol-4-yl]-8,10-dichloro-6-oxo-1,3,4,12,13,13a-hexahydropyrazino[2,1-d][1,5]benzoxazocine-2-carboxylate (724 mg, 1.084 mmol) is dissolved in DCM (4 mL) and TFA (2 mL, 26.45 mmol) and stirred at ambient temperature. After 6 hours, the mixture is concentrated in vacuo. The crude is loaded onto a SCX column, washed with MeOH, and eluted with 7N $NH_3$ in MeOH. The filtrate is concentrated in vacuo to give the title compound (500 mg, 98%). ES/MS m/z ($^{35}Cl/^{37}Cl$) 467/469 [M+H]$^+$.

TABLE 19

Compounds synthesized in a manner essentially analogous to that of Preparation 175

| Preparation | Structure | Compound Name | ES/MS m/z (M + H) |
|---|---|---|---|
| 176 | 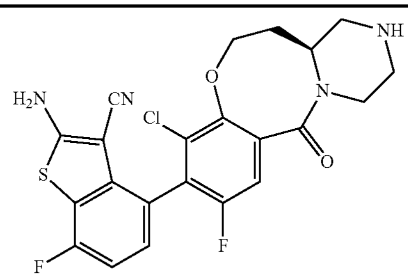 | 4-[(13aS)-10-Chloro-8-fluoro-6-oxo-2,3,4,12,13,13a-hexahydro-1H-pyrazino[2,1-d][1,5]benzoxazocin-9-yl]-2-amino-7-fluoro-benzothiophene-3-carbonitrile | 475.0/477.0 |

TABLE 19-continued

Compounds synthesized in a manner essentially analogous to that of Preparation 175

| Preparation | Structure | Compound Name | ES/MS m/z (M + H) |
|---|---|---|---|
| 177 | 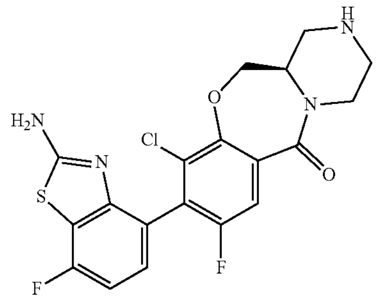 [SMILES: Nc1nc2c(-c3c(F)cc4c(c3Cl)OC[C@H]3CNCCN3C4=O)ccc(F)c2s1] | (4aR)-8-(2-Amino-7-fluoro-1,3-benzothiazol-4-yl)-7-chloro-9-fluoro-1,2,3,4,4a,5-hexahydropyrazino[2,1-c][1,4]benzoxazepine-11-one | 437.2/439.2 |
| 178 | 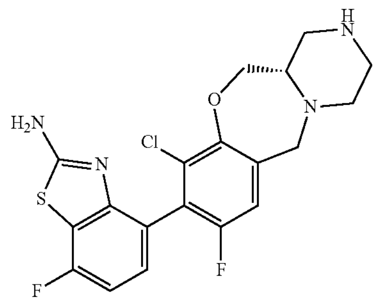 [SMILES: Nc1nc2c(-c3c(F)cc4c(c3Cl)OC[C@@H]3CNCCN3C4)ccc(F)c2s1] | 4-[(4aS)-7-Chloro-9-fluoro-2,3,4,4a,5,11-hexahydro-1H-pyrazino[2,1-c][1,4]benzoxazepine-8-yl]-7-fluoro-1,3-benzothiazol-2-amine | 423.2/425.2 |
| 179 | 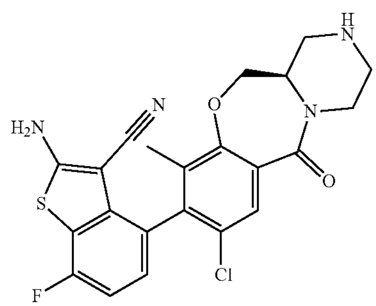 [SMILES: Cc1c2c(cc(Cl)c1-c1ccc(F)c3sc(N)c(C#N)c13)C(=O)N1CCNC[C@@H]1CO2] | 4-[(4aR)-9-Chloro-7-methyl-11-oxo-1,2,3,4,4a,5-hexahydropyrazino[2,1-c][1,4]benzoxazepine-8-yl]-2-amino-7-fluoro-benzothiophene-3-carbonitrile | 457.2/459.2 |
| 180 | 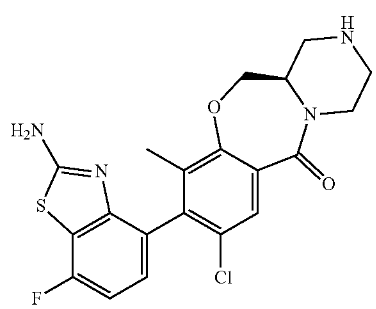 | (4aR)-8-(2-Amino-7-fluoro-1,3-benzothiazol-4-yl)-9-chloro-7-methyl-1,2,3,4,4a,5-hexahydropyrazino[2,1-c][1,4]benzoxazepine-11-one | 433.2/435.2 |
| 181 | 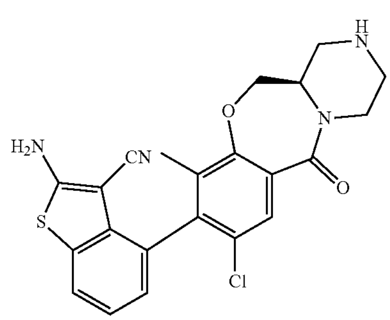 [SMILES: Cc1c2c(cc(Cl)c1-c1cccc3sc(N)c(C#N)c13)C(=O)N1CCNC[C@@H]1CO2] | (4aR)-8-(2-Amino-3-methyl-benzothiophen-4-yl)-9-chloro-7-methyl-1,2,3,4,4a,5-hexahydropyrazino[2,1-c][1,4]benzoxazepine-11-one | 439.1/441.2 |

TABLE 19-continued

Compounds synthesized in a manner essentially analogous to that of Preparation 175

| Preparation | Structure | Compound Name | ES/MS m/z (M + H) |
|---|---|---|---|
| 182 | 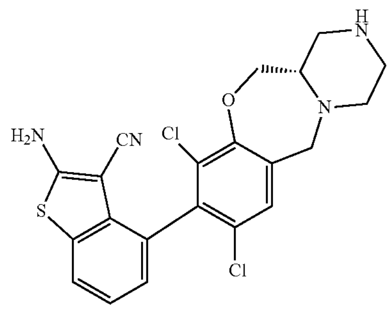 [SMILES: N#Cc1c(N)sc2cccc(-c3c(Cl)cc4c(c3Cl)OC[C@@H]3CNCCN3C4)c12] | 4-[(4aS)-7,9-Dichloro-2,3,4,4a,5,11-hexahydro-1H-pyrazino[2,1-c][1,4]benzoxazepine-8-yl]-2-amino-benzothiophene-3-carbonitrile | 445.0/447.0 |
| 183 | 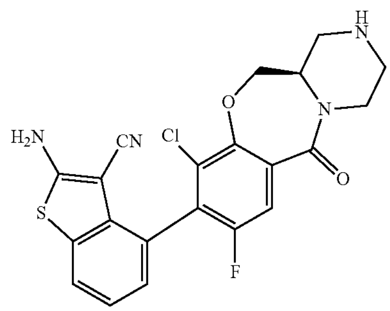 [SMILES: N#Cc1c(N)sc2cccc(-c3c(F)cc4c(c3Cl)OC[C@H]3CNCCN3C4=O)c12] | 4-[(4aR)-7-Chloro-9-fluoro-11-oxo-1,2,3,4,4a,5-hexahydropyrazino[2,1-c][1,4]benzoxazepine-8-yl]-2-amino-benzothiophene-3-carbonitrile | 443.2/445.2 |
| 184 | 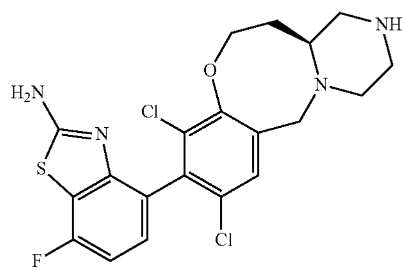 [SMILES: Nc1nc2c(-c3c(Cl)cc4c(c3Cl)OCC[C@H]3CNCCN3C4)ccc(F)c2s1] | 4-[(13aS)-8,10-Dichloro-1,2,3,4,6,12,13,13a-octahydropyrazino[2,1-d][1,5]benzoxazocin-9-yl]-7-fluoro-1,3-benzothiazol-2-amine | 453.0/455.0 |
| 185 | 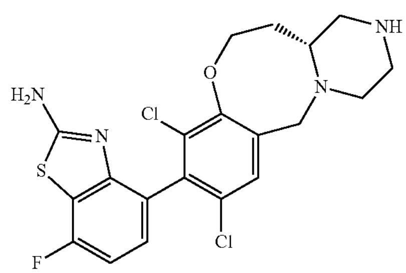 [SMILES: Nc1nc2c(-c3c(Cl)cc4c(c3Cl)OCC[C@@H]3CNCCN3C4)ccc(F)c2s1] | 4-[(13aR)-8,10-Dichloro-1,2,3,4,6,12,13,13a-octahydropyrazino[2,1-d][1,5]benzoxazocin-9-yl]-7-fluoro-1,3-benzothiazol-2-amine | 453.0/455.0 |
| 186 | 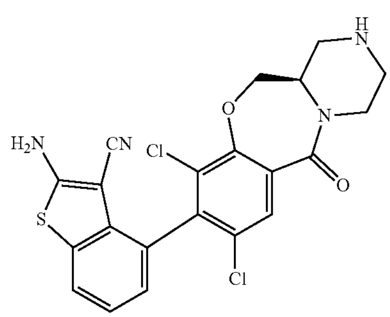 [SMILES: N#Cc1c(N)sc2cccc(-c3c(Cl)cc4c(c3Cl)OC[C@H]3CNCCN3C4=O)c12] | 4-[(4aR)-7,9-Dichloro-11-oxo-1,2,3,4,4a,5-hexahydropyrazino[2,1-c][1,4]benzoxazepine-8-yl]-2-amino-benzothiophene-3-carbonitrile | 458.9/460.9 |

Preparation 187

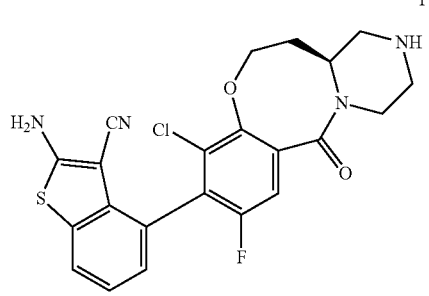

4-[(13aS)-10-Chloro-8-fluoro-6-oxo-2,3,4,12,13,13a-hexahydro-1H-pyrazino[2,1-d][1,5]benzoxazocin-9-yl]-2-amino-benzothiophene-3-carbonitrile To a suspension of tert-butyl (13aS)-9-[2-(tert-butoxycarbonylamino)-3-cyano-benzothiophen-4-yl]-10-chloro-8-fluoro-6-oxo-1,3,4,12,13,13a-hexahydropyrazino[2,1-d][1,5]benzoxazocine-2-carboxylate (2.64 g, 4.02 mmol) in DCM (10.0 mL) at 0° C. is added TFA (10 mL) dropwise. The mixture is stirred at ambient temperature for 1 hour. The mixture is concentrated in vacuo, dissolved in EtOAc, and concentrated in vacuo again. This procedure is repeated once more. The resulting residue is purified by silica gel flash column chromatography, eluting first with 0-80% (10% MeOH in DCM)/DCM, and second with 0-100% [10% (7N $NH_3$ in MeOH) in DCM]/DCM to give the title compound (1.58 g, 86%). ES/MS m/z ($^{35}Cl/^{37}Cl$) 457.0/459.0 [M+H]$^+$.

TABLE 20

Compounds synthesized in a manner essentially analogous to that of Preparation 187

| Preparation | Structure | Compound Name | ES/MS m/z (M + H) |
|---|---|---|---|
| 188 | 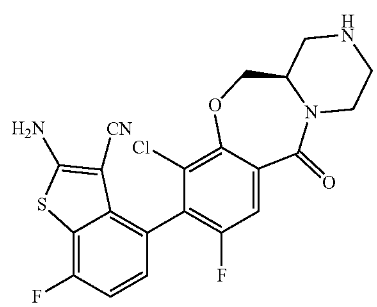 [SMILES: N#Cc1c(N)sc2c(F)ccc(-c3c(F)cc4c(c3Cl)OC[C@H]3CNCCN3C4=O)c12] | 4-[(4aR)-9-Chloro-7-fluoro-11-oxo-1,2,3,4,4a,5-hexahydropyrazino[2,1-c][1,4]benzoxazepine-8-yl]-2-amino-7-fluoro-benzothiophene-3-carbonitrile | 461.0/463.0 |
| 189 | 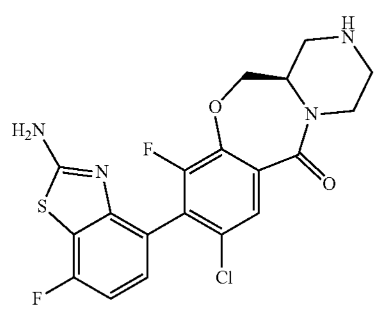 [SMILES: Nc1nc2c(-c3c(Cl)cc4c(c3F)OC[C@H]3CNCCN3C4=O)ccc(F)c2s1] | (4aR)-8-(2-Amino-7-fluoro-1,3-benzothiazol-4-yl)-9-chloro-7-fluoro-1,2,3,4,4a,5-hexahydropyrazino[2,1-c][1,4]benzoxazepine-11-one | 437.0/439.0 |
| 190 | 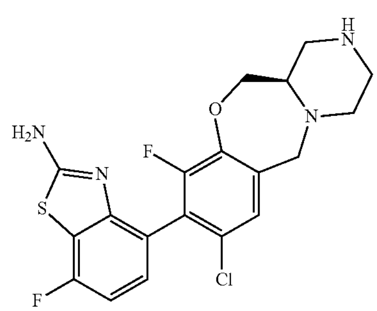 [SMILES: Nc1nc2c(-c3c(Cl)cc4c(c3F)OC[C@H]3CNCCN3C4)ccc(F)c2s1] | 4-[(4aR)-9-Chloro-7-fluoro-2,3,4,4a,5,11-hexahydro-1H-pyrazino[2,1-c][1,4]benzoxazepine-8-yl]-7-fluoro-1,3-benzothiazol-2-amine | 423.0/425.0 |

TABLE 20-continued

Compounds synthesized in a manner essentially analogous to that of
Preparation 187

| Preparation | Structure | Compound Name | ES/MS m/z (M + H) |
|---|---|---|---|
| 191 | 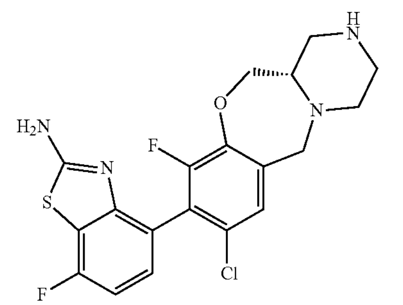 [SMILES: Nc1nc2c(-c3c(Cl)cc4c(c3F)OC[C@@H]3CNCCN3C4)ccc(F)c2s1] | 4-[(4aS)-9-Chloro-7-fluoro-2,3,4,4a,5,11-hexahydro-1H-pyrazino[2,1-c][1,4]benzoxazepine-8-yl]-7-fluoro-1,3-benzothiazol-2-amine | 423.0/425.0 |
| 192 | 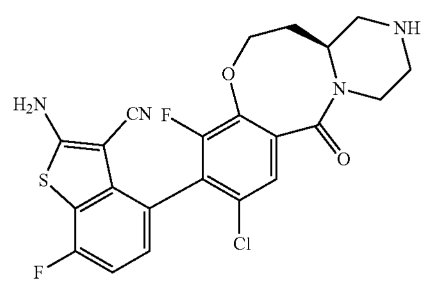 [SMILES: N#Cc1c(N)sc2c(F)ccc(-c3c(Cl)cc4c(c3F)OCC[C@H]3CNCCN3C4=O)c12] | 4-[(13aS)-8-Chloro-10-fluoro-6-oxo-2,3,4,12,13,13a-hexahydro-1H-pyrazino[2,1-d][1,5]benzoxazocin-9-yl]-2-amino-7-fluoro-benzothiophene-3-carbonitrile | 475.0/477.0 |
| 193 | 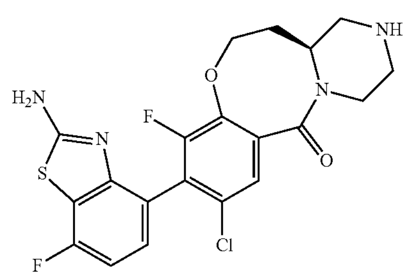 [SMILES: Nc1nc2c(-c3c(Cl)cc4c(c3F)OCC[C@H]3CNCCN3C4=O)ccc(F)c2s1] | (13aS)-9-(2-Amino-7-fluoro-1,3-benzothiazol-4-yl)-8-chloro-10-fluoro-2,3,4,12,13,13a-hexahydro-1H-pyrazino[2,1-d][1,5]benzoxazocin-6-one | 451.0/453.0 |
| 194 | 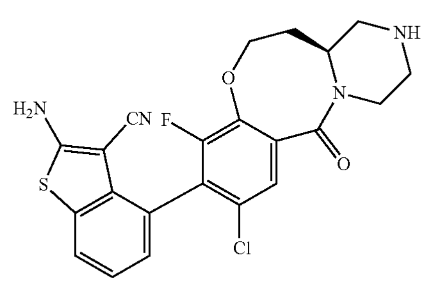 [SMILES: N#Cc1c(N)sc2cccc(-c3c(Cl)cc4c(c3F)OCC[C@H]3CNCCN3C4=O)c12] | 4-[(13aS)-8-Chloro-10-fluoro-6-oxo-2,3,4,12,13,13a-hexahydro-1H-pyrazino[2,1-d][1,5]benzoxazocin-9-yl]-2-amino-benzothiophene-3-carbonitrile | 457.0/459.0 |
| 195 | 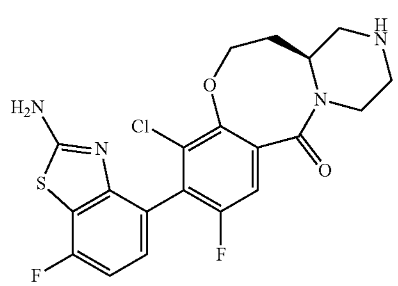 | (13aS)-9-(2-Amino-7-fluoro-1,3-benzothiazol-4-yl)-10-chloro-8-fluoro-2,3,4,12,13,13a-hexahydro-1H-pyrazino[2,1-d][1,5]benzoxazocin-6-one | 451.0/453.0 |

TABLE 20-continued

Compounds synthesized in a manner essentially analogous to that of Preparation 187

| Preparation | Structure | Compound Name | ES/MS m/z (M + H) |
|---|---|---|---|
| 196 | 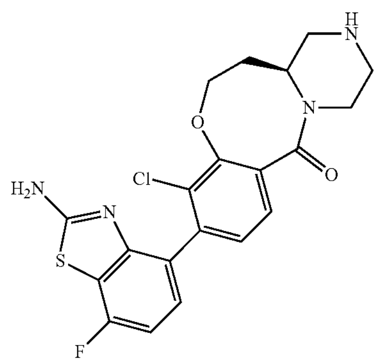 [SMILES: Nc1nc2c(-c3ccc4c(c3Cl)OCC[C@H]3CNCCN3C4=O)ccc(F)c2s1] | (13aS)-9-(2-Amino-7-fluoro-1,3-benzothiazol-4-yl)-10-chloro-2,3,4,12,13,13a-hexahydro-1H-pyrazino[2,1-d][1,5]benzoxazocin-6-one | 433.0/435.0 |
| 197 | 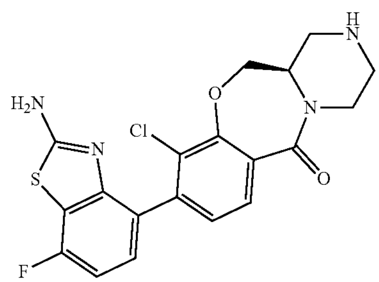 [SMILES: Nc1nc2c(-c3ccc4c(c3Cl)OC[C@H]3CNCCN3C4=O)ccc(F)c2s1] | (4aR)-8-(2-Amino-7-fluoro-1,3-benzothiazol-4-yl)-7-chloro-1,2,3,4,4a,5-hexahydropyrazino[2,1-c][1,4]benzoxazepine-11-one | 419.0/421.0 |
| 198 | 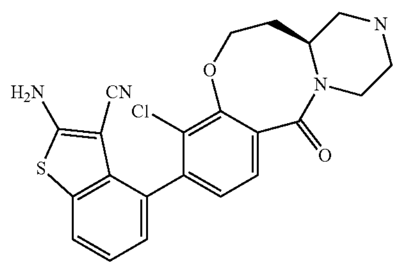 [SMILES: N#Cc1c(N)sc2cccc(-c3ccc4c(c3Cl)OCC[C@H]3CNCCN3C4=O)c12] | 4-[(13aS)-10-Chloro-6-oxo-2,3,4,12,13,13a-hexahydro-1H-pyrazino[2,1-d][1,5]benzoxazocin-9-yl]-2-amino-benzothiophene-3-carbonitrile | 439.0/441.0 |
| 199 | 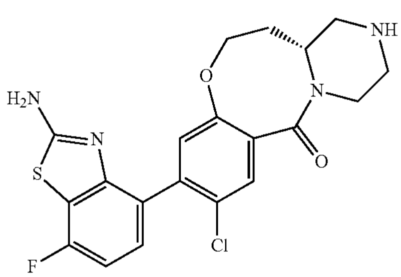 [SMILES: Nc1nc2c(-c3cc4c(cc3Cl)C(=O)N3CCNC[C@H]3CCO4)ccc(F)c2s1] | (13aR)-9-(2-Amino-7-fluoro-1,3-benzothiazol-4-yl)-8-chloro-2,3,4,12,13,13a-hexahydro-1H-pyrazino[2,1-d][1,5]benzoxazocin-6-one | 433.0/435.0 |
| 200 | 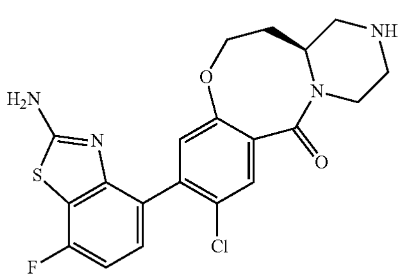 [SMILES: Nc1nc2c(-c3cc4c(cc3Cl)C(=O)N3CCNC[C@@H]3CCO4)ccc(F)c2s1] | (13aS)-9-(2-Amino-7-fluoro-1,3-benzothiazol-4-yl)-8-chloro-2,3,4,12,13,13a-hexahydro-1H-pyrazino[2,1-d][1,5]benzoxazocin-6-one | 432.9/435.0 |

TABLE 20-continued

Compounds synthesized in a manner essentially analogous to that of Preparation 187

| Preparation | Structure | Compound Name | ES/MS m/z (M + H) |
|---|---|---|---|
| 201 | 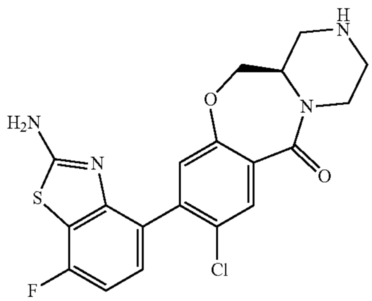 [SMILES: Nc1nc2c(-c3cc4c(cc3Cl)C(=O)N3CCNC[C@@H]3CO4)ccc(F)c2s1] | (4aR)-8-(2-Amino-7-fluoro-1,3-benzothiazol-4-yl)-9-chloro-1,2,3,4,4a,5-hexahydropyrazino[2,1-c][1,4]benzoxazepine-11-one | 418.9/420.9 |
| 202 | 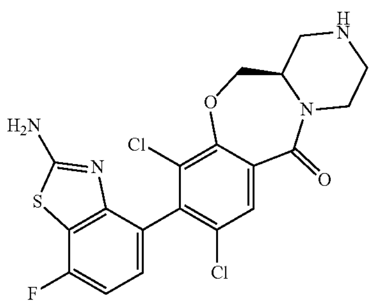 [SMILES: Nc1nc2c(-c3c(Cl)cc4c(c3Cl)OC[C@H]3CNCCN3C4=O)ccc(F)c2s1] | (4aR)-8-(2-Amino-7-fluoro-1,3-benzothiazol-4-yl)-7,9-dichloro-1,2,3,4,4a,5-hexahydropyrazino[2,1-c][1,4]benzoxazepine-11-one | 452.8/454.8 |
| 203 | 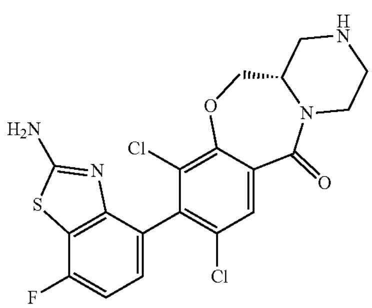 [SMILES: Nc1nc2c(-c3c(Cl)cc4c(c3Cl)OC[C@@H]3CNCCN3C4=O)ccc(F)c2s1] | (4aS)-8-(2-Amino-7-fluoro-1,3-benzothiazol-4-yl)-7,9-dichloro-1,2,3,4,4a,5-hexahydropyrazino[2,1-c][1,4]benzoxazepine-11-one | 452.8/454.8 |
| 204 | 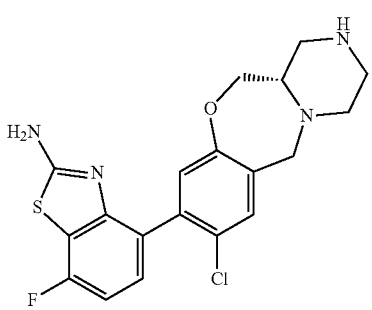 [SMILES: Nc1nc2c(-c3cc4c(cc3Cl)CN3CCNC[C@H]3CO4)ccc(F)c2s1] | 4-[(4aS)-9-Chloro-2,3,4,4a,5,11-hexahydro-1H-pyrazino[2,1-c][1,4]benzoxazepine-8-yl]-7-fluoro-1,3-benzothiazol-2-amine | 405.0/407.0 |
| 205 | 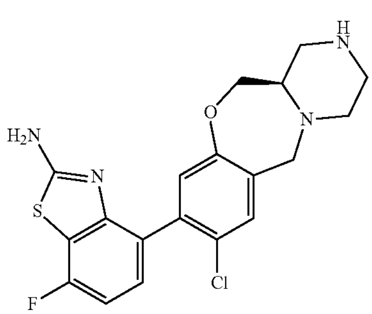 [SMILES: Nc1nc2c(-c3cc4c(cc3Cl)CN3CCNC[C@@H]3CO4)ccc(F)c2s1] | 4-[(4aR)-9-Chloro-2,3,4,4a,5,11-hexahydro-1H-pyrazino[2,1-c][1,4]benzoxazepine-8-yl]-7-fluoro-1,3-benzothiazol-2-amine | 405.0/407.0 |

TABLE 20-continued

Compounds synthesized in a manner essentially analogous to that of Preparation 187

| Preparation | Structure | Compound Name | ES/MS m/z (M + H) |
|---|---|---|---|
| 206 | 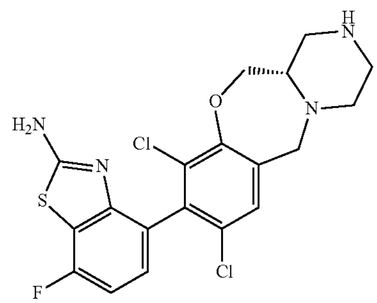 [SMILES: Nc1nc2c(-c3c(Cl)cc4c(c3Cl)OC[C@@H]3CNCCN3C4)ccc(F)c2s1] | 4-[(4aS)-7,9-Dichloro-2,3,4,4a,5,11-hexahydro-1H-pyrazino[2,1-c][1,4]benzoxazepine-8-yl]-7-fluoro-1,3-benzothiazol-2-amine | 438.9/441.0 |
| 207 | 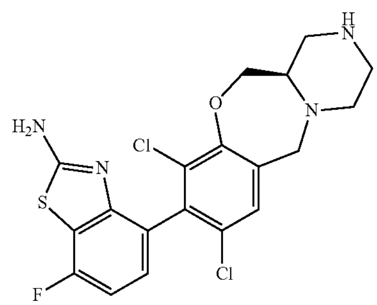 [SMILES: Nc1nc2c(-c3c(Cl)cc4c(c3Cl)OC[C@H]3CNCCN3C4)ccc(F)c2s1] | 4-[(4aR)-7,9-Dichloro-2,3,4,4a,5,11-hexahydro-1H-pyrazino[2,1-c][1,4]benzoxazepine-8-yl]-7-fluoro-1,3-benzothiazol-2-amine | 438.8/440.9 |
| 208 | 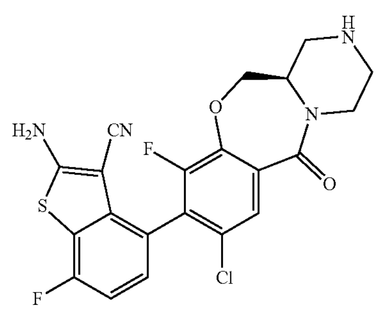 [SMILES: N#Cc1c(N)sc2c(F)ccc(-c3c(Cl)cc4c(c3F)OC[C@H]3CNCCN3C4=O)c12] | 4-[(4aR)-9-Chloro-7-fluoro-11-oxo-1,2,3,4,4a,5-hexahydropyrazino[2,1-c][1,4]benzoxazepine-8-yl]-2-amino-7-fluoro-benzothiophene-3-carbonitrile | 461.0/463.0 |
| 209 | 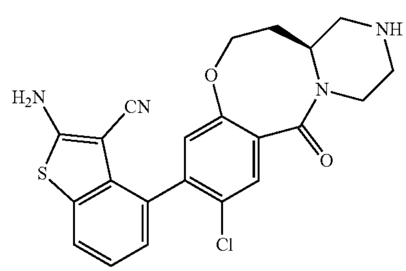 [SMILES: N#Cc1c(N)sc2cccc(-c3cc4c(cc3Cl)C(=O)N3CCNC[C@@H]3CCO4)c12] | 4-[(13aS)-8-Chloro-6-oxo-2,3,4,12,13,13a-hexahydro-1H-pyrazino[2,1-d][1,5]benzoxazocin-9-yl]-2-amino-benzothiophene-3-carbonitrile | 439.0/441.0 |
| 210 | 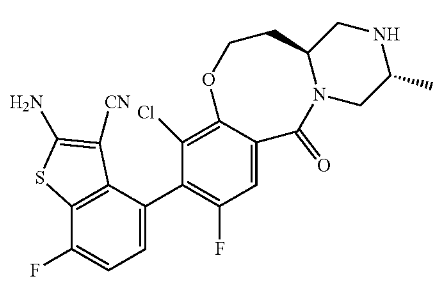 [SMILES: C[C@@H]1CN2C(=O)c3cc(F)c(-c4ccc(F)c5sc(N)c(C#N)c45)c(Cl)c3OCC[C@H]2CN1] | 4-[(3R,13aS)-10-Chloro-8-fluoro-3-methyl-6-oxo-2,3,4,12,13,13a-hexahydro-1H-pyrazino[2,1-d][1,5]benzoxazocin-9-yl]-2-amino-7-fluoro-benzothiophene-3-carbonitrile | 489.0/491.0 |

TABLE 20-continued

Compounds synthesized in a manner essentially analogous to that of Preparation 187

| Preparation | Structure | Compound Name | ES/MS m/z (M + H) |
|---|---|---|---|
| 211 | 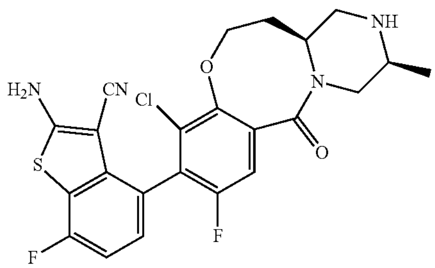 [SMILES: C[C@H]1CN2C(=O)c3cc(F)c(-c4ccc(F)c5sc(N)c(C#N)c45)c(Cl)c3OCC[C@H]2CN1] | 4-[(3S,13aS)-10-Chloro-8-fluoro-3-methyl-6-oxo-2,3,4,12,13,13a-hexahydro-1H-pyrazino[2,1-d][1,5]benzoxazocin-9-yl]-2-amino-7-fluoro-benzothiophene-3-carbonitrile | 489.2/491.2 |
| 212 | 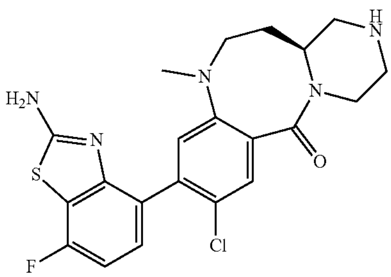 [SMILES: CN1CC[C@H]2CNCCN2C(=O)c2cc(Cl)c(-c3ccc(F)c4sc(N)nc34)cc21] | (13aS)-9-(2-Amino-7-fluoro-1,3-benzothiazol-4-yl)-8-chloro-11-methyl-2,3,4,12,13,13a-hexahydro-1H-pyrazino[2,1-d][1,5]benzodiazocin-6-one | 446.0/448.0 |
| 213 | 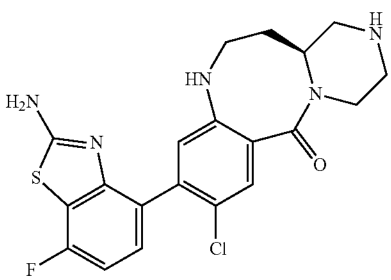 [SMILES: Nc1nc2c(-c3cc4c(cc3Cl)C(=O)N3CCNC[C@@H]3CCN4)ccc(F)c2s1] | (13aS)-9-(2-Amino-7-fluoro-1,3-benzothiazol-4-yl)-8-chloro-1,2,3,4,11,12,13,13a-octahydropyrazino[2,1-d][1,5]benzodiazocin-6-one | 432.0/434.0 |
| 214 | 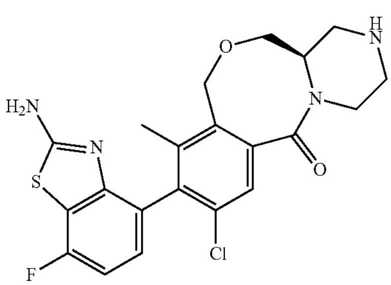 [SMILES: Cc1c2c(cc(Cl)c1-c1ccc(F)c3sc(N)nc13)C(=O)N1CCNC[C@@H]1COC2] | (13aR)-9-(2-Amino-7-fluoro-1,3-benzothiazol-4-yl)-8-chloro-10-methyl-2,3,4,11,13,13a-hexahydro-1H-pyrazino[2,1-d][2,5]benzoxazocin-6-one | 447.2/449.2 |
| 215 | 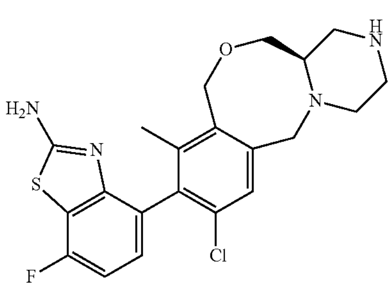 [SMILES: Cc1c2c(cc(Cl)c1-c1ccc(F)c3sc(N)nc13)CN1CCNC[C@@H]1COC2] | 4-[(13aR)-8-Chloro-10-methyl-1,2,3,4,6,11,13,13a-octahydropyrazino[2,1-d][2,5]benzoxazocin-9-yl]-7-fluoro-1,3-benzothiazol-2-amine | 433.2/435.2 |

TABLE 20-continued

Compounds synthesized in a manner essentially analogous to that of Preparation 187

| Preparation | Structure | Compound Name | ES/MS m/z (M + H) |
|---|---|---|---|
| 216 | 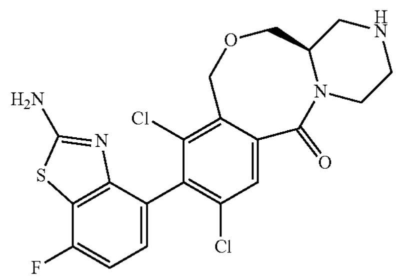 [SMILES: Nc1nc2c(-c3c(Cl)cc4c(c3Cl)COC[C@H]3CNCCN3C4=O)ccc(F)c2s1] | (13aR)-9-(2-Amino-7-fluoro-1,3-benzothiazol-4-yl)-8,10-dichloro-2,3,4,11,13,13a-hexahydro-1H-pyrazino[2,1-d][2,5]benzoxazocin-6-one | 467.2/469.2 |
| 217 | 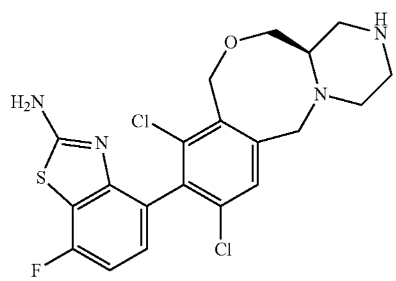 [SMILES: Nc1nc2c(-c3c(Cl)cc4c(c3Cl)COC[C@H]3CNCCN3C4)ccc(F)c2s1] | 4-[(13aR)-8,10-Dichloro-1,2,3,4,6,11,13,13a-octahydropyrazino[2,1-d][2,5]benzoxazocin-9-yl]-7-fluoro-1,3-benzothiazol-2-amine | 453.2/455.2 |
| 218 | 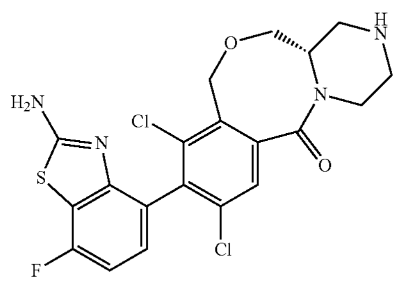 [SMILES: Nc1nc2c(-c3c(Cl)cc4c(c3Cl)COC[C@@H]3CNCCN3C4=O)ccc(F)c2s1] | (13aS)-9-(2-Amino-7-fluoro-1,3-benzothiazol-4-yl)-8,10-dichloro-2,3,4,11,13,13a-hexahydro-1H-pyrazino[2,1-d][2,5]benzoxazocin-6-one | 467.2/469.2 |

Preparation 219

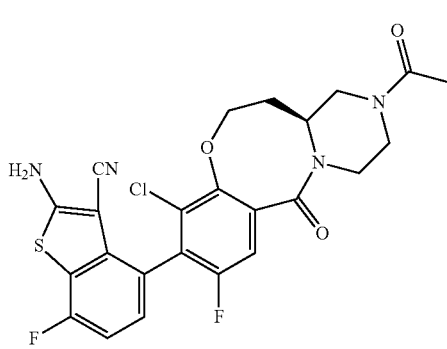

4-[(13aS)-10-Chloro-2-(2-cyanoacetyl)-8-fluoro-6-oxo-1,3,4,12,13,13a-hexahydropyrazino[2,1-d][1,5]benzoxazocin-9-yl]-2-amino-7-fluoro-benzothiophene-3-carbonitrile Cyanoacetic acid (138 mg, 1.61 mmol), 1-hydroxybenzotriazole (222 mg, 1.61 mmol), DIEA (0.5 mL, 3 mmol), and 1-(3-dimethylaminopropyl)-3-ethylcarbodiimide hydrochloride (306 mg, 1.60 mmol) are added to a suspension of 4-[(13aS)-10-chloro-8-fluoro-6-oxo-2,3,4,12,13,13a-hexahydro-1H-pyrazino[2,1-d][1,5]benzoxazocin-9-yl]-2-amino-7-fluoro-benzothiophene-3-carbonitrile (500 mg, 1.05 mmol) in DCM (10 mL). The reaction mixture is stirred at ambient temperature for 18 hours before diluting with DCM and washing with saturated aqueous ammonium chloride solution and saturated aqueous sodium chloride solution. The organics are dried over sodium sulfate, filtered, and concentrated in vacuo. The residue is dissolved in DCM (5 mL) and a few drops of MeOH then hexane is added to precipitate out the product. The precipitate is filtered to give the title compound as a white solid (410 mg, 72%). ES/MS m/z ($^{35}$Cl/$^{37}$Cl) 542.4/544.4 [M+H]$^+$.

Preparation 220

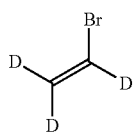

1-Bromo-1,2,2-trideuterio-ethylene 1,2-Dibromoethane-d$_4$ (25.0 g, 130.28 mmol) is added dropwise to a solution of potassium hydroxide (15.19 g, 243.63 mmol) in 95% ethanol-OD (95 mL) and D₂O (5 mL) at 33° C. The mixture was first stirred at 60° C. for 1.5 hours, and then at 63° C. for 1.5 hours to give the title compound as a colorless oil, which was continuously distilled from the reaction during the course of heating and collected in a receiving flask cooled in a dry ice-acetone bath (7.3 g, 50%).

Preparation 221

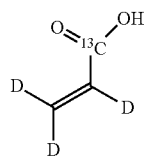

2,3,3-Trideuterioprop-2-enoic acid-¹³C

Magnesium turnings (1.67 g, 69.71 mmol), a crystal of iodine, and anhydrous THF (20 mL) are placed in a flask. Meanwhile a solution of 1-bromo-1,2,2-trideuterio-ethylene (7.3 g, 66.39 mmol) in anhydrous THF (30 mL) is prepared. The mixture containing the magnesium is heated to 50° C. and a portion of the vinyl bromide solution (2 mL) is added. The mixture is heated at 50° C. until the Grignard reaction is initiated and the mixture begins to reflux (65° C.). The remaining vinyl bromide solution in THF is added dropwise at 55 to 65° C. over 1.5 hours. The resulting mixture is heated at 65° C. for 1.5 hours to make sure that the reaction is complete. This freshly prepared (1,2,2-trideuteriovinyl) magnesium bromide solution in THF is cooled to room temperature and used immediately.

Carbon dioxide-¹³C gas is bubbled through anhydrous THF (50 mL) at −65° C. for 5 minutes. The above freshly prepared (1,2,2-trideuteriovinyl)magnesium bromide solution in THE (66.39 mmol) is added dropwise at which time the reaction temperature rises to −20° C. The mixture is warmed to −10° C. and stirred for 10 minutes. Carbon dioxide-¹³C gas is bubbled through the mixture for an additional 2 minutes. The mixture is warmed to ambient temperature and stirred for 10 minutes. Hydroquinone (10 mg) is added, followed by the dropwise addition of 6M sulfuric acid (6.5 mL) to quench the reaction while maintaining the temperature below 20° C. The mixture is diluted with diethyl ether (400 mL) and sodium sulfate (100 g) is added. The mixture is stirred at ambient temperature for 5 minutes, filtered, and concentrated in vacuo at 0 to 5° C. to give the crude product (7.5 g) as a yellow oil. The crude product is purified by a short-path vacuum distillation to give the title compound as a colorless oil (1.2 g, 24%).

Preparation 222

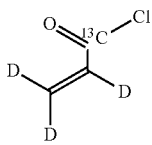

2,3,3-Trideuterioprop-2-enoic acid chloride-¹³C

Oxalyl chloride (0.24 mL, 2.85 mmol) is added to a solution of 2,3,3-trideuterioprop-2-enoic acid-¹³C (0.181 g, 2.38 mmol) and DMF (1 drop) in anhydrous DCM (10 mL) at 0° C. and the mixture is stirred at room temperature for 1 hour. The title compound is used directly in the next step as a solution.

Preparation 223

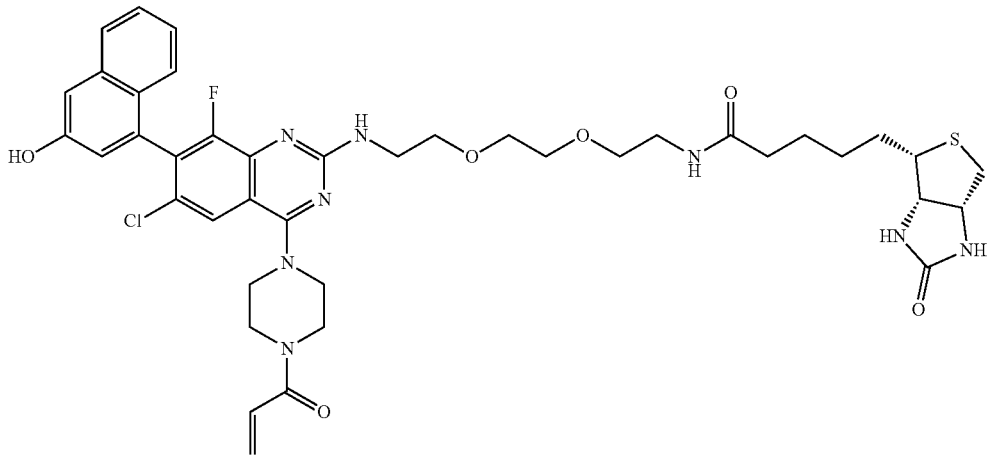

Kras Probe
N-(2-{2-[2-({6-Chloro-8-fluoro-7-(3-hydroxynapthalen-1-yl)-4-[4-(prop-2-enoyl)piperazin-1-yl]quinazolin-2-yl}amino)ethoxy]ethoxy}ethyl)-5-[(3aS,4S,6aR)-2-oxohexahydro-1H-thieno[3,4-d]imidazol-4-yl]pentanamide Step A: tert-Butyl 4-(7-bromo-2,6-dichloro-8-fluoroquinazolin-4-yl)piperazine-1-carboxylate (0.51 g, 1.1 mmol) and IPA (5 mL) are combined in a microwave vessel. DIPEA (0.55 mL, 3.3 mmol) and 5-[(3aS,4S,6aR)-2-oxohexahydro-1H-thieno[3,4-d]imidazol-4-yl]-N-[2-[2-(2-aminoethoxy) ethoxy]ethyl]pentanamide (0.48 g, 1.32 mmol) are added and the mixture is heated to 120° C. in a microwave reactor for six hours. After this time the mixture is diluted with saturated aqueous ammonium chloride solution and 25% IPA in CHCl₃ and the layers are separated. The organic layer is washed with saturated aqueous sodium chloride solution, dried over anhydrous sodium sulfate, filtered, and concentrated in vacuo. The resulting residue is purified by normal phase chromatography, eluting with a 50-100% B in A gradient (A: hexanes, B: 10% MeOH in DCM), to give the tert-butyl 4-{7-bromo-6-chloro-8-fluoro-2-[(2-{2-[2-({5-[(3aS,4 S, 6aR)-2-oxohexahydro-1H-thieno[3,4-d]imidazol-4-yl]pentanoyl}amino) ethoxy]ethoxy}ethyl)amino]quinazolin-4-yl}piperazine-1-carboxylate as a yellow solid (0.68 g, 78%). ES/MS m/z: 819 (M+H).

Step B: tert-Butyl 4-{7-bromo-6-chloro-8-fluoro-2-[(2-{2-[2-({5-[(3aS,4S,6aR)-2-oxohexahydro-1H-thieno[3,4-d]imidazol-4-yl]pentanoyl}amino)ethoxy]ethoxy}ethyl)amino]quinazolin-4-yl}piperazine-1-carboxylate (0.30 g, 0.37 mmol), 1,4-dioxane (4 mL) and water (0.75 mL) are combined. Potassium carbonate (0.24 g, 1.11 mmol), 4-(4,4,5,5-tetramethyl-1,3,2-dioxaborolan-2-yl)naphthalen-2-ol (0.20 g, 0.74 mmol), and tetrakis(triphenylphosphine) palladium(0) (0.085 g, 0.074 mmol) are added and the mixture is stirred at 85° C. under nitrogen for 12 hours. After this time, the mixture is cooled to ambient temperature and filtered to remove solids. The filtrate is diluted with saturated aqueous ammonium chloride solution and EtOAc and the layers are separated. The organic layer is washed with saturated aqueous sodium chloride solution, dried over anhydrous sodium sulfate, filtered, and concentrated in vacuo. The resulting residue is purified by normal phase chromatography, eluting with a 90-100% B in A gradient (A: hexanes, B: 10% MeOH in DCM), to give tert-butyl 4-{6-chloro-8-fluoro-7-(3-hydroxynaphthalen-1-yl)-2-[(2-{2-[2-({5-[(3aS,4S,6aR)-2-oxohexahydro-1H-thieno[3,4-d]imidazol-4-yl]pentanoyl}amino)ethoxy]ethoxy}ethyl)amino]quinazolin-4-yl}piperazine-1-carboxylate as a yellow solid (0.31 g, 96%). ES/MS m/z: 881 (M+H).

Step C: A solution of tert-butyl 4-{6-chloro-8-fluoro-7-(3-hydroxynaphthalen-1-yl)-2-[(2-{2-[2-({5-[(3aS,4 S,6aR)-2-oxohexahydro-1H-thieno[3,4-d]imidazol-4-yl]pentanoyl}amino)ethoxy]ethoxy}ethyl)amino]quinazolin-4-yl}piperazine-1-carboxylate (0.31 g, 0.35 mmol) in MeOH (4 mL) is cooled to 0° C. HCl (3 M in MeOH, 6 mL, 17.5 mmol) is added and the mixture is stirred at 0° C. for 30 minutes before allowing to warm to ambient temperature. After ~18 hours, the reaction mixture is concentrated in vacuo. The residue is diluted with DCM and concentrated in vacuo again. The resulting residue is diluted with hexanes and stirred at ambient temperature for two hours. The resulting solid is filtered and dried under vacuum to give N-{2-[2-(2-{[6-chloro-8-fluoro-7-(3-hydroxynaphthalen-1-yl)-4-(piperazin-1-yl)quinazolin-2-yl]amino}ethoxy)ethoxy]ethyl}-5-[(3 aS,4 S,6aR)-2-oxohexahydro-1H-thieno[3,4-d]imidazol-4-yl]pentanamide hydrogen chloride. This hydrochloride salt (0.19 g, 0.23 mmol) is neutralized by combining with DIEA (0.16 mL, 0.92 mmol) in DCM (2.5 mL). The mixture is cooled to −78° C. and acryloyl chloride (0.5 M in DCM, 0.4 mL, 0.21 mmol) is added. After 30 minutes, the mixture is warmed to ambient temperature. After one hour, the mixture is diluted with MeOH (1 mL) and concentrated in vacuo. The resulting residue is purified by reverse phase chromatography, eluting with a 35-60% B in A gradient (A: 10 mM aqueous NH₄HCO₃ with 5% MeOH; B: ACN), to give the title compound as a white solid (0.027 g, 14%). ES/MS m/z: 835 (M+H).

Example 1

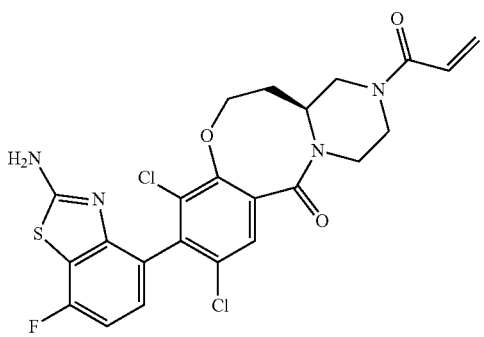

Example 1

(13aS)-9-(2-Amino-7-fluoro-1,3-benzothiazol-4-yl)-8,10-dichloro-2-prop-2-enoyl-1,3,4,12,13,13a-hexahydropyrazino[2,1-d][1,5]benzoxazocin-6-one (13aS)-9-(2-Amino-7-fluoro-1,3-benzothiazol-4-yl)-8,10-dichloro-2,3,4,12,13,13a-hexahydro-1H-pyrazino[2,1-d][1,5]benzoxazocin-6-one (500 mg, 1.070 mmol) is dissolved in DCM (5 mL) and TEA (0.75 mL, 5.4 mmol). The mixture is cooled to −78° C. and then acryloyl chloride (0.085 mL, 1.0 mmol) is added and the mixture is stirred at −78° C. After 5 minutes a few drops of isopropyl alcohol are added at −78° C. and then the mixture is concentrated in vacuo and submitted to reversed phase chromatography to give a mixture of two atropisomers. The mixture of atropisomers is separated using Chiralpak® IC, 4.6×150 mm, 40% EtOH/CO₂, 5 mL/min, 225 nm. The second compound off the column is identified as the active atropisomer (165 mg, 55%). ES/MS m/z ($^{35}$Cl/$^{37}$Cl) 521/523 [M+H]⁺ (>98% e.e.). The less active atropisomer is first off the column (133 mg, 44%). ES/MS m/z ($^{35}$Cl/$^{37}$Cl) 521/523 [M+H]⁺ (>98% e.e.).

TABLE 21

Compounds synthesized in a manner essentially analogous to that of Example 1

| Example | Structure | Compound Name | ES/MS m/z (M + H) |
| --- | --- | --- | --- |
| 2 | (structure shown) | (4aR)-8-(2-Amino-7-fluoro-1,3-benzothiazol-4-yl)-7-chloro-9-fluoro-3-prop-2-enoyl-2,4,4a,5-tetrahydro-1H-pyrazino[2,1-c][1,4]benzoxazepine-11-one | 491.2/493.2 |

TABLE 21-continued

Compounds synthesized in a manner essentially analogous to that of Example 1

| Example | Structure | Compound Name | ES/MS m/z (M + H) |
|---|---|---|---|
| 3 | 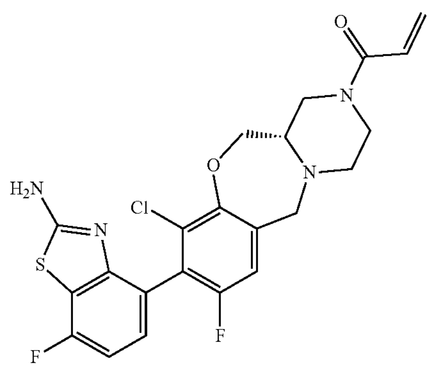 [SMILES: C=CC(=O)N1CCN2Cc3cc(F)c(-c4ccc(F)c5sc(N)nc45)c(Cl)c3OC[C@@H]2C1] | 1-[(4aS)-8-(2-Amino-7-fluoro-1,3-benzothiazol-4-yl)-7-chloro-9-fluoro-1,2,4,4a,5,11-hexahydropyrazino[2,1-c][1,4]benzoxazepine-3-yl]prop-2-en-1-one | 477.2/479.2 |
| 4 | 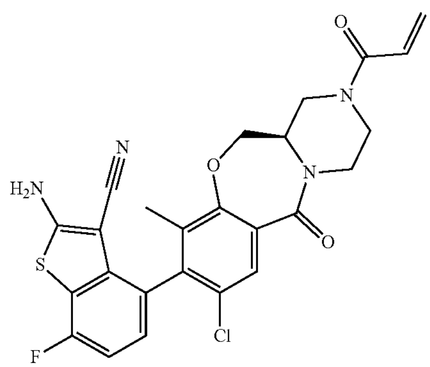 [SMILES: C=CC(=O)N1CCN2C(=O)c3cc(Cl)c(-c4ccc(F)c5sc(N)c(C#N)c45)c(C)c3OC[C@H]2C1] | 4-[(4aR)-9-Chloro-7-methyl-11-oxo-3-prop-2-enoyl-2,4,4a,5-tetrahydro-1H-pyrazino[2,1-c][1,4]benzoxazepine-8-yl]-2-amino-7-fluoro-benzothiophene-3-carbonitrile | 511.0/513.0 |
| 5 | 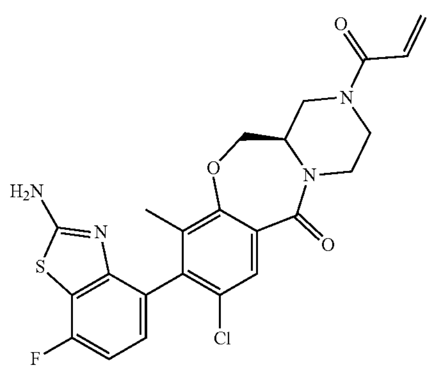 [SMILES: C=CC(=O)N1CCN2C(=O)c3cc(Cl)c(-c4ccc(F)c5sc(N)nc45)c(C)c3OC[C@H]2C1] | (4aR)-8-(2-Amino-7-fluoro-1,3-benzothiazol-4-yl)-9-chloro-7-methyl-3-prop-2-enoyl-2,4,4a,5-tetrahydro-1H-pyrazino[2,1-c][1,4]benzoxazepine-11-one | 487.0/489.0 |
| 6 | 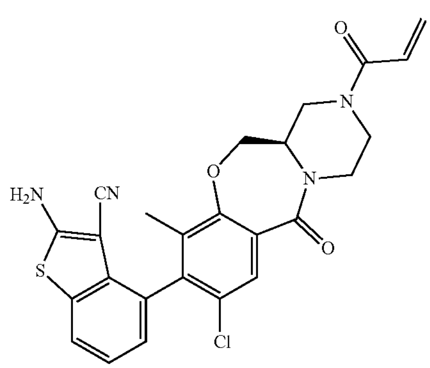 [SMILES: C=CC(=O)N1CCN2C(=O)c3cc(Cl)c(-c4cccc5sc(N)c(C#N)c45)c(C)c3OC[C@H]2C1] | (4aR)-8-(2-Amino-3-methyl-benzothiophen-4-yl)-7-chloro-9-methyl-3-prop-2-enoyl-2,4,4a,5-tetrahydro-1H-pyrazino[2,1-c][1,4]benzoxazepine-11-one | 493.0/495.0 |

TABLE 21-continued

Compounds synthesized in a manner essentially analogous to that of Example 1

| Example | Structure | Compound Name | ES/MS m/z (M + H) |
|---|---|---|---|
| 7 | 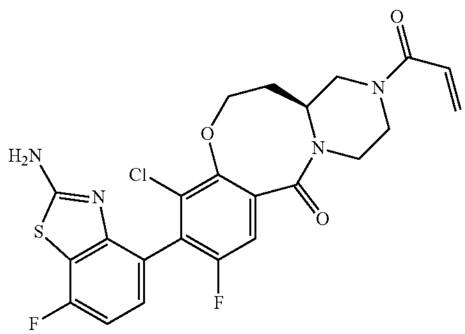 [SMILES: C=CC(=O)N1CCN2C(=O)c3cc(F)c(-c4ccc(F)c5sc(N)nc45)c(Cl)c3OCC[C@H]2C1] | (13aS)-9-(2-Amino-7-fluoro-1,3-benzothiazol-4-yl)-10-chloro-8-fluoro-2-prop-2-enoyl-1,3,4,12,13,13a-hexahydropyrazino[2,1-d][1,5]benzoxazocin-6-one | 505.2/507.2 |
| 8 | 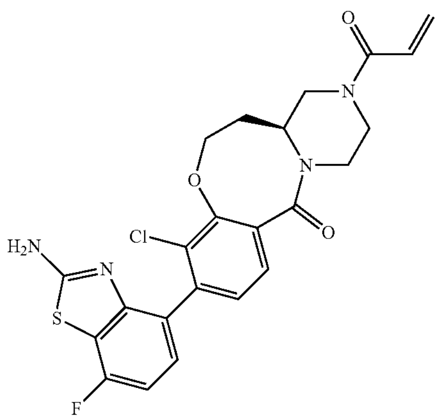 [SMILES: C=CC(=O)N1CCN2C(=O)c3ccc(-c4ccc(F)c5sc(N)nc45)c(Cl)c3OCC[C@H]2C1] | (13aS)-9-(2-Amino-7-fluoro-1,3-benzothiazol-4-yl)-10-chloro-2-prop-2-enoyl-1,3,4,12,13,13a-hexahydropyrazino[2,1-d][1,5]benzoxazocin-6-one | 487.0/489.0 |
| 9 | 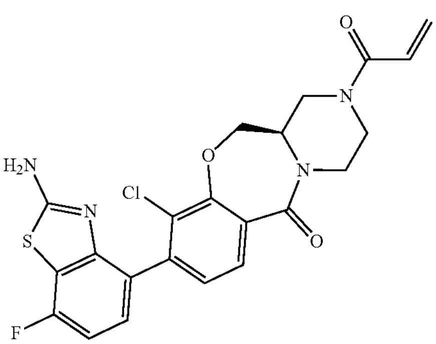 [SMILES: C=CC(=O)N1CCN2C(=O)c3ccc(-c4ccc(F)c5sc(N)nc45)c(Cl)c3OC[C@H]2C1] | (4aR)-8-(2-Amino-7-fluoro-1,3-benzothiazol-4-yl)-7-chloro-3-prop-2-enoyl-2,4,4a,5-tetrahydro-1H-pyrazino[2,1-c][1,4]benzoxazepine-11-one | 473.0/475.0 |
| 10 | 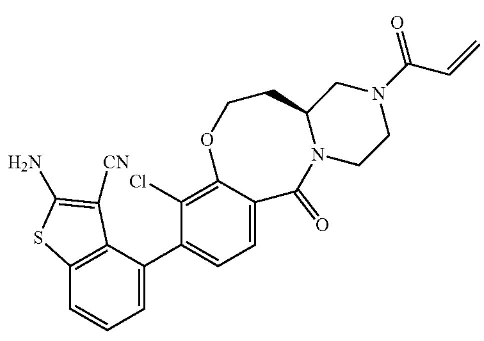 [SMILES: C=CC(=O)N1CCN2C(=O)c3ccc(-c4cccc5sc(N)c(C#N)c45)c(Cl)c3OCC[C@H]2C1] | 4-[(13aS)-10-Chloro-6-oxo-2-prop-2-enoyl-1,3,4,12,13,13a-hexahydropyrazino[2,1-d][1,5]benzoxazocin-9-yl]-2-amino-benzothiophene-3-carbonitrile | 493.0/495.0 |

TABLE 21-continued

Compounds synthesized in a manner essentially analogous to that of Example 1

| Example | Structure | Compound Name | ES/MS m/z (M + H) |
|---|---|---|---|
| 11 | 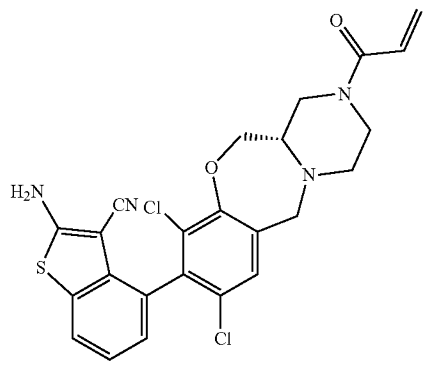 [SMILES: C=CC(=O)N1CCN2Cc3cc(Cl)c(-c4cccc5sc(N)c(C#N)c45)c(Cl)c3OC[C@@H]2C1] | 4-[(4aS)-7,9-Dichloro-3-prop-2-enoyl-1,2,4,4a,5,11-hexahydropyrazino[2,1-c][1,4]benzoxazepine-8-yl]-2-amino-benzothiophene-3-carbonitrile | 499.2/501.2 |
| 12 | 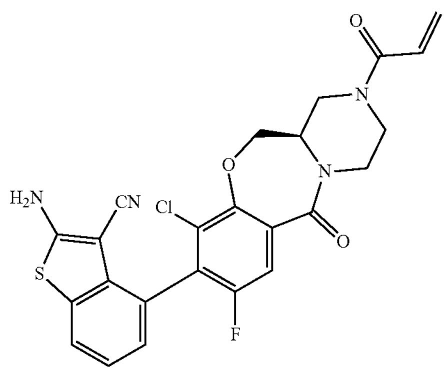 [SMILES: C=CC(=O)N1CCN2C(=O)c3cc(F)c(-c4cccc5sc(N)c(C#N)c45)c(Cl)c3OC[C@H]2C1] | 4-[(4aR)-7-Chloro-9-fluoro-11-oxo-3-prop-2-enoyl-2,4,4a,5-tetrahydro-1H-pyrazino[2,1-c][1,4]benzoxazepine-8-yl]-2-amino-benzothiophene-3-carbonitrile | 497.2/499.2 |
| 13 | 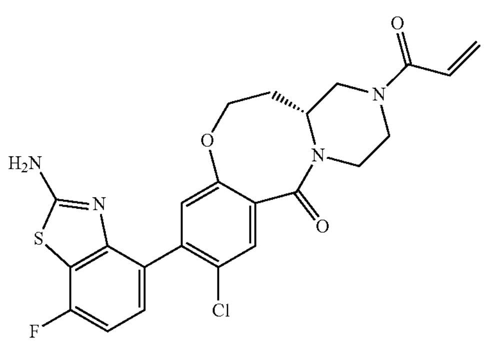 [SMILES: C=CC(=O)N1CCN2C(=O)c3cc(Cl)c(-c4ccc(F)c5sc(N)nc45)cc3OCC[C@@H]2C1] | (13aR)-9-(2-Amino-7-fluoro-1,3-benzothiazol-4-yl)-8-chloro-2-prop-2-enoyl-1,3,4,12,13,13a-hexahydropyrazino[2,1-d][1,5]benzoxazocin-6-one | 487.0/489.0 |
| 14 | 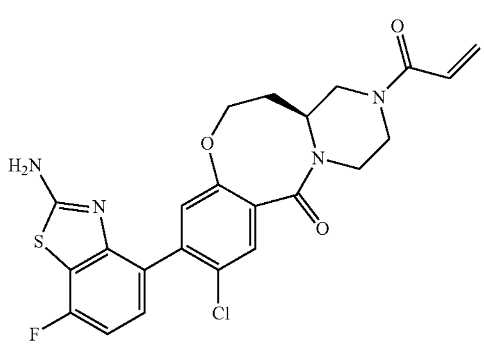 [SMILES: C=CC(=O)N1CCN2C(=O)c3cc(Cl)c(-c4ccc(F)c5sc(N)nc45)cc3OCC[C@H]2C1] | (13aS)-9-(2-Amino-7-fluoro-1,3-benzothiazol-4-yl)-8-chloro-2-prop-2-enoyl-1,3,4,12,13,13a-hexahydropyrazino[2,1-d][1,5]benzoxazocin-6-one | 487.0/489.0 |

TABLE 21-continued

Compounds synthesized in a manner essentially analogous to that of Example 1

| Example | Structure | Compound Name | ES/MS m/z (M + H) |
|---|---|---|---|
| 15 | 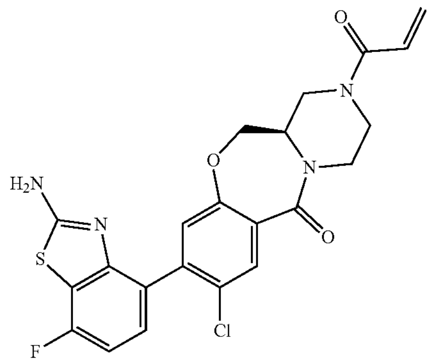 [SMILES: C=CC(=O)N1CCN2C(=O)c3cc(Cl)c(-c4ccc(F)c5sc(N)nc45)cc3OC[C@H]2C1] | (4aR)-8-(2-Amino-7-fluoro-1,3-benzothiazol-4-yl)-9-chloro-3-prop-2-enoyl-2,4,4a,5-tetrahydro-1H-pyrazino[2,1-c][1,4]benzoxazepine-11-one | 473.0/475.0 |
| 16 | 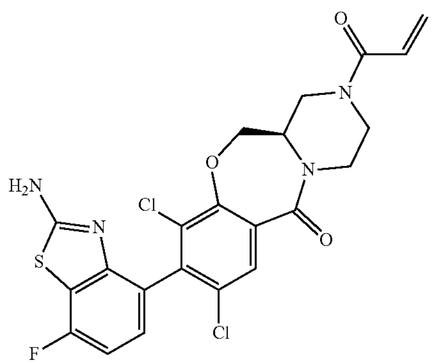 [SMILES: C=CC(=O)N1CCN2C(=O)c3cc(Cl)c(-c4ccc(F)c5sc(N)nc45)c(Cl)c3OC[C@H]2C1] | (4aR)-8-(2-Amino-7-fluoro-1,3-benzothiazol-4-yl)-7,9-dichloro-3-prop-2-enoyl-2,4,4a,5-tetrahydro-1H-pyrazino[2,1-c][1,4]benzoxazepine-11-one | 507.0/509.0 |
| 17 | 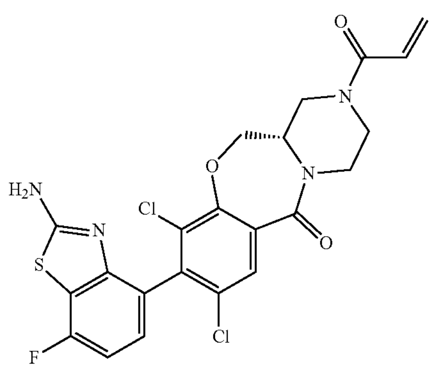 [SMILES: C=CC(=O)N1CCN2C(=O)c3cc(Cl)c(-c4ccc(F)c5sc(N)nc45)c(Cl)c3OC[C@@H]2C1] | (4aS)-8-(2-Amino-7-fluoro-1,3-benzothiazol-4-yl)-7,9-dichloro-3-prop-2-enoyl-2,4,4a,5-tetrahydro-1H-pyrazino[2,1-c][1,4]benzoxazepine-11-one | 506.9/508.8 |
| 18 | 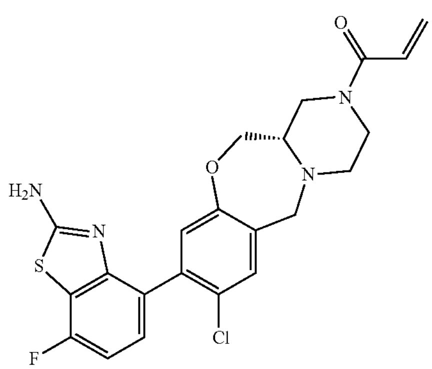 [SMILES: C=CC(=O)N1CCN2Cc3cc(Cl)c(-c4ccc(F)c5sc(N)nc45)cc3OC[C@@H]2C1] | 1-[(4aS)-8-(2-Amino-7-fluoro-1,3-benzothiazol-4-yl)-9-chloro-1,2,4,4a,5,11-hexahydropyrazino[2,1-c][1,4]benzoxazepine-3-yl]prop-2-en-1-one | 459.0/461.0 |

TABLE 21-continued

Compounds synthesized in a manner essentially analogous to that of Example 1

| Example | Structure | Compound Name | ES/MS m/z (M + H) |
|---|---|---|---|
| 19 | 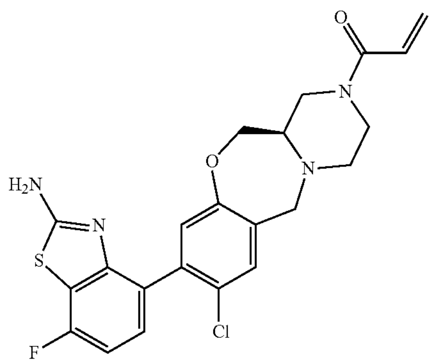 [SMILES: C=CC(=O)N1CCN2Cc3cc(Cl)c(-c4ccc(F)c5sc(N)nc45)cc3OC[C@H]2C1] | 1-[(4aR)-8-(2-Amino-7-fluoro-1,3-benzothiazol-4-yl)-9-chloro-1,2,4,4a,5,11-hexahydropyrazino[2,1-c][1,4]benzoxazepine-3-yl]prop-2-en-1-one | 459.0/461.0 |
| 20 | 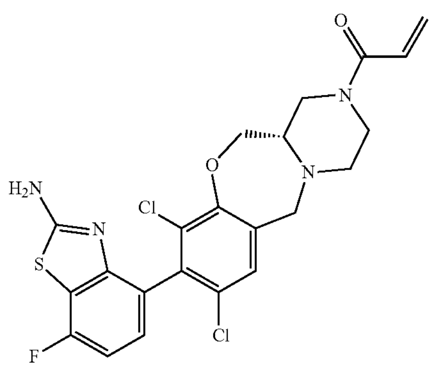 [SMILES: C=CC(=O)N1CCN2Cc3cc(Cl)c(-c4ccc(F)c5sc(N)nc45)c(Cl)c3OC[C@@H]2C1] | 1-[(4aS)-8-(2-Amino-7-fluoro-1,3-benzothiazol-4-yl)-7,9-dichloro-1,2,4,4a,5,11-hexahydropyrazino[2,1-c][1,4]benzoxazepine-3-yl]prop-2-en-1-one | 493.0/495.0 |
| 21 | 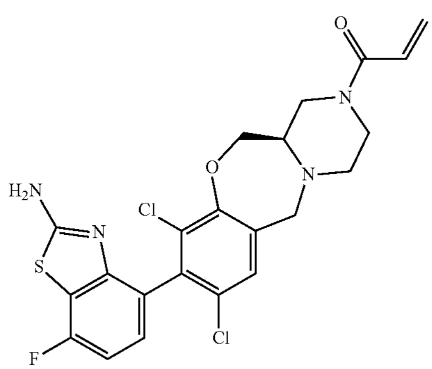 [SMILES: C=CC(=O)N1CCN2Cc3cc(Cl)c(-c4ccc(F)c5sc(N)nc45)c(Cl)c3OC[C@H]2C1] | 1-[(4aR)-8-(2-Amino-7-fluoro-1,3-benzothiazol-4-yl)-7,9-dichloro-1,2,4,4a,5,11-hexahydropyrazino[2,1-c][1,4]benzoxazepine-3-yl]prop-2-en-1-one | 493.0/495.0 |
| 22 | 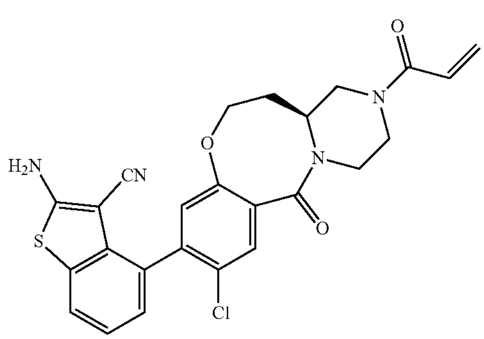 [SMILES: C=CC(=O)N1CCN2C(=O)c3cc(Cl)c(-c4cccc5sc(N)c(C#N)c45)cc3OCC[C@H]2C1] | 4-[(13aS)-8-Chloro-6-oxo-2,3,4,12,13,13a-hexahydro-1H-pyrazino[2,1-d][1,5]benzoxazocin-9-yl]-2-amino-benzothiophene-3-carbonitrile | 493.0/495.0 |

TABLE 21-continued

Compounds synthesized in a manner essentially analogous to that of Example 1

| Example | Structure | Compound Name | ES/MS m/z (M + H) |
|---|---|---|---|
| 23 | 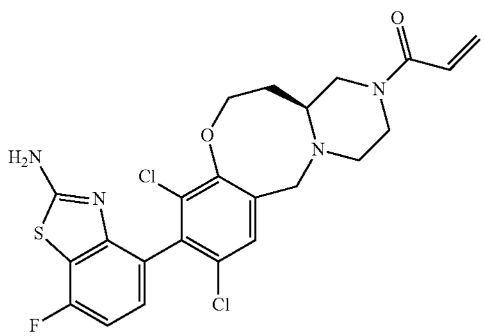 [SMILES: C=CC(=O)N1CCN2Cc3cc(Cl)c(-c4ccc(F)c5sc(N)nc45)c(Cl)c3OCC[C@H]2C1] | 1-[(13aS)-9-(2-Amino-7-fluoro-1,3-benzothiazol-4-yl)-8,10-dichloro-3,4,6,12,13,13a-hexahydro-1H-pyrazino[2,1-d][1,5]benzoxazocin-2-yl]prop-2-en-1-one | 507.0/509.0 |
| 24 | 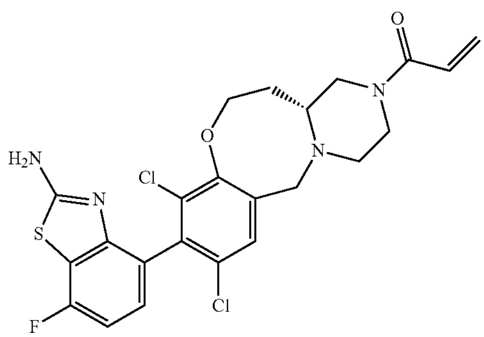 [SMILES: C=CC(=O)N1CCN2Cc3cc(Cl)c(-c4ccc(F)c5sc(N)nc45)c(Cl)c3OCC[C@@H]2C1] | 1-[(13aR)-9-(2-Amino-7-fluoro-1,3-benzothiazol-4-yl)-8,10-dichloro-3,4,6,12,13,13a-hexahydro-1H-pyrazino[2,1-d][1,5]benzoxazocin-2-yl]prop-2-en-1-one | 507.0/509.0 |
| 25 | 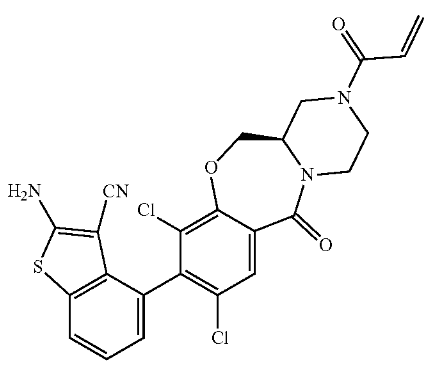 [SMILES: C=CC(=O)N1CCN2C(=O)c3cc(Cl)c(-c4cccc5sc(N)c(C#N)c45)c(Cl)c3OC[C@H]2C1] | 4-[(4aR)-7,9-Dichloro-11-oxo-3-prop-2-enoyl-2,4,4a,5-tetrahydro-1H-pyrazino[2,1-c][1,4]benzoxazepine-8-yl]-2-amino-benzothiophene-3-carbonitrile | 513.0/515.0 |
| 26 | 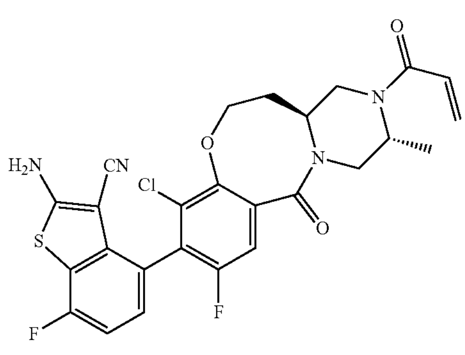 [SMILES: C=CC(=O)N1C[C@@H]2CCOc3c(cc(F)c(-c4ccc(F)c5sc(N)c(C#N)c45)c3Cl)C(=O)N2C[C@H]1C] | 4-[(3R,13aS)-10-Chloro-8-fluoro-3-methyl-6-oxo-2-prop-2-enoyl-1,3,4,12,13,13a-hexahydropyrazino[2,1-d][1,5]benzoxazocin-9-yl]-2-amino-7-fluoro-benzothiophene-3-carbonitrile | 543.0/545.0 |

TABLE 21-continued

Compounds synthesized in a manner essentially analogous to that of Example 1

| Example | Structure | Compound Name | ES/MS m/z (M + H) |
|---|---|---|---|
| 27 | 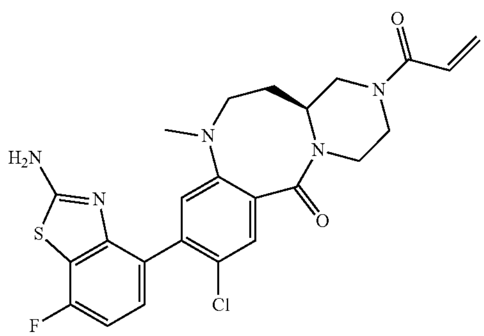 [SMILES: C=CC(=O)N1CCN2C(=O)c3cc(Cl)c(-c4ccc(F)c5sc(N)nc45)cc3N(C)CC[C@H]2C1] | (13aS)-9-(2-Amino-7-fluoro-1,3-benzothiazol-4-yl)-8-chloro-11-methyl-2-prop-2-enoyl-1,3,4,12,13,13a-hexahydropyrazino[2,1-d][1,5]benzodiazocin-6-one | 500.0/502.0 |
| 28 | 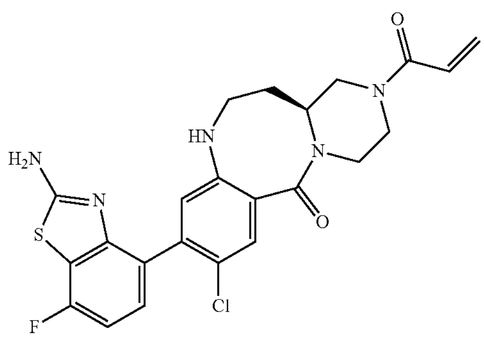 [SMILES: C=CC(=O)N1CCN2C(=O)c3cc(Cl)c(-c4ccc(F)c5sc(N)nc45)cc3NCC[C@H]2C1] | (13aS)-9-(2-Amino-7-fluoro-1,3-benzothiazol-4-yl)-8-chloro-2-prop-2-enoyl-3,4,11,12,13,13a-hexahydro-1H-pyrazino[2,1-d][1,5]benzodiazocin-6-one | 486.0/488.0 |
| 29 | 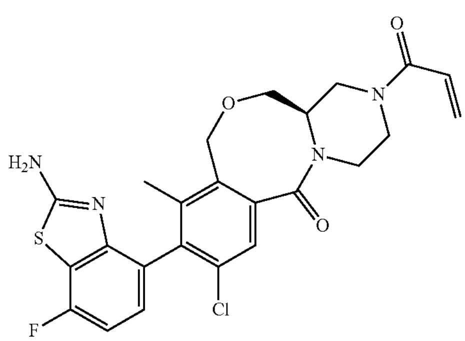 [SMILES: C=CC(=O)N1CCN2C(=O)c3cc(Cl)c(-c4ccc(F)c5sc(N)nc45)c(C)c3COC[C@H]2C1] | (13aR)-9-(2-Amino-7-fluoro-1,3-benzothiazol-4-yl)-8-chloro-10-methyl-2-prop-2-enoyl-1,3,4,11,13,13a-hexahydropyrazino[2,1-d][2,5]benzoxazocin-6-one | 501.0/503.0 |
| 30 | 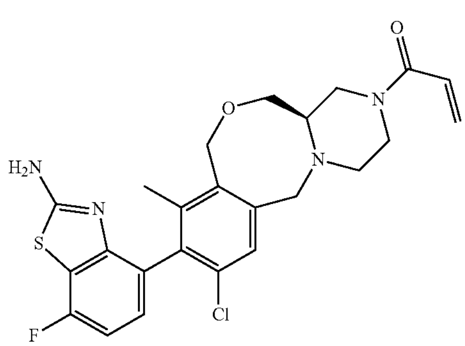 [SMILES: C=CC(=O)N1CCN2Cc3cc(Cl)c(-c4ccc(F)c5sc(N)nc45)c(C)c3COC[C@H]2C1] | 1-[(13aR)-9-(2-Amino-7-fluoro-1,3-benzothiazol-4-yl)-8-chloro-10-methyl-3,4,6,11,13,13a-hexahydro-1H-pyrazino[2,1-d][2,5]benzoxazocin-2-yl]prop-2-en-1-one | 487.0/489.0 |

TABLE 21-continued

Compounds synthesized in a manner essentially analogous to that of Example 1

| Example | Structure | Compound Name | ES/MS m/z (M + H) |
|---|---|---|---|
| 31 | 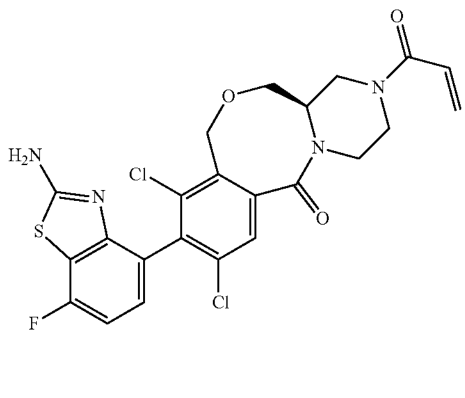 | (13aR)-9-(2-Amino-7-fluoro-1,3-benzothiazol-4-yl)-8,10-dichloro-2-prop-2-enoyl-1,3,4,11,13,13a-hexahydropyrazino[2,1-d][2,5]benzoxazocin-6-one | 521.2/523.2 |
| 32 | 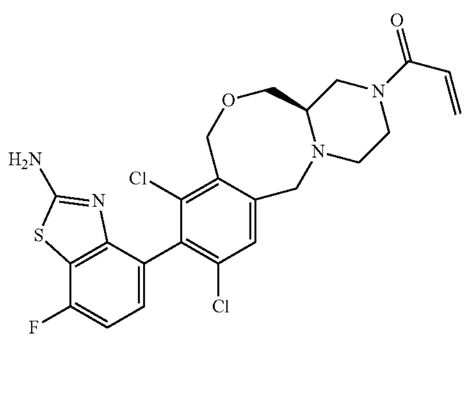 [SMILES: C=CC(=O)N1CCN2Cc3cc(Cl)c(-c4ccc(F)c5sc(N)nc45)c(Cl)c3COC[C@H]2C1] | 1-[(13aR)-9-(2-Amino-7-fluoro-1,3-benzothiazol-4-yl)-8,10-dichloro-3,4,6,11,13,13a-hexahydro-1H-pyrazino[2,1-d][2,5]benzoxazocin-2-yl]prop-2-en-1-one | 507.0/509.0 |
| 33 | 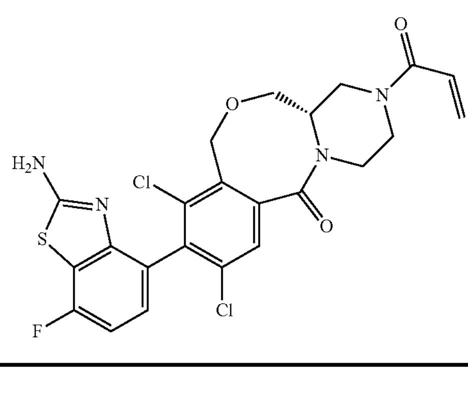 | (13aS)-9-(2-Amino-7-fluoro-1,3-benzothiazol-4-yl)-8,10-dichloro-2-prop-2-enoyl-1,3,4,11,13,13a-hexahydropyrazino[2,1-d][2,5]benzoxazocin-6-one | 521.0/523.0 |

In some cases, DIEA is used in place of TEA.

Example 34

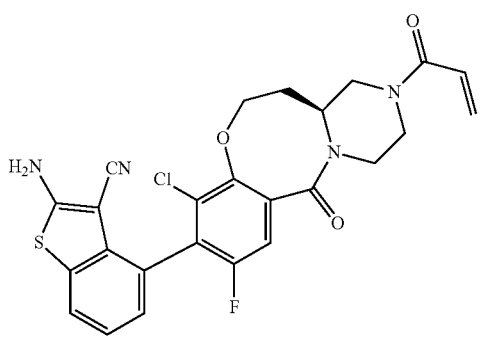

4-[(13aS)-10-Chloro-8-fluoro-6-oxo-2-prop-2-enoyl-1,3,4,12,13,13a-hexahydropyrazino[2,1-d][1,5]benzoxazocin-9-yl]-2-amino-benzothiophene-3-carbonitrile A suspension of 4-[(13aS)-10-chloro-8-fluoro-6-oxo-2,3,4,12,13,13a-hexahydro-1H-pyrazino[2,1-d][1,5]benzoxazocin-9-yl]-2-amino-benzothiophene-3-carbonitrile (1.58 g, 3.46 mmol) in EtOAc (35 mL), THF (15 mL) and water (40 mL) is charged with potassium carbonate (1.90 g, 13.7 mmol). The mixture is stirred rapidly and cooled to 0° C. Acryloyl chloride in DCM (13.0 mL, 3.25 mmol, 0.25M) is added dropwise through a dropping funnel. After 10 minutes of stirring in an ice bath, the mixture is diluted with EtOAc and poured into a separatory funnel. The layers are separated and the aqueous layer is again extracted with EtOAc. The combined organic extracts are washed with saturated aqueous sodium chloride solution, dried over magnesium sulfate, filtered, and concentrated in vacuo. The residue is purified by silica gel flash column chromatography, eluting first with 0-100% (10% MeOH in DCM)/DCM, and second with 0-100% [10% (7N $NH_3$ in MeOH) in DCM]/DCM to give the desired product as fluffy solid. The solid is sonicated in ether for 30 minutes, filtered, and dried in high vacuum to give the title compound (1.60 g, 91%). ES/MS m/z ($^{35}$Cl/$^{37}$Cl) 511.0/513.0 $[M+H]^+$.

TABLE 22

Compounds synthesized in a manner essentially analogous to that of Example 34

| Example | Structure | Compound Name | ES/MS m/z (M + H) |
|---|---|---|---|
| 35 | 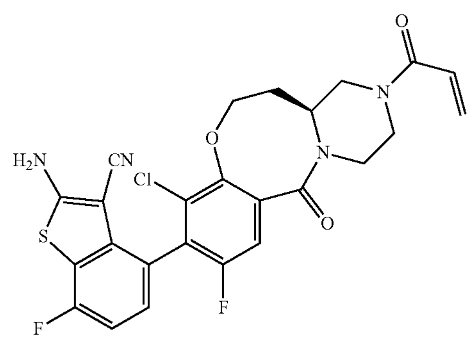 [SMILES: C=CC(=O)N1CCN2C(=O)c3cc(F)c(-c4ccc(F)c5sc(N)c(C#N)c45)c(Cl)c3OCC[C@H]2C1] | 4-[(13aS)-10-Chloro-8-fluoro-6-oxo-2-prop-2-enoyl-1,3,4,12,13,13a-hexahydropyrazino[2,1-d][1,5]benzoxazocin-9-yl]-2-amino-7-fluoro-benzothiophene-3-carbonitrile | 529.0/531.0 |
| 36 | 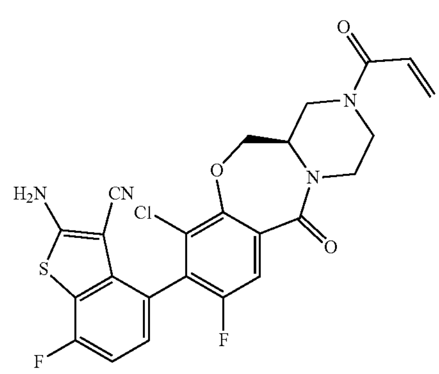 [SMILES: C=CC(=O)N1CCN2C(=O)c3cc(F)c(-c4ccc(F)c5sc(N)c(C#N)c45)c(Cl)c3OC[C@H]2C1] | 4-[(4aR)-7-Chloro-9-fluoro-11-oxo-3-prop-2-enoyl-2,4,4a,5-tetrahydro-1H-pyrazino[2,1-c][1,4]benzoxazepine-8-yl]-2-amino-7-fluoro-benzothiophene-3-carbonitrile | 515.0/517.0 |

TABLE 22-continued

Compounds synthesized in a manner essentially analogous to that of Example 34

| Example | Structure | Compound Name | ES/MS m/z (M + H) |
|---|---|---|---|
| 37 | 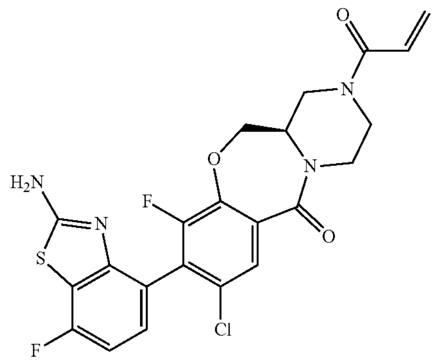 | (4aR)-8-(2-Amino-7-fluoro-1,3-benzothiazol-4-yl)-9-chloro-7-fluoro-3-prop-2-enoyl-2,4,4a,5-tetrahydro-1H-pyrazino[2,1-c][1,4]benzoxazepine-11-one | 491.0/493.0 |
| 38 | 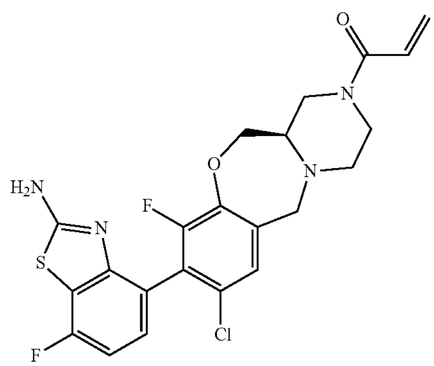 | 1-[(4aR)-8-(2-Amino-7-fluoro-1,3-benzothiazol-4-yl)-9-chloro-7-fluoro-1,2,4,4a,5,11-hexahydropyrazino[2,1-c][1,4]benzoxazepine-3-yl]prop-2-en-1-one | 477.0/479.0 |
| 39 | 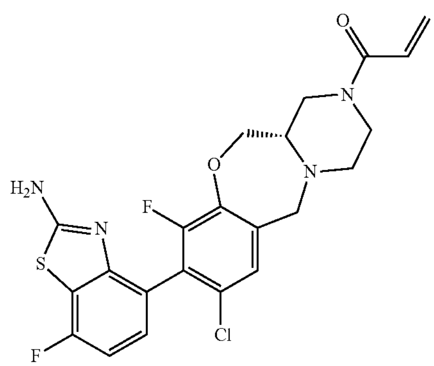 [SMILES: C=CC(=O)N1CCN2Cc3cc(Cl)c(-c4ccc(F)c5sc(N)nc45)c(F)c3OC[C@@H]2C1] | 1-[(4aS)-8-(2-Amino-7-fluoro-1,3-benzothiazol-4-yl)-9-chloro-7-fluoro-1,2,4,4a,5,11-hexahydropyrazino[2,1-c][1,4]benzoxazepine-3-yl]prop-2-en-1-one | 477.0/479.0 |
| 40 | 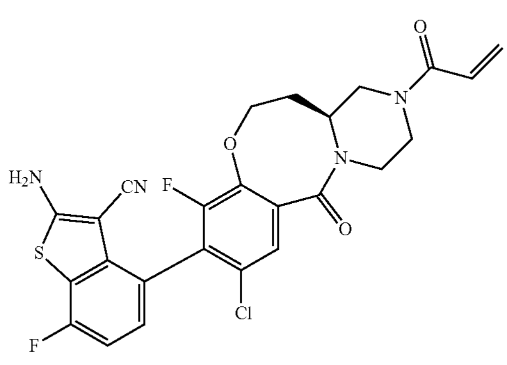 [SMILES: C=CC(=O)N1CCN2C(=O)c3cc(Cl)c(-c4ccc(F)c5sc(N)c(C#N)c45)c(F)c3OCC[C@H]2C1] | 4-[(13aS)-8-Chloro-10-fluoro-6-oxo-2-prop-2-enoyl-1,3,4,12,13,13a-hexahydropyrazino[2,1-d][1,5]benzoxazocin-9-yl]-2-amino-7-fluoro-benzothiophene-3-carbonitrile | 529.0/531.0 |

TABLE 22-continued

Compounds synthesized in a manner essentially analogous to that of Example 34

| Example | Structure | Compound Name | ES/MS m/z (M + H) |
|---|---|---|---|
| 41 | 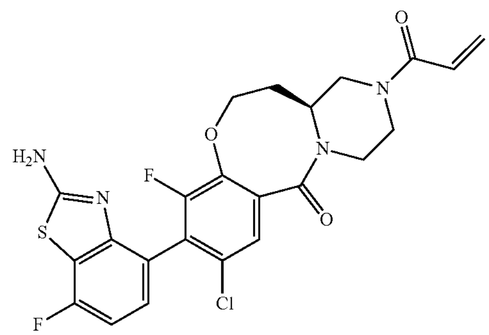 [SMILES: C=CC(=O)N1CCN2C(=O)c3cc(Cl)c(-c4ccc(F)c5sc(N)nc45)c(F)c3OCC[C@H]2C1] | (13aS)-9-(2-Amino-7-fluoro-1,3-benzothiazol-4-yl)-8-chloro-10-fluoro-2-prop-2-enoyl-1,3,4,12,13,13a-hexahydropyrazino[2,1-d][1,5]benzoxazocin-6-one | 505.0/507.0 |
| 42 | 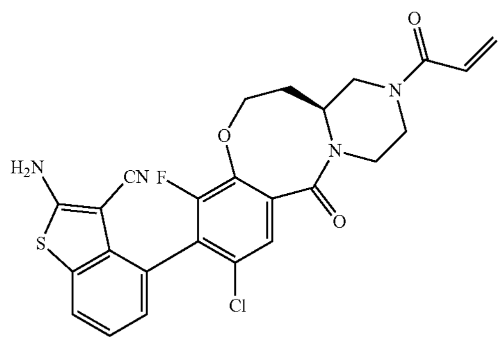 [SMILES: C=CC(=O)N1CCN2C(=O)c3cc(Cl)c(-c4cccc5sc(N)c(C#N)c45)c(F)c3OCC[C@H]2C1] | 4-[(13aS)-8-Chloro-10-fluoro-6-oxo-2-prop-2-enoyl-1,3,4,12,13,13a-hexahydropyrazino[2,1-d][1,5]benzoxazocin-9-yl]-2-amino-benzothiophene-3-carbonitrile | 511.0/513.0 |
| 43 | 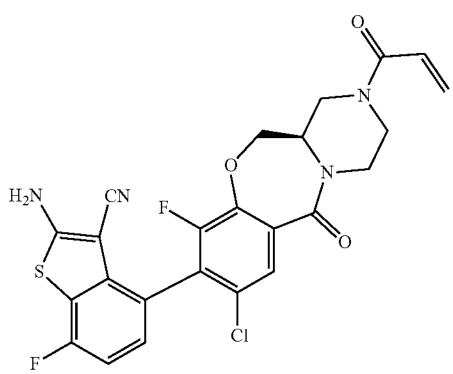 [SMILES: C=CC(=O)N1CCN2C(=O)c3cc(Cl)c(-c4ccc(F)c5sc(N)c(C#N)c45)c(F)c3OC[C@H]2C1] | 4-[(4aR)-9-Chloro-7-fluoro-11-oxo-3-prop-2-enoyl-2,4,4a,5-tetrahydro-1H-pyrazino[2,1-c][1,4]benzoxazepine-8-yl]-2-amino-7-fluoro-benzothiophene-3-carbonitrile | 515.0/517.0 |
| 44 | 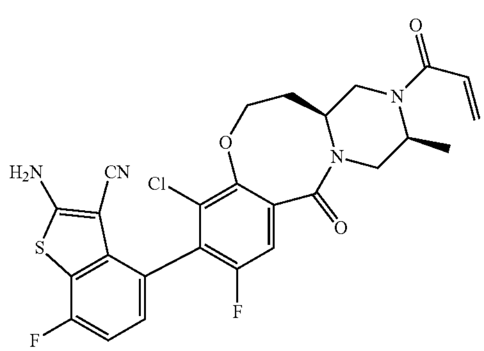 [SMILES: C=CC(=O)N1C[C@@H]2CCOc3c(cc(F)c(-c4ccc(F)c5sc(N)c(C#N)c45)c3Cl)C(=O)N2C[C@@H]1C] | 4-[(3S,13aS)-10-Chloro-8-fluoro-3-methyl-6-oxo-2-prop-2-enoyl-1,3,4,12,13,13a-hexahydropyrazino[2,1-d][1,5]benzoxazocin-9-yl]-2-amino-7-fluoro-benzothiophene-3-carbonitrile | 542.4/544.4 |

TABLE 22-continued

Compounds synthesized in a manner essentially analogous to that of Example 34

| Example | Structure | Compound Name | ES/MS m/z (M + H) |
|---|---|---|---|
| 45 | 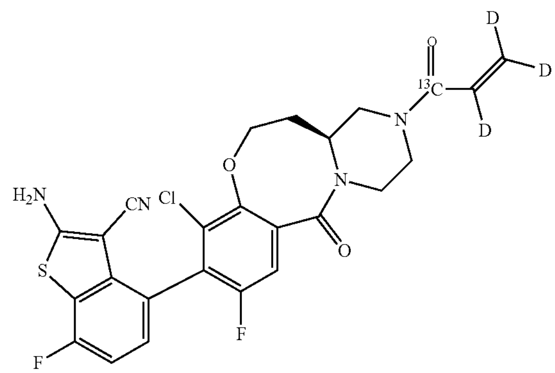 [SMILES: [2H]C([2H])=C([2H])[13C](=O)N1CCN2C(=O)c3cc(F)c(-c4ccc(F)c5sc(N)c(C#N)c45)c(Cl)c3OCC[C@H]2C1] | 4-[(13aS)-10-Chloro-8-fluoro-6-oxo-2-(2,3,3-trideuterioprop-2-enoyl)-1,3,4,12,13,13a-hexahydropyrazino[2,1-d][1,5]benzoxazocin-9-yl]-2-amino-7-fluoro-benzothiophene-3-carbonitrile-$^{13}$C | 533.1/535.1 |

Example 46

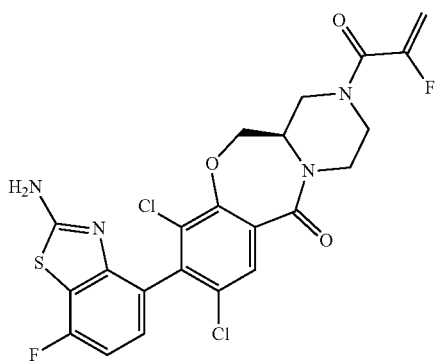 [SMILES: C=C(F)C(=O)N1CCN2C(=O)c3cc(Cl)c(-c4ccc(F)c5sc(N)nc45)c(Cl)c3OC[C@H]2C1]

To a solution (4aR)-8-(2-amino-7-fluoro-1,3-benzothiazol-4-yl)-7,9-dichloro-1,2,3,4,4a,5-hexahydropyrazino[2,1-c][1,4]benzoxazepine-11-one (46 mg, 0.10 mmol), 2-fluoroprop-2-enoic acid (11 mg, 0.12 mmol), DIEA (53 μL, 0.30 mmol) in DMF (1 mL) cooled in an ice-bath at 0° C. is added a 50 wt. % propylphosphonic anhydride solution in EtOAc (91 μL, 0.15 mmol). After 45 min, the reaction mixture is concentrated in vacuo. The crude mixture is purified by reverse phase chromatography, eluting with a 20-80% B in A gradient (A: 10 mM aqueous $NH_4HCO_3$ with 5% MeOH; B: ACN), to give the title compound as a white solid (25 mg, 47%). ES/MS m/z: 525 (M+H)

TABLE 23

Compounds synthesized in a manner essentially analogous to that of Example 46

| Example | Structure | Compound Name | ES/MS m/z (M + H) |
|---|---|---|---|
| 47 | 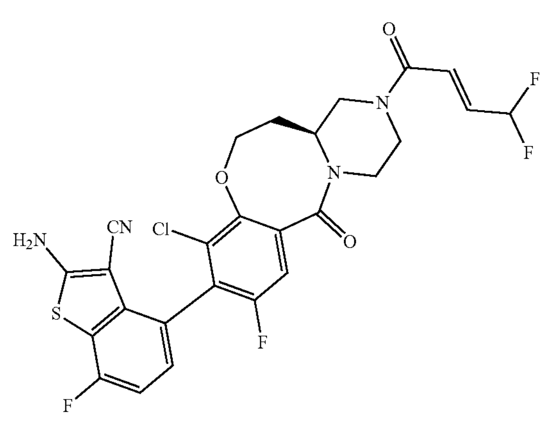 [SMILES: N#Cc1c(N)sc2c(F)ccc(-c3c(F)cc4c(c3Cl)OCC[C@H]3CN(C(=O)/C=C/C(F)F)CCN3C4=O)c12] | 4-[(13aS)-10-Chloro-2-[(E)-4,4-difluorobut-2-enoyl]-8-fluoro-6-oxo-1,3,4,12,13,13a-hexahydropyrazino[2,1-d][1,5]benzoxazocin-9-yl]-2-amino-7-fluoro-benzothiophene-3-carbonitrile | 579.5/581.4 |

TABLE 23-continued

Compounds synthesized in a manner essentially analogous to that of Example 46

| Example | Structure | Compound Name | ES/MS m/z (M + H) |
|---|---|---|---|
| 48 | 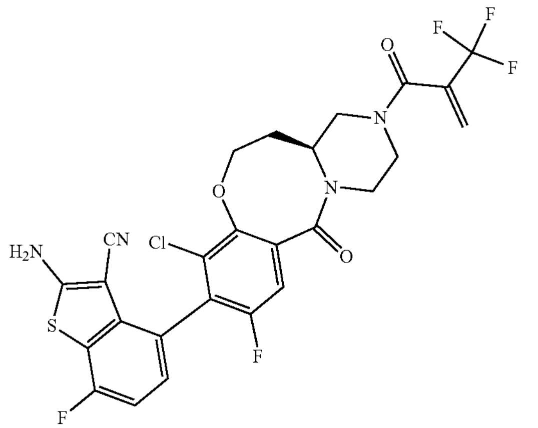 [SMILES: C=C(C(=O)N1CCN2C(=O)c3cc(F)c(-c4ccc(F)c5sc(N)c(C#N)c45)c(Cl)c3OCC[C@H]2C1)C(F)(F)F] | 4-[(13aS)-10-Chloro-8-fluoro-6-oxo-2-[2-(trifluoromethyl)prop-2-enoyl]-1,3,4,12,13,13a-hexahydropyrazino[2,1-d][1,5]benzoxazocin-9-yl]-2-amino-7-fluoro-benzothiophene-3-carbonitrile | 597.5/599.5 |
| 49 | 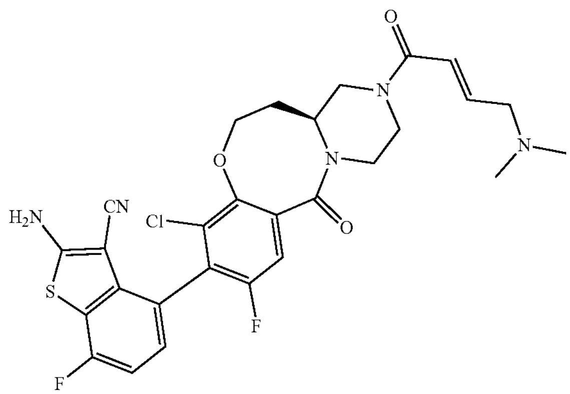 [SMILES: CN(C)C/C=C/C(=O)N1CCN2C(=O)c3cc(F)c(-c4ccc(F)c5sc(N)c(C#N)c45)c(Cl)c3OCC[C@H]2C1] | 4-[(13aS)-10-Chloro-2-[(E)-4-(dimethylamino)but-2-enoyl]-8-fluoro-6-oxo-1,3,4,12,13,13a-hexahydropyrazino[2,1-d][1,5]benzoxazocin-9-yl]-2-amino-7-fluoro-benzothiophene-3-carbonitrile | 586.6/588.6 |
| 50 | 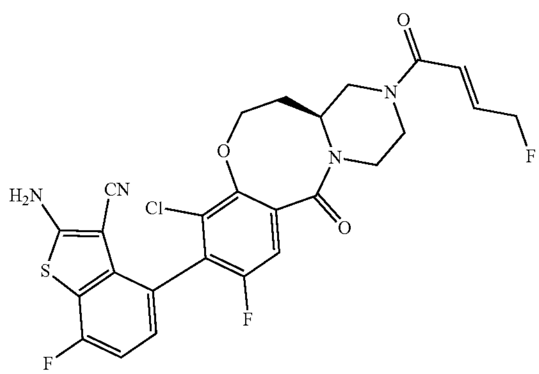 [SMILES: N#Cc1c(N)sc2c(F)ccc(-c3c(F)cc4c(c3Cl)OCC[C@H]3CN(C(=O)/C=C/CF)CCN3C4=O)c12] | 4-[(13aS)-10-Chloro-8-fluoro-2-[(E)-4-fluorobut-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 561.5/563.5 |
| 51 | 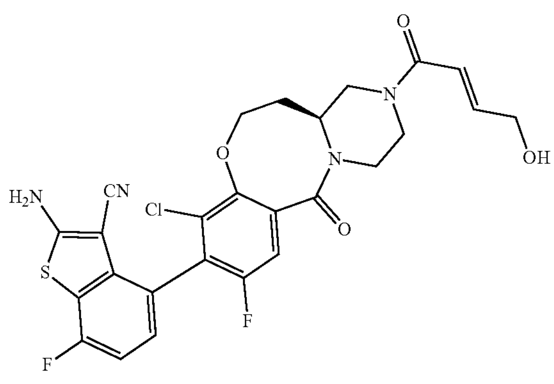 [SMILES: N#Cc1c(N)sc2c(F)ccc(-c3c(F)cc4c(c3Cl)OCC[C@H]3CN(C(=O)/C=C/CO)CCN3C4=O)c12] | 4-[(13aS)-10-Chloro-8-fluoro-2-[(E)-4-hydroxybut-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 559.4/561.4 |

TABLE 23-continued

Compounds synthesized in a manner essentially analogous to that of Example 46

| Example | Structure | Compound Name | ES/MS m/z (M + H) |
|---|---|---|---|
| 52 | 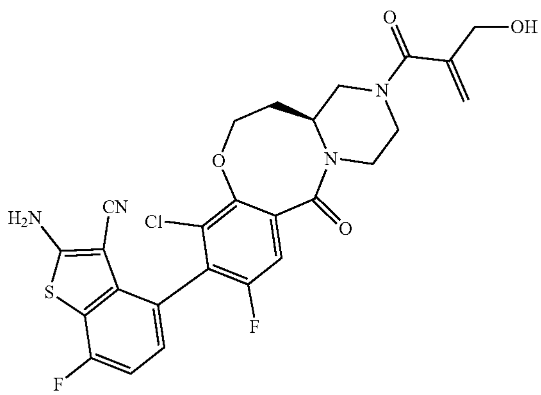 [SMILES: C=C(CO)C(=O)N1CCN2C(=O)c3cc(F)c(-c4ccc(F)c5sc(N)c(C#N)c45)c(Cl)c3OCC[C@H]2C1] | 4-[(13aS)-10-Chloro-8-fluoro-2-[2-(hydroxymethyl)prop-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 559.4/561.4 |
| 53 | 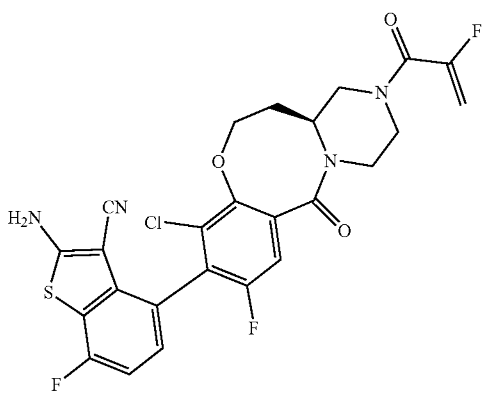 [SMILES: C=C(F)C(=O)N1CCN2C(=O)c3cc(F)c(-c4ccc(F)c5sc(N)c(C#N)c45)c(Cl)c3OCC[C@H]2C1] | 4-[(13aS)-10-Chloro-8-fluoro-2-(2-fluoroprop-2-enoyl)-6-oxo-1,3,4,12,13,13a-hexahydropyrazino[2,1-d][1,5]benzoxazocin-9-yl]-2-amino-7-fluoro-benzothiophene-3-carbonitrile | 547.0/549.0 |
| 54 | 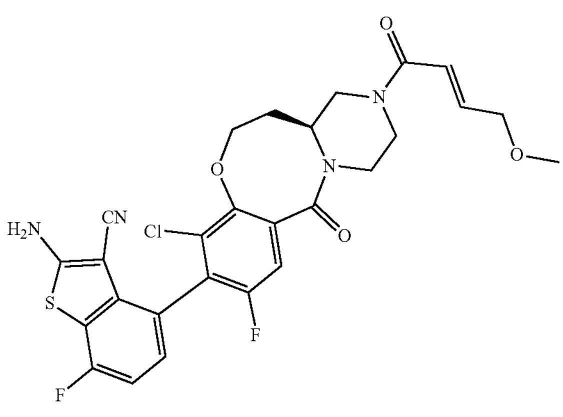 [SMILES: COC/C=C/C(=O)N1CCN2C(=O)c3cc(F)c(-c4ccc(F)c5sc(N)c(C#N)c45)c(Cl)c3OCC[C@H]2C1] | 4-[(13aS)-10-Chloro-8-fluoro-2-[(E)-4-methoxybut-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 573.6/575.6 |

TABLE 23-continued

Compounds synthesized in a manner essentially analogous to that of Example 46

| Example | Structure | Compound Name | ES/MS m/z (M + H) |
|---|---|---|---|
| 55 | 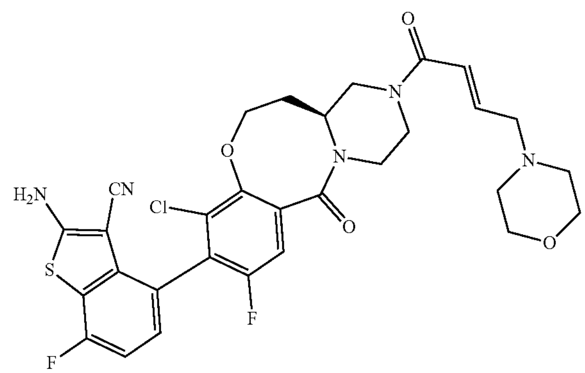 [SMILES: N#Cc1c(N)sc2c(F)ccc(-c3c(F)cc4c(c3Cl)OCC[C@H]3CN(C(=O)/C=C/CN5CCOCC5)CCN3C4=O)c12] | 4-[(13aS)-10-Chloro-8-fluoro-2-[(E)-4-morpholinobut-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 628.6/630.6 |
| 56 | 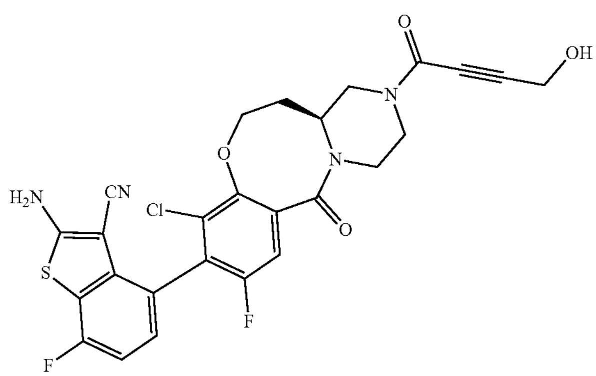 [SMILES: N#Cc1c(N)sc2c(F)ccc(-c3c(F)cc4c(c3Cl)OCC[C@H]3CN(C(=O)C#CCO)CCN3C4=O)c12] | 4-[(13aS)-10-Chloro-8-fluoro-2-(4-hydroxybut-2-ynoyl)-6-oxo-1,3,4,12,13,13a-hexahydropyrazino[2,1-d][1,5]benzoxazocin-9-yl]-2-amino-7-fluoro-benzothiophene-3-carbonitrile | 557.5/559.4 |
| 57 | 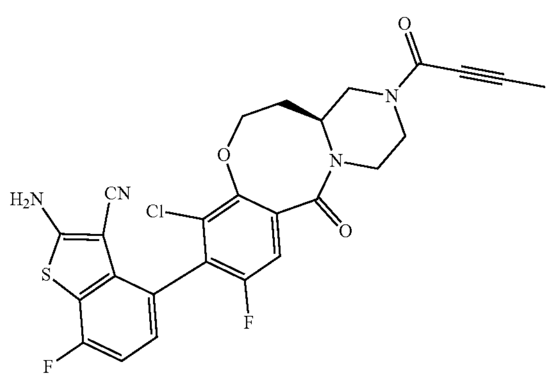 [SMILES: CC#CC(=O)N1CCN2C(=O)c3cc(F)c(-c4ccc(F)c5sc(N)c(C#N)c45)c(Cl)c3OCC[C@H]2C1] | 4-[(13aS)-2-But-2-ynoyl-10-chloro-8-fluoro-6-oxo-1,3,4,12,13,13a-hexahydropyrazino[2,1-d][1,5]benzoxazocin-9-yl]-2-amino-7-fluoro-benzothiophene-3-carbonitrile | 541.4/543.4 |

Example 58

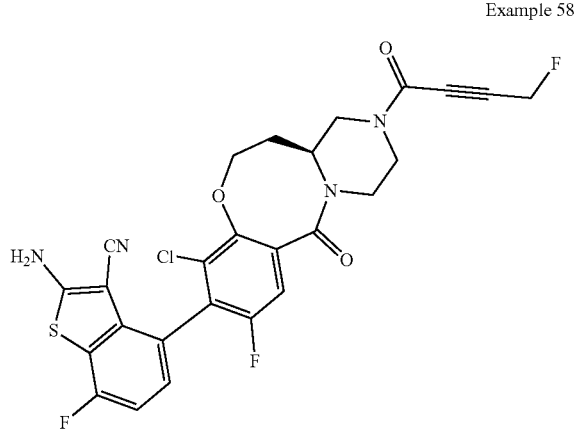

4-[(13aS)-10-Chloro-8-fluoro-2-(4-fluorobut-2-ynoyl)-6-oxo-1,3,4,12,13,13a-hexahydropyrazino[2,1-d][1,5]benzoxazocin-9-yl]-2-amino-7-fluoro-benzothiophene-3-carbonitrile Diethylaminosulfur trifluoride (0.03 mL, 0.2 mmol) is added dropwise via syringe to a sealed vial containing a 0° C. solution of 4-[(13aS)-10-chloro-8-fluoro-2-(4-hydroxybut-2-ynoyl)-6-oxo-1,3,4,12,13,13a-hexahydropyrazino[2,1-d][1,5]benzoxazocin-9-yl]-2-amino-7-fluoro-benzothiophene-3-carbonitrile (120 mg, 0.215 mmol) in DCE (2 mL). The reaction mixture is stirred for 30 minutes and then diluted with water and 25% IPA/chloroform solution. The organics are separated, dried over anhydrous sodium sulfate, filtered, and concentrated in vacuo. The resulting residue is purified via silica gel flash chromatography eluting with 0-100% 10% 7M $NH_3$ in DCM/DCM and further purified via reverse phase chromatography to give the title compound as a white solid (7 mg, 6%). ES/MS m/z ($^{35}Cl/^{37}Cl$) 559.4/561.4 [M+H]$^+$.

Example 60

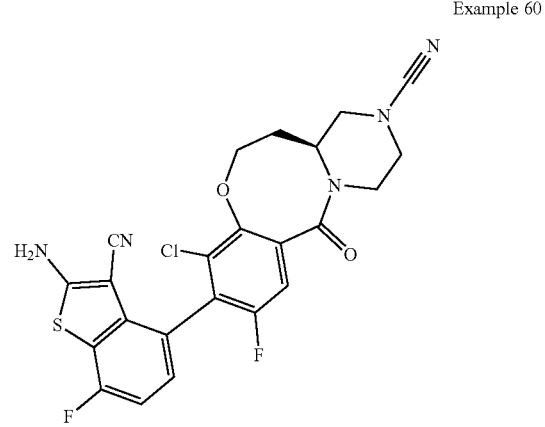

(13aS)-9-(2-Amino-3-cyano-7-fluoro-benzothiophen-4-yl)-10-chloro-8-fluoro-6-oxo-1,3,4,12,13,13a-hexahydropyrazino[2,1-d][1,5]benzoxazocine-2-carbonitrile Cyanogen bromide (3M in DCM, 0.15 mL, 0.45 mmol) is added to a flask containing 4-[(13aS)-10-chloro-8-fluoro-6-oxo-2,3,4,12,13,13a-hexahydro-1H-pyrazino[2,1-d][1,5]benzoxazocin-9-yl]-2-amino-7-fluoro-benzothiophene-3-carbonitrile (100 mg, 0.211 mmol) and 1N NaOH (1 mL) in DCM (1 mL). The mixture is stirred at ambient temperature for 18 hours then diluted with water and 25% IPA/chloroform solution. The organics are separated, dried over anhydrous sodium sulfate, filtered, and concentrated in vacuo. The resulting residue is via reverse phase chromatography to give the title compound as a white solid (29 mg, 27%). ES/MS m/z ($^{35}Cl/^{37}Cl$) 517.0/519.0 [M+H]$^+$.

TABLE 24

Compound synthesized in a manner essentially analogous to that of Example 57

| Example | Structure | Compound Name | ES/MS m/z (M + H) |
|---|---|---|---|
| 59 | 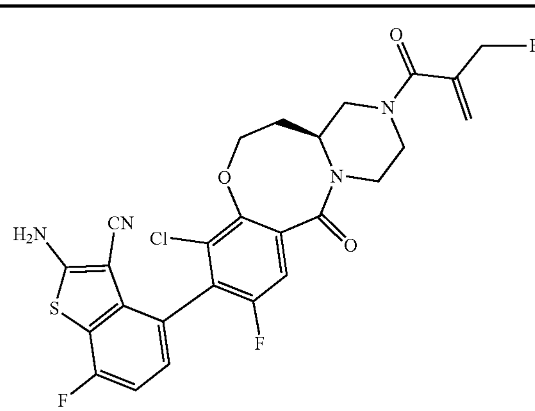 | 4-[(13aS)-10-Chloro-8-fluoro-2-[2-(fluoromethyl)prop-2-enoyl]-6-oxo-1,3,4,12,13,13a-hexahydropyrazino[2,1-d][1,5]benzoxazocin-9-yl]-2-amino-7-fluoro-benzothiophene-3-carbonitrile | 561.4/563.5 |

Example 61

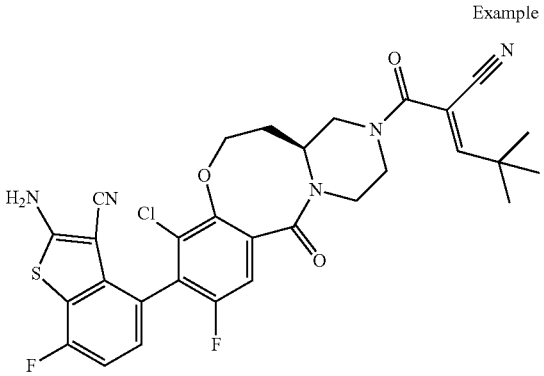

4-[(13aS)-10-Chloro-2-[(E)-2-cyano-4,4-dimethyl-pent-2-enoyl]-8-fluoro-6-oxo-1,3,4,12,13,13a-hexahydropyrazino[2,1-d][1,5]benzoxazocin-9-yl]-2-amino-7-fluoro-benzothiophene-3-carbonitrile A 20 mL microwave vial is charged with 4-[(13aS)-10-chloro-2-(2-cyanoacetyl)-8-fluoro-6-oxo-1,3,4,12,13,13a-hexahydropyrazino[2,1-d][1,5]benzoxazocin-9-yl]-2-amino-7-fluoro-benzothiophene-3-carbonitrile (0.410 g, 0.756 mmol), EtOH (8 mL), piperidine (0.15 mL, 1.5 mmol) and trimethylacetaldehyde (0.7 mL, 6 mmol) and sealed with a septum cap. The reaction mixture is heated in a microwave reactor at 120° C. for 60 minutes, an additional 90 minutes at 120° C., and another 1 hour at 100° C. before concentrating in vacuo. The resulting residue is purified via silica gel flash chromatography eluting with 0-50% acetone: DCM to give the title product as a pale yellow solid (117 mg, 25%). ES/MS m/z ($^{35}$Cl/$^{37}$Cl) 610.6/612.6 [M+H]$^+$.

Biological Assays

The following assays demonstrate that the exemplified compounds are inhibitors of KRas G12C and inhibit growth of certain tumors in vitro and/or in vivo.

KRas G12C Probe Occupancy TR-FRET Assay

The purpose of this assay is to measure the ability of an inhibitor to compete with a probe for binding to and covalently modifying KRas G12C at codon 12. The signal is generated by the time-resolved transfer of fluorescence between europium on an antibody bound to KRas G12C Europium-labeled Anti-Histidine Tag Antibody LanthaScreen (the Eu Anti-His antibody) and fluorescent Tracer 647 (Alexa Fluor™) bound to KRas G12C through streptavidin and a biotinylated inhibitor (the "KRas Probe", see Preparation 223).

Inhibitors are tested in dose response format from 10 mM stocks in 100% DMSO. The Labycyte Echo® 555 is used to dilute and transfer 100 nL per well containing a 10 point, 2.8-fold serial dilution to an assay plate. Two copies of the assay plate are prepared to measure the potency after 5 and 60 minutes incubation of the inhibitor with KRas G12C. His-tagged KRas G12C (20 nM) is added to the plates in assay buffer (20 mM Tris-HCl, pH 7.5, 0.01% TX-100, and 1 mM DTT). After 5 or 60 minutes incubation, 1 µM KRas Probe is added and allowed to covalently modify free KRas G12C for 1 hour. This is diluted 4-fold in buffer containing Eu Anti-His antibody and Streptavidin-Coated Tracer 647 (both from Life Technologies) to achieve KRas G12C (5 nM), Anti-His Antibody (2 nM), KRas Probe (300 nM), and Streptavidin Coated Tracer 647 (500 nM). After 30 minutes, the fluorescent signal is read on an Envision™ Plate Reader (excitation at 340 nM, tracer emission (em) at 665 nM, and antibody emission at 615 nM). Maximum control wells lack inhibitor and minimum control wells lack both inhibitor and KRas G12C. The signal ratio (em at 665/em at 615) is converted to percent inhibition using the following equation: % Inhibition=100−[(Test Compound Signal−Median Minimum Signal)/(Median Maximum Signal−Median Minimum Signal)×100]. The IC$_{50}$ is determined by fitting the percent inhibition at each inhibitor concentration to the four parameter nonlinear logistic equation using Genedata Screener®: y=(A+((B−A)/(1+((C/x)^D)))) where, y=% inhibition, A=minimum asymptote, B=maximum asymptote, C=relative IC$_{50}$ or the inhibitor concentration producing 50% inhibition within the fitted range of both asymptotes, and D=Hill Slope. Compounds within the scope of this invention are evaluated in this assay substantially as described above. Exemplified compounds of the invention evaluated in this assay exhibit KRas G12C inhibitor activity by competing with a probe for binding to and covalently modifying KRas G12C at codon 12. The compound of Example 1, for example, evaluated in this assay exhibits an IC$_{50}$ of less than 0.015 µM, at 5 and 60 minutes, n=4.

H358 Cellular Phospho-ERK AphaLISA®

The purpose of this assay is to measure the ability of test compounds to inhibit the phosphorylation of p-ERK1/2, a downstream effector of KRas in human lung cancer cells H358 (ATCC CRL-5807). Briefly, the AlphaLISA® SureFire® Ultra™ p-ERK 1/2 (Thr202/Tyr204) assay is a sandwich immunoassay for quantitative detection of phospho-ERK 1/2 (phosphorylated on Thr202/Tyr204 in ERK1, or Thr185/Tyr187 in ERK2) in cellular lysates using Alpha Technology (Perkin Elmer Cat #ALSU-PERK-A50K).

H358 cells are plated at 40K cells per well in 100 µL media (RPMI 1640, GIBCO Cat #22400-071) containing 10% FBS (GIBCO Cat #: 10082-147) in a 96 well plate (Costar #3596) and are incubated overnight in humid trays at 37° C., 5% CO$_2$. The next morning, 10 µL of serially-diluted (3-fold) test compounds (50 µM top concentration) and 10 µL of controls (Maximum signal wells: 5% DMSO and Minimum signal wells: 2 µM of N-(3-{3-cyclopropyl-5-[(2-fluoro-4-iodophenyl)amino]-6,8-dimethyl-2,4,7-trioxo-3,4,6,7-tetrahydropyrido[4,3-D]pyrimidin-1(2H)-yl}phenyl)acetamide (trametinib, as a positive control) are added to the cell plate and incubated for 2 hours in humid trays at 37° C./5% CO$_2$. Lysis Buffer is prepared at ambient temperature containing a protease and phosphatase inhibitor cocktail. Culture medium is removed by inverting and shaking the cell plate in the sink and then blotting onto a paper towel. Lysis buffer is added to the cell plate (50 µL per well) and the plate is incubated at ambient temperature for 10 minutes on a shaker. For p-ERK detection, acceptor beads are diluted into a suspension mixture with buffer. Using a STARlet liquid handler, 5 µL of acceptor beads and 2 µL of cell lysate are transferred as a single-step in-tip dilution to a 384 well assay plate. The assay plate is sealed with foil and is incubated at ambient temperature for 2 hours. Donor beads are diluted into a suspension mixture with buffer. Using the STARlet, 5 µL of donor beads are added to the assay plate that is then sealed, wrapped with foil. The plate is incubated at ambient temperature for 2 hours in the dark. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Min Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. The compounds of the Examples exhibit an ability to inhibit the phosphorylation of p-ERK1/2. The compound of Example 1, for example, exhibit a relative $IC_{50}$ in this assay of 0.00178 μM n=3. This data show that the compounds of the Examples exhibit KRas G12C inhibition activity in this cellular assay.

H358 Cellular Active RAS GTPase ELISA

The purpose of this assay is to measure the ability of test compounds to inhibit constitutive RAS GTPase activity in human lung cancer cells H358 (ATCC CRL-5807). The RAS GTPase ELISA kit (Active Motif Cat #52097) contains a 96-well plate pre-coated with glutathione in order to capture a kit-supplied GST-Raf-RBD protein. Activated RAS (GTP-bound) in cell extracts specifically bind to the Raf-RBD. Bound RAS is detected with a primary antibody that recognizes human KRas. A secondary antibody conjugated with HRP recognizes the primary antibody and a development solution provides a chemiluminescent readout.

H358 cells are plated at 80,000 cells/well in 90 μL serum free media (RPMI 1640, GIBCO) and incubated overnight at 37° C./5% $CO_2$. The next morning, 10 μL of serially-diluted (3-fold) test compounds (500 μM top concentration) and 10 μL of controls (Maximum signal wells: 5% DMSO and Minimum signal wells: 500 μM 1-[4-[6-chloro-8-fluoro-7-(3-hydroxy-1-naphthyl)quinazolin-4-yl]piperazin-1-yl] prop-2-en-1-one, WO2015054572 as an inhibitor) are added to the cell plate and incubated for 2 hours at 37° C./5% $CO_2$. Complete Lysis/Binding Buffer is prepared containing Protease Inhibitor cocktail and GST-Raf-RBD and stored on ice. One hour before cell plate incubation is completed, 50 μL of GST-Raf-RBD is diluted in lysis/binding buffer, and buffer is added to the ELISA assay plate and which is incubated for 1 hour at 4° C. with gently rocking. After 2 hours, the cells are washed with 100 μL ice-cold PBS and lysed with 100 μL lysis/binding buffer. The cell plate is shaken for 10 minutes at ambient temperature. The cell plate is then centrifuged at 1500 rpm for 10 minutes at ambient temperature. During this time, 1×Wash Buffer is prepared at ambient temperature and then is used to wash (3×100 μL) the GST-Raf-RBD coated assay plate. After washing, 50 μL of cell lysate is added to the GST-Raf-RBD coated assay plate and incubated for 1 hour at ambient temperature with gentle shaking. During this incubation period, 1×Antibody Binding Buffer is prepared and brought to ambient temperature. The assay plate is washed 3×100 μL with 1×Wash Buffer and then 50 μL of Primary Antibody (diluted 1:500 in 1×Antibody Binding buffer) is added. The plate is incubated for 1 hour at ambient temperature. The assay plate is washed 3×100 μL with 1×Wash Buffer and then 50 μL of Secondary Antibody (diluted 1:5000 in 1×Antibody Binding buffer) is added and incubated for 1 hour at ambient temperature. The assay plate is washed 4×100 μL with 1×Wash buffer and then 50 μL of chemiluminescent working solution is added at ambient temperature. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Minimum Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. The compounds of the Examples exhibit an ability to inhibit constitutive RAS GTPase activity. The compound of Example 1, for example, exhibit a relative $IC_{50}$ of 0.00672 μM, n=4 in this assay. This data show that the compounds of the Examples exhibit KRas-GTP inhibition activity in this human lung cancer cell culture.

3D H358 Cell Proliferation Assay

The purpose of this assay is to evaluate test compound inhibition in a 3D proliferation assay using human lung cancer cells, H358, (ATCC CRL-5807). Signal reflecting cell proliferation is detected with the CellTiterGlo® 3D reagent (Promega G9683). The cells are grown in RPMI 1640 (GIBCO®) supplemented with 10% heat inactivated FBS and 0.1 mg/mL penicillin/streptomycin. H358 cells are cultured in the growth phase and five thousand cells per well are plated in a black well clear round bottom 96-well ultra-low attachment surface plate (Corning® Cat 4520) with 80 μL/well of culture media. Cells are incubated overnight at 37° C. in a humidity chamber. 20 μL/well of serially diluted test compound is added to the plate which is then incubated for 96 hours. Plates are brought to ambient temperature and an equal volume of ambient temperature CellTiterGlo® 3D reagent is added. Plates are shaken at 750 RPM for 10 minutes at ambient temperature. After a 1 hour incubation at ambient temperature to stabilize the signal, the luminescent signal is measured on the EnVision™ plate reader. The signal is converted to percent inhibition using the following equation: % Inhibition=100−[(Test Compound Signal−Median Minimum Signal)/(Median Maximum Signal−Median Minimum Signal)×100]. The Max Signal is a control well without inhibitor. The Minimum Signal is a control well containing a reference inhibitor (trametinib) sufficient to fully inhibit cell proliferation. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. The compound of Example 1, for example, exhibit a relative $IC_{50}$ Viability Assay® (Promega #G7572 for 2D) according to manufacturer's instructions and an EnVision™ plate reader. Nonlinear regression and sigmoidal dose-response curves are used to calculate the half maximal inhibitory concentration ($IC_{50}$) with GraphPad Prism 4® software.

TABLE 25

In vitro anti-proliferation activities of Examples 1, 34-36 in a panel of KRas G12C mutation tumor cell lines

| Cell Line | Example 1 | | Example 34 | | Example 35 | | Example 36 | |
|---|---|---|---|---|---|---|---|---|
| | % inh. @ 10 μM | IC50 (μM) | % inh. @ 10 μM | IC50 (μM) | % inh. @ 10 μM | IC50 (μM) | % inh. @ 10 μM | IC50 (μM) |
| H358 (lung) | 94.5 | 0.004 | 95.6 | 0.002 | 96.4 | 0.002 | 89.1 | 0.008 |
| SW1463 (colon) | 95.3 | 0.006 | 90.1 | 0.004 | 94.3 | 0.005 | 82.7 | 0.014 |
| MiaPaca-2 (pancr) | 77.2 | 0.018 | 82.9 | 0.01 | 85.8 | 0.011 | 79.6 | 0.081 |
| H23 (lung) | 98.2 | 0.045 | 96.8 | 0.026 | 98 | 0.024 | 96.7 | 0.1 |
| LU99 (lung) | 89.9 | 0.303 | 91.9 | 0.201 | 96.6 | 0.173 | 99.1 | 0.349 |
| SW837 (rectum) | 60.8 | 0.25 | 59.6 | 0.2 | 64.2 | 0.33 | 58.7 | 0.57 |
| HCC44 (lung) | 46.4 | >10 | 41 | >10 | 64.3 | 2.23 | 80.6 | 2.839 |
| LXFA-983L (lung) | 78.6 | 3.609 | 68.8 | >10 | 83.1 | >10 | 88 | >10 |
| H2122 (lung) | 80.4 | 1.17 | 78.1 | 0.66 | 79.7 | 0.9 | 92.8 | 1.36 |
| SW756 (cervix) | 51.9 | 1.63 | 56.9 | 1.08 | 56.7 | 1.55 | 58.1 | 2.52 |
| Calu-1 (lung) | 45.4 | >10 | 50.6 | 1.14 | 56 | 0.48 | 77.4 | 2.925 |
| H1792 (lung) | 63.6 | 3.011 | 56.7 | 4.354 | 81.7 | 1.41 | 97.4 | 2.032 |
| UM-UC-3 (bladder) | 54.3 | 0.73 | 56.1 | 0.51 | 80.4 | 1.09 | 91.6 | 1.86 |
| KYSE-410 (esoph) | 64.6 | 5.84 | 63.2 | >10 | 68.3 | 7.974 | 43.1 | >10 |
| H1373 (lung) | 68.8 | 1.813 | 67.7 | 6.739 | 86.3 | 3.544 | 82.6 | 5.494 |
| SW1573 (lung) | 35 | >10 | 60.8 | 7.823 | 44.7 | >10 | 54.3 | 9.35 |
| H2030 (lung) | 32.9 | >10 | 41.1 | >10 | 40.3 | >10 | 55.8 | >10 |
| A549 (lung) | 19.1 | >10 | 18.8 | >10 | 31.6 | >10 | 62.1 | 9.5 |

0.0083 μM in this assay. This data show that the compound of Example 1 inhibits the proliferation of H358 human lung cancer cells.

CellTiterGlo® Cell Proliferation Assay

The purpose of this assay is to evaluate the growth of KRas G12C mutant tumor lines following treatment with a test compound. A panel of tumor cell lines harboring KRas G12C or other KRas mutations are collected (Table 25). All cell lines are from ATCC or other sources indicated.

Typically cells are cultured in RPMI1640 or Dulbecco's modified Eagle's medium (DMEM, GIBCO) supplemented with 10% FBS (GIBCO, Invitrogen). For 2D culture cells ($4\times10^3$/well) maintained in growth medium described above, are plated onto 96 well tissue culture plates (Corning® Cat. 3603) a day before the treatment. The cells are treated with compound for 96 hours, and then are analyzed for viability using the CellTiterGlo® Luminescent Cell The data indicate that the compounds of Examples 1, 34-36 inhibit the growth of many KRas G12C mutant tumor cell lines listed in Table 26.

As summarized in Table 25, the compounds of Example 1, 34-36 exhibit anti-proliferation activities in most of the tumor cells with KRas G12C mutation in 2D culture condition. In A549 cells with KRas G12S mutation, the compounds of Examples 1, 34-36 exhibit little activity, suggesting that Examples 1, 34-36 selectively inhibit tumor cells with KRas G12C mutation.

Inhibition of KRas G12C Pharmacodynamic (PD) Markers in H358 Xenograph Model and Pancreatic Cancer MiaPaca-2 Xenograft Model The purpose of these assays is to evaluate in vivo target inhibition of an orally administered test compound. Human lung cancer H358 cells, or pancreatic cancer MiaPaca-2 cells, are implanted into nude mice xenograft tumor models.

H358 or MiaPaca-2 cells (10×10⁶ in a 1:1 Matrigel® mix, 0.2 mL total volume) are implanted by subcutaneous injection in hind leg of nude female mice (Harlan Laboratories). A total of 3-4 mice in each group are used for target engagement and PD study. Treatment is initiated with oral administration (gavage) of a test compound or vehicle (20% Captisol®, 25 mM phosphate, pH 2.0 in 0.2 mL) when the tumor size reaches approximately 300 mg.

For in vivo target inhibition and PD analysis, tumors are ground by mortar and pestle on dry ice and tumor fragments are added to 800 μL of lysis buffer containing 1% Triton™ X-100, 25 mM Tris pH7.5, 150 mM sodium chloride, 1 mM EDTA, and 1 mM EGTA with Halt protease and phosphatase inhibitor cocktail (Thermo Scientific, cat. no. 1861281) in lysing matrix D tubes (MP Biomedical®, cat. no. 6913-500) with one additional large bead (MP Biomedical® ¼" ceramic sphere bead cat. no. 6540-412) per tube. Tumor fragments are homogenized in a Thermo Bio101® fast prep (FP120) at setting 4 for 15 min while cold for a total of 2 times. Lysates are spun at 14,000 rpm for 10 minutes at 4° C. to clarify. Protein estimation is done on the lysate supernatant using a BioRad Dc® protein assay and lysates are diluted in complete lysis/binding buffer from the Ras GTPase Chemi ELISA Kit® (Active Motif, cat. no. 52097). The active KRas ELISA is performed as follows: glutathione-coated ELISA wells are incubated with diluted RAF1-GST in complete lysis/binding buffer for 1 hour at 4° C. with gentle agitation. Wells are washed 3 times with wash buffer and 100 μg of lysates are added to each well and incubated at ambient temperature for 1 hour with mild agitation. The wells are washed an additional 3 times, then primary antibody, diluted in antibody binding buffer, is added to each well. The plates are incubated for 1 hour. The wells are washed 3 more times before adding HRP-conjugated secondary antibody, diluted in antibody binding buffer, to each well. The plates are incubated at ambient temperature for 1 hour. ELISA wells are washed 4 times, chemiluminescent reagent is added and then luminescence is read. For pERK Meso Scale Discovery ELISA, 25 μg of protein containing 0.1% SDS is used; Meso Scale Discovery Whole Cell Lysate Kit for pERK is provided by Meso Scale Discovery.

Dose Dependent In Vivo Target Inhibition and Pharmacodynamic Effects in Lung Cancer H358 Xenograft Model The purpose of this assay is to evaluate the dose dependent in vivo target inhibition and pharmacodynamic effects in a lung cancer model. The test compound is dosed in lung cancer H358 mouse xenograft model at a dose range from 12.5 to 100 mg/kg. The tumor samples are collected 8 hours post a single dose. The tumor lysates are prepared and the inhibition of pERK and active KRas is measured as described above. The results are provided in Table 26; the compound of Example 34 exhibit a dose dependent inhibition of pERK and active KRas after a single dose treatment from 12.5 to 100 mg/kg at 8 hours. The compound of Example 35 also exhibit good inhibition of pERK and active KRas after a single dose treatment from 12.5 to 100 mg/kg. 82.2%-90.6% pERK inhibition, and 73.4%-94% active KRas inhibition are observed at these dose levels.

TABLE 26

Dose Dependent Inhibition of pERK, pMEK And Active Kras in H358 Xenograft Mice Model

| Compound | Dose (mg/kg) | Time | % Inhibition Active RAS | % Inhibition of pERK |
|---|---|---|---|---|
| Vehicle | 0 | 8 | 0 | 0 |
| Example 35 | 12.5 | 8 | 81 | 82.2 |
|  | 25 | 8 | 73.4 | 85.3 |
|  | 50 | 8 | 94 | 90.6 |
|  | 100 | 8 | 91.9 | 88.9 |
| Example 34 | 12.5 | 8 | 14.2 | 26.9 |
|  | 25 | 8 | 35.1 | 53.2 |
|  | 50 | 8 | 31.5 | 54 |
|  | 100 | 8 | 69.3 | 74.8 |

Time Dependent In Vivo Target Inhibition and Pharmacodynamic Effects in Lung Cancer H358 Xenograft Mouse Model The purpose of this assay is to evaluate the time dependent in vivo target inhibition and pharmacodynamic effects in a lung cancer model. The compounds of Examples 35 and 36 are also dosed at 30 mg/kg in a time course experiment. After a single dose, the tumor samples are harvested at 2, 4, 8, 12 and 24 hour post doing. The tumor lysates are prepared and the inhibition of pERK and active KRas is measured as described above. The results are provided in Table 27. The compound of Example 35 exhibit a time dependent inhibition of pERK and active KRas after a single dose treatment of 30 mg/kg. At 30 mg/kg, 82.6% pERK inhibition is observed at 8 hours, and the pERK inhibition decreases to 65.2% at 24 hours. For active KRas, 80.2% inhibition is achieved at 8 hours, and the active KRas inhibition decreases to 54.9% at 24 hours. The compound of Example 36 also exhibit a time dependent inhibition of pERK and active KRas after a single dose treatment of 30 mg/kg. At 30 mg/kg, 82.6% pERK inhibition is observed at 8 hours, and the pERK inhibition decreases to 48.8% at 24 hours. For active KRas, 88.5% inhibition is achieved at 8 hours, and the active KRas inhibition decreases to 43.2% at 24 hours.

TABLE 27

Time Dependent Inhibition of pERK And Active KRas in the H358 Model

| Compound | Dose (mg/kg) | Time (h) | % Inhibition of Active Ras | % inhibition of pERK |
|---|---|---|---|---|
| Vehicle | 0 | 4 or 8 | 0 | 0 |
| Example 35 | 30 | 2 | 7.6 | 67.9 |
|  | 30 | 4 | 65.7 | 73.2 |
|  | 30 | 8 | 80.2 | 82.6 |
|  | 30 | 12 | 39.3 | 71.1 |
|  | 30 | 24 | 54.9 | 65.2 |
| Example 36 | 30 | 2 | 72.6 | 79.7 |
|  | 30 | 4 | 72.4 | 84.2 |
|  | 30 | 8 | 88.5 | 86.9 |
|  | 30 | 24 | 43.2 | 48.8 |

In Vivo Target Inhibition and Pharmacodynamic Effects in Pancreatic Cancer MiaPaca-2 Xenograft Mouse Model The purpose of this assay is to evaluate the does and time dependent in vivo target inhibition and pharmacodynamic effects in a pancreatic cancer model. The compound of Examples 35 is dosed at 5, 10 or 30 mg/kg in a time course experiment. After a single dose, the tumor samples are harvested at 2, 4, 8, 12 and 24 hours post doing. The tumor lysates are prepared and the inhibition of pERK and active KRas is measured as described above. The results are provided in Table 28. The compound of Example 35 exhibit a dose and time dependent inhibition of pERK and active KRas after a single dose treatment of 5, 10 or 30 mg/kg. At 5 mg/kg, 63.8% inhibition of active Ras and 50.9% inhibition of pERK are observed at 4 hours. At 10 mg/kg, 85.5% inhibition of active Ras and 58.5% inhibition of pERK are observed at 4 hours. At 30 mg/kg, 90.9% inhibition of active Ras and 58.7% inhibition of pERK are observed at 4 hours, and 60.7% inhibition of active Ras maintained at 24 hours.

TABLE 28

Dose and Time Dependent Inhibition of pERK And Active KRas in MiaPaca-2 Model

| Dose (mg/kg) | Treatment Time (hours) | % Inhibition of active RAS | % Inhibition of pERK |
|---|---|---|---|
|  | 4 | 0 | 0 |
| 5 | 2 | 24 3 | 51 |
| 5 | 4 | 63.8 | 50.9 |
| 5 | 8 | 57 | 59 |
| 5 | 12 | 34.3 | 47.4 |
| 5 | 24 | 4.3 | −30.2 |
| 10 | 2 | 67.8 | 68.5 |
| 10 | 4 | 85.5 | 58.5 |
| 10 | 8 | 78.9 | 57.6 |
| 10 | 12 | 44.7 | 49 |
| 10 | 24 | 22.8 | −14.9 |
| 30 | 2 | 76 | 59.5 |
| 30 | 4 | 90.9 | 58.7 |
| 30 | 8 | 89 | 54.3 |
| 30 | 12 | 68.9 | 58.4 |
| 30 | 24 | 60.7 | 15.6 |

Anti-tumor Growth Activity in Lung Cancer H358 Xenograft Mouse Model

The purpose of this assay is to determine anti-tumor activities of test compounds (Example 34, 35, and 36) in a lung cancer H358 mouse xenograft model. H358 lung tumor cells (10×10$^6$) are implanted by subcutaneous injection in hind leg of nude female mice (Taconic Biosciences). A total of 4 mice in each group are used for the efficacy study. Treatment is initiated with oral administration (gavage) of the test compound or vehicle (20% Captisol®, 25 mM phosphate, pH 2.0 in 0.2 mL volume) once or twice daily for 28 days when the tumor size reaches approximately 300 mg. Tumor growth and body weight are monitored over time to evaluate efficacy and signs of toxicity. The summarized results are provided in Table 29. At 100 mg/kg on a once daily dosing schedule, −6.28 to −30.96% tumor growth regression was observed for compound Example 34. At 30 mg/kg on a twice daily dosing schedule, −67.68 to −72.14% tumor regression was observed for compound Example 35. At 30 mg/kg on a twice daily dosing schedules, −68.96% tumor progression was achieved for compound Example 36. No significant animal body weight loss was observed through the whole study for these compounds.

TABLE 29

Anti-tumor Growth Activity in Lung Cancer H358 Xenograft Mouse Model

| Treatment | Dose (mg/kg) | Dosing Schedule | % Regression (Day 12) | % Regression (Day 26) |
|---|---|---|---|---|
| Example 35 | 30 | PO, BID | −72.14 | −67.68 |
| Example 36 | 30 | PO, BID | −68.96 | NA |
| Example 34 | 100 | PO, QD | −30.96 | −6.28 |

Anti-Tumor Growth Activities in Other Lung Cancer Models and Models of Colorectal, Pancreatic, Bladder and Esophageal Cancers In addition to H358 xenograft model, the compound of Example 35 is tested in other xenograft or patient-derived xenograft (PDX) models of lung, colorectal, pancreatic, bladder, and esophageal cancer at different doses. For xenograft models of H1373, HCC44, MiaPaca-2, SW1463, KYSE-410 and UM-UC-3, typically 5-10×10$^6$ cells in a 1:1 matrigel mix (0.2 mL total volume) are implanted by subcutaneous injection in hind leg of nude mice. Generally, a total of 4 mice each group are used for efficacy study. Treatment is initiated with oral administration (gavage) of testing compound or vehicle (20% captisol, 25 mM phosphate, pH2.0) in 0.2 mL volume when tumor size reaches approximately 200-300 mg. Tumor growth and body weight are monitored over time to evaluate efficacy and signs of toxicity. For EL3187 PDX model, frozen vials containing tumor fragments are thawed at 37° C. in a water bath. The tumor fragments are transferred to 50 mL Falcon tube and the ice cold DMEM medium is slowly added into the tube to a total volume of 35 mL. Then the tumor fragments are centrifuged at 130×g for 2 minutes at 4° C. and supernatant is aspirated. This washing step is repeated twice and the tumor fragments are resuspended in 10 mL DMEM for implantation into athymic nude-Foxn1nu mice (Envigo RMS, Inc., Mount Comfort, Ind.). Once tumor volumes reach 800 to 1000 mm$^3$, animals are sacrificed and tumors are harvested using aseptic technique. Fresh tumors are cut into 10 to 15 mm$^3$ fragments and placed into cold Gibco hibernate medium. The tumor fragments are subcutaneously implanted into animals with a 10 g trochar needle. When tumor size reaches 200 to 300 mm$^3$, the animals are randomized for compound treatment.

The anti-tumor growth or regression activities of the compound of Example 35 are summarized in Table 30. Among models listed in Table 31, EL3187 is a patient-derived xenograft (PDX) model, and all other are tumor xenograft models. As illustrated in Table 31, the compound of Example 35 demonstrates dose-dependent anti-tumor activities in all of the models, suggesting that the compound of Example 35 is active against cancers with KRasG12C mutation, including lung, colorectal, pancreatic, bladder and esophageal cancer.

TABLE 30

Anti-Tumor Growth Activity by the Compound of Example 35 in Lung, Colorectal, Pancreatic, bladder and Esophageal Cancer Xenograft or PDX Models.

| Xenograft/ PDX model (tumor type) | Example 35 tumor growth inhibition (%) or regression (−%) | | | | | | | | | |
|---|---|---|---|---|---|---|---|---|---|---|
| | 1 mg/kg | | 3 mg/kg | | 5 mg/kg | | 10 mg/kg | | 30 mg/kg | |
| | QD × 28 | BID × 28 | QD × 28 | BID × 28 | QD × 28 | BID × 28 | QD × 28 | BID × 28 | QD × 28 | BID × 28 |
| H1373 (lung) | | | | | 97.9 | −26.3 | −21.3 | −49 | −49.7 | |
| HCC44 (lung) | | | | | 28.3 | 57.5 | 32.7 | 61.8 | 77 | 84.1 |
| EL3187 (lung) | 52 | 89.2 | −39.8 | −91 | | | −96 | −96 | | |
| MiaPaca-2 (pancreas) | | | | | 81.7 | −36.1 | −27 | −45.2 | −42 | −43.6 |
| SW1463 (CRC) | | | | | 52.5 | 48.8 | 78.3 | 79.5 | 89.8 | 98.8 |
| SW837 (CRC) | | | | | 18.2 | 83.6 | 95.2 | 62.1 | 83.5 | −23.8 |
| KYSE-410 (Esophagus) | | | | | | | 25.3 | 51.5 | 66.7 | 61.8 |
| UM-UC-3 (bladder) | | | | | 34.3 | 45.3 | 33.6 | 75 | 83.1 | 85 |

In Vitro Combination Efficacy of the Compound of Example 35 with Other Targeted Therapies In addition to monotherapy, the compound of Example 35 is assessed for its combination efficacy with other targeted therapies, such as CDK4 and CDK6 inhibitor abemaciclib, EGFR small molecule inhibitors erlotinib or afatinib, EGFR monoclonal antibody cetuximab, and the ERK inhibitor LY3214996. Eleven cell lines for this study are obtained from ATCC and grown under ATCC recommended conditions. All cell lines have a KRAS G12C mutation, and they are six lung cancer cell lines (H358, H1373, H1792, H2030, H2122, SW1573 and HCC44), two colorectal cancer cell lines (SW837 and SW1463), one pancreatic cancer cell line (MiaPaca-2), and one esophageal cancer cell line (KYSE410). The proliferation assay is performed as a 4 day growth assay using Cell TiterGlo® as the readout. Briefly, cells are plated in 96-well cell culture plates and allowed to adhere overnight at 37° C. The following day, cells are treated with compounds, either single treatments or combination treatments. First, the testing compounds are serially diluted in DMSO, followed by dilution into media as a 5×concentration with 1% DMSO, and finally added to cells in media to dilute to 1×. The cells are incubated at 37° C. for 4 more days. At the end of the incubation period, Cell TiterGlo® reagent is mixed and added to the wells. After 10 minutes, the luminescence is read by a Perkin Elmer Envision instrument. Absolute $IC_{50}$ values generated by a 4-parameter logistics model for the single and combination treatments are compared, followed by combination indexes for each combination treatment and cell line. The combination $IC_{50}$ values are adjusted based on the total concentration of each compound when added together. (Example: for a 1:1 concentration ratio of compound 1 and compound 2, the combination $IC_{50}$ is increased by a factor of 2). The combination index (CI) measures the degree to which the potency of a combination therapy differs from the expected-if-additive potency and is based on the Loewe definition of additivity.

$$CI = \frac{C_{A,y}}{IC_{A,y}} + \frac{C_{B,y}}{IC_{B,y}}$$

Where $C_{A,y}$ and $C_{B,y}$ are the concentrations of therapies A and B that produce an effect, y, when given in combination $IC_{A,y}$ and $IC_{B,y}$ are the concentrations of A and B that produce an effect, y, when given individually In some cases, if an estimated $IC_{50}$ value is used for CI calculation, the calculated CI is called Potentiation Index. The biological interpretation of the combination or potentiation index is as follows: synergistic if the combination or potentiation index <0.5, additive if the combination or potentiation index is between 0.5 and 2, and antagonistic if the combination index or potentiation is >2.

As shown in Table 31, combination of the compound of Example 35 and abemaciclib has additive or synergistic efficacy in inhibiting tumor cells with KRasG12C mutation. Among eleven cell lines tested, additive effects are observed in five cell lines, with a Combination Index (CI) between 0.5 and 1.2, and a synergistic effect is observed in six cell lines, with CI<0.5, suggesting that combination of the compound of Example 35 and abemaciclib may provide benefit to cancer patients with a KRas G12C mutation.

TABLE 31

In Vitro Combination of the Compound of Example 35 and the CDK4/CDK6 Inhibitor Abemaciclib

| Cell Line Name | Compound | Compound IC50 (μM) | Example 35 IC50 (μM) | Combo IC50 (μM) | Combination or Potentiation Index |
|---|---|---|---|---|---|
| SW1463 | Abemaciclib | 0.16253 | 0.001089422 | 0.001861309 | 0.859990152 |
| SW837 | Abemaciclib | 3.2175 | 0.413147553 | 0.276563347 | 0.377680849 |
| H358 | Abemaciclib | 0.47697 | 0.003199233 | 0.006847357 | 1.077334012 |
| HCC44 | Abemaciclib | 3.64845 | 1.764025208 | 2.86634865 | 1.205263179 |
| NCI-H1373 | Abemaciclib | 4.27817 | 0.403993227 | 0.11698021 | 0.158451664 |
| NCI-H1792 | Abemaciclib | 0.40097 | 0.118134759 | 0.041106255 | 0.225239313 |
| NCI-H2030 | Abemaciclib | 1.81728 | 0.819557983 | 0.357361105 | 0.316343687 |
| NCI-H2122 | Abemaciclib | 0.32737 | 0.031200861 | 0.02784263 | 0.488708133 |
| SW1573 | Abemaciclib | 0.35607 | 10.7632 | 0.614058717 | 0.890789114 |
| KYSE-410 | Abemaciclib | 1.94423 | 4.89618484 | 0.773507455 | 0.277914318 |
| MIAPACA2 | Abemaciclib | 0.28033 | 0.00748134 | 0.01060427 | 0.727628496 |

As shown in Table 32, the combination of the compound of Example 35 and the EGFR small molecule inhibitor erlotinib or afatinib has an additive or a synergistic effect in inhibiting tumor cells harboring a KRasG12C mutation. For the erlotinib combination, among eleven cell lines tested, an additive effect is observed in five cell lines, with a Combination or Potentiation Index between 0.5 and 1.15, and a synergistic effect is observed in six cell lines, with Combination or Potentiation Index <0.5. For the afatinib combination, among nine cell lines tested, an addition effect is observed in four cell lines, with a CI between 0.5 and 1.1, and a synergistic effect is observed in five cell lines, with a CI<0.5. These data suggest that combination of Example 35 and an EGFR small molecule inhibitor may provide benefit to cancer patients with a KRas G12C mutation.

TABLE 32

In Vitro Combination of the Compound of Example 35 and the EGFR Small Molecule Inhibitor Erlotinib or Afatinib

| Cell Line Name | Compound | Compound IC50 (μM) | Example 35 IC50 (μM) | Combo IC50 (μM) | Combination or Potentiation Index |
|---|---|---|---|---|---|
| SW1463 | Erlotinib | 0.40193 | 0.001089 | 0.002231 | 1.026498376 |
| SW837 | Erlotinib | >10 | 0.413148 | 0.140876 | 0.170491111 |
| H358 | Erlotinib | 2.19247 | 0.003199 | 0.007357 | 1.151488525 |
| HCC44 | Erlotinib | >10 | 1.764025 | 1.567802 | 0.444381951 |
| NCI-H1373 | Erlotinib | >10 | 0.403993 | 0.411429 | 0.509203323 |
| NC1-H1792 | Erlotinib | >10 | 0.118135 | 0.090106 | 0.381370715 |
| NCI-H2030 | Erlotinib | >10 | 0.819558 | 0.424816 | 0.259174125 |
| NCI-H2122 | Erlotinib | 12.1511 | 0.031201 | 0.030705 | 0.493309984 |
| SW1573 | Erlotinib | >10 | 10.7632 | 11.32891 | 0.526279729 |
| KYSE-410 | Erlotinib | >10 | 4.896185 | 1.153993 | 0.11784619 |
| MIAPACA2 | Erlotinib | >10 | 0.007481 | 0.015373 | 1.027399401 |
| SW1463 | Afatinib | 0.05612 | 0.003248 | 0.003838 | 0.625028705 |
| SW837 | Afatinib | 1.28333 | 0.321329 | 0.06905 | 0.134347371 |
| H358 | Afatinib | 0.30551 | 0.002231 | 0.004945 | 1.11655131 |
| NCI-H1373 | Afatinib | 2.21668 | 0.255708 | 0.090101 | 0.196502052 |
| NCI-H1792 | Afatinib | 3.39177 | 0.903764 | 0.2928 | 0.205152445 |
| NCI-H2122 | Afatinib | 1.45096 | 0.03372 | 0.019501 | 0.295874375 |
| SW1573 | Afatinib | 1.58254 | 12.736 | 2.456936 | 0.872720042 |
| KYSE-410 | Afatinib | 0.65031 | 4.058337 | 0.041564 | 0.03707842 |
| MIAPACA2 | Afatinib | 1.94391 | 0.005951 | 0.011389 | 0.959906159 |

As shown in Table 33, the combination of the compound of Example 35 and the EGFR antibody cetuximab has additive or synergistic efficacy in inhibiting tumor cells with the KRas G12C mutation. Among eleven cell lines tested, five cell lines have additive effects with Potentiation Index (CI) between 0.5 and 1.06, and six cell line have synergistic effects with Potentiation Index <0.5, suggesting that combination of Example 35 and Cetuximab may provide benefit to cancer patients with KRasG12C mutation.

TABLE 33

In Vitro Combination of Example 35 and EGFR Antibody Cetuximab

| Cell Line Name | Compound | Compound IC50 (μM) | Example 35 IC50 (μM) | Combo IC50 (μM) | Potentiation Index |
|---|---|---|---|---|---|
| SW1463 | Cetuximab | >20 | 0.001089422 | <0.00152 | <0.4663 |
| SW837 | Cetuximab | >20 | 0.413147553 | 0.059912256 | 0.048338062 |
| H358 | Cetuximab | >20 | 0.003199233 | 0.004884468 | 0.508920734 |
| HCC44 | Cetuximab | >20 | 1.764025208 | 5.643865533 | 1.066474845 |
| NCI-H1373 | Cetuximab | >20 | 0.403993227 | 0.433760358 | 0.357894084 |
| NCI-H1792 | Cetuximab | >20 | 0.118134759 | 0.054252171 | 0.153079899 |
| NCI-H2030 | Cetuximab | >20 | 0.819557983 | 2.161595154 | 0.879171131 |
| NCI-H2122 | Cetuximab | >20 | 0.031200861 | 0.021630045 | 0.23108385 |
| SW1573 | Cetuximab | >20 | 10.7632 | 23.86318501 | 0.739036253 |
| KYSE-410 | Cetuximab | >20 | 4.89618484 | 1.117690734 | 0.076092629 |
| MIAPACA2 | Cetuximab | >20 | 0.00748134 | 0.018187633 | 0.810355342 |

As shown in Table 34, the combination of the compound of Example 35 and the ERK inhibitor LY3219446 has additive or synergistic efficacy in inhibiting tumor cells with the KRas G12C mutation. Among ten cell lines tested, an additive effect is observed in 5 cell lines, with a CI between 0.5 and 1.2, and a synergistic effect is observed in 5 cell lines, with a Combination or Potentiation Index <0.5, suggesting that combination of Example 35 and an ERK inhibitor may provide benefit to cancer patients with the KRas G12C mutation.

TABLE 34

In Vitro Combination of the Compound of Example 35 and ERK Inhibitor LY3214996

| Cell Line Name | Compound | Compound IC50 (uM) | Example 35 IC50 (uM) | Combo_IC50 (uM) | Combination or Potentiation_Index |
|---|---|---|---|---|---|
| SW1463 | LY3214996 | 0.42099 | 0.001089 | 0.001225 | 0.563579 |
| SW837 | LY3214996 | 3.4288 | 0.413148 | 0.149674 | 0.202965 |
| H358 | LY3214996 | 1.67124 | 0.001854 | 0.004485 | 1.210955 |
| HCC44 | LY3214996 | 3.26824 | 1.764025 | 1.988401 | 0.867799 |
| NCI-H1373 | LY3214996 | 9.2603 | 0.403993 | 0.304663 | 0.393514 |
| NCI-H1792 | LY3214996 | 3.51533 | 0.862901 | 1.310947 | 0.946077 |
| NCI-H2122 | LY3214996 | 1.60091 | 0.108719 | 0.068988 | 0.338821 |
| SW1573 | LY3214996 | >10 | 10.7632 | 8.05786 | 0.374325 |
| KYSE-410 | LY3214996 | 4.59338 | 4.896185 | 2.178332 | 0.459569 |
| MIAPACA2 | LY3214996 | 0.8405 | 0.00628 | 0.014545 | 1.166658 |

In Vitro Combination Efficacy of the Compound of Example 35 with Chemotherapies The compound of Example 35 is also combined with chemotherapy, including pemetrexed, carboplatin or cisplatin, in three lung cancer cell lines, H1792, H358 and H2122, in vitro. As shown in Table 35, for the pemetrexed combination, additive or synergistic effects are observed based on the CI. Similar combinational effects are observed with carboplatin and cisplatin combination.

TABLE 35

In Vitro Combination of the Compound of Example 35 and Chemotherapies (Combination Index).

| | Cell_lines | | |
|---|---|---|---|
| | NCI-H1792 | NCI-H358 | NCI-H2122 |
| ABS_IC50_Example 35 (uM) | 0.8399 | 0.001 | 0.209 |
| ABS_IC50_pemetrexed (uM) | 20 | 20 | 0.003739 |
| ABS_IC50_Combo (uM) | 1.305 | 0.001 | 0.000084 |
| Combination Index | 0.809 | 0.5 | 0.011 |
| ABS_IC50_carboplatin (uM) | 20 | 20 | 20 |
| ABS_IC50_Combo (uM) | 2.6 | 0.001 | 0.0363 |
| Combination Index | 1.616 | 0.5 | 0.087 |
| ABS_IC50_cisplatin (uM) | 0.312 | 0.773 | 1.163 |
| ABS_IC50_Combo (uM) | 0.134 | 0.001 | 0.15 |
| Combination Index | 0.296 | 0.5 | 0.422 |

In Vivo Combination Efficacy of Example 35 with Other Targeted Therapies

The compound of Example 35 is evaluated in combination with the CDK4/CDK6 inhibitor abemaciclib, the EGFR small molecule inhibitors erlotinib or afatinib, the anti-EGFR monoclonal antibody cetuximab, or the ERK inhibitor LY3214996, in a PDX animal model. A total of six in vivo xenograft or PDX models—four lung models (H358, H1373, LU99, and EL3187 PDX), one colorectal model (SW1463) and one pancreatic model (MiaPaca-2)—are utilized. Table 36 is a summary of all these in vivo combination study results.

The combination of the compound of Example 35 and the CDK4/6 inhibitor abemaciclib is studied in all six models. In all six models, the combination is better than for either the compound of Example 35 or abemaciclib alone. In four lung cancer models and in one pancreatic cancer model, synergy and significant tumor growth regression are observed for the combination. In the colorectal SW1463 model, better anti-tumor activity is observed than for either the compound of Example 35 or abemaciclib alone.

The combination of the compound of Example 35 and the EGFR small molecule inhibitor erlotinib is conducted in all six models. In all six models, the combination is better than for either the compound of Example 35 or erlotinib alone. In three lung cancer models and one pancreatic cancer model, synergy and significant tumor growth regression are observed for the combination. In the colorectal cancer SW1463 model and the lung cancer LU99 model, the combination is better than for either the compound of Example 35 or erlotinib alone. In the lung cancer H358 xenograft model, an additive effect and better anti-tumor activity is observed the combination of the compound of Example 3 and the EGFR small molecule inhibitor afatinib, relative to either compound alone.

In vivo combination studies of Example 35 and EGFR antibody cetuximab are conducted in H358 lung cancer xenograft model and SW1463 colorectal cancer xenograft model. In both models, tumor growth regression and better combination efficacy are observed for the combination. The combination is better than either the compound Example 35 or cetuximab alone.

The combination of the compound of Example 35 and the ERK inhibitor (ERKi) LY3214996 is studied in all six models. In all six models, synergy or additive effect is observed for the combination, and the combination is better than either the compound of Example 35 or ERK inhibitor alone. In three lung cancer models (H358, H1373 and EL3187), one pancreatic cancer model and one colorectal model, significant tumor growth regression are observed.

TABLE 36

In Vivo Anti-Tumor Activities of the Compound of Example 35 in Combination with Other Targeted Therapies in Tumor Xenograft or PDX Models

| | | | Tumor Growth Inhibition (%) and Regression (−%) in xenograft or PDX models | | | | | |
|---|---|---|---|---|---|---|---|---|
| Treatment | Dose (mg/kg) | Dose | H358 (Lung) | H1373 (Lung) | EL3187 (Lung PDX) | Mia Paca-2 (Pancr) | SW1463 (CRC) | LU99 (Lung) |
| Example 35 | 3 | QD × 28 | — | — | — | 85.2 | — | — | — |
| | 10 | QD × 28 | 74.9 | 46.6 | 98.5 | | −27 | 44 | 68.7 |
| | 30 | QD × 28 | — | — | — | — | — | — | 76.2 |
| ERKi | 100 | QD × 28 | 71.1 | — | 85.2 | 85.4 | 46.5 | — | 92.7 | 28.6 |
| abemaciclib | 50 | QD × 28 | 77 | — | 77.6 | 41.3 | 45.1 | 53 | — | (−21.5)* |
| erlotinib | 25 | QD × 28 | 76.9 | — | 50.6 | 29.5 | (−77.7)* | 40.9 | | (−23.1)* |
| cetuximab | 20 | QD × 28 | — | 87 | — | — | — | 97.9 | 94.7 | — |
| afatinib | 25 | QD × 28 | — | 77.4 | — | — | — | — | — |
| Example 35 + ERKi | 10 + 100 | | — | −22.1 | — | −70.2 | −83.3 | −65.4 | −24.8 | −3.7 |
| Example 35 + abemaciclib | 10 + 50 | | — | −61.8 | — | −54.4 | −96 | −59.8 | 81 | — | −37.4 |
| Example 35 + erlotinib | 10 + 25 | | — | −64 | — | −48.9 | −89.9 | −62.2 | 88 | — | 98.9 |

TABLE 36-continued

In Vivo Anti-Tumor Activities of the Compound of Example 35 in Combination with Other Targeted Therapies in Tumor Xenograft or PDX Models

| Treatment | Dose (mg/kg) | Dose | H358 (Lung) | H1373 (Lung) | EL3187 (Lung PDX) | Mia Paca-2 (Pancr) | SW1463 (CRC) | | LU99 (Lung) |
|---|---|---|---|---|---|---|---|---|---|
| Example 35 + cetuximab | 30 + 20 | — | −34.6 | — | — | — | −20.2 | −42.8 | — |
| Example 35 + afatinib | 10 + 25 | — | 91.3 | — | — | — | — | — | — |

*Indicates average tumor volume was larger than vehicle control group

Combination Efficacy with Immuno-Therapies, Anti-PD-1 or Anti-PD-L1 Antibody

A mouse syngeneic model is used to evaluate the effects of KRas G12C inhibition and immuno-therapy combination. In this model, the KRas G12D mutation is converted to KRas G12C mutation by CRISPR knock-in in the CT-26 cell line, a mouse colorectal tumor cell line. The KRas G12C knock-in is confirmed by genetic and functional characterization. The engineered cell line is named CT-26-H4/KRas G12C. These cells are implanted to the Balb/c mice, and the compound treatment is started 6 days post tumor cell implantation. In this study, the compound of Example 35 is combined with either anti-PD-L1 antibody (RMP1-14 (BioXcell Cat. No. BE0146)) or an anti-PD-1 antibody (Holmgaard R B, et al., *J. Immunotherapy Cancer* 2018; 6(47): 1-15), with the dose schedule listed in Table 37. As shown in Table 37 the compound of Example 35 demonstrates significant single agent activity, with an average of 89.4% tumor growth inhibition, and no complete response at 30 mg/kg at the end of 3 week dose. An anti-mouse PD-L1 antibody 178G7 shows 36.1% tumor growth inhibition, with no complete response, and anti-PD-1 antibody RMP1-14 shows 70.7% tumor growth inhibition and 10% (1 out of 10) complete response at the end of the dose (day 21) or day 59. However, the combination of the compound of Example 35 with either the anti-PD-L1 or the anti-PD-1 antibody achieves significantly better anti-tumor activity. At the end of 3 week dose, the combination of the compound of Example 35 with the anti-PD-L1 or anti-PD-1 antibody shows −33.9% and −19.4% tumor regression, and 30% and 40% complete response, respectively. After 3 weeks, compound treatment is stopped and all tumors in monotherapy groups, with exception of 1 animal in the anti-PD-1, group started to regrow. However, many tumors in the two combination groups show no signs of regrowth. 38 days after the last dose (day 59), the combination groups have 40% and 60% complete response, indicating that many tumors in combination groups are eliminated. These results suggest that treatment with the compound of Example 35, in combination with either an anti-PD-L1 or an anti-PD-1 antibody, may be beneficial for cancer patients with the KRas G12C mutation.

TABLE 37

In Vivo Anti-Tumor Activity of the Compound of Example 35 in Combination with Immuno-Therapy (Anti-PD-1 or Anti-PD-L1 antibody) in CT-26-H4/KRasG12C Syngeneic Model

| Treatment | Dose | Dose Frequency | TGI (T/C) (%) | % Regression | Complete Regression (day 21) | Complete Regression (day 59) |
|---|---|---|---|---|---|---|
| Vehicle | | PO, QD × 21 | — | — | 0/10 | 0/10 |
| Example 35 | 30 mg/kg | PO, QD × 21 | 89.4 (11.6) | — | 0/10 | 0/10 |
| PD-L1 antibody (178G7) | 500 μg/mouse | IP, Q7D × 3 | 36.1 (63.9) | — | 0/10 | 0/10 |
| PD-1 antibody (RMP1-14) | 250 μg/mouse | IP, BIW × 3 | −70.7 (29.3) | — | 1/10 | 1/10 |
| Example 35 + PD-L1 antibody (178G7) | 30 mg/kg 500 μg/mouse | PO, QD × 21 IP, Q7D × 3 | — | −33.9 | 3/10 | 4/10 |
| Example 35 + PD-1 antibody (RMP1-14) | 30 mg/kg 250 μg/mouse | PO, QD × 21 IP, BIW × 3 | — | −19.4 | 4/10 | 6/10 |

What is claimed is:

1. A compound of the formula:

[Chemical structure]

wherein:
A is —OCH$_2$—, —N(R$_6$)CH$_2$—, —OCH$_2$CH$_2$—, —N(R$_6$)CH$_2$CH$_2$—, —CH$_2$OCH$_2$—, or —CH$_2$N(R$_6$)CH$_2$—;
B is —CH$_2$— or —C(O)—,
Y is —C(CN)— or —N—;
R$_1$ is —CN, —C(O)C≡CR$_8$, or a group of the formula

[Chemical structure]

R$_2$ is H, methyl, or —CH$_2$CN;
R$_3$ and R$_5$ are each independently H, halogen, —C$_{0-3}$ alkyl-cyclopropyl, —C$_{1-6}$ alkyl optionally substituted 1-3 times with R$_{10}$, or —O—C$_{1-6}$ alkyl optionally substituted 1-3 times with R$_{10}$;
R$_4$ is H, halogen, or —C$_{1-6}$ alkyl optionally substituted 1-3 times with R$_{10}$;
R$_6$ is H or —C$_{1-6}$ alkyl optionally substituted 1-3 times with R$_{10}$;
R$_7$ is H, halogen, —NR$_{11}$R$_{12}$, —CH$_2$NR$_{11}$R$_{12}$, —C$_{1-6}$ alkyl optionally substituted 1-3 times with R$_{10}$ or R$_{13}$, —C$_{0-3}$ alkyl cyclopropyl, or —O—C$_{1-6}$ alkyl optionally substituted 1-3 times with R$_{10}$ or R$_{13}$;
R$_8$ is H, —C$_{1-4}$ alkyl optionally substituted 1-3 times with R$_{10}$, or —C$_{3-6}$ cycloalkyl optionally substituted 1-3 times with R$_{10}$;
R$_9$ is H, halogen, —CN, —C$_{0-3}$ alkyl-C$_{3-6}$ cycloalkyl, or —C$_{1-6}$ alkyl optionally substituted 1-3 times with R$_{10}$;
R$_{10}$ is independently at each occurrence halogen, oxygen, hydroxy, —C$_{1-4}$ alkyl, or —O—C$_{1-4}$ alkyl;
R$_{11}$ and R$_{12}$ are each independently H, —C$_{1-4}$ alkyl, or —C$_{1-4}$ heteroalkyl, wherein R$_{11}$ and R$_{12}$ may combine to form a cycloheteroalkyl; and
R$_{13}$ is independently at each occurrence —N—C$_{1-4}$ alkyl, or a pharmaceutically acceptable salt thereof.

2. The compound according to claim 1, wherein A is —OCH$_2$CH$_2$—, or a pharmaceutically acceptable salt thereof.

3. The compound according to claim 1, wherein B is —C(O)—, or a pharmaceutically acceptable salt thereof.

4. The compound according to claim 1, wherein Y is —C(CN)—, or a pharmaceutically acceptable salt thereof.

5. The compound according to claim 1, wherein Y is —N—, or a pharmaceutically acceptable salt thereof.

6. The compound according to claim 1, wherein R$_1$ is a group of the formula

[Chemical structure]

and wherein R$_7$ is H, F, Cl, methyl, ethoxy, ethyl, isopropyl, or cyclopropyl, or a pharmaceutically acceptable salt thereof.

7. The compound according to claim 6, wherein R$_9$ is H, F, Cl, —CHF$_2$, —CF$_3$, or —CH$_2$OH, or a pharmaceutically acceptable salt thereof.

8. The compound according to claim 1, wherein R$_1$ is —CN, —C(O)C≡CR$_8$, or a pharmaceutically acceptable salt thereof.

9. The compound according to claim 1, wherein R$_2$ is H or methyl, or a pharmaceutically acceptable salt thereof.

10. The compound according to claim 1, wherein R$_3$ is H, F, Cl, methyl, methoxy, ethyl, isopropyl, or cyclopropyl or a pharmaceutically acceptable salt thereof.

11. The compound according to claim 1, wherein R$_4$ is H, F, or Cl, or a pharmaceutically acceptable salt thereof.

12. The compound according to claim 1, wherein R$_5$ is H, —CHF$_2$, —CH$_2$F, —CH$_2$OH, or —CH$_2$OCH$_3$, or a pharmaceutically acceptable salt thereof.

13. The compound according to claim 1, of the formula:

[Chemical structure]

wherein:
A is —OCH$_2$— or —OCH$_2$CH$_2$—;
Y is C(CN) or N;
R$_3$ is Cl or F;
R$_4$ is H or F when Y is C(CN); and
R$_4$ is F when Y is N,
or a pharmaceutically acceptable salt thereof.

14. The compound according to claim 13, wherein A is

[Chemical structure] or [Chemical structure].

15. The compound according to claim 1 selected from:

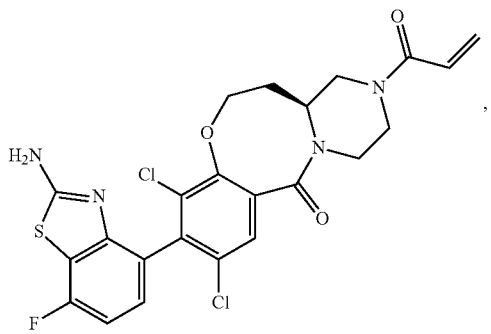

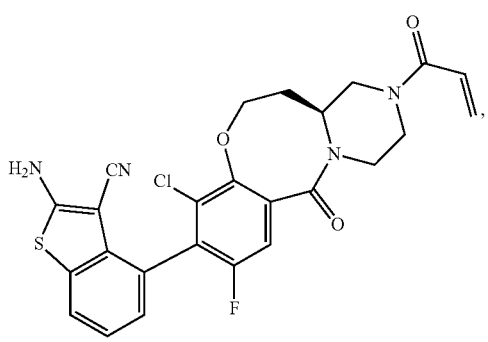

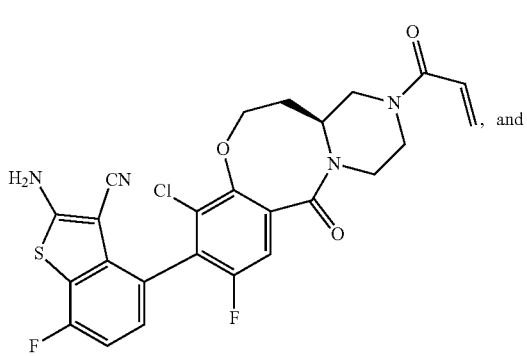, and

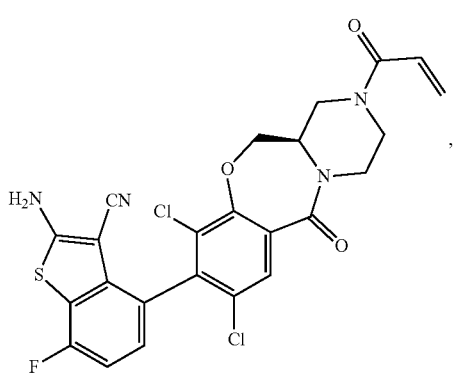

or a pharmaceutically acceptable salt thereof.

16. The compound according to claim 15, which is:

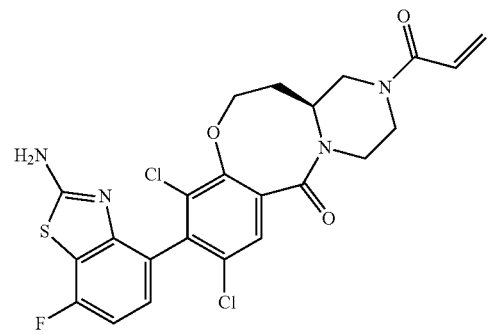

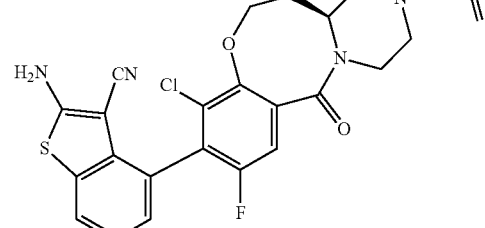

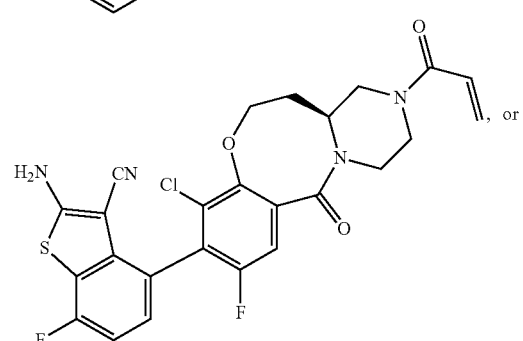, or

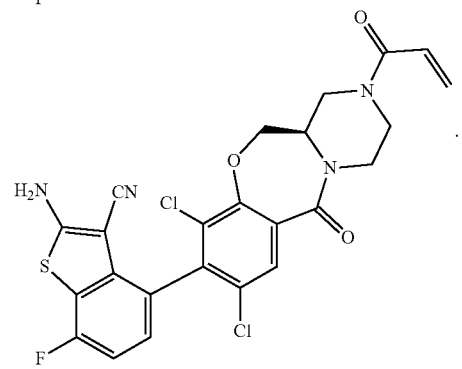

17. A method of treating a patient for cancer, comprising administering to a patient in need thereof, an effective amount of a compound according to claim 1, or a pharmaceutically acceptable salt thereof, wherein the cancer has a KRAS G12C mutation and is selected from the group consisting of lung cancer, pancreatic cancer, cervical cancer, esophageal cancer, endometrial cancer, ovarian cancer, cholangiocarcinoma, and colorectal cancer.

18. The method according to claim 17 wherein the cancer is non-small cell lung cancer, and wherein one or more cells express KRas G12C mutant protein.

19. The method according to claim 17 wherein the cancer is colorectal cancer, and wherein one or more cells express KRas G12C mutant protein.

20. The method according to claim 17 wherein the cancer is pancreatic cancer, and wherein one or more cells express KRas G12C mutant protein.

21. The method according to claim 17 wherein the patient has a cancer that was determined to have one or more cells expressing the KRas G12C mutant protein prior to administration of the compound or a pharmaceutically acceptable salt thereof.

22. A method of treating a patient with a cancer that has a KRAS G12C mutation comprising administering to a patient in need thereof an effective amount of a compound according to claim 1, or a pharmaceutically acceptable salt thereof.

23. The method according to claim 17, wherein the patient is also administered an effective amount of one or more of a PD-1 inhibitor, a PD-L1 inhibitor, a CD4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof, a platinum agent, or pemetrexed, or a pharmaceutically acceptable salt thereof.

* * * * *

UNITED STATES PATENT AND TRADEMARK OFFICE
CERTIFICATE OF CORRECTION

Page 1 of 2

PATENT NO. : 11,731,984 B2
APPLICATION NO. : 17/111676
DATED : August 22, 2023
INVENTOR(S) : Boulet et al.

It is certified that error appears in the above-identified patent and that said Letters Patent is hereby corrected as shown below:

On the Title Page

Item (73), under Assignee:
Delete "LIlly" and insert -- Lilly --.

In the Claims

Column 207, Line 24:
In Claim 1, delete "—C(O)—," and insert -- —C(O)—; --.

Column 209, Lines 51-65 (structure):

In Claim 15, delete " 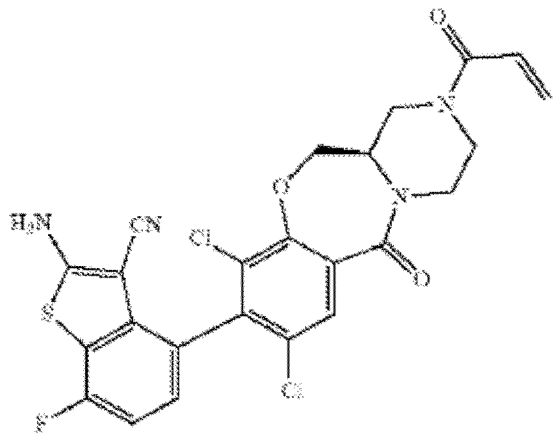 " and insert

Signed and Sealed this
Twenty-sixth Day of December, 2023

Katherine Kelly Vidal
*Director of the United States Patent and Trademark Office*

CERTIFICATE OF CORRECTION (continued)
U.S. Pat. No. 11,731,984 B2

Page 2 of 2

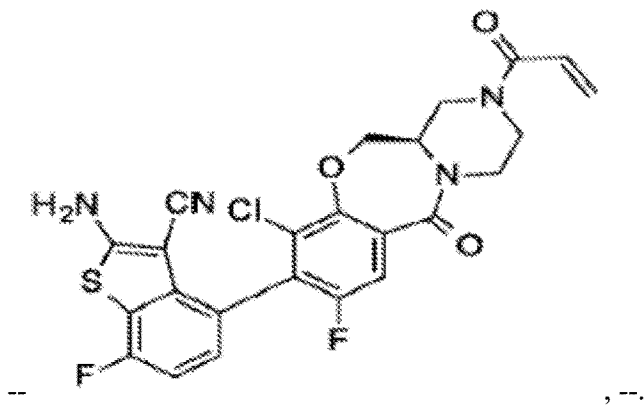

Column 210, Lines 41-55 (structure):

In Claim 16, delete " 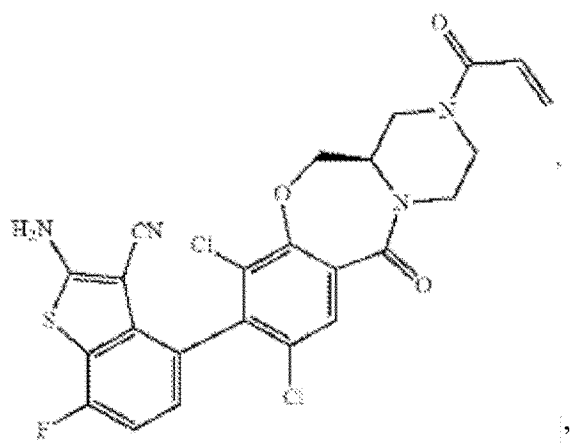 " and insert

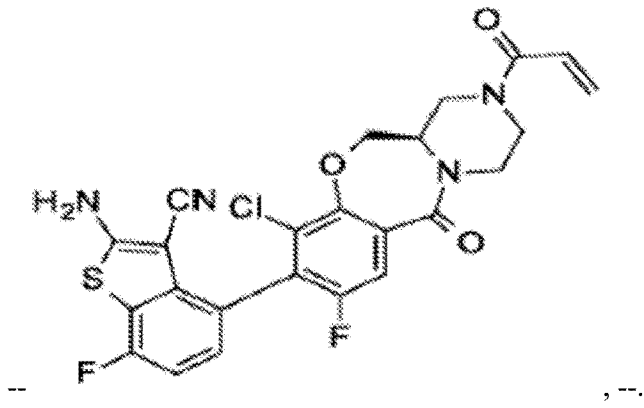

-- , --.